(12) United States Patent
Lai et al.

(10) Patent No.: US 11,732,264 B2
(45) Date of Patent: *Aug. 22, 2023

(54) COMPOSITIONS AND METHODS FOR TREATING COVID-19

(71) Applicant: Vast Sea Biotechnology, Inc., Rockville, MD (US)

(72) Inventors: Norman Zhennan Lai, N. Potomac, MD (US); Yuebin Tan, Gaithersburg, MD (US); Ying Wang, Washington, DC (US)

(73) Assignee: Vast Sea Biotechnology, Inc., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/512,963

(22) Filed: Oct. 28, 2021

(65) Prior Publication Data

US 2022/0127614 A1 Apr. 28, 2022

Related U.S. Application Data

(63) Continuation of application No. 17/350,114, filed on Jun. 17, 2021.

(60) Provisional application No. 63/041,587, filed on Jun. 19, 2020.

(51) Int. Cl.
| | | |
|---|---|---|
| *C12N 15/11* | (2006.01) | |
| *C12N 15/113* | (2010.01) | |
| *A61K 38/48* | (2006.01) | |
| *A61K 31/375* | (2006.01) | |
| *A61K 31/4415* | (2006.01) | |
| *A61K 31/714* | (2006.01) | |
| *A61K 31/593* | (2006.01) | |
| *A61K 33/30* | (2006.01) | |
| *A61K 31/198* | (2006.01) | |
| *A61K 36/534* | (2006.01) | |
| *A61P 31/14* | (2006.01) | |
| *C12N 15/86* | (2006.01) | |
| *A23L 33/18* | (2016.01) | |
| *A61K 31/7088* | (2006.01) | |
| *A61K 38/55* | (2006.01) | |
| *A61K 48/00* | (2006.01) | |

(52) U.S. Cl.
CPC .......... *C12N 15/1131* (2013.01); *A23L 33/18* (2016.08); *A61K 31/198* (2013.01); *A61K 31/375* (2013.01); *A61K 31/4415* (2013.01); *A61K 31/593* (2013.01); *A61K 31/7088* (2013.01); *A61K 31/714* (2013.01); *A61K 33/30* (2013.01); *A61K 36/534* (2013.01); *A61K 38/4813* (2013.01); *A61K 38/556* (2013.01); *A61P 31/14* (2018.01); *C12N 15/86* (2013.01); *C12Y 304/17023* (2013.01); *A23V 2002/00* (2013.01); *A61K 48/00* (2013.01); *C12N 2310/14* (2013.01); *C12N 2310/321* (2013.01); *C12N 2310/322* (2013.01); *C12N 2310/3517* (2013.01); *C12N 2320/32* (2013.01); *C12N 2750/14143* (2013.01)

(58) Field of Classification Search
CPC ... C12N 15/1131; A23L 33/18; A61K 38/556; A61P 31/14
See application file for complete search history.

(56) References Cited

U.S. PATENT DOCUMENTS

| | | |
|---|---|---|
| 2003/0138894 A1 | 7/2003 | Parry et al. |
| 2006/0084620 A1 | 4/2006 | McCray et al. |
| 2006/0258611 A1 | 11/2006 | Kung et al. |
| 2010/0261214 A1 | 10/2010 | Loibner et al. |

FOREIGN PATENT DOCUMENTS

| | | | |
|---|---|---|---|
| WO | WO-2021188966 A1 | * | 9/2021 |
| WO | WO-2021224918 A1 | * | 11/2021 |

OTHER PUBLICATIONS

Gen Bank Accession No. AAQ89076.1 (2003, pp. 1-2) (Year: 2003).*
AL-Azzam S. et al., "Peptides to Combat Viral Infectious Diseases", Peptides 134:170402 (2020).
Chen W. et al., "Computational Identification of Small Interfering RNA Targets in SARS-CoV-2", Virologica Sinica 35(3):359-361 (Apr. 15, 2020).
Cox R.M. et al., "Therapeutically Administered Ribonucleotide Analogue MK-4482/EIDD-2801 Blocks SARS-CoV-2 Transmission in Ferrets", Nature Microbiology 6:11-18 (Jan. 2021).
Idris A. et al., "A SARS-CoV-2 Targeted siRAN-Nanoparticle Therapy for COVID-19", (14 pages) (2021).

(Continued)

*Primary Examiner* — Ekaterina Poliakova-Georgantas
(74) *Attorney, Agent, or Firm* — Scully, Scott, Murphy & Presser, P.C.

(57) ABSTRACT

This disclosure is directed to inhibitory oligonucleotides, inhibitory peptides, compositions and methods for preventing or treating Coronavirus disease 2019 (COVID-19). In one aspect, the disclosure is directed to compositions that comprise inhibitory oligonucleotides against one or more SARS-CoV-2 virus genes. In another aspect, the disclosure is directed to compositions that comprise inhibitory peptides that inhibit SARS-COV-2 entry into cells. Another aspect of the disclosure is directed to gene therapy methods for treating COVID-19, and vectors for carrying out the same. Finally, the disclosure provides nutritional supplements to support human immunity and prevent or inhibit viral infections.

16 Claims, 86 Drawing Sheets

Specification includes a Sequence Listing.

(56) References Cited

OTHER PUBLICATIONS

Ju B. et al., "Human Neutralizing Antibodies Elicited by SARS-CoV-2 Infection", Nature 584(7819):115-119 (Aug. 6, 2020).
Larue R.C. et al., "Rationally Designed ACE2-Derived Peptides Inhibit SARS-CoV-2", Bioconjugate Chemistry 32:215-223 (2021).
Li W. et al., "Angiotensin-Converting Enzyme 2 is a Functional Receptor for the SARS Coronavirus", Nature 426(6965):450-454 (Nov. 27, 2003).
Lykken E A et al., "Recent Progress and Considerations for AAV Gene Therapies Targeting the Central Nervous System", Journal of Neurodevelopment Disorders 10:16 (2018).
Malonis R.J. et al., "Peptide-Based Vaccines: Current Progress and Future Challenges", Chemical Reviews 120:3210-3229 (2020).
Morris D. et al., "Glutathione and Infection", Biochimica et Biophysica Acta 1830:3329-3349 (2013).
Philippe S. et al., "Lentiviral Vectors With a Defective Integrase Allow Efficient and Sustained Transgene Expression In Vitro and In Vivo", PNAS 103(47):17684-17689 (Nov. 21, 2006).
Shi Z. et al., "N-Acetylcysteine to Combat COVID-19: An Evidence Review", Therapeutics and Clinical Risk Management 16:1047-1055 (2020).
Wu F. et al., "A New Coronavirus Associated With Human Respiratory Disease in China", Nature 579(7798):265-269 (Mar. 12, 2020).
Yan R. et al., "Structural Basis for the Recognition of SARS-CoV-2 by Full-Length Human ACE2", Science 367:1444-1448 (Mar. 27, 2020).
Yi C. et al., "Key Residues of the Receptor Binding Motif in the Spike Protein of SARS-CoV-2 that Interact with ACE2 and Neutralizing Antibodies", Cellular & Molecular Immunology 17(6):621-630 (May 15, 2020).
Yoshimoto F.K., "The Proteins of Severe Acute Respiratory Syndrome Coronavirus-2 (SARS CoV-2 or n-COV19), the Cause of COVID-19", The Protein Journal 39(3):198-216 (May 23, 2020).
GenBank Accession No. MN908947.3 (11 pages) (Mar. 18, 2020).
International Search Report & Written Opinion dated Oct. 28, 2021 received in International Application No. PCT/US2021/037747.

* cited by examiner

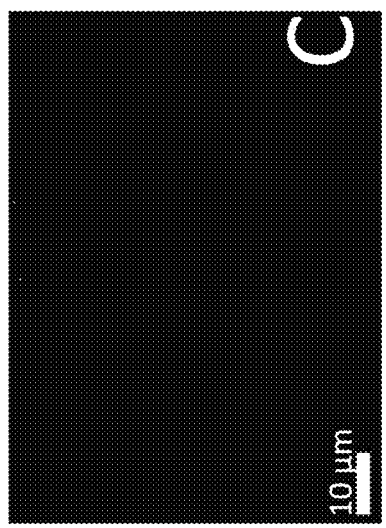
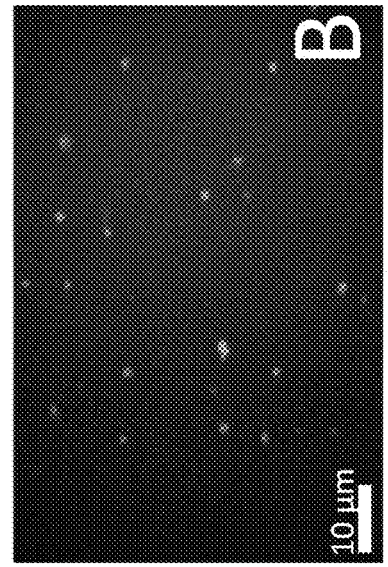
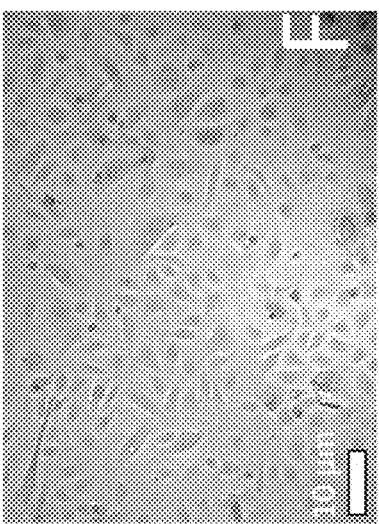
FIG. 3A  FIG. 3B  FIG. 3C
Human Primary Small Airway Epithermal Cells (HSAEC) (10X):
Overexpression of N-protein + VS_ASO_1-FANA with lipofectamine
Overexpression of N-protein + VS_ASO_1-FANA without lipofectamine or Poly-Arginine
Overexpression N-protein only
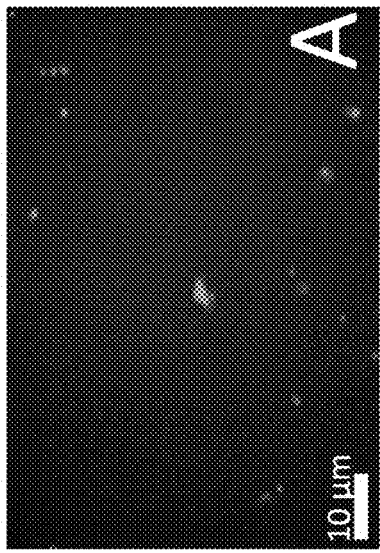
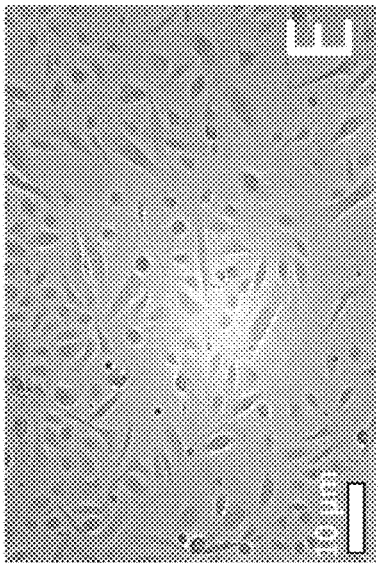
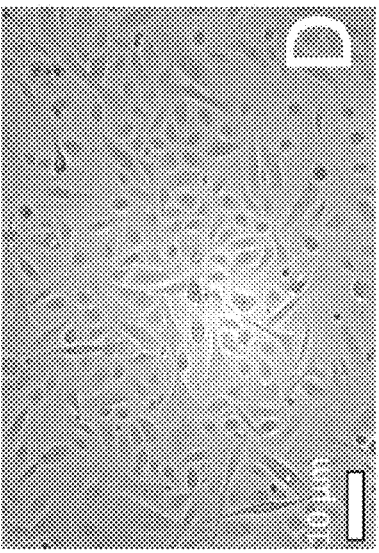
FIG. 3D  FIG. 3E  FIG. 3F

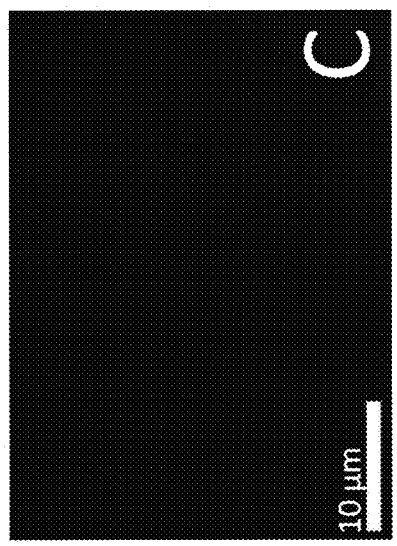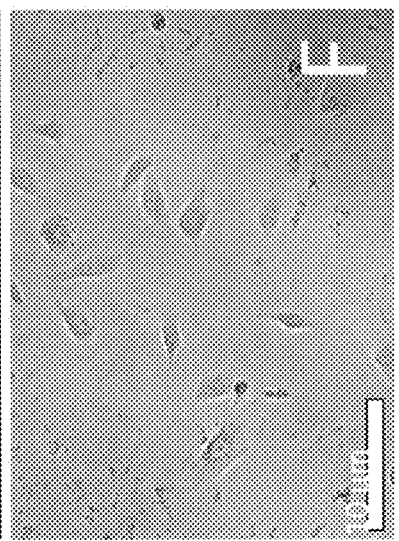
FIG. 4A — Overexpression of N-protein + VS_DsiRNA-Cy5 with lipofectamine
FIG. 4B — Overexpression of N-protein + VS_DsiRNA-Cy5 with Poly-Arginine (5µl/well)
FIG. 4C — Overexpression N-protein only
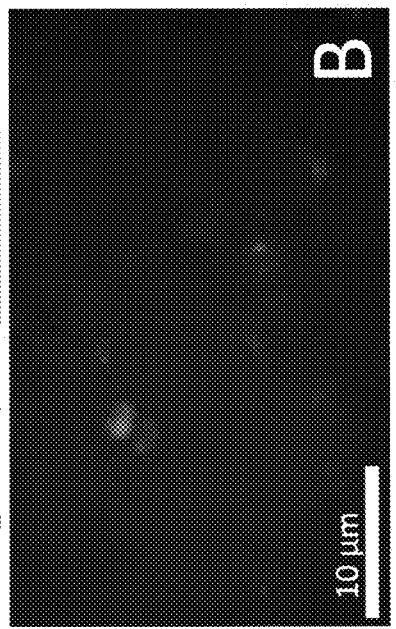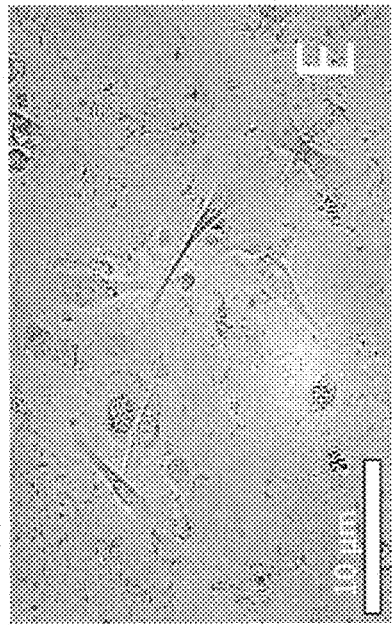
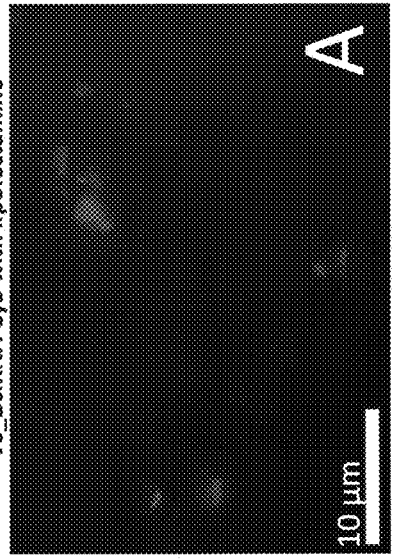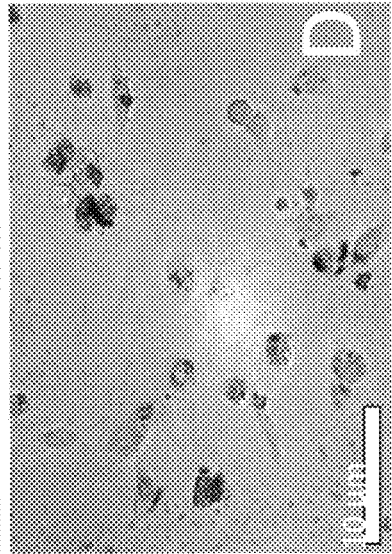
FIG. 4D
FIG. 4E
FIG. 4F

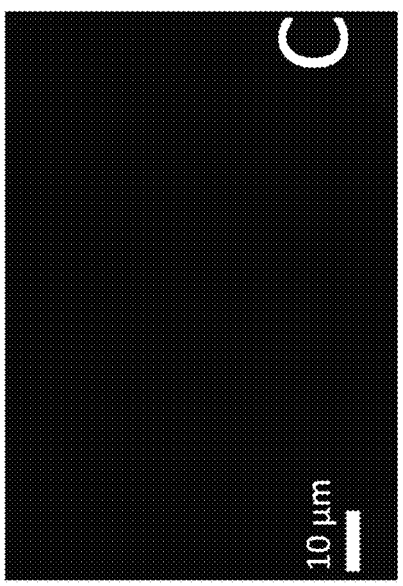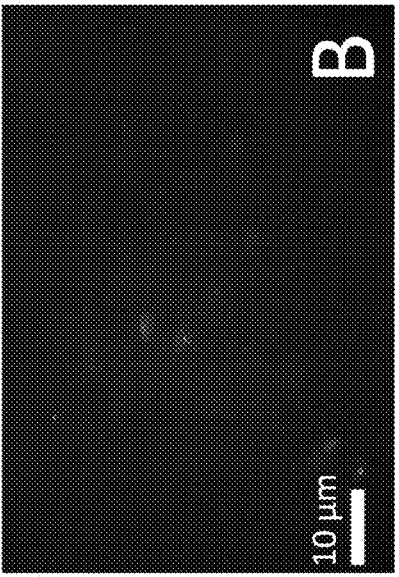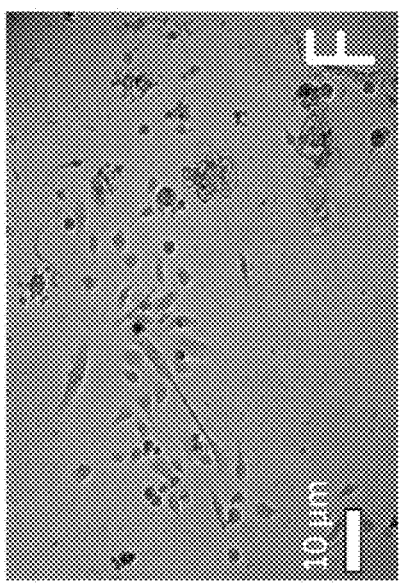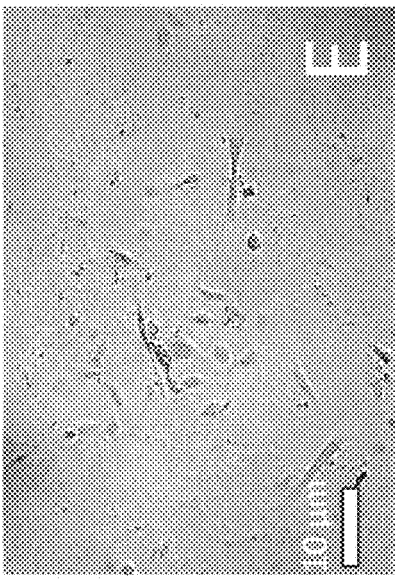
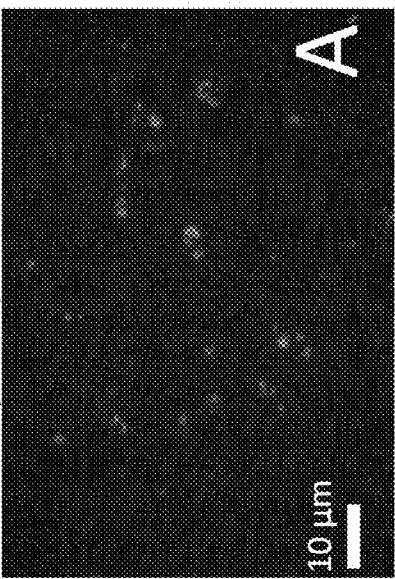
FIG. 5A Overexpression of N-protein + VS_DsiRNA-Cy5 with lipofectamine
FIG. 5B Overexpression of N-protein + VS_DsiRNA-Cy5 with Poly-Arginine (5µl/well)
FIG. 5C Overexpression of N-protein only
FIG. 5D
FIG. 5E
FIG. 5F

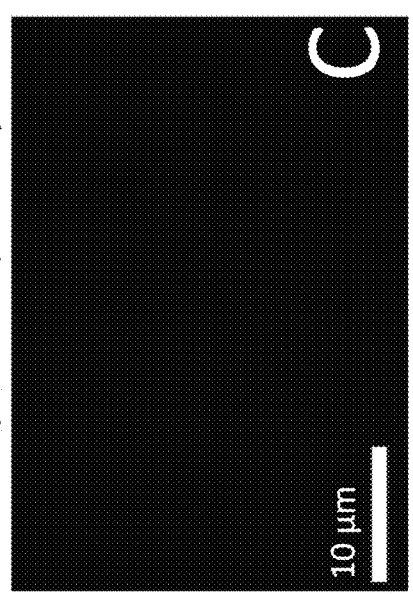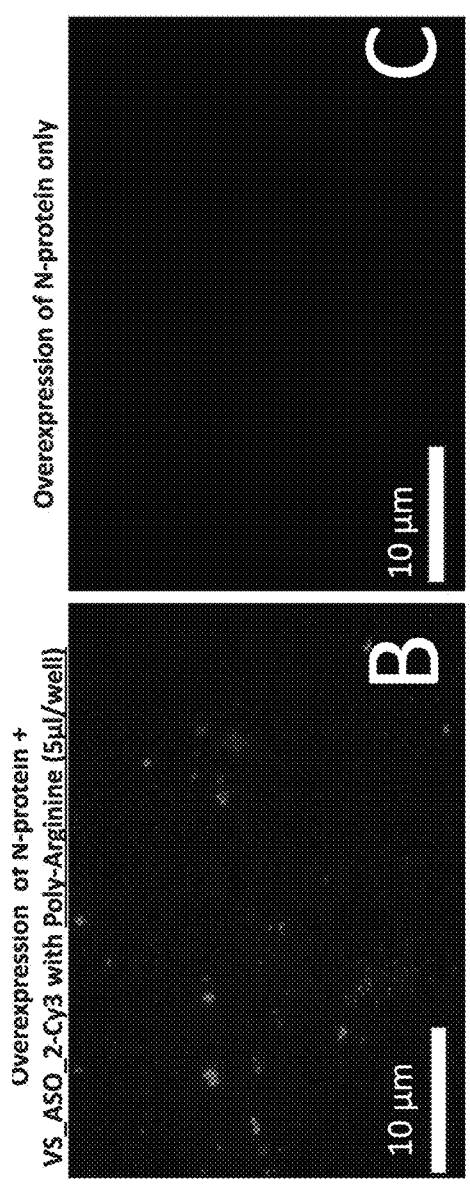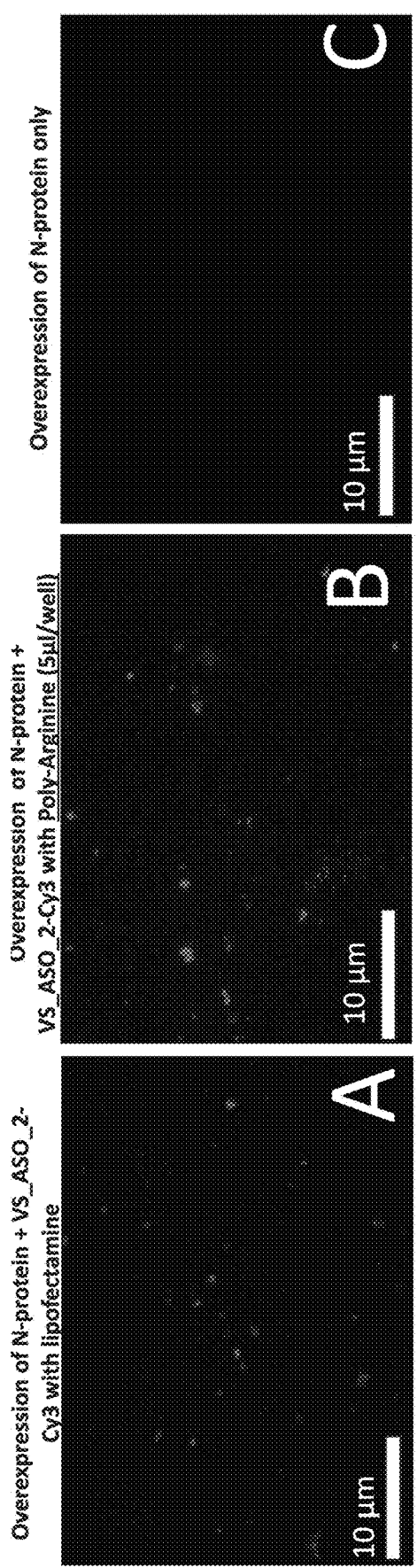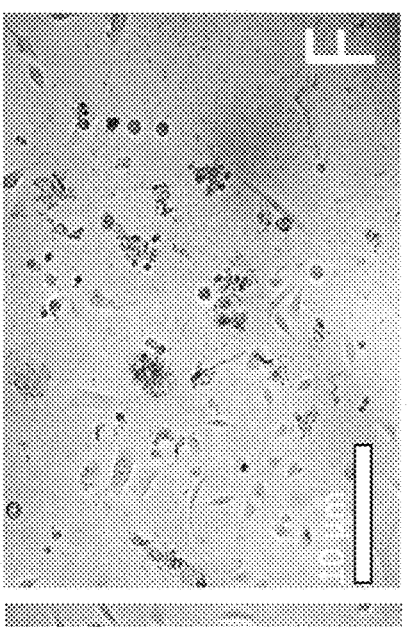
FIG. 7A  FIG. 7B  FIG. 7C  FIG. 7D  FIG. 7E  FIG. 7F N-protein Overexpression only Overexpression of N-protein + VS_ASO_1_FANA-FITC without lipofectamine or arginine N-protein Overexpression only Overexpression of N-protein + VS_ASO_1-FANA-FITC without lipofectamine or arginine

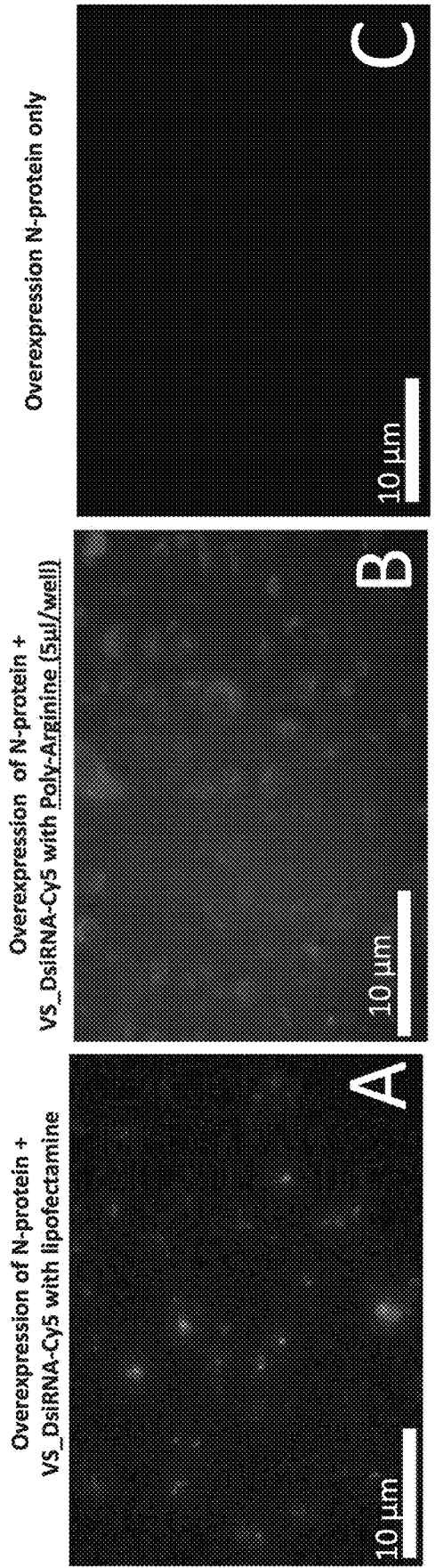
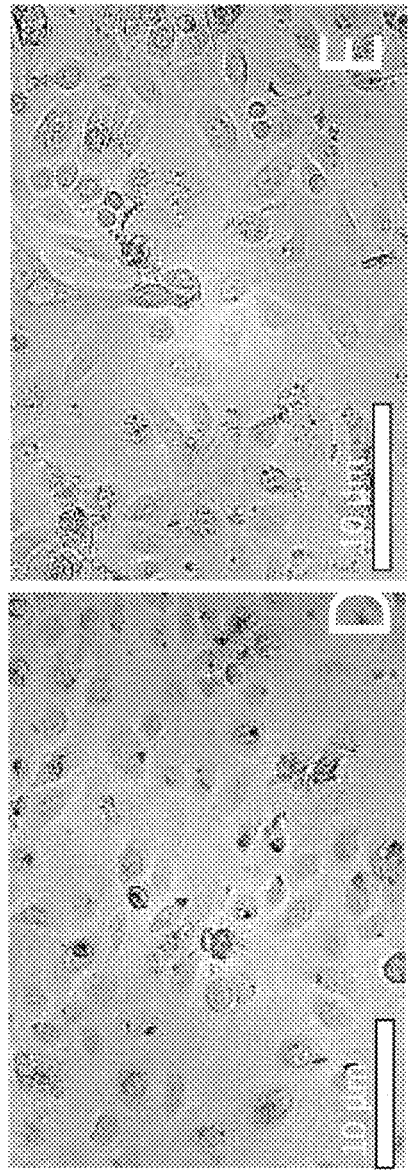
FIG. 23A Overexpression of N-protein + VS_DsiRNA-Cy5 with lipofectamine
FIG. 23B Overexpression of N-protein + VS_DsiRNA-Cy5 with Poly-Arginine (5µl/well)
FIG. 23C Overexpression N-protein only
FIG. 23D
FIG. 23E
FIG. 23F Overexpression of N-protein only Overexpression of N-protein + V5_ASO_2-Cy3 with Poly-Arginine (5µl/well)

Overexpression of N-protein + V5_ASO_2-Cy3 with lipofectamine

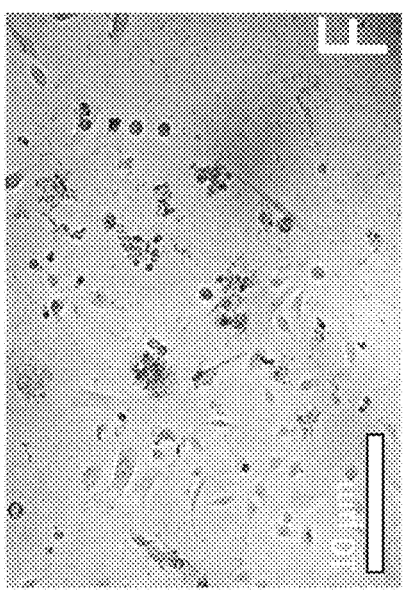
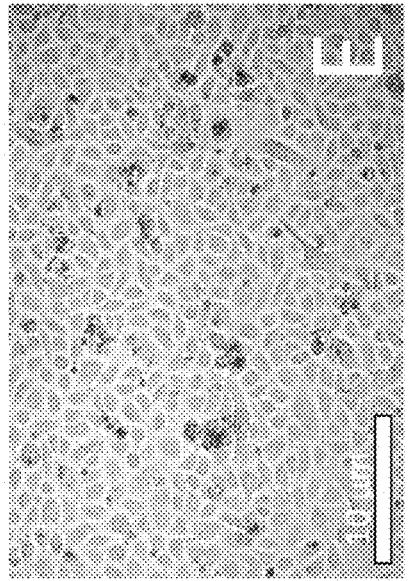
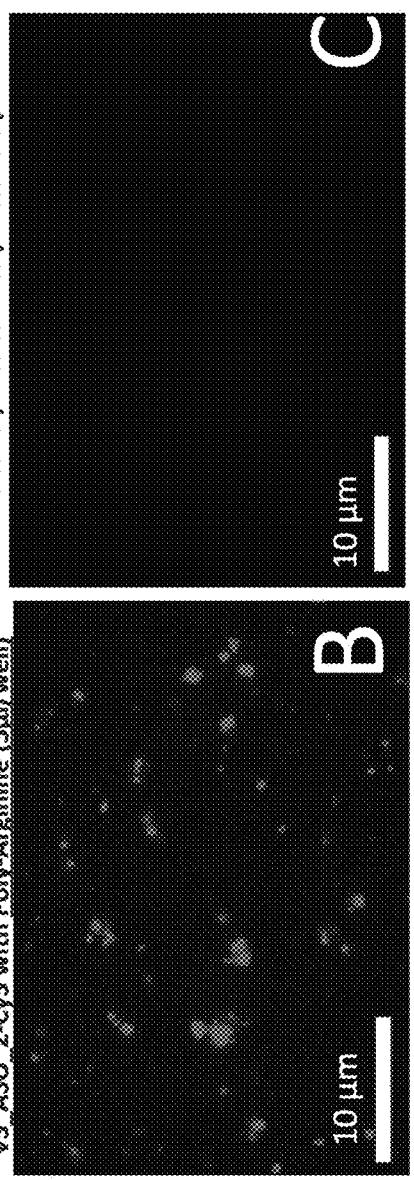
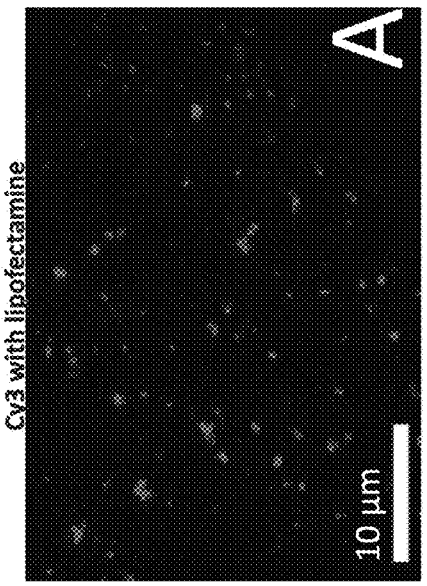
FIG. 26A Overexpression of N-protein + VS_ASO_2-Cy3 with lipofectamine
FIG. 26B Overexpression of N-protein + VS_ASO_2-Cy3 with Poly-Arginine (5µl/well)
FIG. 26C Overexpression of N-protein only
FIG. 26D
FIG. 26E
FIG. 26F Overexpression of N-protein + VS_ASO_1-FANA-FITC without lipofectamine or arginine N-protein Overexpression only N-protein Overexpression only Overexpression of N-protein + VS_ASO_1-FANA-FITC without lipofectamine or arginine

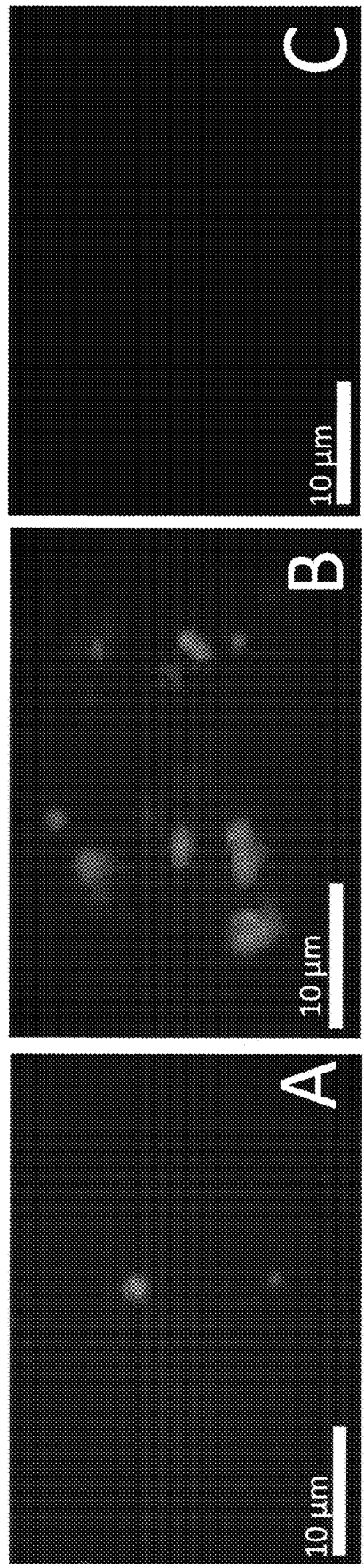
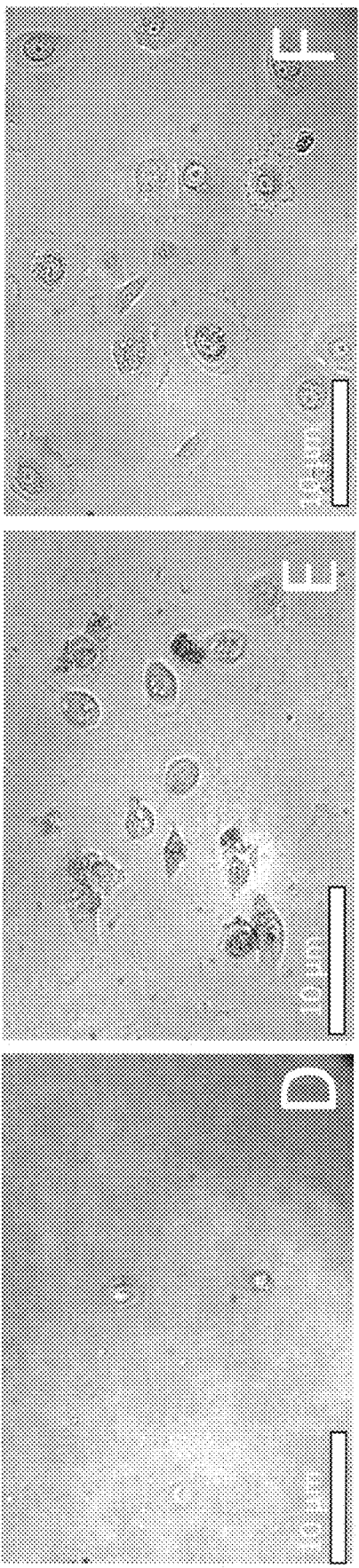
FIG. 38A — Overexpression of N-protein + VS_DsiRNA-Cy5 with lipofectamine
FIG. 38B — Overexpression of N-protein + VS_DsiRNA-Cy5 with Poly-Arginine (5µl/well)
FIG. 38C — Overexpression N-protein only
FIG. 38D
FIG. 38E
FIG. 38F FIG. 40A Overexpression of N-protein + VS_ASO_2-Cy3 with lipofectamine FIG. 40B Overexpression of N-protein + VS_ASO_2-Cy3 with Poly-Arginine (5µl/well)

FIG. 40C Overexpression of N-protein only

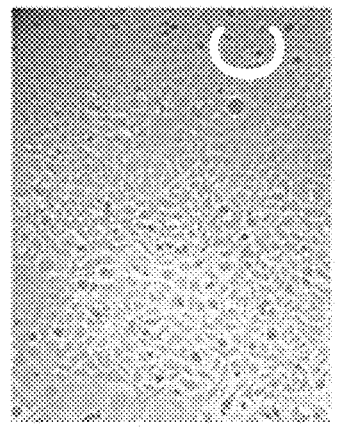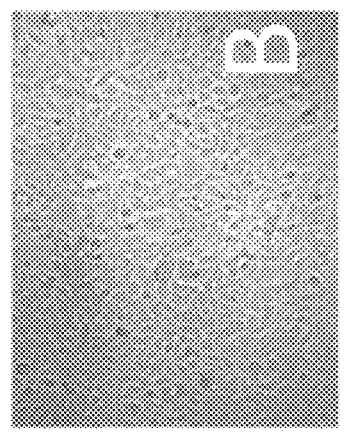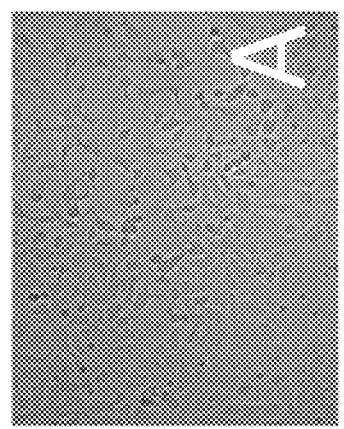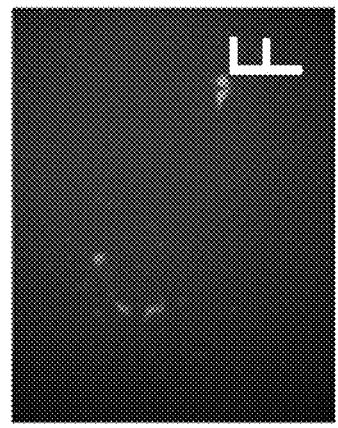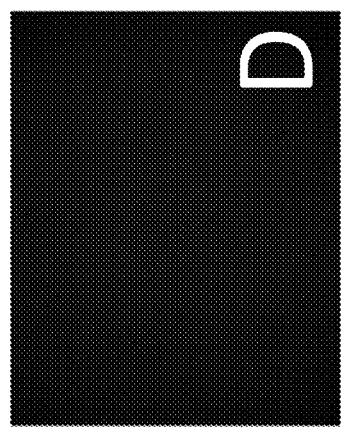
FIG. 45A VS_ASO_3
FIG. 45B VS_RNAi_3
FIG. 45C Scramble nucleotide (SN)
FIG. 45D
FIG. 45E
FIG. 45F
Bright field
GFP view

VS_ASO_3

VS_RNAi_3

SN

Bright field

GFP view

FIG. 47

| | | | | |
|---|---|---|---|---|
| 1 | mfvflvllpl | vssqcvnltt | rtqlppaytn | sftrgvyypd | kvfrssvlhs | tqdlflpffs |
| 61 | nvtwfhaihv | sgtngtkrfd | npvlpfndgv | yfasteksni | irgwifgttl | dsktqslliv |
| 121 | nnatnvvikv | cefqfcndpf | lgvyyhknnk | swmesefrvy | ssannctfey | vsqpflmdle |
| 181 | gkqgnfknlr | efvfknidgy | fkiyskhtpi | nlvrdlpqgf | saleplvdlp | iginitrfqt |
| 241 | llalhrsylt | pgdsssgwta | gaaayyvgyl | qprtflllkyn | engtitdavd | caldplsetk |
| 301 | ctlksftvek | giyqtsnfrv | qptesivrfp | nitnlcpfge | vfnatrfasv | yawnrkrisn |
| 361 | cvadysvlyn | sasfstfkcy | gvsptkindl | cftnvyadsf | virgdevrqi | apgqtgkiad |
| 421 | ynyklpddft | gcviawnsnn | ldskvggnyn | ylyrlfrksn | ikpferdist | eiyqagstpc |
| 481 | ngvegfncyf | plqsygfqpt | ngvgyqpyrv | vvlsfellha | patvcgpkks | tnlvknkcvn |
| 541 | fnfngltgtg | vltesnkkfl | pfqqfgrdia | dttdavrdpq | tleilditpc | sfggvsvitp |
| 601 | gintsnqvav | lyqdvnctev | pvaihadqlt | ptwrvystgs | nvfqtragcl | igaehvnnsy |
| 661 | ecdipigagi | casyqtqtns | prrarsvasq | siiaytmslg | aensvaysnn | siaiptnfti |
| 721 | svtteilpvs | mktksvdctm | yicgdstecs | nlllqygsfc | tqlnraltgi | aveqdkntqe |
| 781 | vfaqvkqiyk | tppikdfggf | nfsqilpdps | kpskrsfied | llfnkvtlad | agfikqygdc |
| 841 | lgdiaardli | caqkfngltv | lpplltdemi | aqytsallag | titsgwtfga | gaalqipfam |
| 901 | qmayrfngig | vtqnvlyenq | klianqfnsa | igkiqdslss | tasalgklqd | vvnqnaqaln |
| 961 | tlvkqlssnf | gaissvlndi | lsrldkveae | vqidrlitgr | lqslqtyvtq | qliraaeira |
| 1021 | sanlaatkms | ecvlgqskrv | dfcgkgyhlm | sfpqsaphgv | vflhvtyvpa | qeknfttapa |
| 1081 | ichdgkahfp | regvfvsngt | hwfvtqrnfy | epqiitdnt | fvsgncdvvi | givnntvydp |
| 1141 | lqpeldsfke | eldkyfknht | spdvdlgdis | ginasvvniq | keidrlneva | knlneslidl |
| 1201 | qelgkyeqyi | kwpwyiwlgf | iagliaivmv | timlccmtsc | csclkgccsc | gscckfdedd |
| 1261 | sepvlkgvkl | hyt | | | | |

FIG. 48A
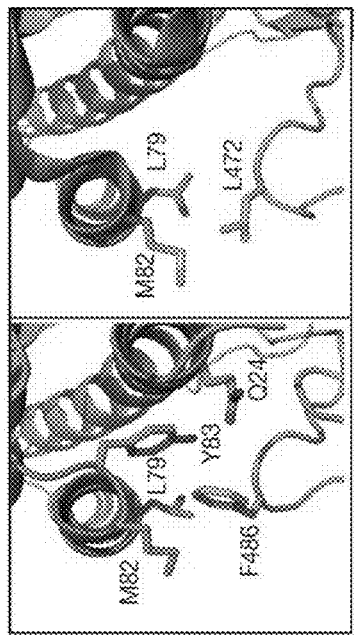
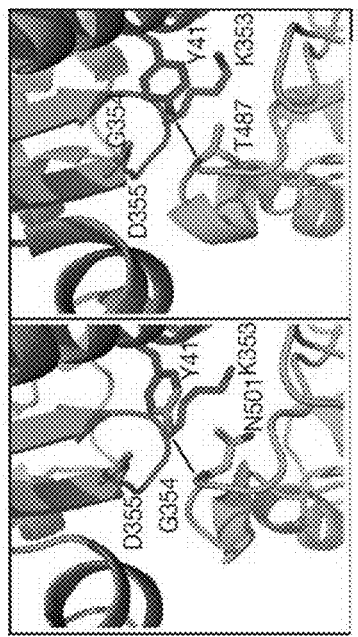
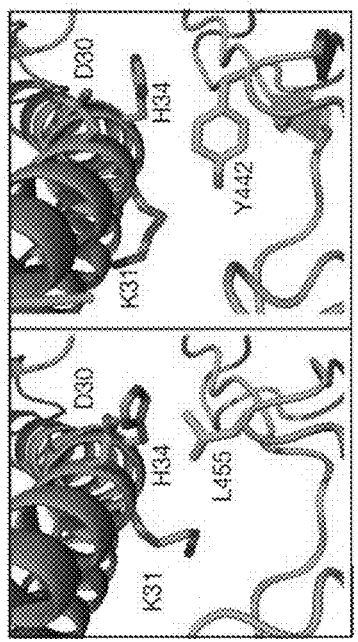
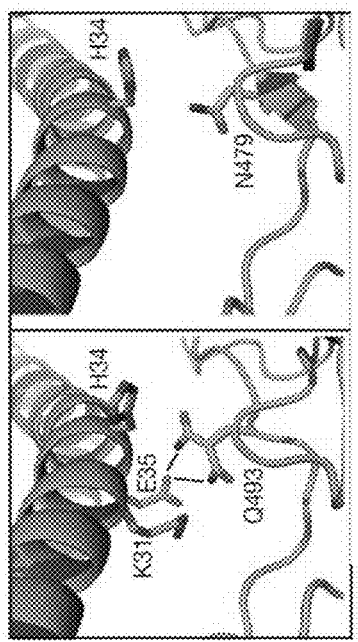
FIG. 48B
| SARS-CoV-2 RBD | ACE2 |
|---|---|
| K417 | Q24 |
| G446 | T27 |
| Y449 | F28 |
| Y453 | D30 |
| L455 | K31 |
| F456 | H34 |
| A475 | E35 |
| F486 | E37 |
| N487 | D38 |
| Y489 | Y41 |
| Q493 | Q42 |
| G496 | L79 |
| Q498 | M82 |
| T500 | Y83 |
| N501 | N330 |
| G502 | K353 |
| Y505 | G354 |
|  | D355 |
|  | R357 |
|  | R393 |

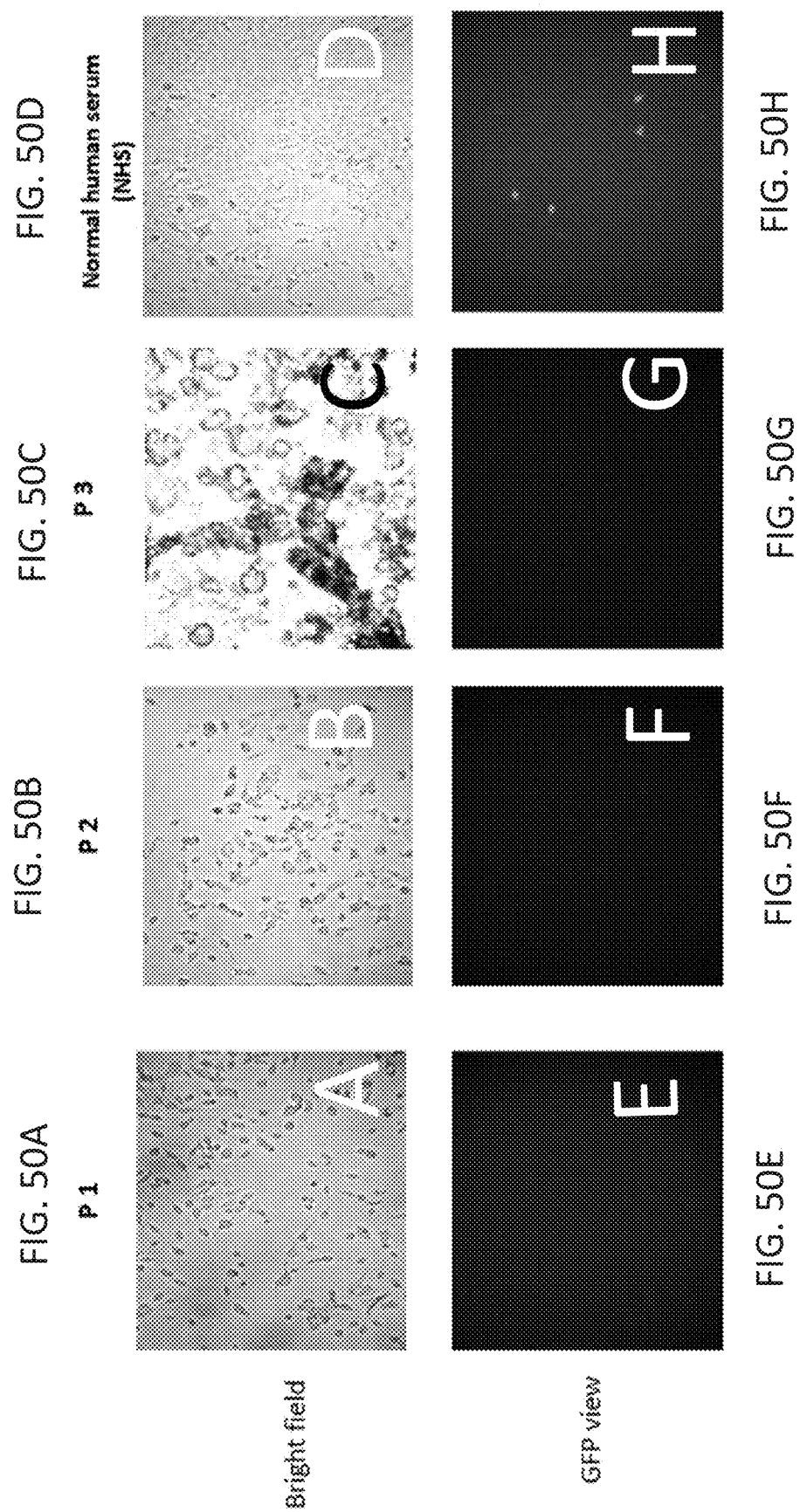

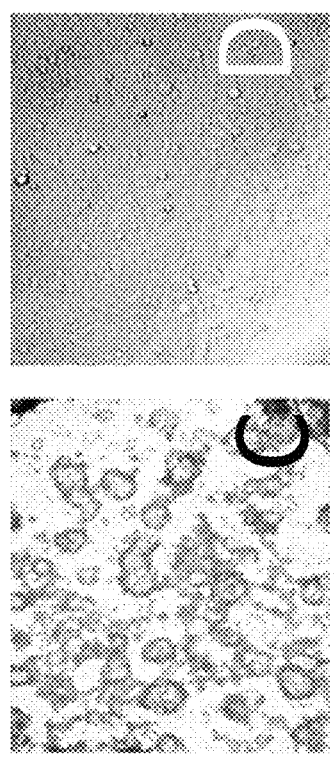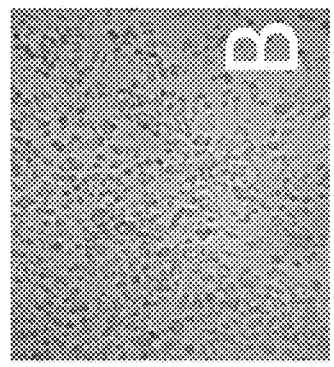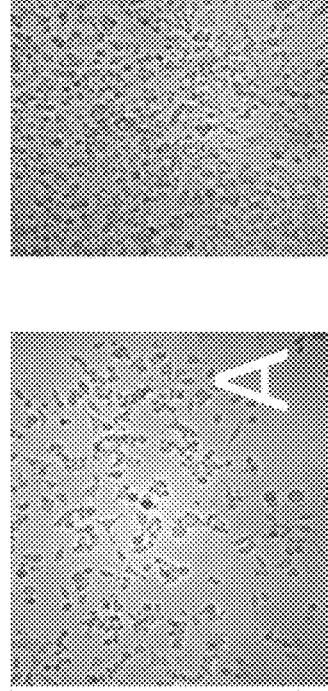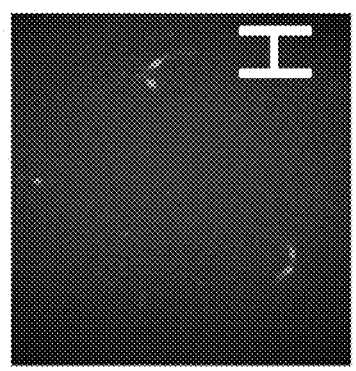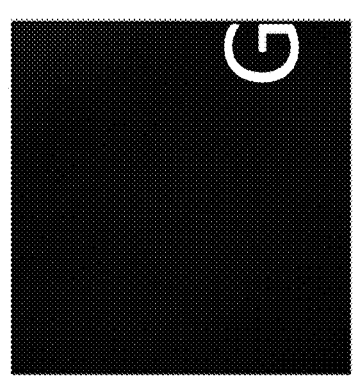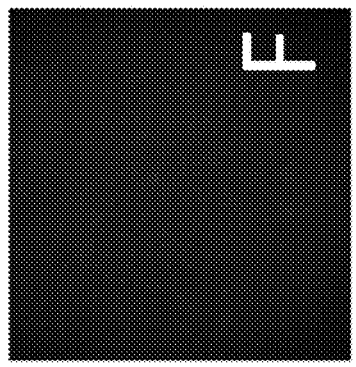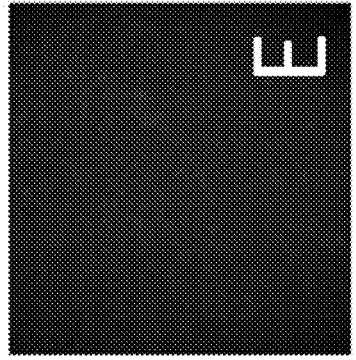
FIG. 51A P1 | FIG. 51B P2 | FIG. 51C P3 | FIG. 51D Normal human serum (NHS)
FIG. 51E | FIG. 51F | FIG. 51G | FIG. 51H
Bright field / GFP view

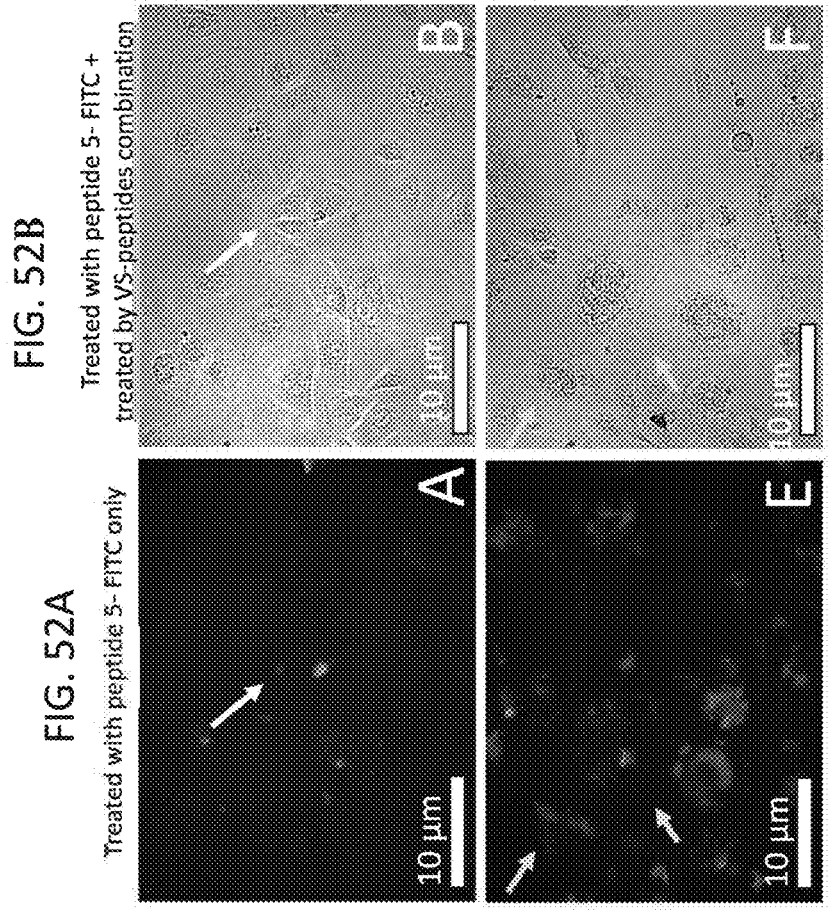

FIG. 59A
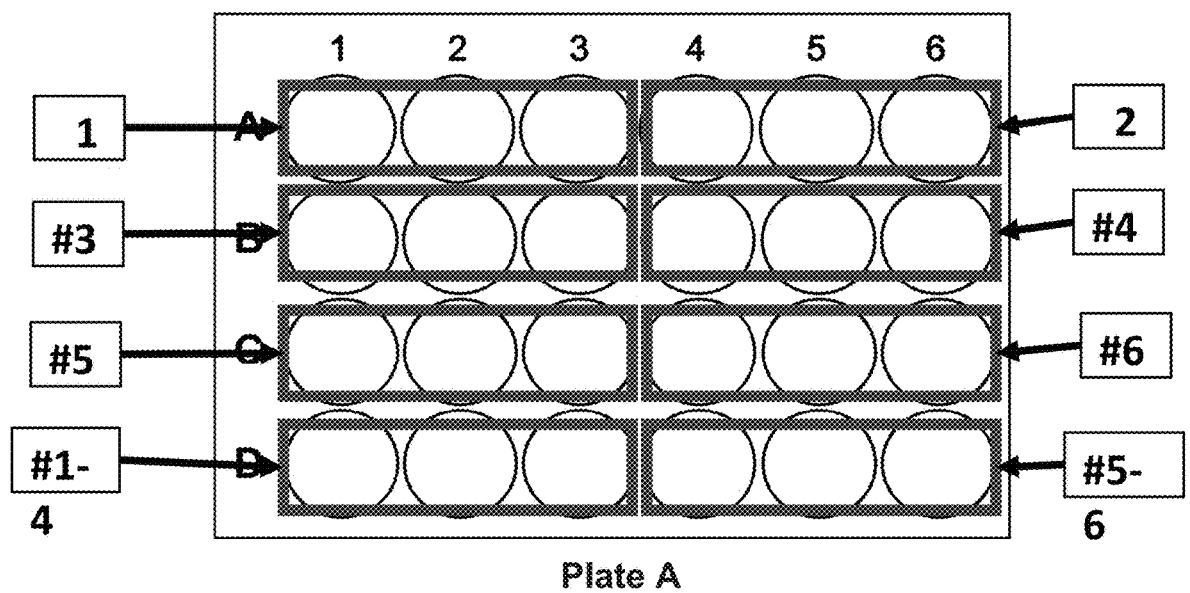
Plate A
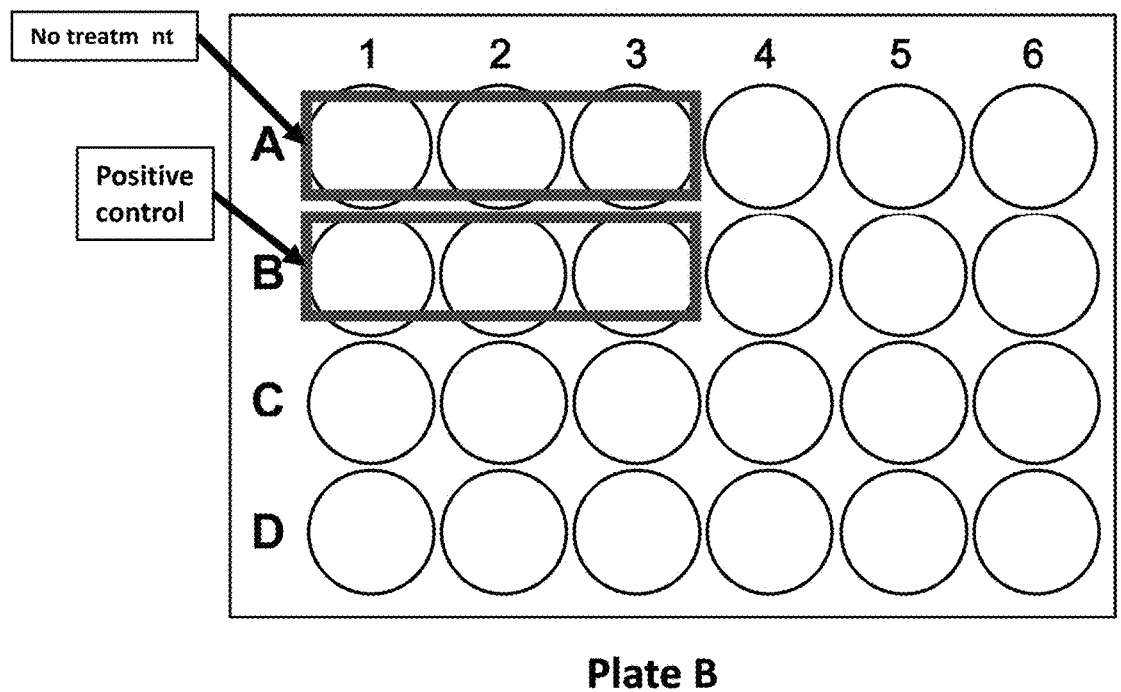
Plate B
FIG. 59B

FIG. 60C
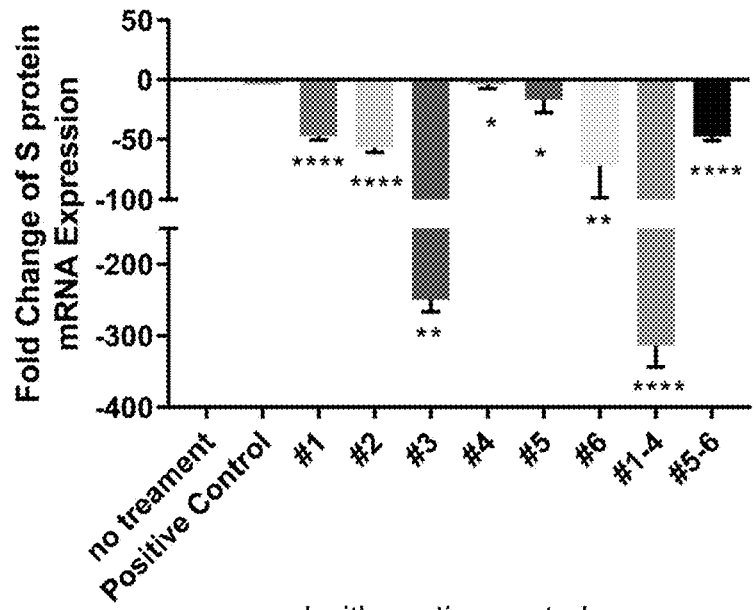
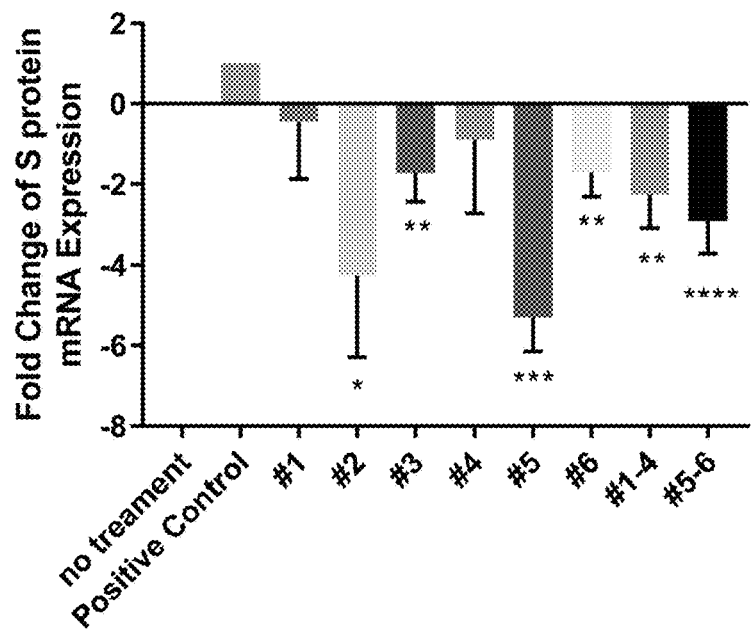
FIG. 60D

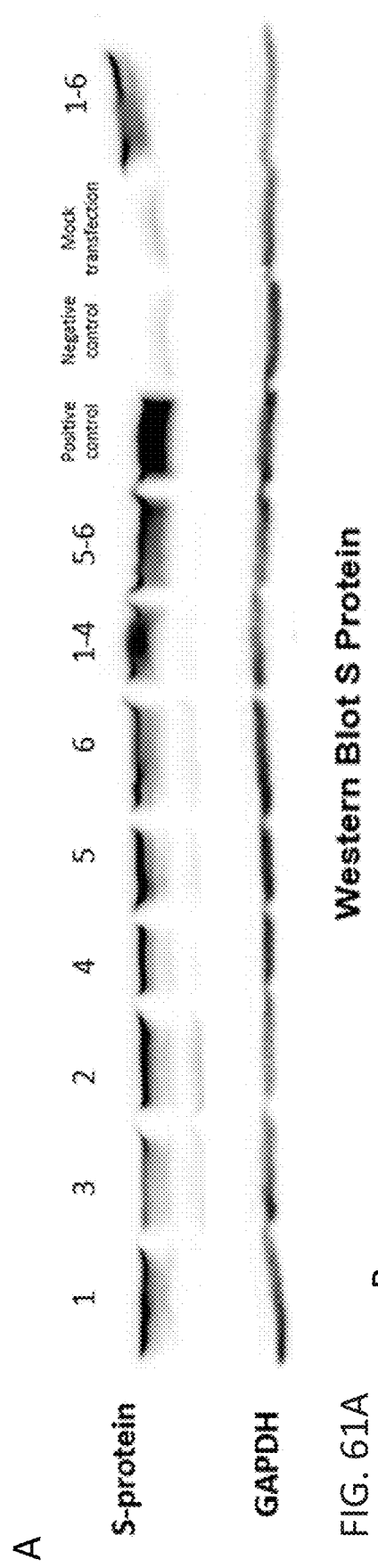
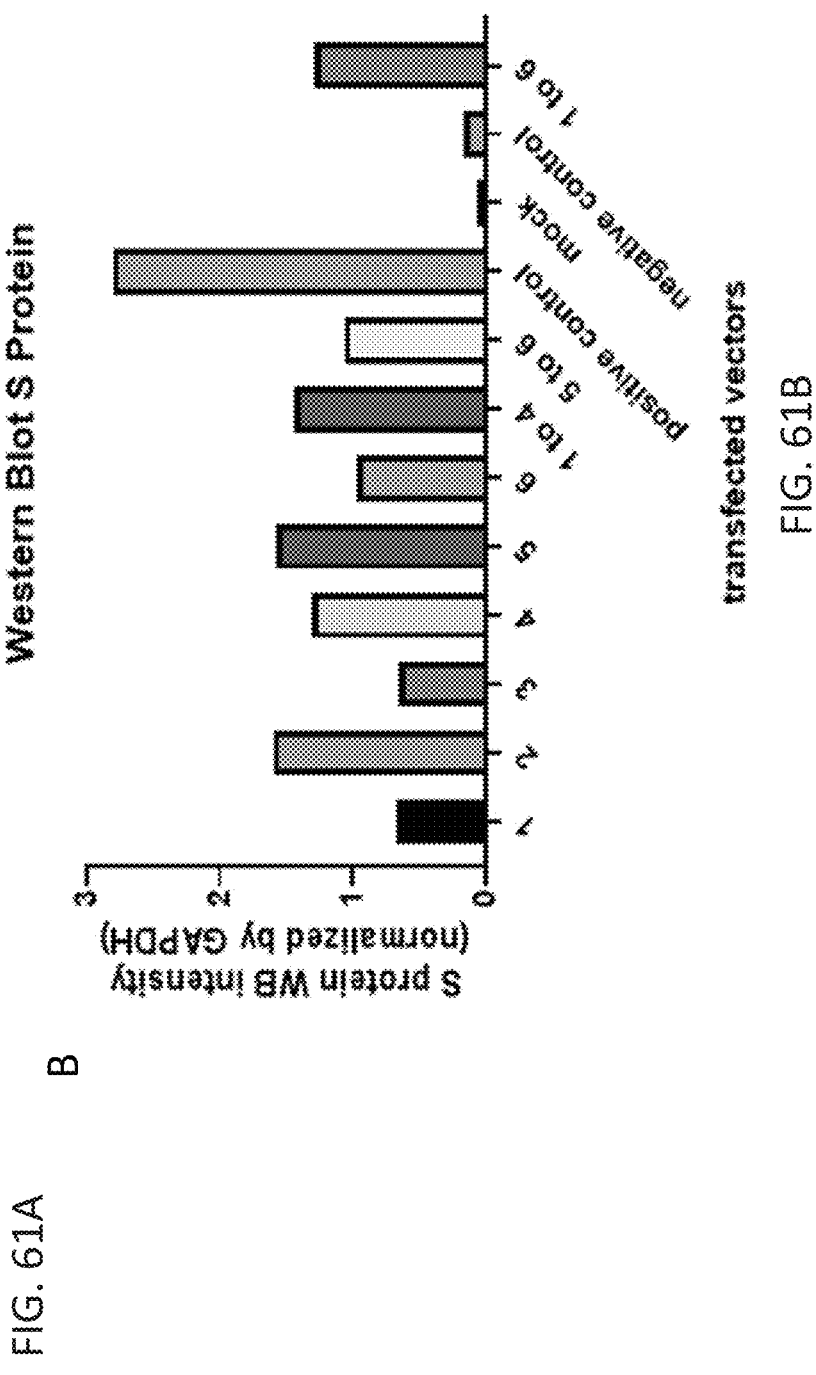
FIG. 61A
FIG. 61B

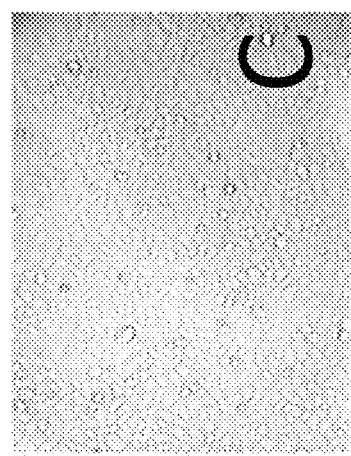
FIG. 63C Control-1
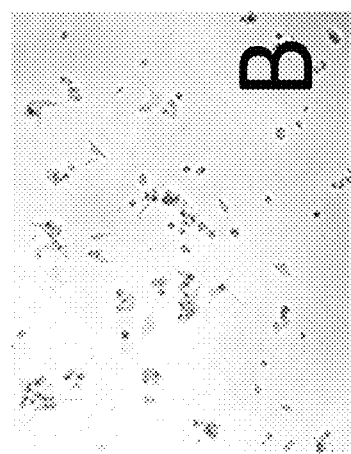
FIG. 63B V2
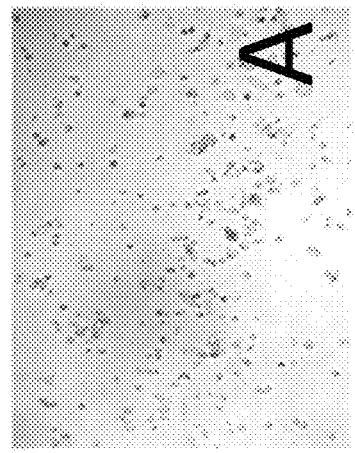
FIG. 63A V1
Bright field
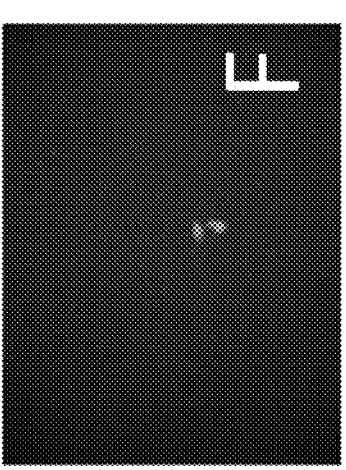
FIG. 63F
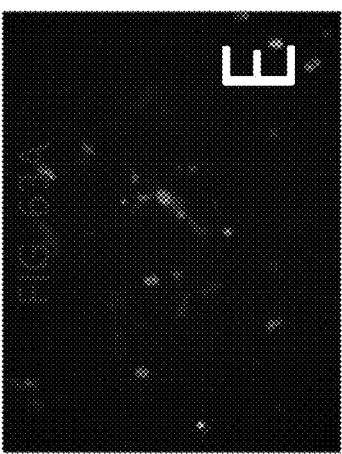
FIG. 63E
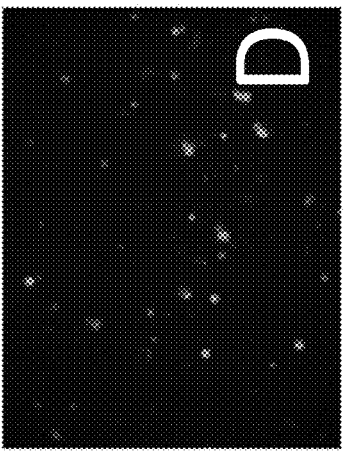
FIG. 63D
GFP view

V1

V2

Control-1

Bright field

GFP view

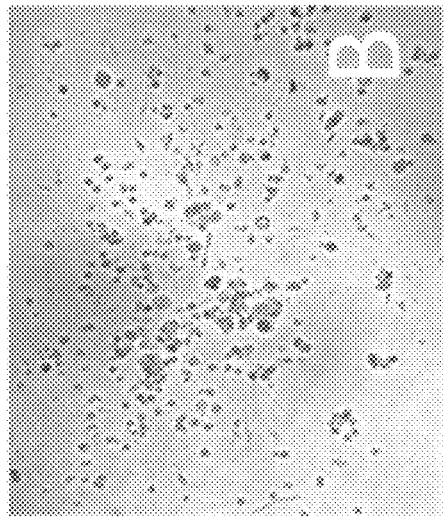
FIG. 65A
Control-2
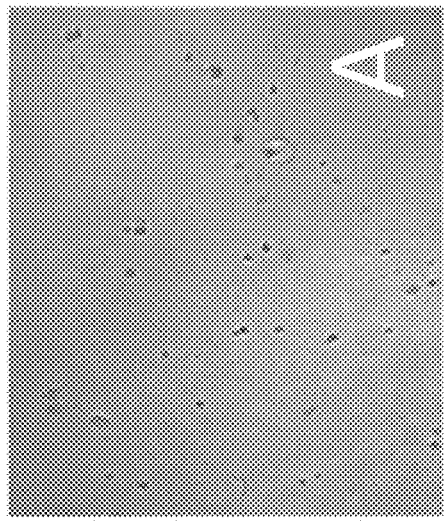
FIG. 65B
Control-3
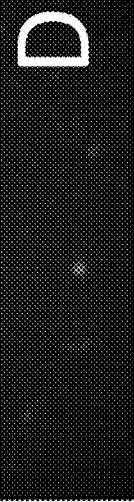
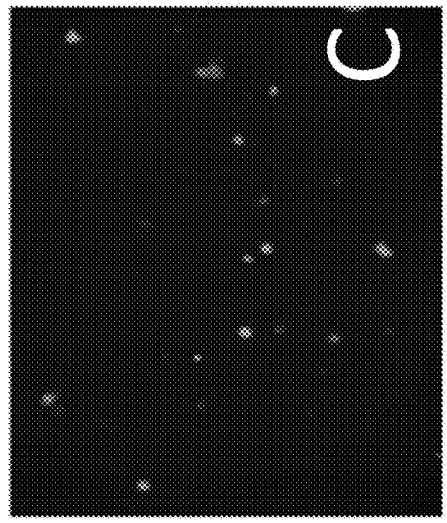
FIG. 65C
FIG. 65D
Bright field
GFP view

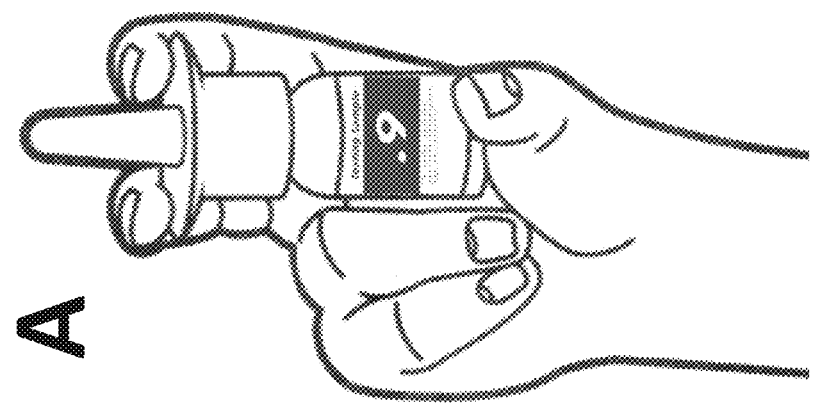
FIG. 72B
FIG. 72C
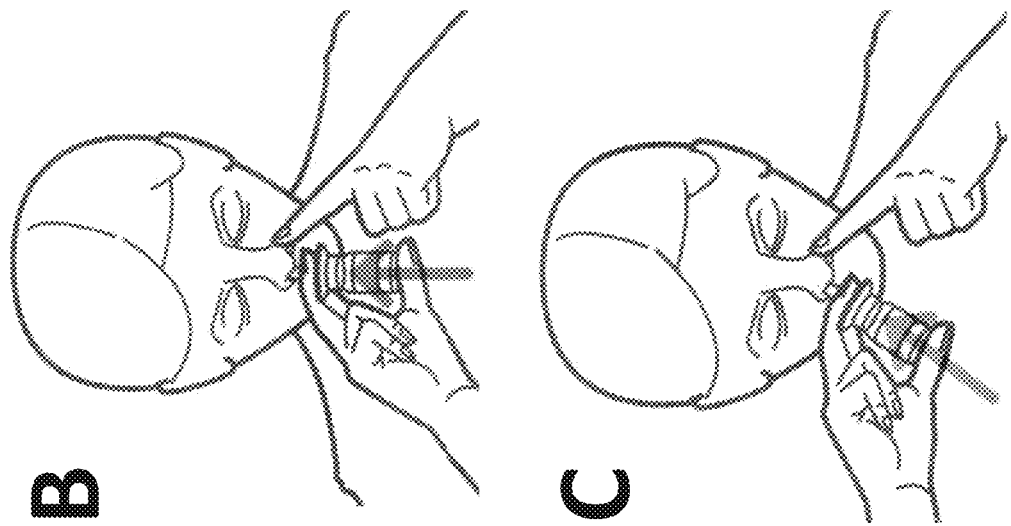
FIG. 72A

FIG. 73A

| p-value | 50 ug/well | 100 ug/well | Binding sites (AA) (see FIGS. 48A – 48B) |
|---|---|---|---|
| Peptide 1 | <0.0001* | <0.0001* | 11 |
| Peptide 2 | 0.001* | <0.0001* | 3 |
| Peptide 3 | 0.1368 | 0.0044* | 1 |
| Peptide 4 | <0.0001* | <0.0001* | 4 |
| Mix | <0.0001* | <0.0001* | N/A |
| BSA | 0.4554 | 0.1115 | N/A |

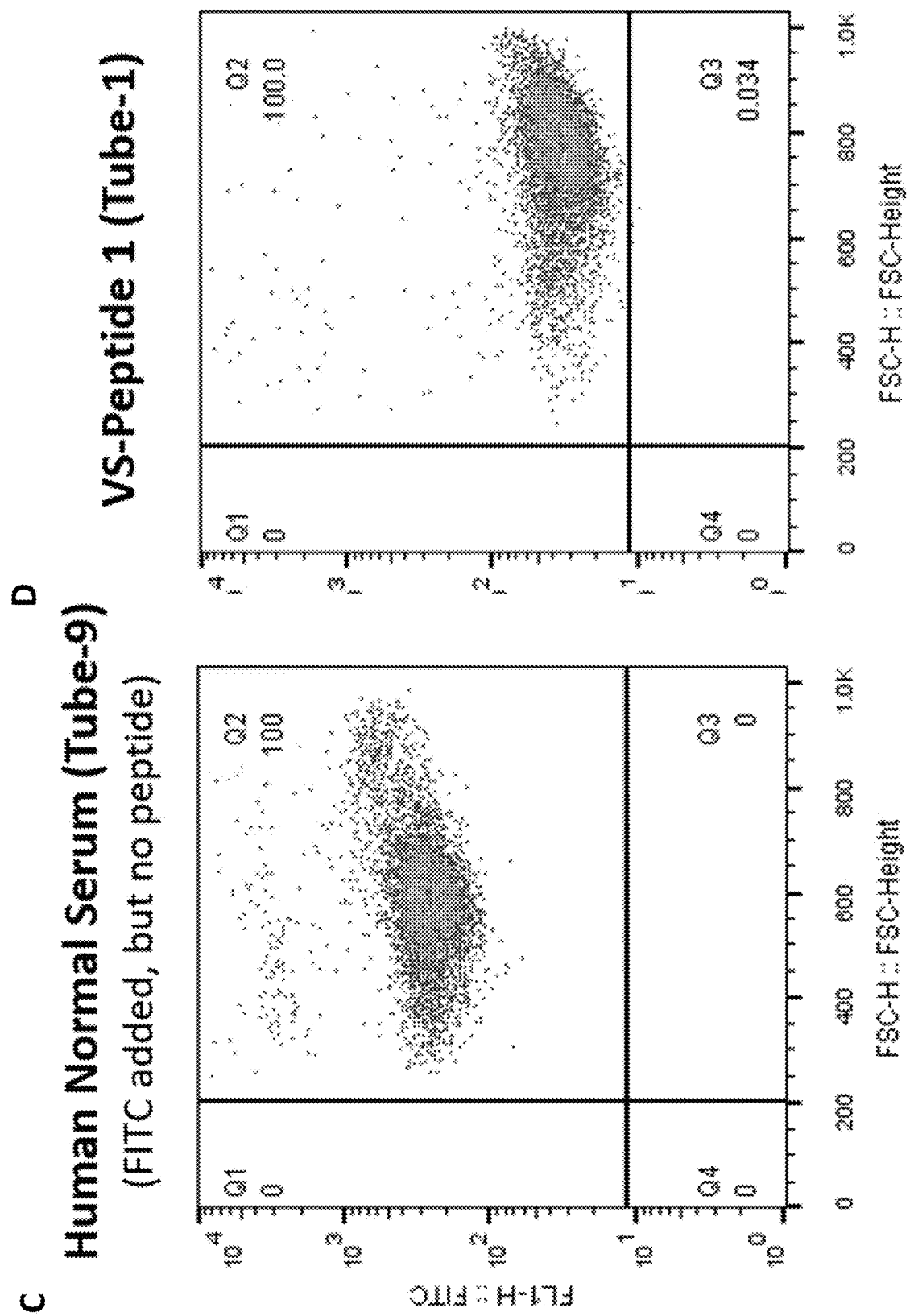

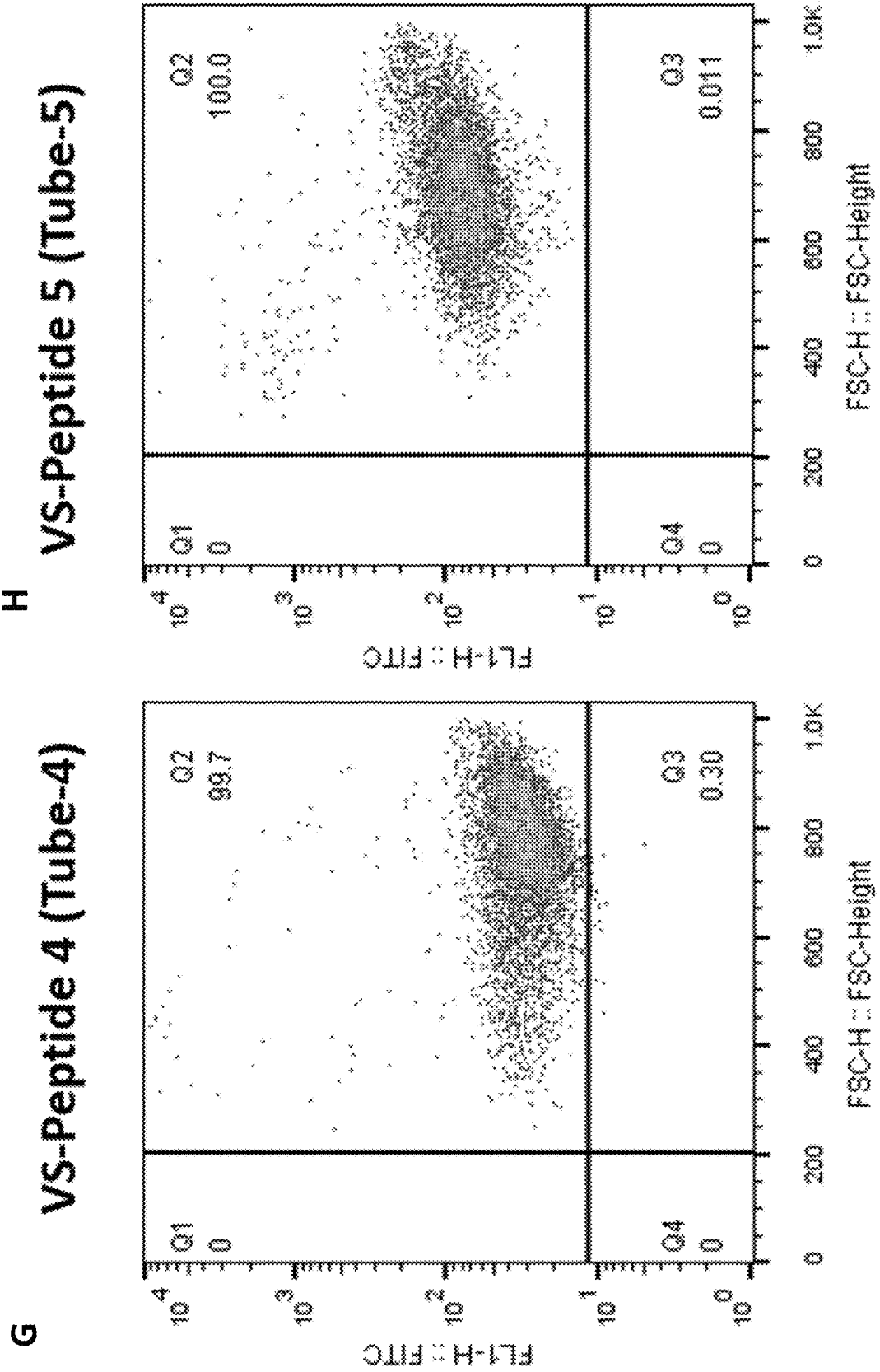

COMPOSITIONS AND METHODS FOR TREATING COVID-19

CROSS REFERENCE TO RELATED APPLICATIONS

This application is a continuation of U.S. patent application Ser. No. 17/350,114, filed Jun. 17, 2021, which claims the benefit of priority from U.S. Provisional Application No. 63/041,587, filed Jun. 19, 2020, the entire contents of which are incorporated herein by reference.

INCORPORATION BY REFERENCE OF SEQUENCE LISTING

The Sequence Listing in an ASCII text file, named as 38534Z_SequenceListing.txt of 114 KB, created on Oct. 25, 2021, and submitted to the United States Patent and Trademark Office via EFS-Web, is incorporated herein by reference.

BACKGROUND

The novel coronavirus disease (COVID-19) is caused by the SARS-Cov-2 virus and is known for inducing multisystem organ dysfunction associated with significant morbidity and mortality. Despite several available vaccines, effective therapeutics targeted specifically to the virus are still lacking. Specifically, effective prophylactics with a few side-effects and therapeutics targeted specifically towards SARS-CoV-2 are needed since some of the current vaccines have been found some serious side-effects, e.g., blood clotting or increasing the heart myocarditis. It has also been observed that IgG antibodies, while abundantly present in the vasculature, are present at a much lesser extent in mucosal tissues, such as epithelial cells of nasal and lung, where most ACE2-expressing cells (i.e., targets of SARS-CoV-2). This means that IgG antibodies against SARS-CoV-2, either induced by vaccination or exogenously provided, may not effectively protect ACE2-expressing cells on the mucosal tissues from a SARS-CoV2 infection.

SUMMARY OF THE DISCLOSURE

An aspect of the disclosure is directed to a composition comprising a plurality of inhibitory oligonucleotides, wherein the plurality of inhibitory oligonucleotides targets at least two SARS-CoV-2 genes selected from the group consisting of ORF1ab, RdRp, the S-protein gene, the N-protein gene, and the E protein gene.

In some embodiments, the plurality of inhibitory oligonucleotides targets all of the ORF1ab, RdRp, S-protein, N-protein and E protein genes. In some embodiments, a selected SARS-CoV-2 gene is targeted by at least two inhibitory oligonucleotides.

In some embodiments, the inhibitory oligonucleotides are selected from an antisense oligonucleotide, a small interfering RNA (siRNA), a Dicer-substrate RNA (DsiRNA), and a microRNA.

In some embodiments, the plurality of inhibitory oligonucleotides comprises at least two oligonucleotides which comprise a nucleotide sequence selected from the group consisting of SEQ ID NOS: 9-16 and modified forms of SEQ ID NOS: 9-16.

In some embodiments, the plurality of inhibitory oligonucleotides comprises eight oligonucleotides as shown in SEQ ID NOS: 9-16 or modified forms of SEQ ID NOS: 9-16.

In some embodiments, the plurality of inhibitory oligonucleotides comprises at least two pairs of Dicer-substrate RNAs (DsiRNAs) selected from the group consisting of DsiRNA pair 1 (SEQ ID NOs: 17 & 18), DsiRNA pair 2 (SEQ ID NOs: 19 & 20), DsiRNA pair 3 (SEQ ID NOs: 21 & 22), DsiRNA pair 4 (SEQ ID NOs: 23 & 24), DsiRNA pair 5 (SEQ ID NOs: 25 & 26), DsiRNA pair 6 (SEQ ID NOs: 27 & 28), DsiRNA pair 7 (SEQ ID NOs: 29 & 30), and DsiRNA pair 8 (SEQ ID NOs: 31 & 32).

In some embodiments, the plurality of inhibitory oligonucleotides comprises Dicer-substrate RNA (DsiRNA) pair 1 (SEQ ID NOs: 17 & 18), DsiRNA pair 2 (SEQ ID NOs: 19 & 20), DsiRNA pair 3 (SEQ ID NOs: 21 & 22), DsiRNA pair 4 (SEQ ID NOs: 23 & 24), DsiRNA pair 5 (SEQ ID NOs: 25 & 26), DsiRNA pair 6 (SEQ ID NOs: 27 & 28), DsiRNA pair 7 (SEQ ID NOs: 29 & 30), and DsiRNA pair 8 (SEQ ID NOs: 31 & 32).

In some embodiments, the inhibitory oligonucleotides are modified oligonucleotides.

In some embodiments, the modified inhibitory oligonucleotides are 2'-Deoxy, 2'-Fluoroarabino Nucleic Acid (FANA)-modified antisense oligonucleotides.

In some embodiments, the modified inhibitory oligonucleotides are 2' O-Methyl RNA modified antisense oligonucleotides selected from the group consisting of SEQ ID NO: 33, SEQ ID NO: 34, SEQ ID NO: 35, SEQ ID NO: 36, SEQ ID NO: 37, SEQ ID NO: 38, SEQ ID NO: 39, and SEQ ID NO: 40.

In some embodiments, at least one inhibitory oligonucleotide within the plurality of oligonucleotides comprises a detectable label.

In some embodiments, the label is a fluorescent label.

In some embodiments, the plurality of inhibitory oligonucleotides is provided in one or more nucleic acid vectors.

In some embodiments, the nucleic acid vectors are selected from a viral vector, a non-viral vector, an integrative vector, or a non-integrative vector.

In some embodiments, the composition further comprises a pharmaceutically acceptable carrier. In some embodiments, the pharmaceutically acceptable carrier comprises nanoparticles or other delivery vehicles to which the plurality of inhibitory oligonucleotides is conjugated.

Another aspect of the specification is directed to a composition comprising at least one peptide mimicking a portion of the ligand binding domain (LBD) of human ACE2 protein, wherein the at least one peptide prevents binding of the S-protein of SARS-CoV-2 to the human ACE2 protein.

In some embodiments, the LBD of human ACE2 comprises the amino acid sequence of SEQ ID NO: 56.

In some embodiments, the composition comprises a plurality of peptides, each mimicking a different portion of the ligand binding domain (LBD) of human ACE2 protein.

In some embodiments, the at least one peptide comprises an amino acid sequence selected from the group consisting of SEQ ID NOs: 41-44, 54, and 63-82.

In some embodiments, the composition comprises a plurality of peptides comprising an amino acid sequence selected from the group consisting of SEQ ID NOs: 41-44, 54, and 63-82.

In some embodiments, the composition comprises at least five peptides, wherein the at least five peptides are selected from peptides comprising an amino acid sequence as shown in SEQ ID NOS: 41-44, 54, and 63-82.

Another aspect of the disclosure is directed to a composition comprising a peptide mimicking a portion of the receptor binding domain (RBD) of the S-Protein of SARS- CoV-2, wherein the peptide prevents binding of the S-protein of SARS-CoV-2 to a human ACE2 protein.

In some embodiments, the RBD of the S protein of SARS-CoV-2 comprises SEQ ID NO: 62.

In some embodiments, the peptide comprises an amino acid sequence as shown in SEQ ID NO: 45.

In some embodiments, the at least one peptide comprises a label or is conjugated with a probe, a nucleic acid or a chemical molecule. In some embodiments, the label is a fluorescent label.

In some embodiments, the composition further comprises a pharmaceutically acceptable carrier. In some embodiments, the pharmaceutically acceptable carrier comprises nanoparticles or other delivery vehicles to which the at least one peptide is conjugated.

Another aspect of the disclosure is directed to a dietary supplement comprising a composition as described herein. In some embodiments, the dietary supplement further comprises at least one additional nutrient selected from Vitamin C, Vitamin B6, Vitamin B12, Vitamin D, Zinc, polypeptides, nucleotide, L-arginine or peppermint oil. In some embodiments, the dietary supplement is formulated for oral, nasal, eye, ear, or topical application.

Another aspect of the disclosure is directed to a method comprising expressing a plurality of inhibitory oligonucleotides in a target cell, wherein the plurality of inhibitory oligonucleotides targets at least two SARS-CoV-2 genes selected from the group consisting of ORF1ab, RdRp, the S-protein gene, the N-protein gene and the E protein gene (aka. the "viral infective functional group"). In some embodiments, a selected SARS-CoV-2 gene is targeted by at least two inhibitory oligonucleotides. In some embodiments, the plurality of inhibitory oligonucleotides targets all of ORF1ab, RdRp, S-protein, N-proteins and E protein genes. In some embodiments, the inhibitory oligonucleotides are selected from an antisense oligonucleotide, a small interfering RNA (siRNA), a Dicer-substrate RNA (DsiRNA), or a microRNA.

In some embodiments, the plurality of inhibitory oligonucleotides comprises at least two oligonucleotides which comprise a nucleotide sequence selected from the group consisting of SEQ ID NOS: 9-16.

In some embodiments, the plurality of inhibitory oligonucleotides comprises eight oligonucleotides as shown in SEQ ID NOS: 9-16.

In some embodiments, the target cell is a human cell. In some embodiments, the target cell is a lung epithelial cell. In some embodiments, the target cell is selected from the group consisting of a small airway epithelial cell, a bronchial/tracheal epithelial cell, and a nasal epithelial cell.

In some embodiments, the plurality of inhibitory oligonucleotides are expressed from at least one vector. In some embodiments, the at least one vector is selected from a viral vector, or a non-viral vector, an integrative vector, or a non-integrative vector.

In some embodiments, the at least one vector is delivered to a subject in need via oral, nasal, intravenous (i.v.) injection or topical administration routes.

Another aspect of the disclosure is directed to a nucleic acid vector encoding a plurality of inhibitory oligonucleotides that targets at least two SARS-CoV-2 genes selected from the group consisting of ORF1ab, RdRp, the S-protein gene, the N-protein gene, and the E protein gene.

Another aspect of the disclosure is directed to a combination of nucleic acid vectors, wherein each nucleic acid vector encodes an inhibitory oligonucleotide that targets at least one SARS-CoV-2 genes selected from the group consisting of ORF1ab, RdRp, the S-protein gene, the N-protein gene, and the E protein gene, and wherein the combination of nucleic acid vectors target at least two SARS-CoV-2 genes.

In some embodiments, the nucleic acid vector is a viral vector.

In some embodiments, the combination of nucleic acid vectors comprises an AAV-based vector selected from AAV1, AAV2, AAV3, AAV4, AAV5, AAV6, AAV7, AAV8, AAV9, AAV10, AAV 11, AAV12, AAV13 and AAV14.

In some embodiments, wherein the nucleic acid vector is a non-viral vector.

Another aspect of the disclosure is directed to a method of treating a SARS-CoV-2 infection in a subject in need thereof, comprising administering a subject an effective amount of a nucleic acid vector or a combination of nucleic acid vectors disclosed herein.

Another aspect of the disclosure is directed to a method for treating a SARS-CoV-2 infection comprising administering to a subject an effective amount of a composition described herein.

Another aspect of the disclosure is directed to a method for treating a SARS-CoV-2 infection comprising administering to a subject an effective amount of a first composition as described herein and a second (different) composition as described herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 2A-2C were captured under the FITC florescent filter, and FIGS. 2D-2F were captured in the same view of bright fields (20×). FIGS. 2A and 2D were taken in well A3 & A4 (as shown in FIG.

Figure 1:
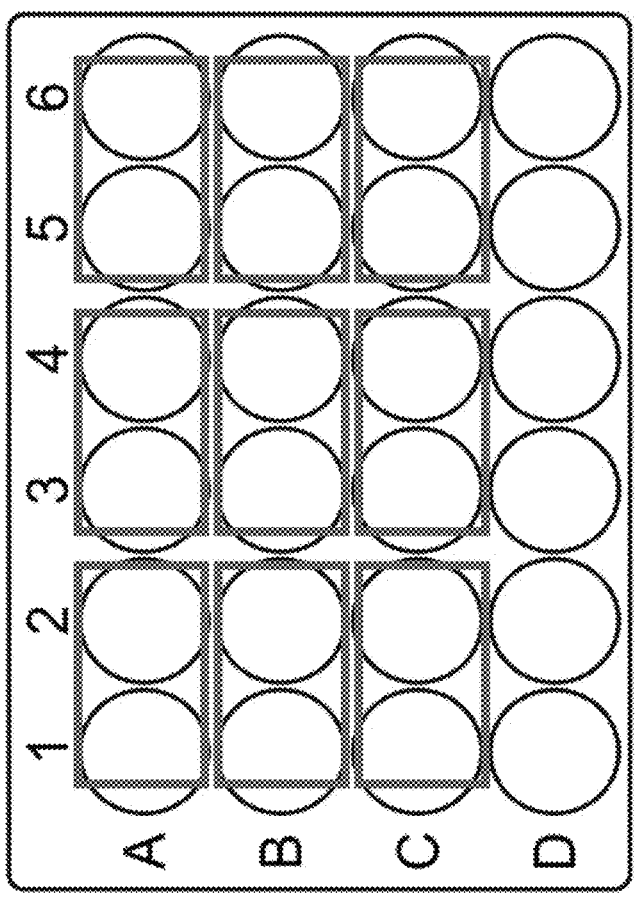
FIG. 1. Experiments designed for investigating cell penetration and therapeutic effects of ASO(s) and siRNA on human primary small airway epithelial cells transfected with viral protein of SARS-CoV-2. The human lung small airway epithelial cells were cultured in the 24 well-dish, and the cells were transfected with the genes encoding the viral proteins of SARS-CoV-2. The VS_ASO_1-FANA-FITC, VS_DsiRNA-Cy5 and VS_ASO_2-Cy3 were into the cells for 24-48 hours before analysis with fluorescent microscope. The VS_ASO_1-FANA-FITC designed with FITC labeled shown in the Table 1, and VS_ASO_2-Cy3 with Cy3 label shown in the Table 2; and VS_DsiRNA-Cy5 with Cy5 label shown in Table 3. A1&A2: No treatment as control; A3&A4: Overexpression of both COVID-19 N-protein and the VS_ASO_1-FANA using lipofectamine reagent; A5&A6: Overexpression of both COVID-19 N-protein and the VS_ASO_1-FANA without any regents; B1&B2: No treatment as control; B3&B4: Overexpression of both COVID-19 N-protein and the VS_DsiRNA-Cy5 using lipofectamine reagent; B5&B6: Overexpression of both COVID-19 N-protein and the VS_DsiRNA-Cy5 using Poly-arginine (5 µl/well) only; C1&C2: No treatment as control; C3&C4: Overexpression of both COVID-19 N-protein and the VS_ASO_2-Cy3 using lipofectamine reagent; C5&C6: Overexpression of both COVID-19 N-protein and the VS_ASO_2-Cy3 using Poly-arginine (5 µl/well) only.
Figure 2A:
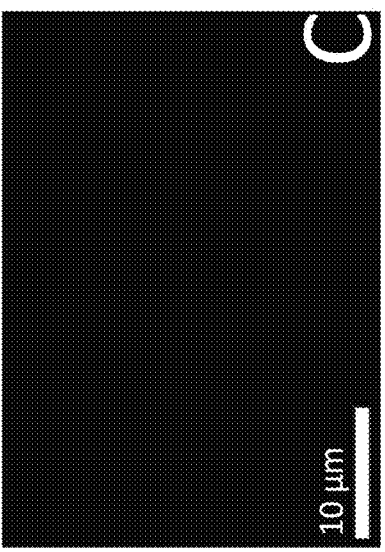
FIGS. 2A-2F. Microscopic analysis showing entry of VS_ASO_1-FANA-FITC into the primary human lung small airway epithermal cells (20×).
Figure 2B:
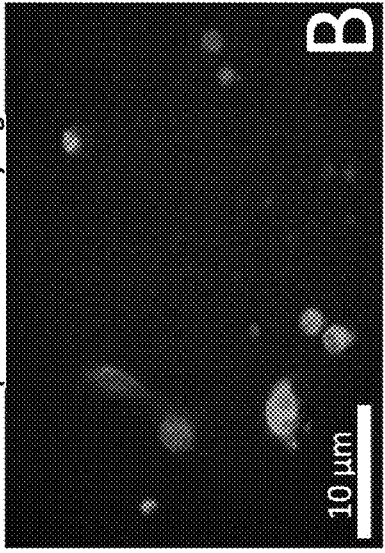
Figure 2C:
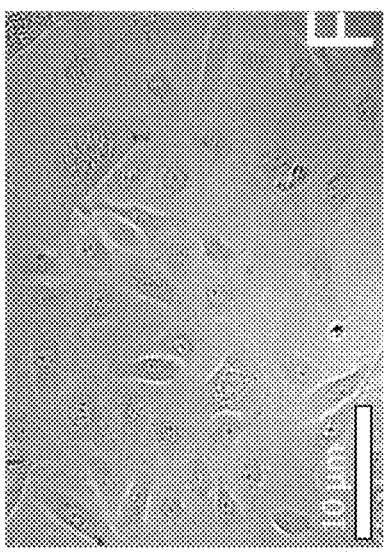
Figure 2D:
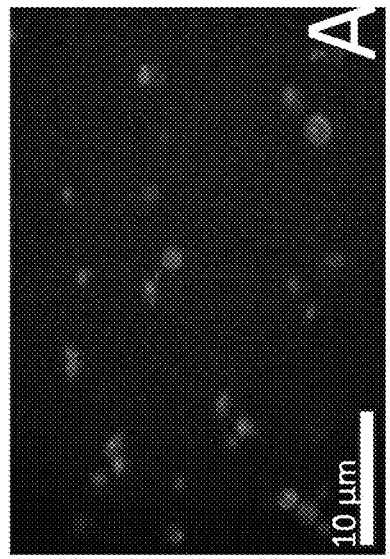
Figure 2E:
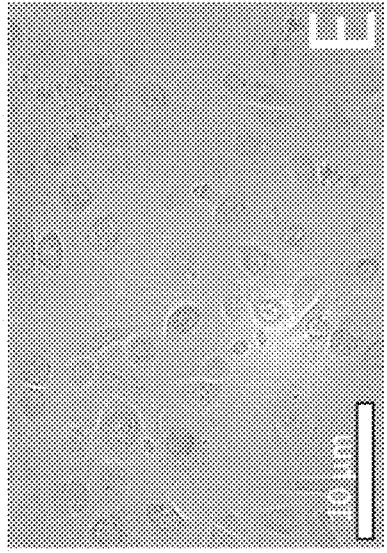
Figure 2F:
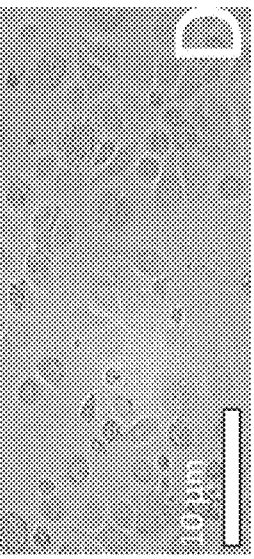

1), FIGS. 2B and 2E were taken in well A5 & A6 (as shown in FIG. 1), and FIGS. 2C and 2F were taken in well A1 & A2 (as shown in FIG. 1).

FIGS. 3A-3F. Microscopic analysis showing entry of VS_ASO_1-FANA-FITC into primary human lung small airway epithermal cells (10×). FIGS. 3A-3C were captured under the FITC florescent filter, and FIGS. 3D-3F were captured in the same view of bright fields (20×). FIGS. 3A and 3D were taken in well A3 & A4 (as shown in FIG. 1), FIGS. 3B and 3E were taken in well A5 & A6 (as shown in FIG. 1), and FIGS. 3C and 3F were taken in well A1 & A2 (as shown in FIG. 1).

FIGS. 4A-4F. Microscopic analysis showing entry of VS_DsiRNA-Cy5 into primary human lung small airway epithermal cells (20×). FIGS. 4A-4C were captured under the Cy5 florescent filter, and FIGS. 4D-4F were captured in the same view of bright fields (20×). FIGS. 4A and 4D were taken in well B3 & B4 (as shown in FIG. 1), FIGS. 4B and 4E were taken in well B5 & B6 (as shown in FIG. 1), and FIGS. 4C and 4F were taken in well B1 & B2 (as shown in FIG. 1).

FIGS. 5A-5F. Microscopic analysis showing entry of VS_DsiRNA-Cy5 into primary human lung small airway epithermal cells (10×). FIGS. 5A-5C were captured under the Cy5 florescent filter, and FIGS. 5D-5F were captured in the same view of bright field images (10×). FIGS. 5A and 5D were taken in well B3 & B4 (as shown in FIG. 1), FIGS. 5B and 5E were taken in well B5 & B6 (as shown in FIG. 1), and FIGS. 5C and 5F were taken in well B1 & B2 (as shown in FIG. 1).

Figure 6C:
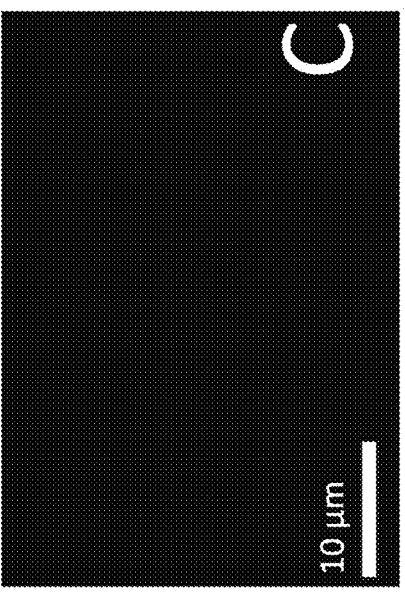
Figure 6B:
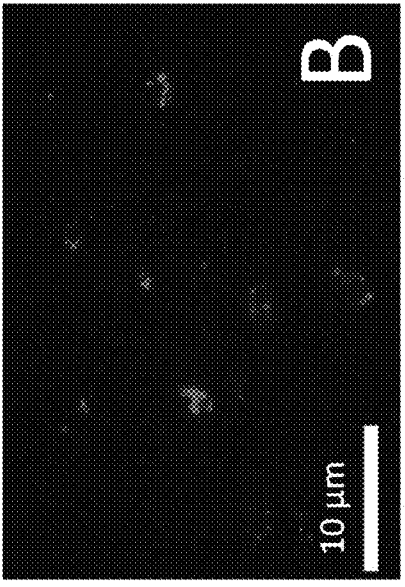
Figure 6A:
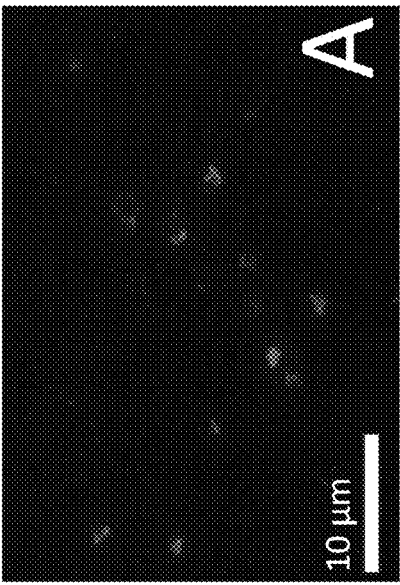
Figure 6F:
Figure 6E:
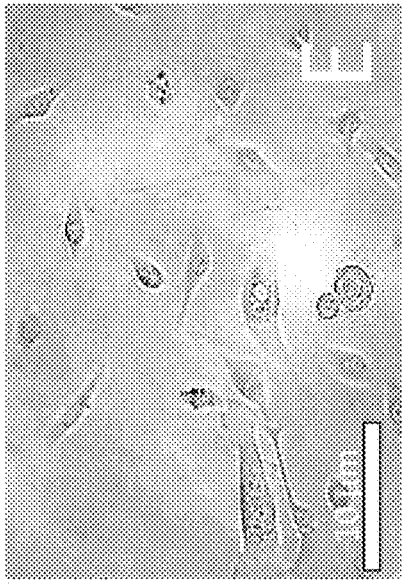
Figure 6D:
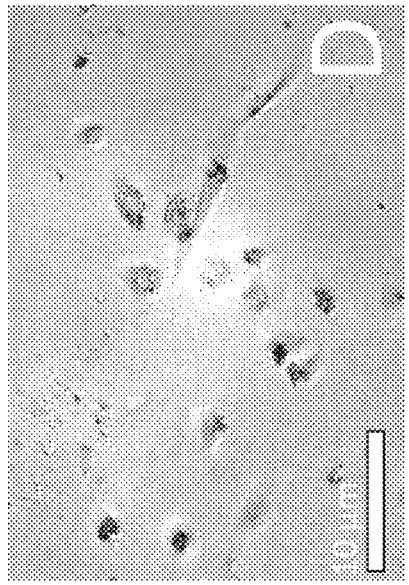

FIGS. 6A-6F. Microscopic analysis showing entry of VS_ASO_2-Cy3 into primary human lung small airway epithermal cells (20×). FIGS. 6A-6C were captured under the Cy3 florescent filter, and FIGS. 6D-6F were captured in the same view of bright fields (20×). FIGS. 6A and 6D were taken in well C3 & C4 (as shown in FIG. 1), FIGS. 6B and 6E were taken in well C5 & C6 (as shown in FIG. 1), and FIGS. 6C and 6F were taken in well C1 & C2 (as shown in FIG. 1).

FIGS. 7A-7F. Microscopic analysis showing entry of VS_ASO_2-Cy3 into primary human lung small airway epithermal cells (10×). The FIGS. 7A-7C were captured under the Cy3 florescent filter, and FIGS. 7D-7F were captured in the same view of bright fields (10×). FIGS. 7A and 7D were taken in well C3 & C4 (as shown in FIG. 1), FIGS. 7B and 7E were taken in well C5 & C6 (as shown in FIG. 1), and FIGS. 7C and 7F were taken in well C1 & C2 (as shown in FIG. 1).

Figure 8:
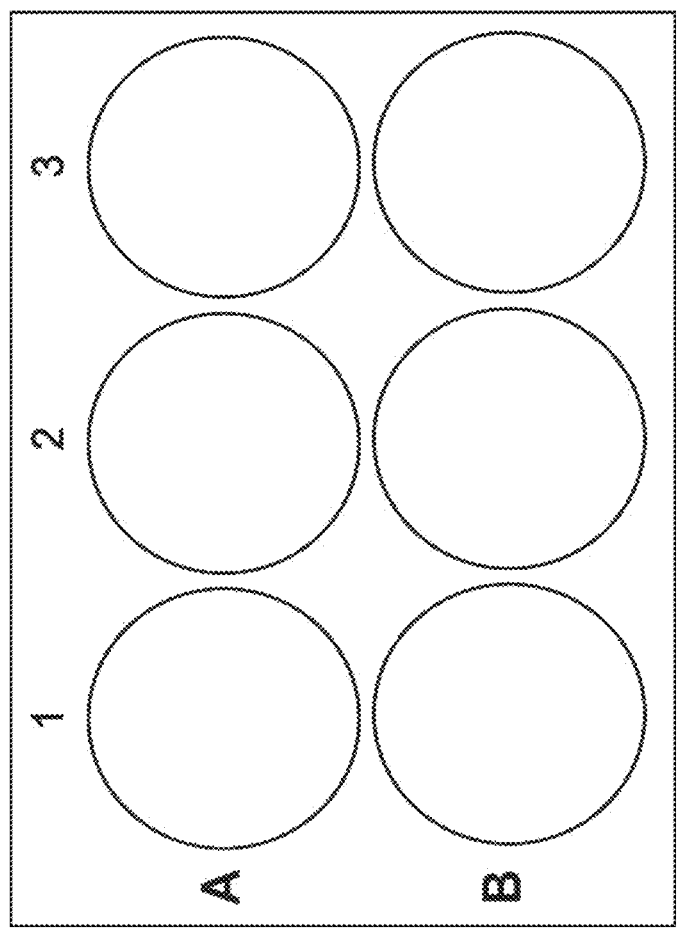

FIG. 8. Experimental design for FACS detection of intercellular delivery of oligos in the human primary lung small airway epithelial cells (HSAEC). The human lung small airway epithelial cells were cultured in the 6-well dish, and the genes encoding the viral proteins of SARS-CoV-2 were delivered by transfection or arginine delivery. The siRNA or ASO were added into the cells for 24-48 hours before analysis with FACS. The VS_ASO_1-FANA-FITC designed with labeled with FITC shown in the Table 1, and VS_ASO_2-Cy3 with modification shown in the Table 2; and VS_DsiRNA-Cy5 shown in Table 3. A1: No treatment as control; A2: Overexpression of N-protein+VS_ASO_1-FANA-FITC without lipofectamine or arginine; A3: Overexpression of N-protein+VS_DsiRNA-Cy5 with lipofectamine; B1: Overexpression of N-protein+VS_DsiRNA-Cy5 with Arginine (10p/well); B2: Overexpression of N-protein+VS_ASO_2-Cy3 with lipofectamine; B3: Overexpression of N-protein+VS_ASO_2-Cy3 with Arginine (10 μl/well).

Figure 9A:
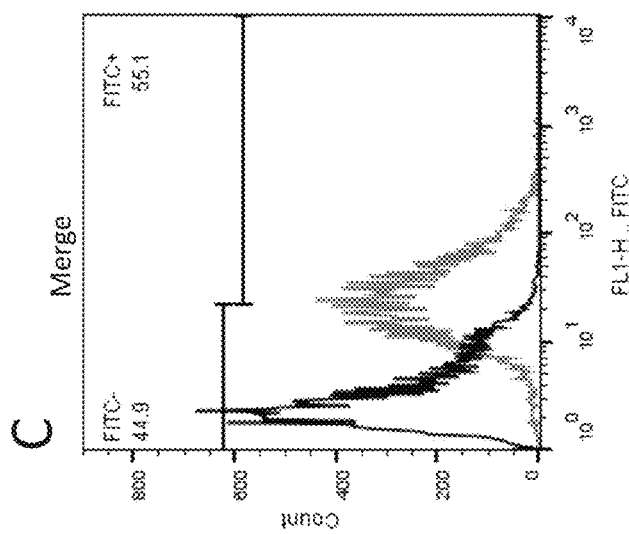
Figure 9B:
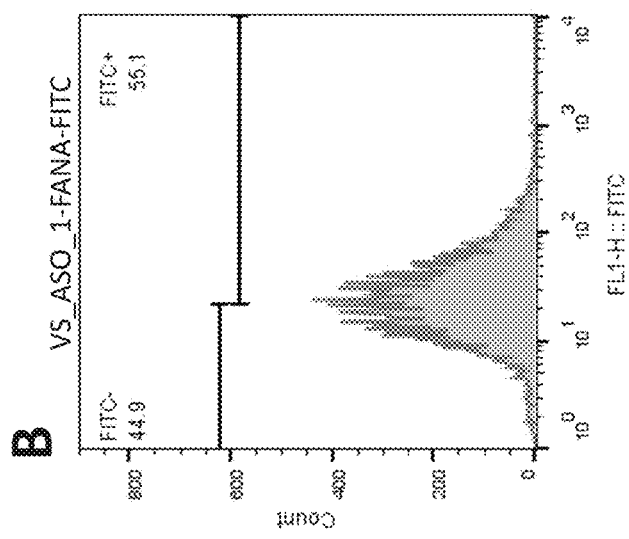
Figure 9C:
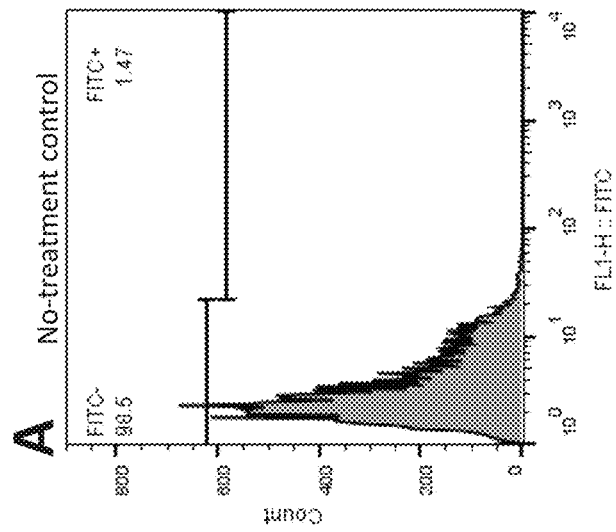

FIGS. 9A-9C. FACS analysis of in vitro treatment with VS_ASO_1-FANA-FITC without lipofectamine or Arginine in human primary lung small airway epithelial cells (HSAEC). FACS analysis of HSAEC treated by VS_ASO_1-FANA-FITC (excitation: 488 nm, emission band pass filter: 530/30, Total event: 20,000). FIG. 9A no-treatment control, FIG. 9B VS_ASO_1-FANA-FITC and FIG. 9C Merge. The FACS data indicate that the intensities of FITC signals were significantly stronger with shifting to the right (B: FL1-H:FITC) when compared with the control FIG. 9A in the cells after treated with the VS_ASO_1-FANA-FITC without lipofectamine or Arginine reagents FIG. 9B. The FIG. 9C is the merged figures of FIGS. 9A and 9B.

Figure 10A:
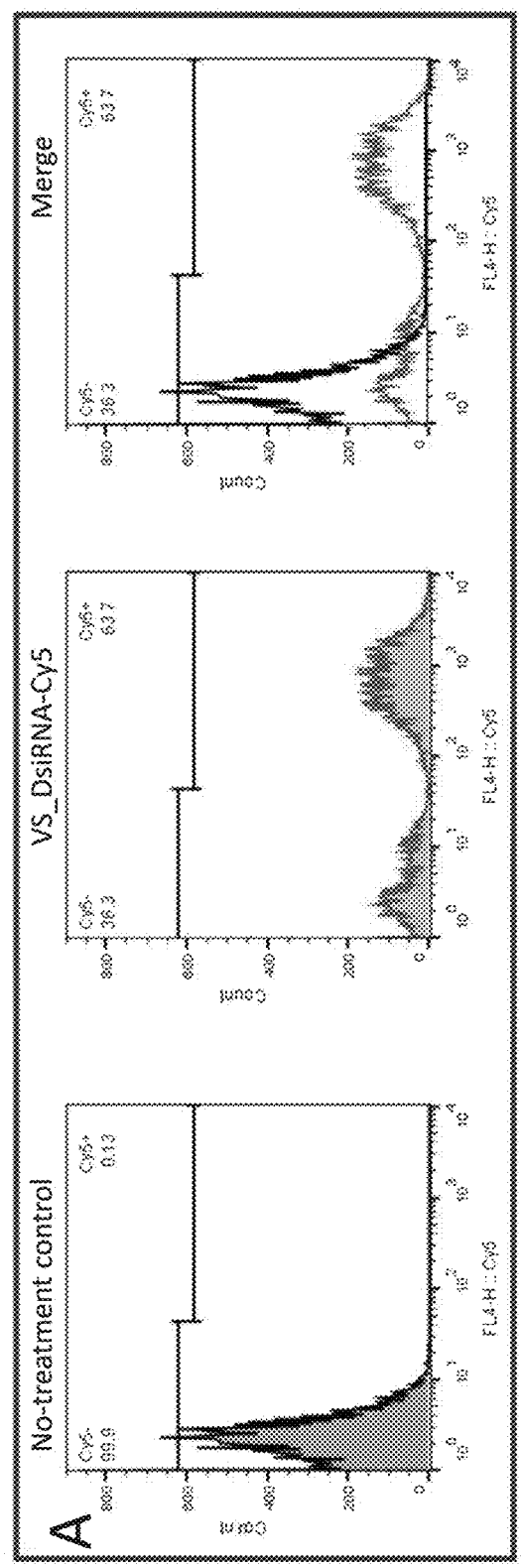
Figure 10B:
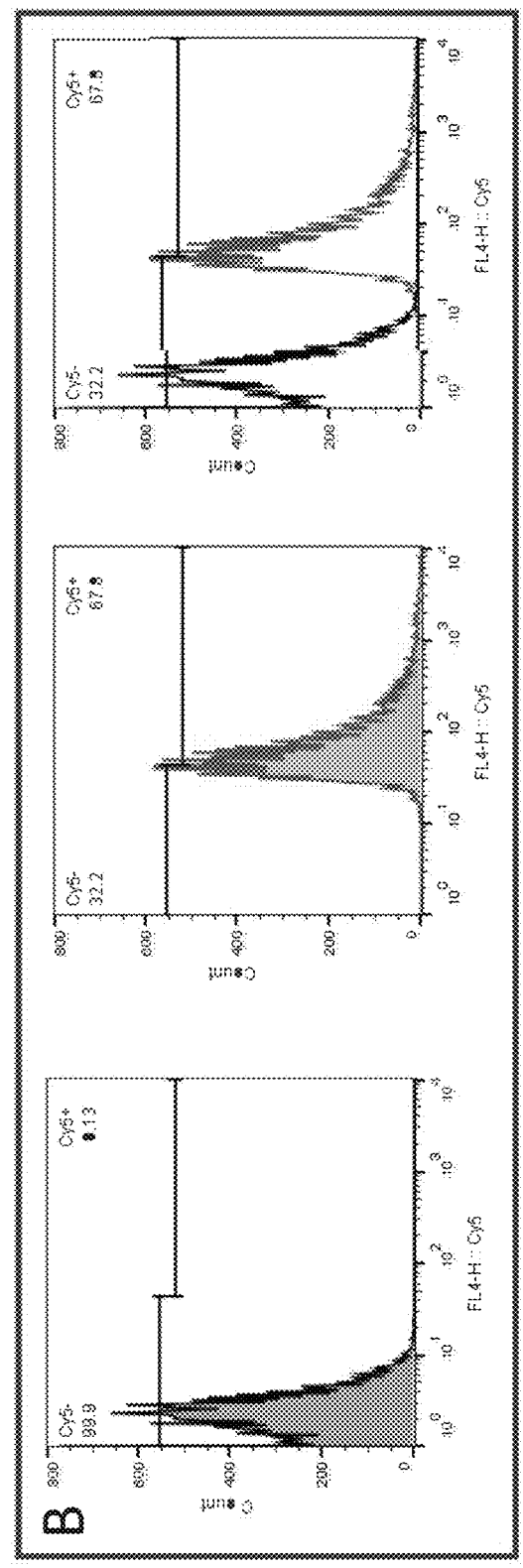

FIGS. 10A-10B. FACS analysis of in vitro treatment with VS_DsiRNA-Cy5 with lipofectamine FIG. 10A or Arginine only FIG. 10B in human primary lung small airway epithelial cells (HSAEC). FACS analysis of HSAEC treated by VS_DsiRNA-Cy5 (excitation: 635 nm, emission band pass filter: 661/16, Total event: 20,000). Left to right panel: no-treatment control, VS_DsiRNA-Cy5 and merge. The FACS data indicates that the intensities of Cy5 signals were significantly higher with shifting to the right (middle panel: FL4-H:Cy5) in both of panel FIGS. 10A and 10B, it also shown that there are more cells with intercellular signals of the oligos in the presence of 10 μl/well Arginine (panel FIG. 10B) when compared with the lipofectamine (panel FIG. 10A).

Figures 11A, 11B:
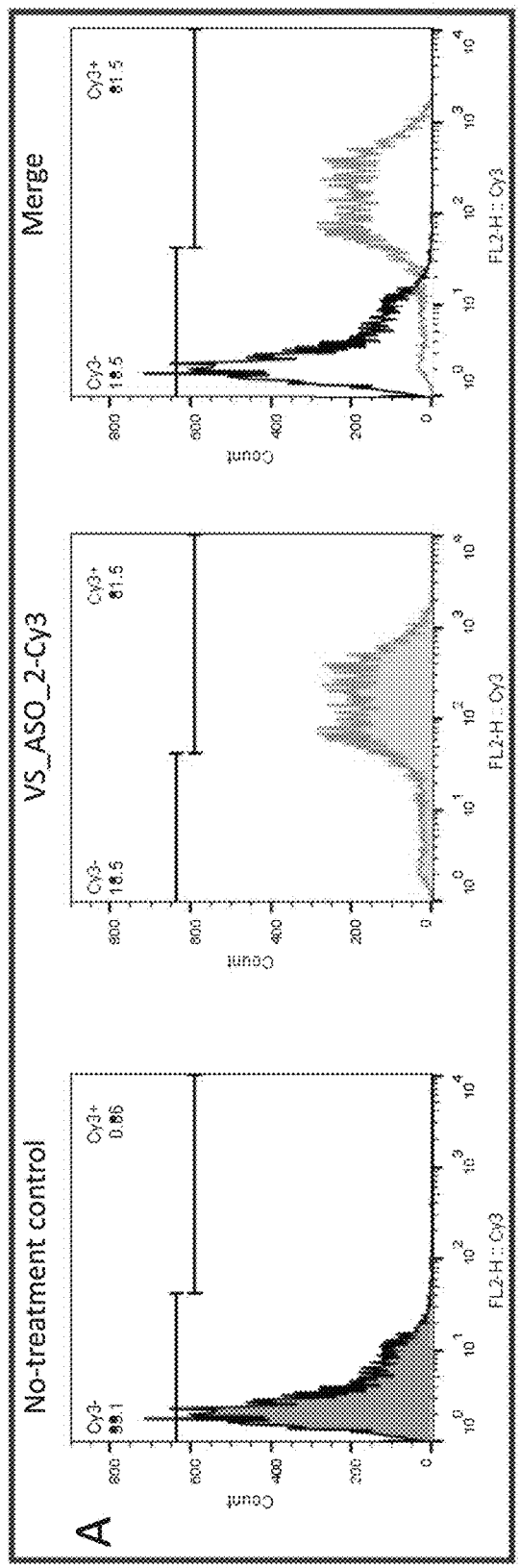

FIGS. 11A-11B. FACS analysis of in vitro treatment with VS_ASO_2-Cy3 with lipofectamine FIG. 11A or Arginine only FIG. 11B in human primary lung small airway epithelial cells (HSAEC). FACS analysis of HSAEC treated by VS_VS_ASO-Cy3 (excitation: 488 nm, emission band pass filter: 585/42, Total event: 20,000). Left to right panel: no-treatment control, VS_ASO_2-Cy3 and merge. The FACS data indicates that the intensities of Cy3 signals were significantly higher with shifting to the right (middle panel: FL2-H:Cy3) in both of FIGS. 11A and 11B, it also shown that there are more cells with intercellular signals of the oligos in the presence of 10 μl/well Arginine (panel FIG. 11B) when compared with the lipofectamine (panel FIG. 11A).

Figure 12:
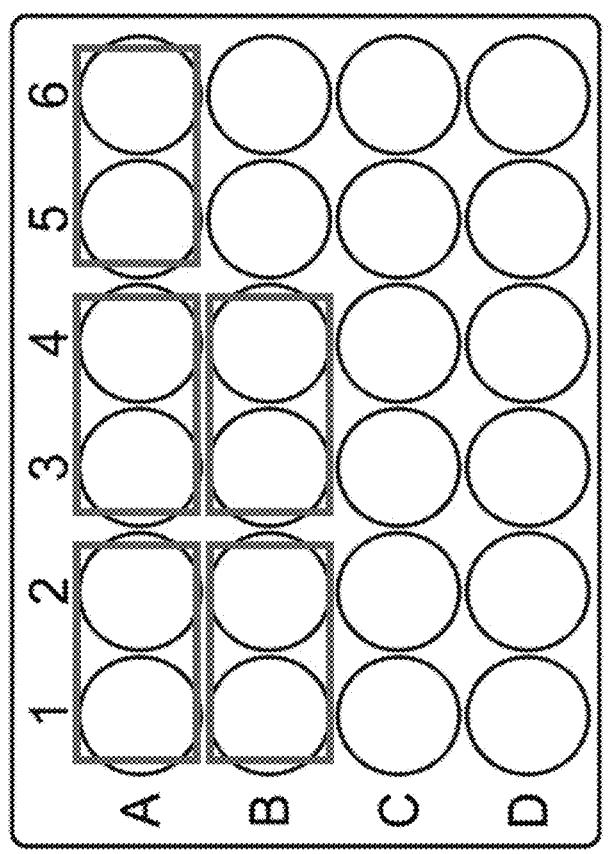

FIG. 12. Experimental design for detection of SARS-CoV-2 N-protein expressed in the human primary lung small airway epithelial cells (HSAEC) by qRT-PCR after treatment. The human lung small airway epithelial cells were cultured in a 24-well dish, and the cells were transfected with the genes encoding the viral protein (N-protein) of SARS-CoV-2. The inhibitory oligonucleotides were added into the cells for 24-48 hours before analysis with RT-PCR. The VS_ASO_1-FANA-FITC designed with FITC labeled shown in the Table 1, and VS_ASO_2-Cy3 with Cy3 modification shown in the Table 2; and VS_DsiRNA-Cy5 with Cy5 modification shown in Table 3. A1&A2: No treatment as control, A3&A4: Overexpression of COVID-19 N-protein, A5&A6: Overexpression of COVID-19 N-protein+/treated by VS_DsiRNA_Cy5 with lipofectamine, B1&B2: Overexpression of COVID-19 N-protein+/treated by VS_ASO_2-Cy3 with lipofectamine, B3&B4: Overexpression of COVID-19 N-protein+/treated by VS_ASO_1-FANA without any reagents.

Figure 13:
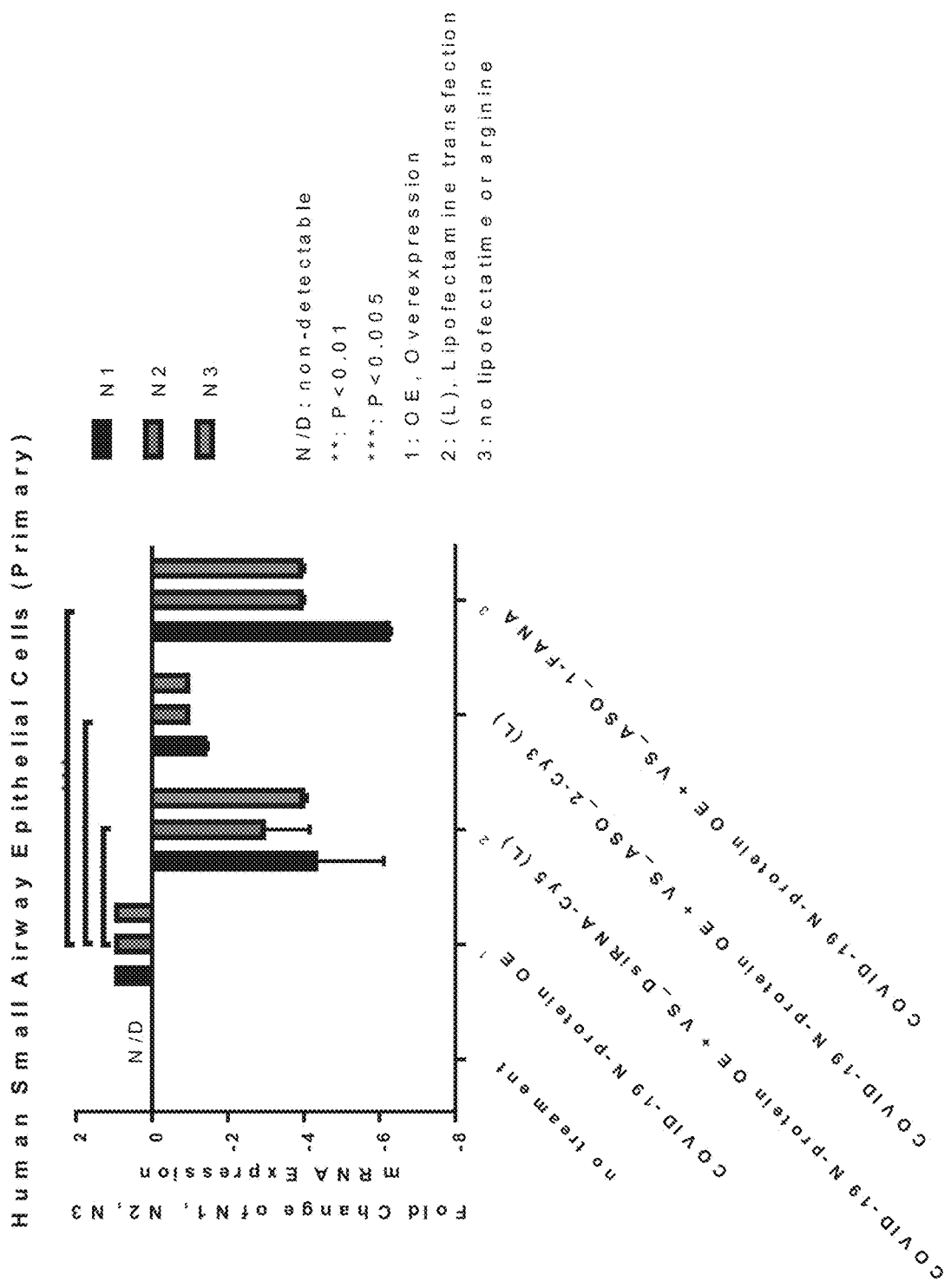

FIG. 13. Detection of SARS-CoV-2 N-protein expressed in the human primary lung small airway epithelial cells (HSAEC) by qRT-PCR after treatment with VS-Nucleotides. Significant down-regulation was observed: about 5-fold in group treated by VS_DsiRNA-Cy5 oligos (p<0.005); about 1.5 fold in the group treated by VS_ASO_2-cy3 oligo (p<0.01), and about 6 fold in the group treated by the VS_ASO_1-FANA-FITC oligo (p<0.005); when compared with the group with SARS-CoV-2 N-protein overexpression only. The cycle threshold of no-treatment is non-detectable, but in this case for calculation purposes, the number "40" was used as the cycle threshold for a base-line control.

Figure 14:
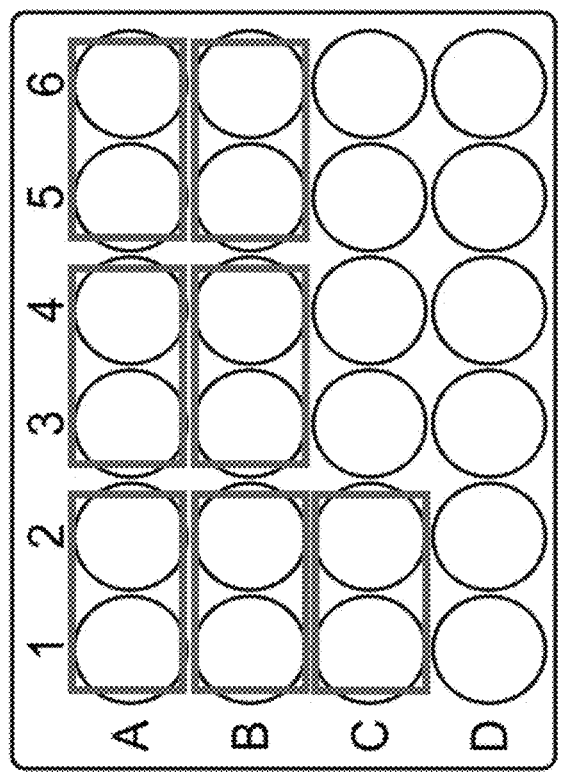

FIG. 14. Experimental design for detection of SARS-CoV-2 S-protein expressed in the primary human lung small airway epithelial cells (HSAEC) by qRT-PCR after treatment. The human primary lung small airway epithelial cells (HSAEC) were cultured in the 24 well-dish, and the cells were transfected with the genes encoding the viral protein (S-protein) of SARS-CoV-2. The inhibitory oligonucleotides were added into the cells for 24-48 hours before analysis with RT-PCR. The VS_ASO_1-FANA (oligo 3) designed shown in the Table 1, and VS_ASO_2 (oligo 3) shown in the Table 2; and VS_DsiRNA (oligo 3) shown in Table 3. A1&A2: No treatment as control, A3&A4: Overexpression of COVID-19 S-protein, A5&A6: Overexpression of COVID-19 S-protein+/treated by VS_DsiRNA (oligo 3) with lipofectamine, B1&B2: Overexpression of COVID-19 S-protein+/treated by VS_DsiRNA (oligo 3) with Arginine (5 µl/well), B3&B4: Overexpression of COVID-19 S-protein+/treated by VS_ASO_2 (oligo 3) with lipofectamine, B5&B6: Overexpression of COVID-19 S-protein+/treated by VS_ASO_2 (oligo 3) with Arginine (5 µl/well), C1&C2: Overexpression of COVID-19 S-protein+/treated by VS_ASO_1-FANA (oligo 3) without any reagents.

Figure 15:
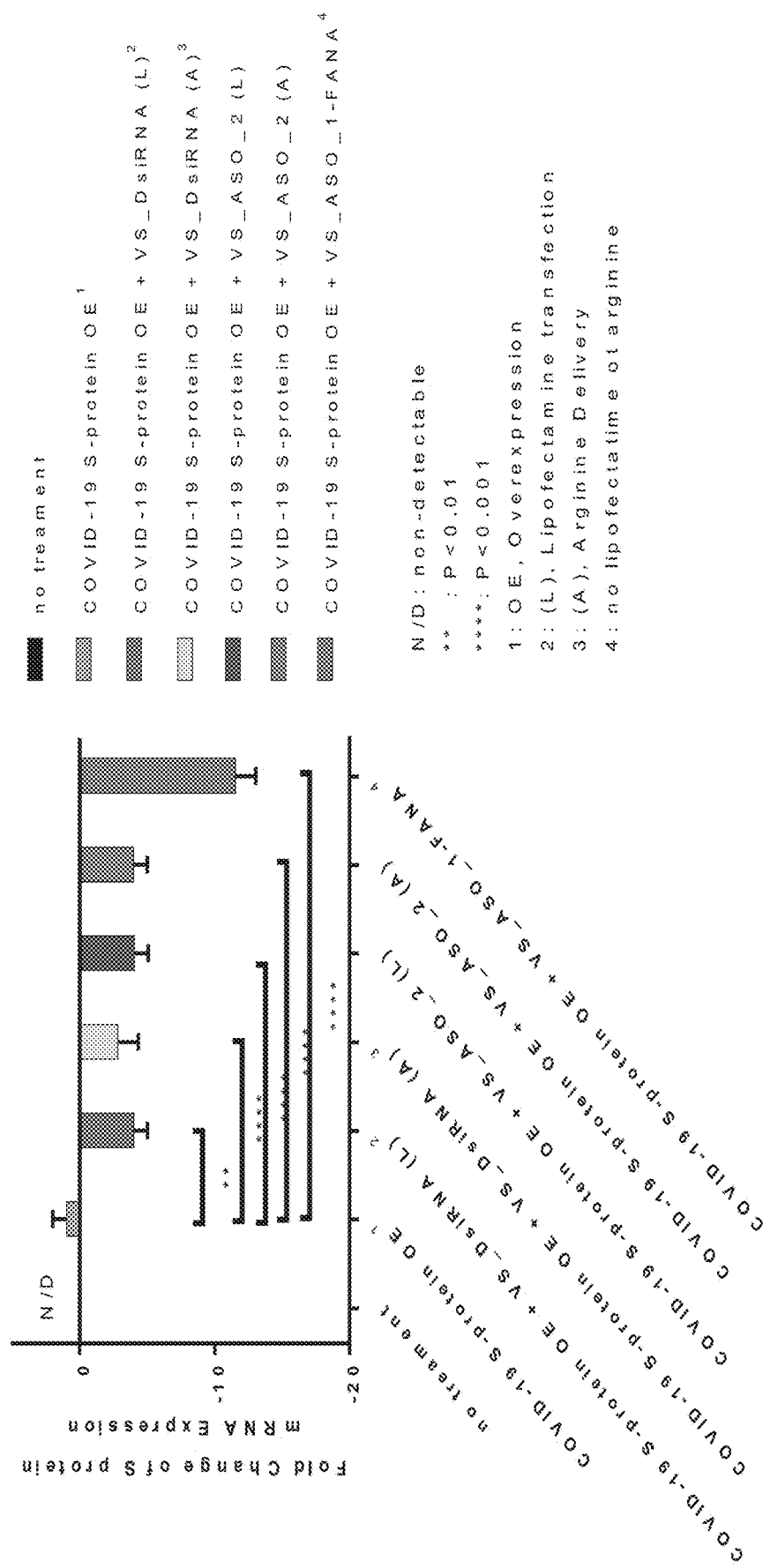

FIG. 15. Detection of SARS-CoV-2 S-protein expressed in the human primary lung small airway epithelial cells (HSAEC) by qRT-PCR after treatment with VS-Nucleotides. Significant down-regulation was observed: about 4 fold in group treated by VS_DsiRNA oligo (purple/L: p<0.01) and about 2.8 fold in the presence of poly-Arginine only (yellow/A: p<0.001); about 4 fold in the group treated by VS_ASO_2 oligo (red/L: p<0.001) and about 4 fold in the in the presence of poly-Arginine only (orange/A: p<0.001); and about 11.5 fold in the group treated by the VS_ASO_1-FANA oligo (green/p<0.001); when compared with the group with SARS-CoV-2 S-protein overexpression only. The cycle threshold of no-treatment is non-detectable, but in this case for calculation purposes, the number "40" was used as the cycle threshold for a base-line control.

Figure 16:
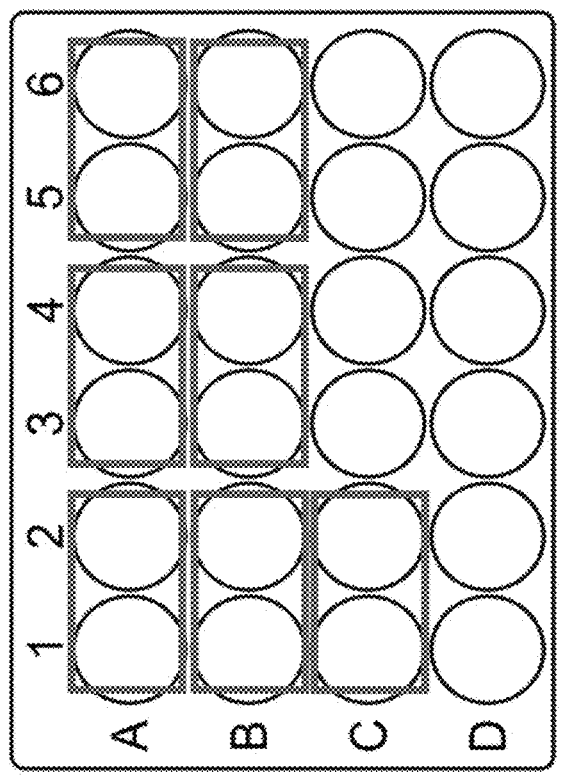

FIG. 16. Experimental design for detection of both of SARS-CoV-2 ORF1ab and RdRp expressed in the primary human lung small airway epithelial cells (HSAEC) by qRT-PCR after treatment. The human primary lung small airway epithelial cells (HSAEC) were cultured in the 24 well-dish, and the cells were transfected with the genes encoding both ORF1ab and RdRp of SARS-CoV-2 viral protein. The inhibitory oligonucleotides were added into the cells for 24-48 hours before analysis with RT-PCR. The VS_ASO_1-FANA (oligo 1, 2, 5 and 6) designed shown in the Table 1, and VS_ASO_2 (oligo 1, 2, 5 and 6) shown in the Table 2; and the VS_DsiRNA (oligo 1, 2, 5 and 6) shown in Table 4. A1&A2: No treatment as control, A3&A4: Overexpression of COVID-19 viral genes encoding both ORF1ab and RdRp, A5&A6: Overexpression of both ORF1ab and RdRp+/treated by VS_DsiRNA (oligo 1, 2, 5 and 6) with lipofectamine, B1&B2: Overexpression of both ORF1ab and RdRp+/treated by VS_DsiRNA (oligo 1, 2, 5 and 6) with Arginine (5 µl/well), B3&B4: Overexpression of both ORF1ab and RdRp+/treated by VS_ASO_2 (oligo 1, 2, 5 and 6) with lipofectamine, B5&B6: Overexpression of both ORF1ab and RdRp+/treated by VS_ASO_2 (oligo 1, 2, 5 and 6) with Arginine (5 µl/well), C1&C2: Overexpression of both ORF1ab and RdRp+/treated by VS_ASO_1-FANA (oligo 1, 2, 5 and 6) without any reagents.

Figure 17:
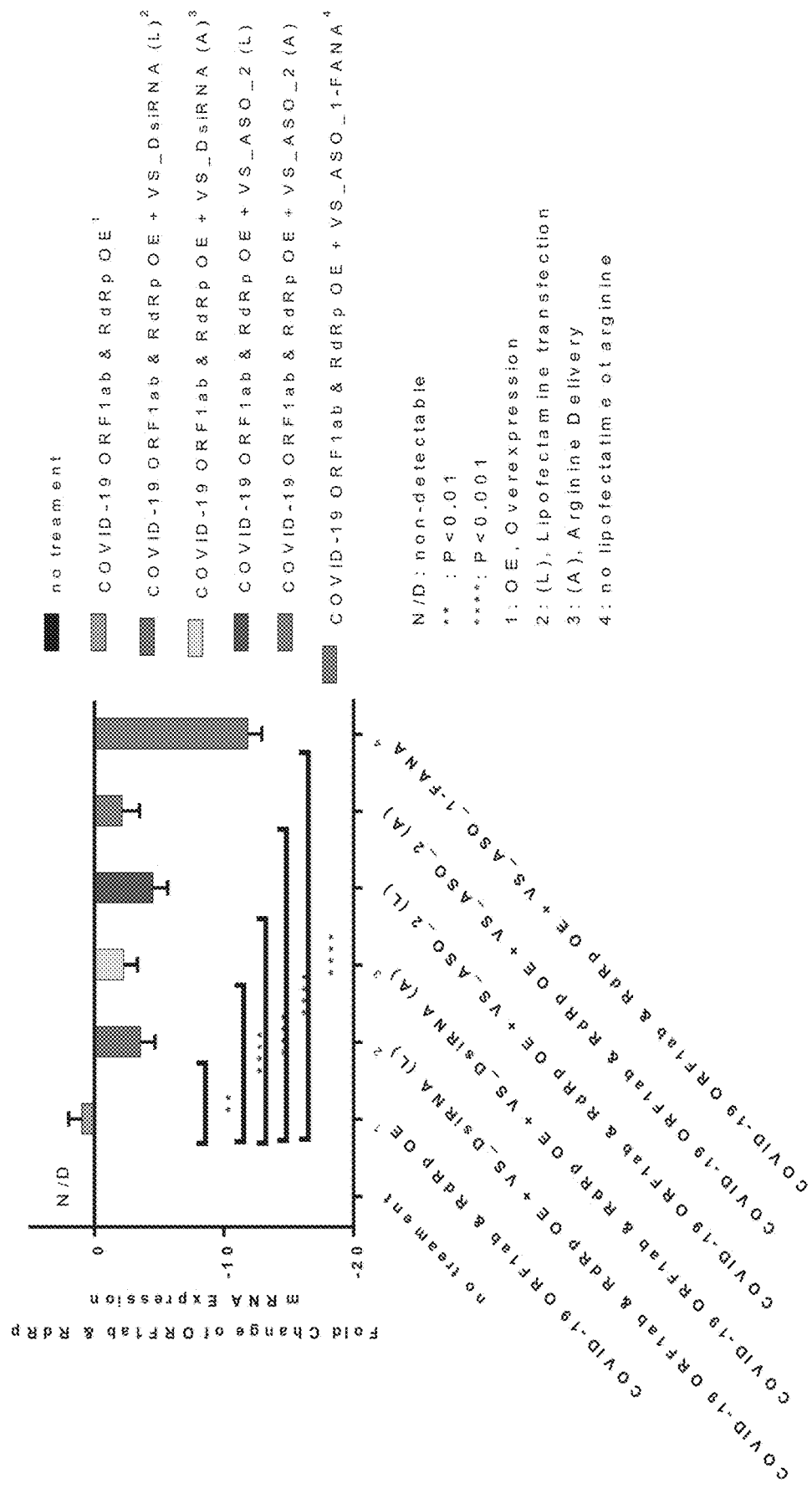

FIG. 17. Detection of SARS-CoV-2 ORF1ab and RdRp expressed in the human primary lung small airway epithelial cells (HSAEC) by qRT-PCR after treatment with inhibitory oligonucleotides. Significant down-regulation was observed: about 3.5 fold in group treated by VS_DsiRNA oligo (purple/L: p<0.01) and about 2.2 fold in the presence of poly-Arginine only (yellow/A: p<0.001); about 4.5 fold in the group treated by VS_ASO_2 oligo (red/L: p<0.001) and about 2.1 fold in the in the presence of poly-Arginine only (orange/A: p<0.001); and about 11.8 fold in the group treated by the VS_ASO_1-FANA oligo (green/p<0.001); when compared with the group with SARS-CoV-2 ORF1ab and RdRp overexpression only. The cycle threshold of no-treatment is non-detectable, but in this case for calculation purposes, the number "40" was used as the cycle threshold for a base-line control.

Figure 18:
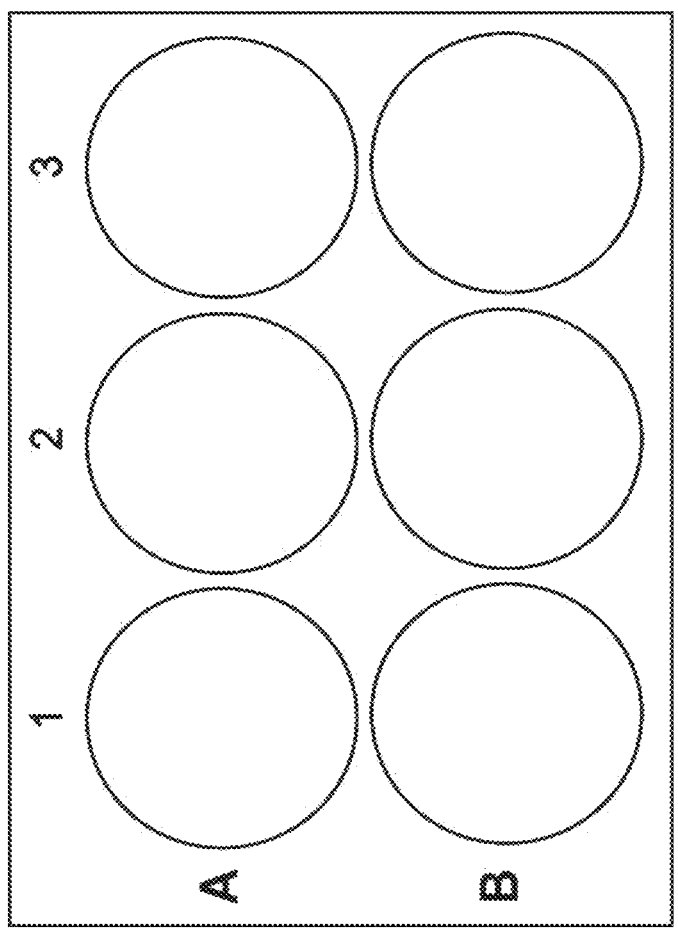

FIG. 18. Experimental design for detection of SARS-CoV-2 N-protein expressed in the primary human lung small airway epithelial cells (HSAEC) by Western Blot after treatment. The human primary lung small airway epithelial cells (HSAEC) were cultured in the 6 well-dish, and the cells were transfected with the genes encoding the viral protein (N-protein) of SARS-CoV-2. The inhibitory oligonucleotides were added into the cells for 24-48 hours before analysis with Western Blot. The VS_ASO_2 (oligo 4 & 8) shown in the Table 2; and VS_DsiRNA (oligo 4 & 8) shown in Table 4. A1: No treatment as control, A2: Overexpression of COVID-19 N-protein, A3: Overexpression of COVID-19 N-protein+/treated by VS_DsiRNA (oligo 4 and 8) with lipofectamine, B1: Overexpression of COVID-19 N-protein+/treated by VS_ASO_2 (oligo 4 and 8) with lipofectamine.

Figure 19:
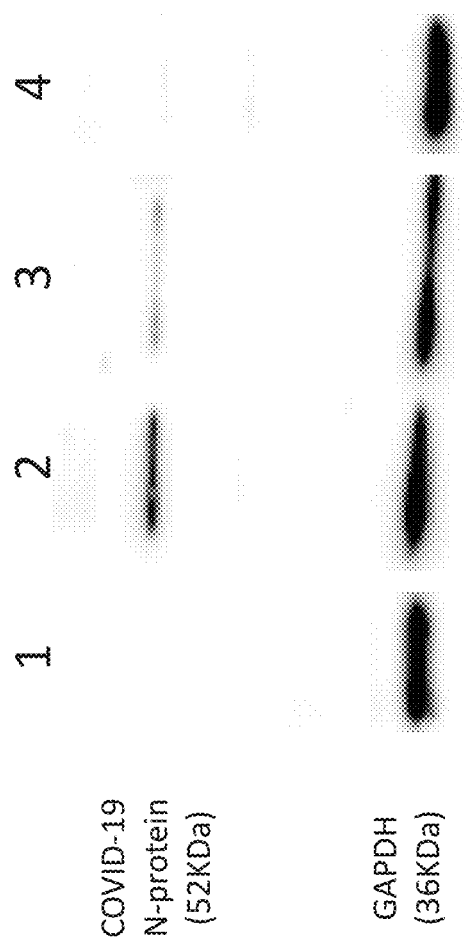

FIG. 19. Detection of SARS-CoV-2 N-protein expressed in the human primary lung small airway epithelial cells (HSAEC) by Western Blot after treatment with inhibitory oligonucleotides: Lane-1: no treatment; Lane-2: SARS-CoV-2 N-protein overexpression (OE); Lane-3: SARS-CoV-2 N-protein OE+/treated by VS_DsiRNA (oligo 4 & 8); Lane-4: SARS-CoV-2 N-protein OE+/treated by the VS_ASO_2 (oligo 4 & 8). The 10 ug total cell-lysis were added into each well. primary antibody: 1 µg/mL anti-SARS-CoV-2-N-protein antibody (ProSci, 3857) and anti-GAPDH antibody (Novus Biologicals, NBP2-27103) with 1:1000 dilution. The secondary antibody: goat-anti-rabbit HRP-conjugated Antibody (R&D System, HAF008) with 1:1000 dilution and goat-anti-mouse IgG HRP-conjugated Antibody (R&D System, HAF007) with 1:1000 dilution. The detection was done using horseradish peroxidase-labeled secondary antibodies and enhanced chemiluminescence detection reagent.

Figure 20:
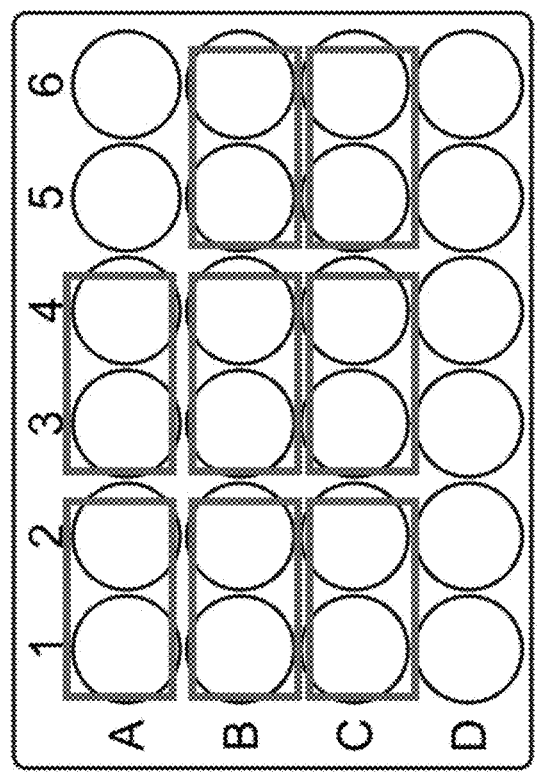

FIG. 20. Experiments designed for investigating cell penetration and therapeutic effects of VS-Nucleotides (inhibitory oligonucleotides) on human primary bronchial/tracheal epithelial cells (HBTEC) transfected with viral protein of SARS-CoV-2 after treatment. The primary human bronchial/tracheal epithelial cells (HBTEC) were cultured in a 24-well dish, and the cells were transfected with the genes encoding the viral proteins of SARS-CoV-2. The VS_ASO_1-FANA-FITC, VS_DsiRNA-Cy5 and VS_ASO_2-Cy3 were added into the cells for 24-48 hours before analysis with fluorescent microscope. VS_ASO_1-FANA-FITC designed with FITC labeled shown in the Table 1, and VS_ASO_2-Cy3 with Cy3 label shown in the Table 2; and VS_DsiRNA-Cy5 with Cy5 label shown in Table 3. A1&A2: No treatment as control, A3&A4: Overexpression of COVID-19 N-protein+/treated by VS_ASO_1-FANA-FITC without lipofectamine or/and Poly-arginine, B1&B2: No treatment as control, B3&B4: Overexpression of COVID-19 N-protein+/treated by VS_DsiRNA-Cy5 with lipofectamine, B5&B6: Overexpression of COVID-19 N-protein+/treated by VS_DsiRNAi-Cy5 with arginine (5 μl/well), C1&C2: No treatment as control, C3&C4: Overexpression of COVID-19 N-protein+/treated by VS_ASO_2-Cy3 with lipofectamine, C5&C6: Overexpression of COVID-19 N-protein+/treated by VS_ASO_2-Cy3 with arginine (5 μl/well).

Figure 21B:
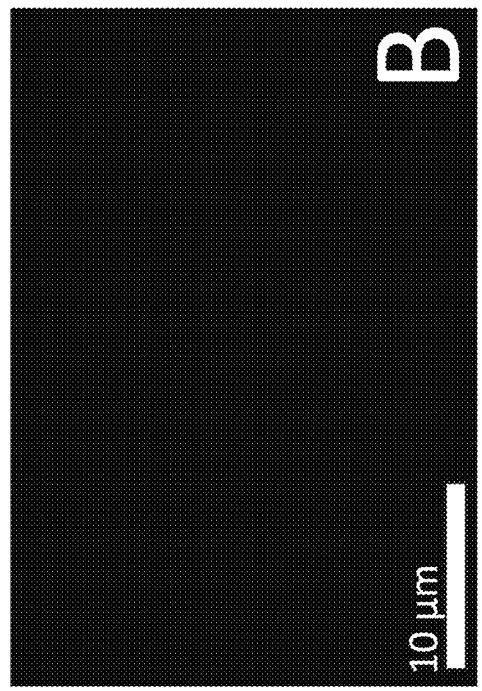
Figure 21D:
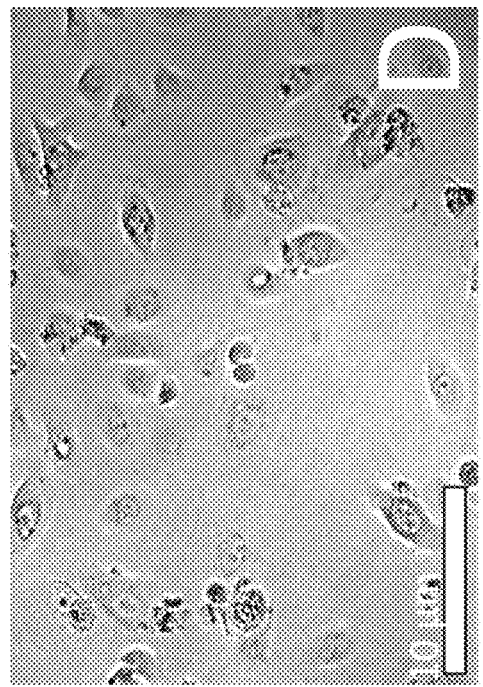
Figure 21A:
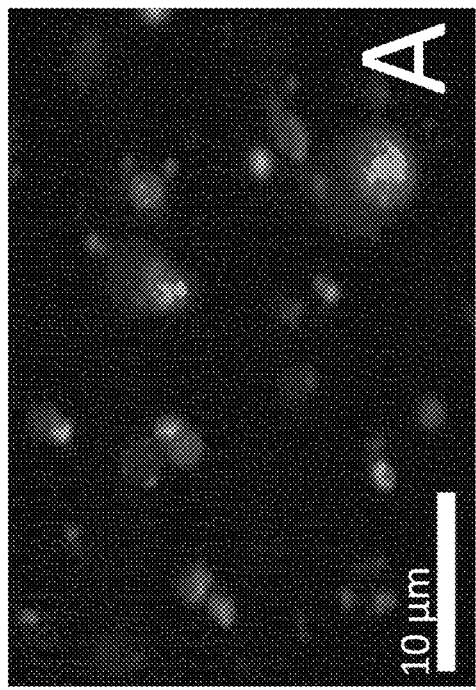
Figure 21C:
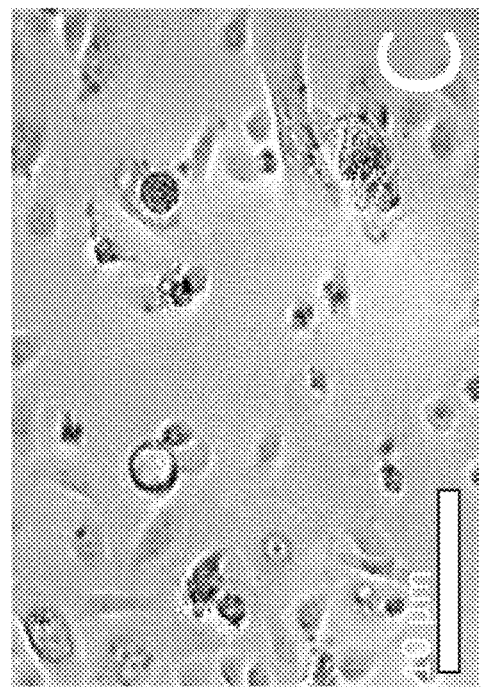

FIGS. 21A-21D. Microscopic analysis showing entry of VS_ASO_1-FANA-FITC into primary human lung bronchial/tracheal epithelial cells (20×). FIGS. 21A-21B were captured under FITC florescent filter, and FIGS. 21C and 21D were captured in the same view of bright fields (20×). FIGS. 21A and 21C were taken in well A1 & A2 (as shown in FIG. 20), and FIGS. 21B and 21D were taken in well A3 & A4 (as shown in FIG. 20).

Figure 22B:
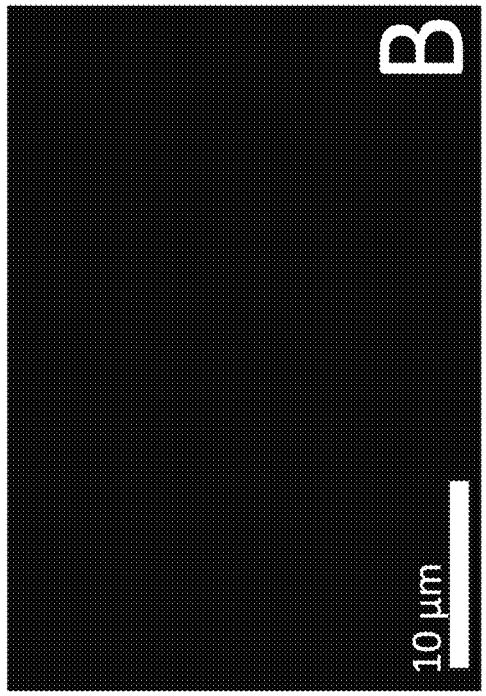
Figure 22D:
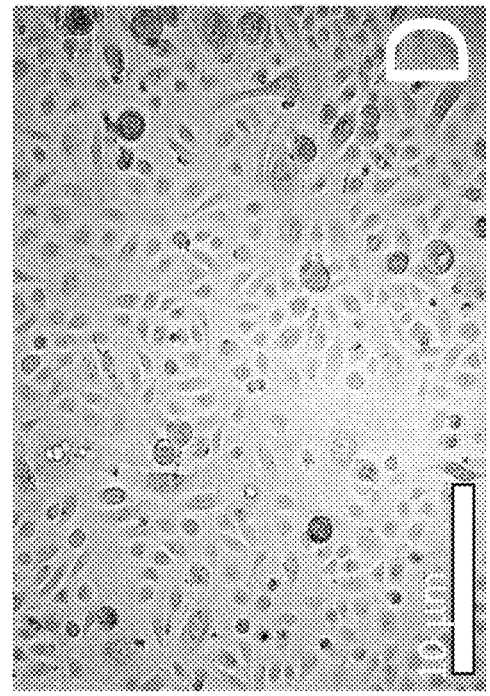
Figure 22A:
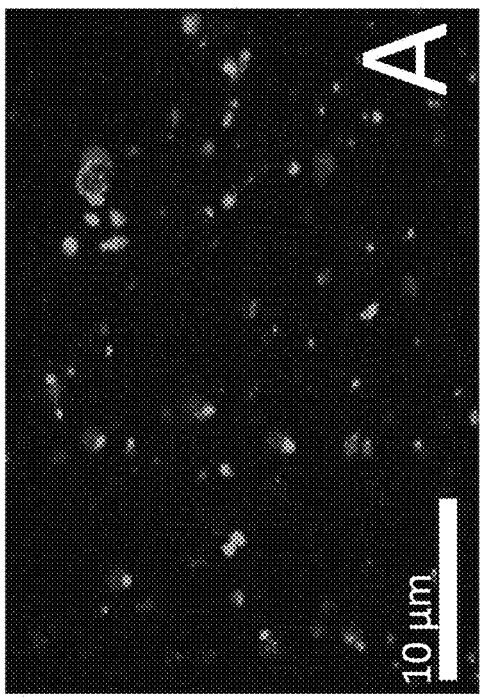
Figure 22C:
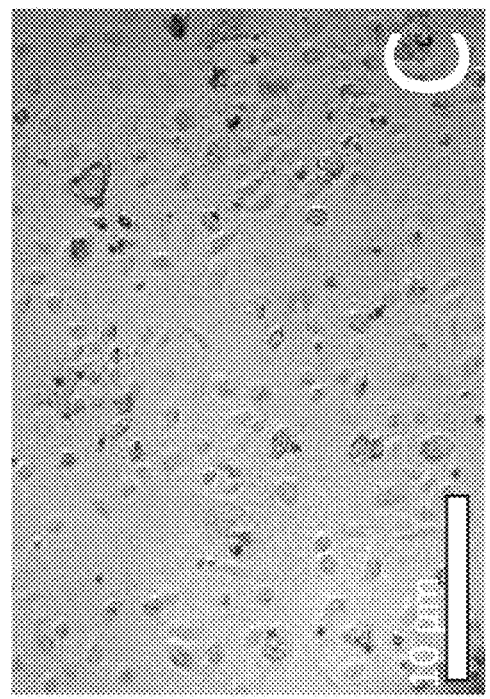

FIGS. 22A-22D. Microscopic analysis showing entry of VS_ASO_1-FANA-FITC into primary human lung bronchial/tracheal epithelial cells (10×). FIGS. 22A-22B were captured under FITC florescent filter, and FIGS. 22C and 22D were captured in the same view of bright fields (10×). FIGS. 22A and 22C were taken in well A1 & A2 (as shown in FIG. 20), and FIGS. 22B and 22D were taken in well A3 & A4 (as shown in FIG. 20).

FIGS. 23A-23F. Microscopic analysis showing entry of VS_DsiRNA-Cy5 into primary human lung bronchial/tracheal epithermal cells (20×). FIGS. 23A-23C were captured under the Cy5 florescent filter, and FIGS. 23D-23F were captured in the same view of bright fields (20×). FIGS. 23A and 23D were taken in well B3 & B4 (as shown in FIG. 20), FIGS. 23B and 23E were taken in well B5 & B6 (as shown in FIG. 20), and FIGS. 23C and 23F were taken in well B1 & B2 (as shown in FIG. 20).

Figure 24C:
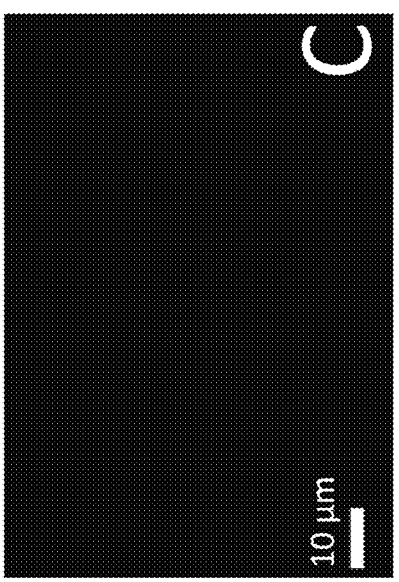
Figure 24B:
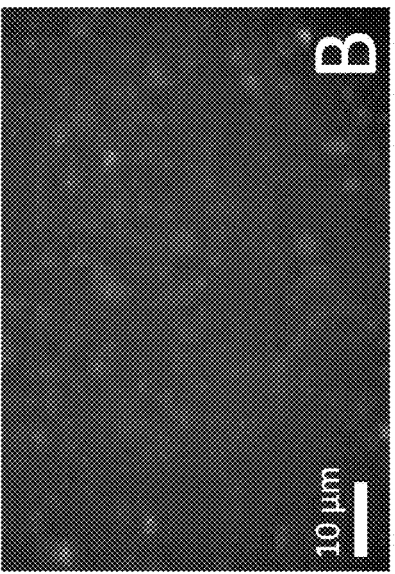
Figure 24A:
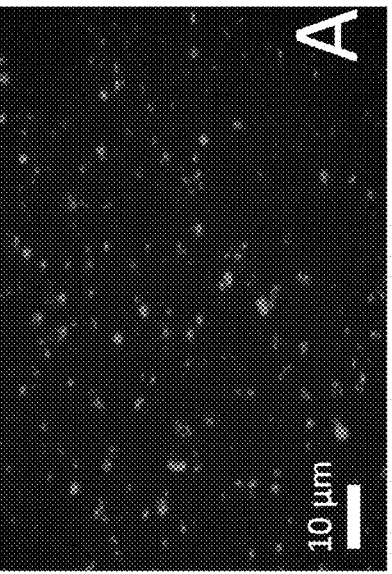
Figure 24F:
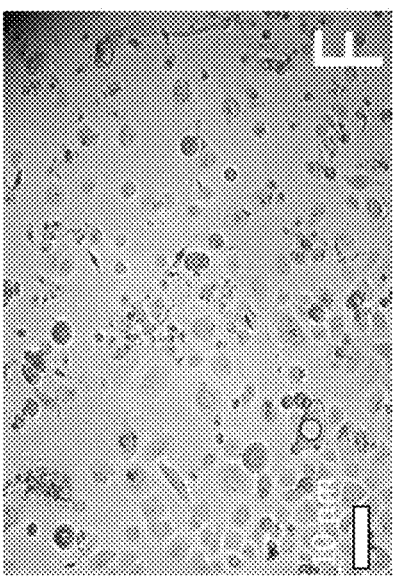
Figure 24E:
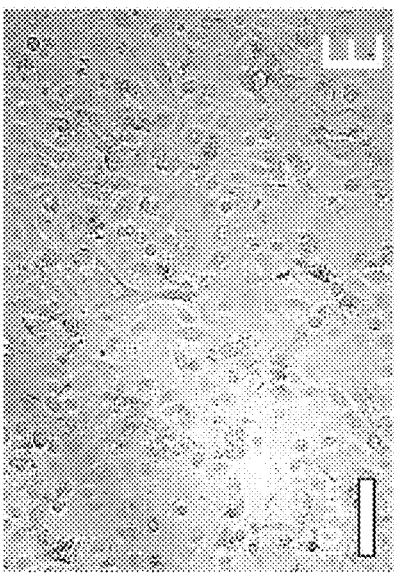
Figure 24D:
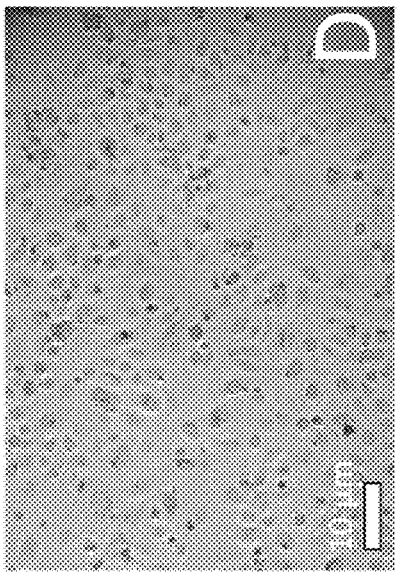

FIGS. 24A-24F. Microscopic analysis showing entry of VS_DsiRNA-Cy5 into primary human lung bronchial/tracheal epithermal cells (10×). FIGS. 24A-24C were captured under the Cy5 florescent filter, and FIGS. 24D-24F were captured in the same view of bright fields (20×). FIGS. 24A and 24D were taken in well B3 & B4 (as shown in FIG. 20), FIGS. 24B and 24E were taken in well B5 & B6 (as shown in FIG. 20), and FIGS. 24C and 24F were taken in well B1 & B2 (as shown in FIG. 20).

Figure 25C:
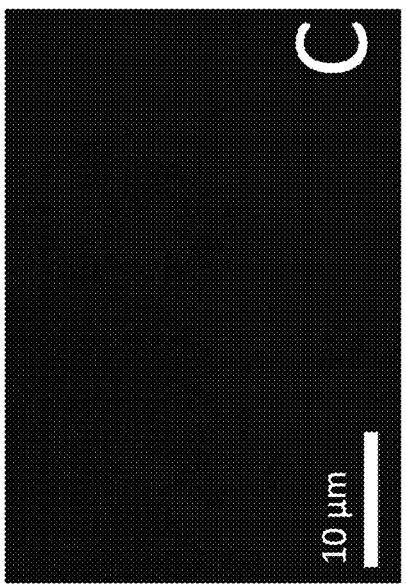
Figure 25B:
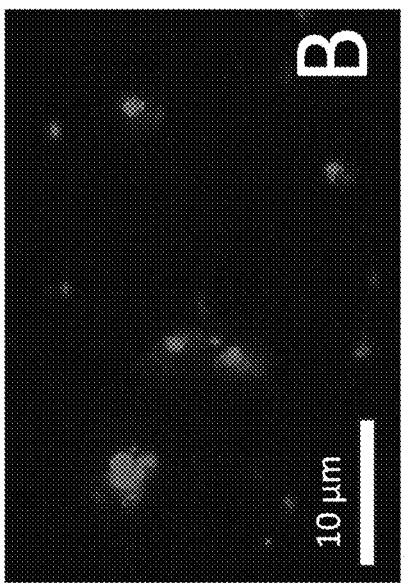
Figure 25A:
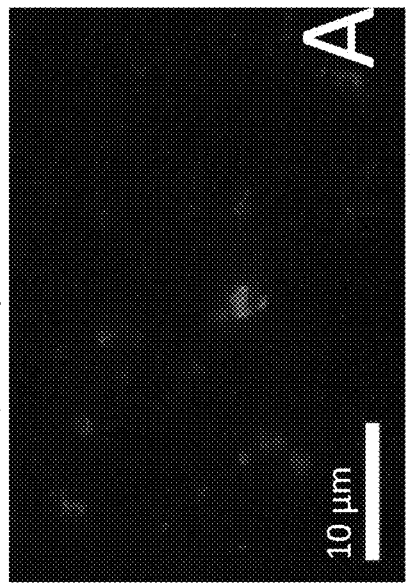
Figure 25F:
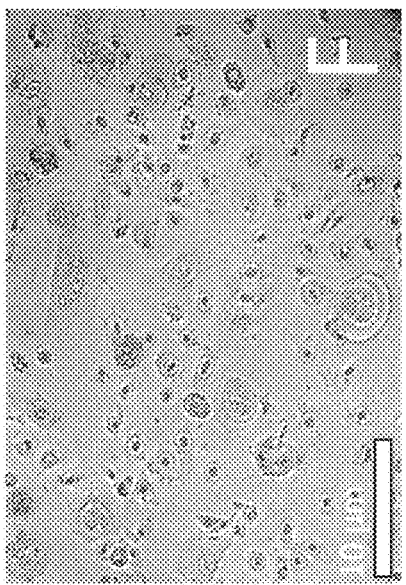
Figure 25E:
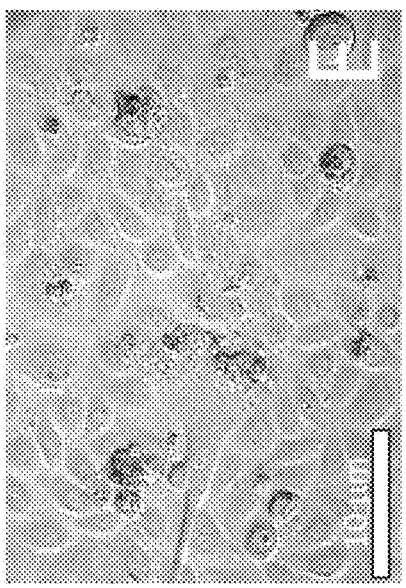
Figure 25D:
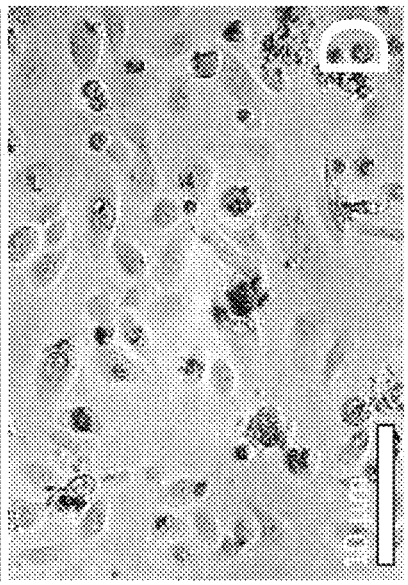

FIGS. 25A-25F. Microscopic analysis showing entry of VS_ASO_2-Cy3 into primary human lung bronchial/tracheal epithermal cells (20×). FIGS. 25A-25C were captured under the Cy3 florescent filter, and FIGS. 25D-25F were captured in the same view of bright fields (20×). FIGS. 25A and 25D were taken in well B3 & B4 (as shown in FIG. 20), FIGS. 25B and 25E were taken in well B5 & B6 (as shown in FIG. 20), and FIGS. 25C and 25F were taken in well B1 & B2 (as shown in FIG. 20).

FIGS. 26A-26F. Microscopic analysis showing entry of VS_ASO_2-Cy3 into primary human lung bronchial/tracheal epithermal cells (10×). FIGS. 26A-26C were captured under the Cy3 florescent filter, and FIGS. 26D-26F were captured in the same view of bright fields (20×). FIGS. 26A and 26D were taken in well B3 & B4 (as shown in FIG. 20), FIGS. 26B and 26E were taken in well B5 & B6 (as shown in FIG. 20), and FIGS. 26C and 26F were taken in well B1 & B2 (as shown in FIG. 20).

Figure 27:
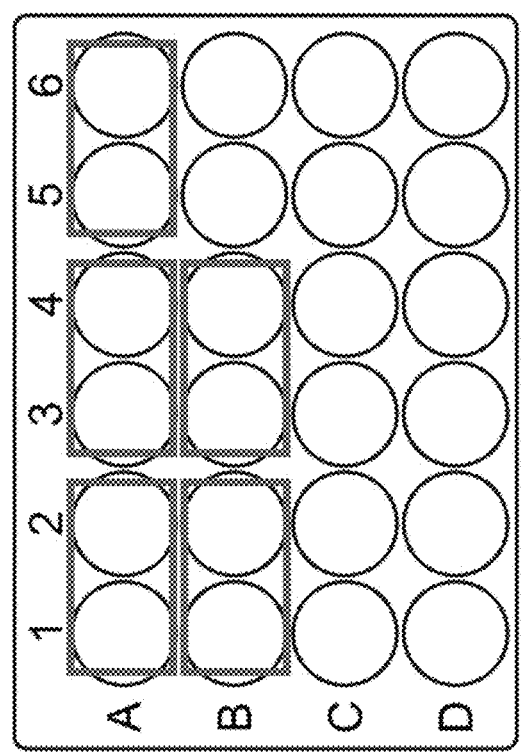

FIG. 27. Experimental design for detection of SARS-CoV-2 N-protein expressed on human primary bronchial/tracheal epithelial cells (HBTEC) by qRT-PCR. The human primary bronchial/tracheal epithelial cells (HBTEC) were cultured in a 24-well dish, and the cells were transfected with the genes encoding the viral protein (N-protein) of SARS-CoV-2. The inhibitory oligonucleotides were added into the cells for 24-48 hours before analysis with RT-PCR. The VS_ASO_1-FANA-FITC designed with FITC labeled shown in the Table 1, and VS_ASO_2-Cy3 with Cy3 modification shown in the Table 2; and VS_DsiRNA-Cy5 with Cy5 modification shown in Table 3. A1&A2: No treatment as control, A3&A4: Overexpression of COVID-19 N-protein, A5&A6: Overexpression of COVID-19 N-protein+/treated by VS_DsiRNA-Cy5 with lipofectamine, B1&B2: Overexpression of COVID-19 N-protein+/treated by VS_Dsi RNA-Cy3 with lipofectamine, B3&B4: Overexpression of COVID-19 N-protein+/treated by VS_ASO_1-FANA without any reagents.

Figure 28:
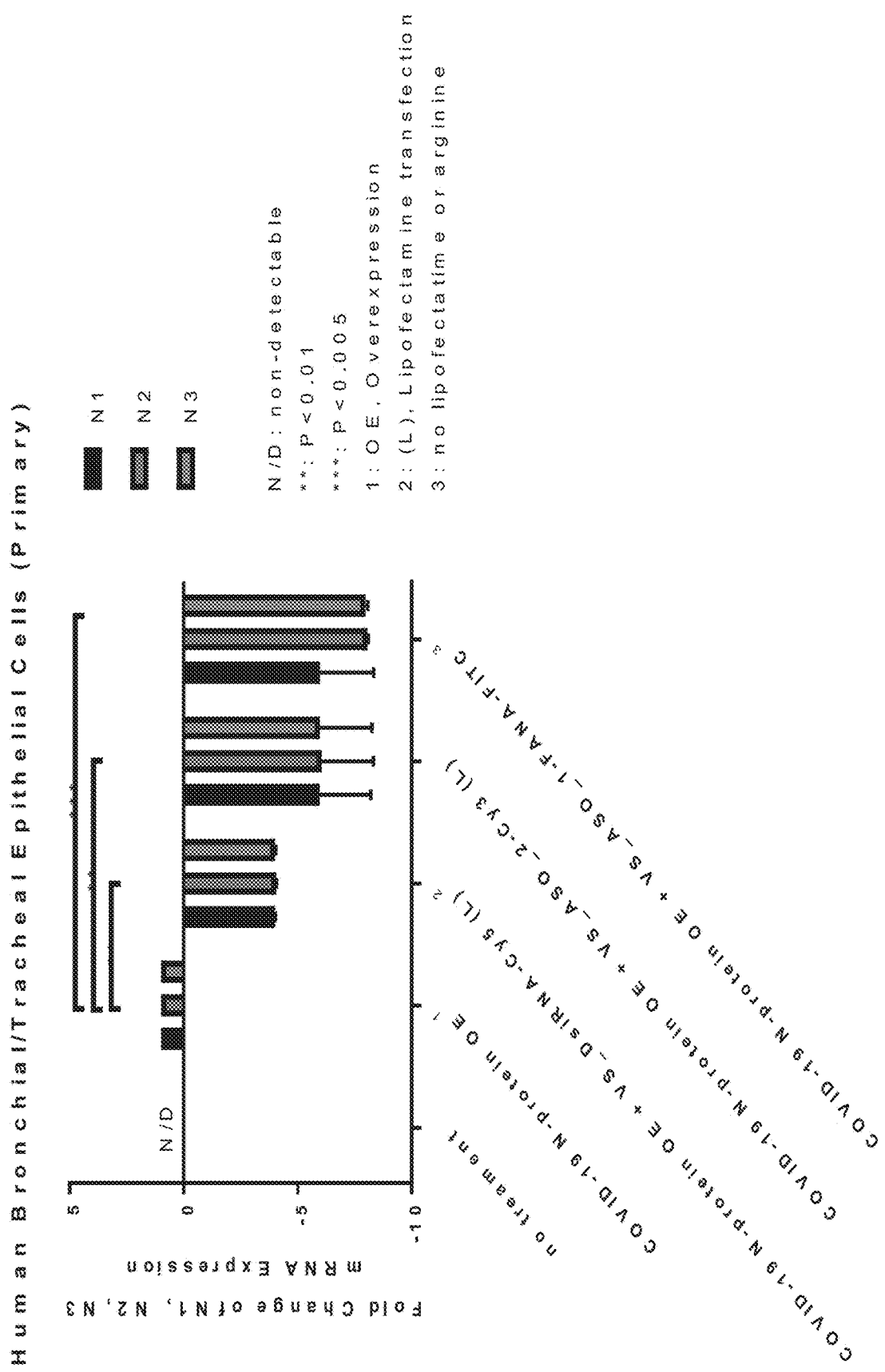

FIG. 28. Detection of SARS-CoV-2 N-protein expressed in the human primary bronchial/tracheal epithelial cells (HBTEC) by qRT-PCR after treatment with inhibitory oligonucleotides. Significant down-regulation was observed: about 4 fold in the group treated by VS_DsiRNA-Cy5 oligos ($p<0.005$); about 6 fold in the group treated by VS_ASO_2-cy3 oligo ($p<0.01$), and about 8 fold in the group treated by the VS_ASO_1-FANA-FITC oligo ($p<0.005$); when compared with the group with SARS-CoV-2 N-protein overexpression only. The cycle threshold of no-treatment is non-detectable, but in this case for calculation purposes, the number "40" was used as the cycle threshold for a base-line control.

Figure 29:
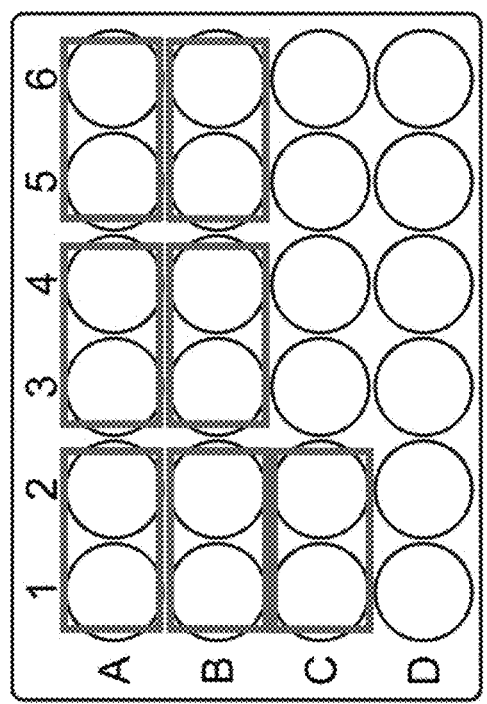

FIG. 29. Experimental design for detection of SARS-CoV-2 S-protein expressed in human primary bronchial/tracheal epithelial cells (HBTEC) by qRT-PCR. The human primary bronchial/tracheal epithelial cells (HBTEC) were cultured in a 24-well dish, and the cells were transfected with the genes encoding the viral protein (S-protein) of SARS-CoV-2. The siRNA or ASO were added into the cells for 24-48 hours before analysis with RT-PCR. The VS_ASO_1-FANA (oligo 3) designed is shown in the Table 1, VS_ASO_2 (oligo 3) is shown in the Table 2; and VS_DsiRNA (oligo 3) is shown in Table 3. A1&A2: No treatment, A3&A4: Overexpression of COVID-19 S-protein, A5&A6: Overexpression of COVID-19 S-protein+/treated by DsiRNA-Cy5 with lipofectamine, B1&B2: Overexpression of COVID-19 S-protein+/treated by VS_DsiRNA-Cy5 with Arginine (5 μl/well), B3&B4: Overexpression of COVID-19 S-protein+/treated by the VS_ASO_2-Cy3 with lipofectamine, B5&B6: Overexpression of COVID-19 S-protein+/treated by VS_ASO_2-Cy3 with Arginine (5 μl/well), C1&C2: Overexpression of COVID-19 S-protein+/treated by VS_ASO_1-FANA without any reagents.

Figure 30:
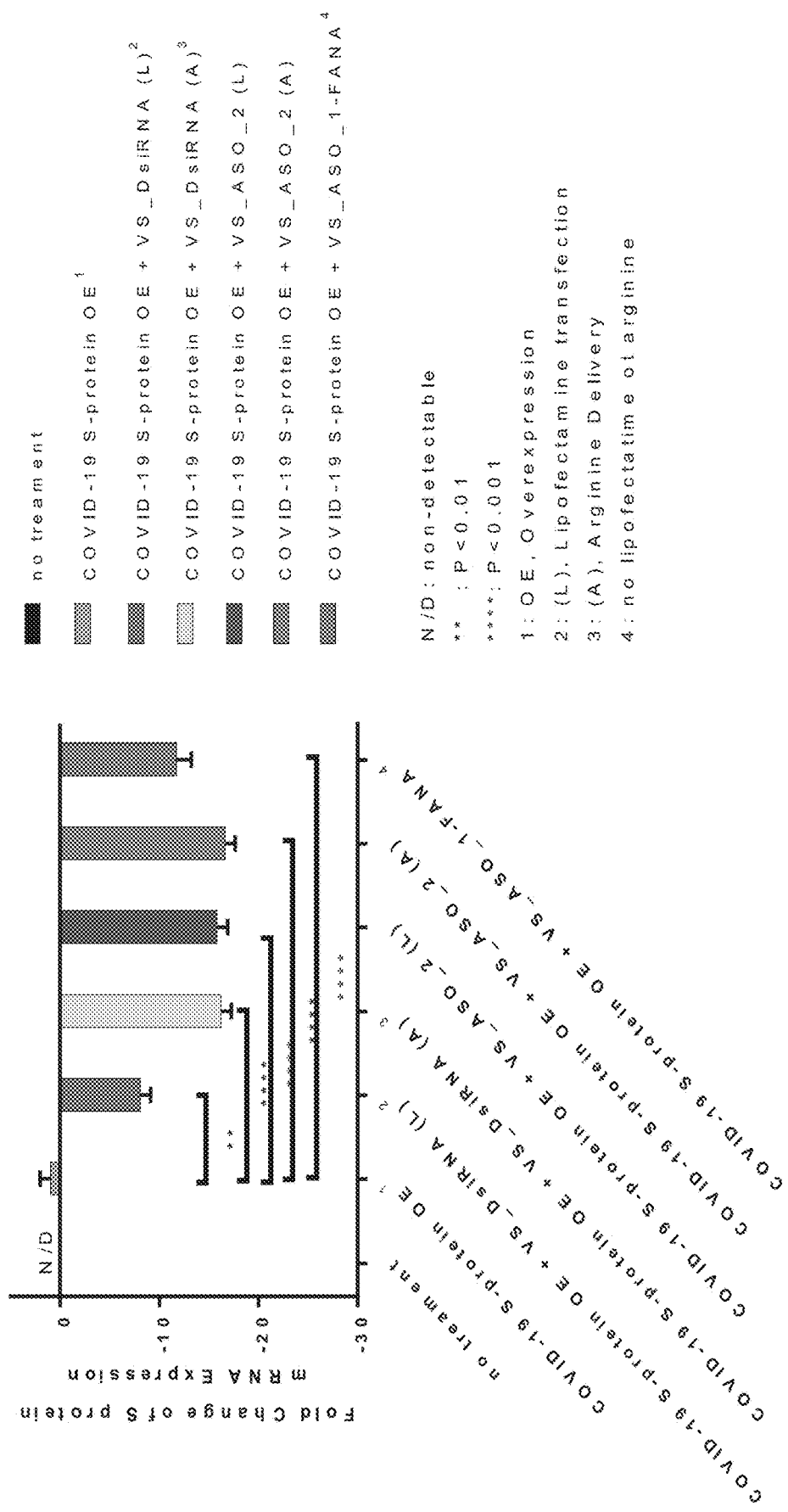

FIG. 30. Detection of SARS-CoV-2 S-protein expressed in the human bronchial/tracheal epithelial cells (HBTEC) by qRT-PCR after treatment with inhibitory oligonucleotides. Significant down-regulation was observed: about 8 fold in the group treated by VS-DsiRNA oligo (purple/L: $p<0.01$), but about 16.3 fold in presence of Poly-arginine only (yellow/$p<0.001$); about 15.8 fold in the group treated by VS_ASO_2 oligo (red/L: $p<0.001$), but about 16.6 fold in presence of Poly-arginine only (orange/A: $p<0.001$); about 11.7 fold in the group treated by the VS_ASO_1 oligo (green/$p<0.001$); when compared with the group with SARS-CoV-2 S-protein overexpression only (1). The cycle threshold of no-treatment is non-detectable, but in this case for calculation purposes, the number "40" was used as the cycle threshold for a base-line control.

Figure 31:
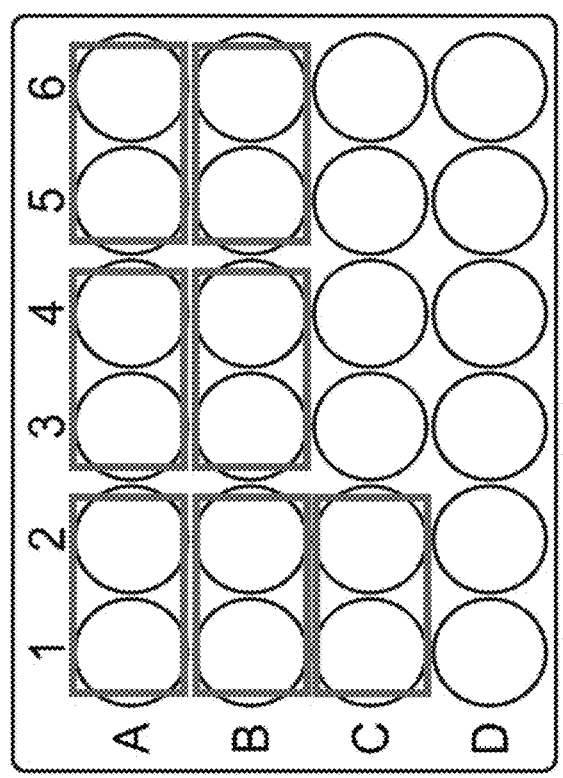
Figure 32:
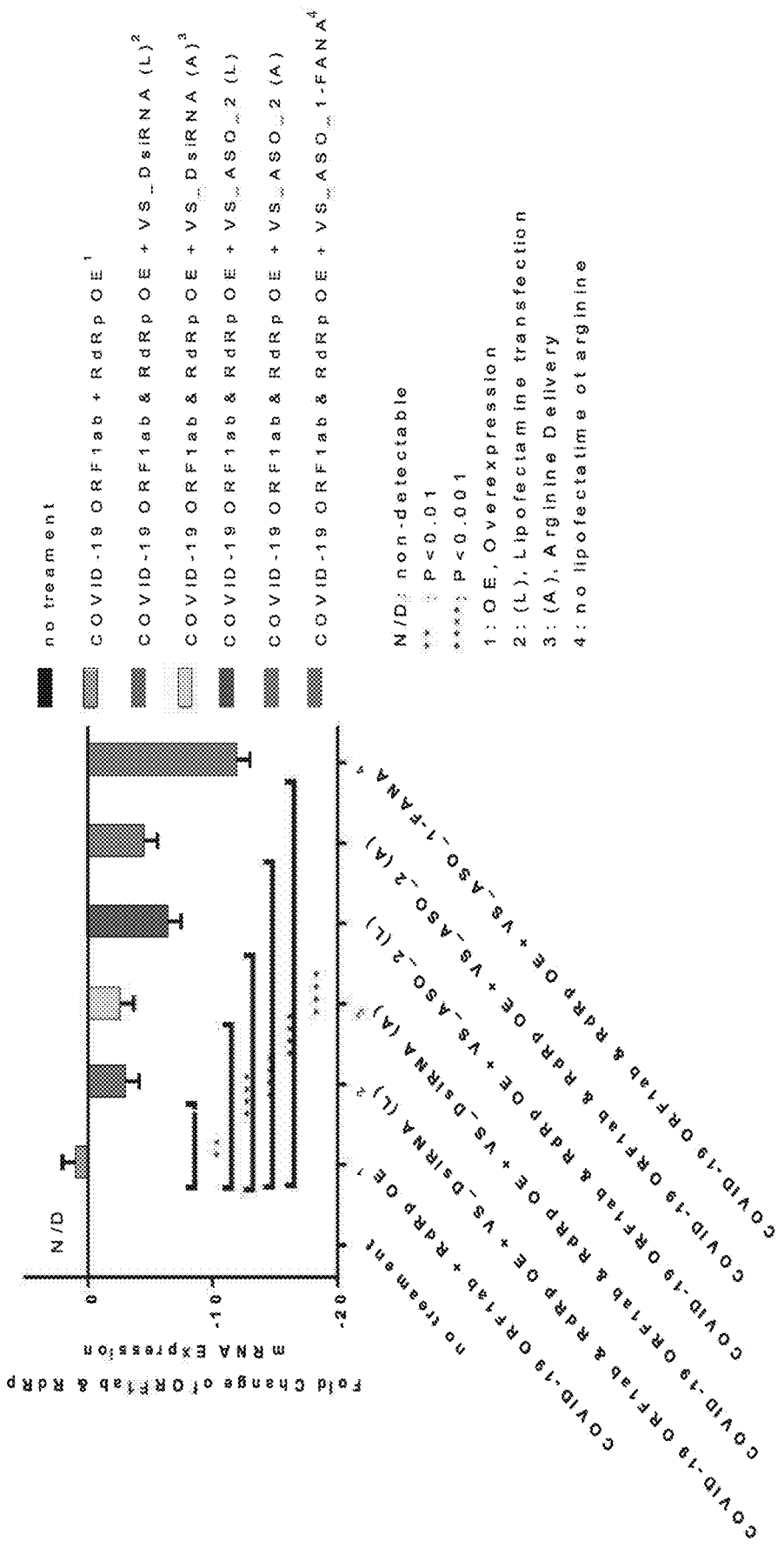
Figure 33:
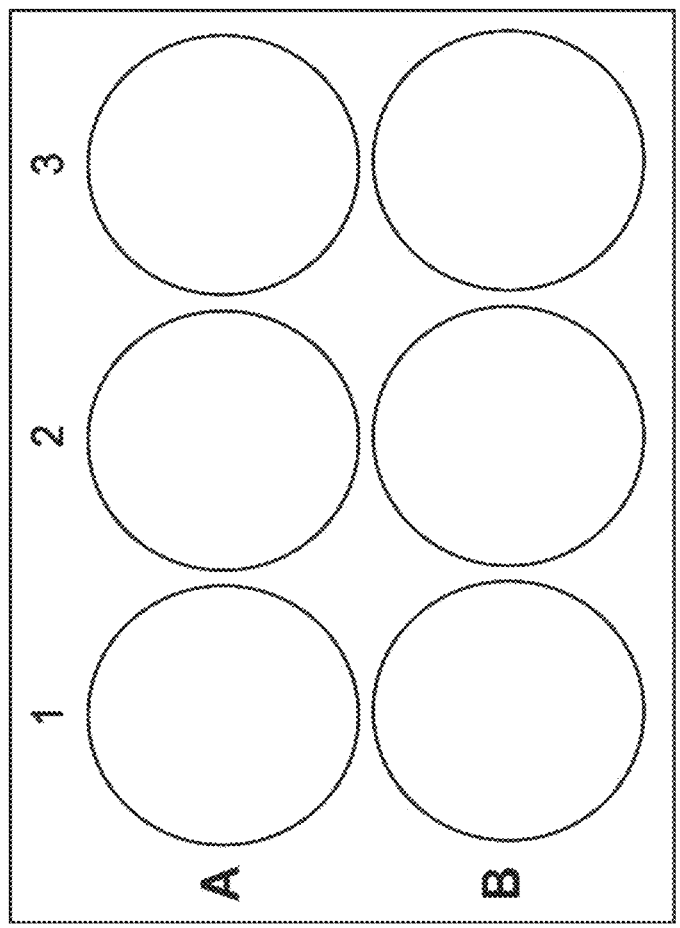
Figure 34:
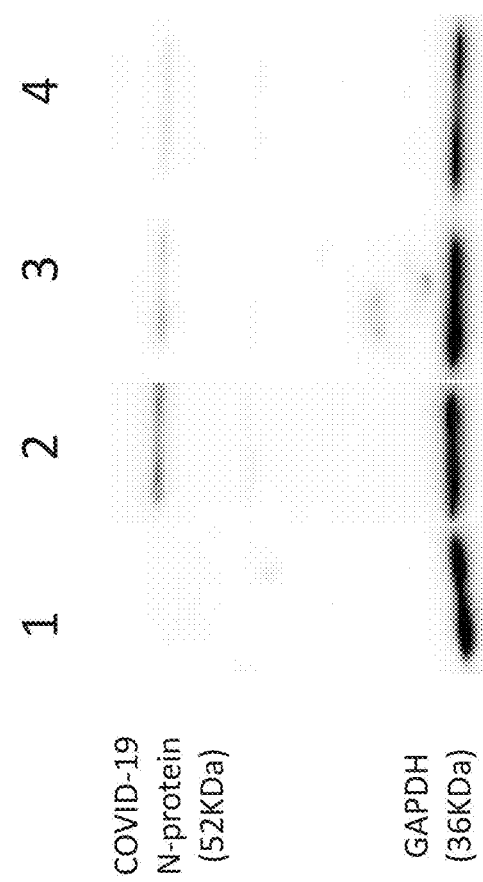
Figure 35:
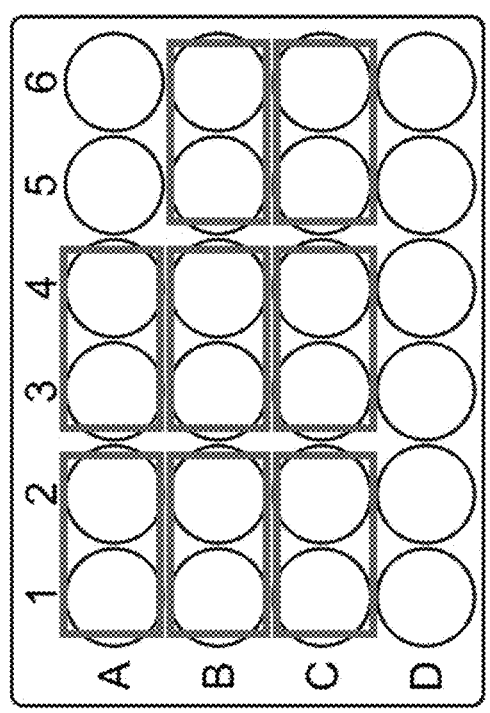
Figures 40D, 40E, 40F:
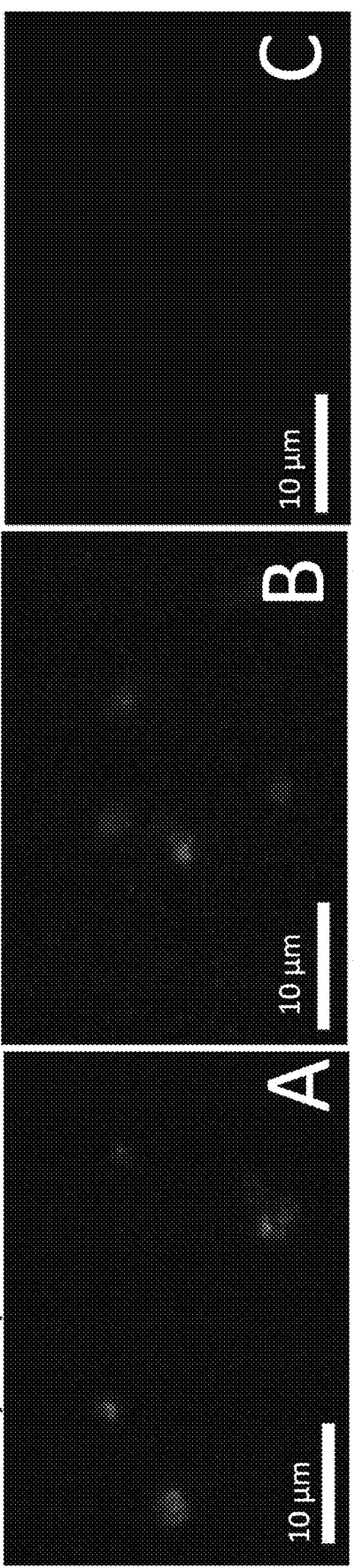

FIG. 31. Experimental design for detection of SARS-CoV-2 ORF1ab and RdRp expressed in the human primary bronchial/tracheal epithelial cells (HBTEC) detected by qRT-PCR after treatment. The human primary bronchial/tracheal epithelial cells (HBTEC) were cultured in the 24 well-dish, and the cells were transfected with the genes encoding the viral protein (ORF1ab and RdRp) of SARS-CoV-2. The inhibitory oligonucleotides were added into the cells for 24-48 hours before analysis with RT-PCR. VS_ASO_1-FANA (oligo 1, 2, 5 and 6) designed is shown in the Table 1, VS_ASO_2 (oligo 1, 2, 5 and 6) is shown in the Table 2; and the VS_DsiRNA (oligo 1, 2, 5 and 6) is shown in Table 4. A1&A2: No treatment as control, A3&A4: Overexpression of COVID-19 viral genes encoding both ORF1ab and RdRp, A5&A6: Overexpression of COVID-19 ORF1ab and RdRp+/treated by VS_DsiRNA (oligo 1, 2, 5 and 6) with lipofectamine, B1&B2: Overexpression of COVID-19 ORF1ab and RdRp+/treated by VS_DsiRNA (oligo 1, 2, 5 and 6) with Arginine (5l/well), B3&B4: Overexpression of COVID-19 ORF1ab and RdRp+/treated by VS_ASO_2 (oligo 1, 2, 5 and 6) with lipofectamine, B5&B6: Overexpression of COVID-19 ORF1ab and RdRp+/treated by VS_ASO_2 (oligo 1, 2, 5 and 6) with Arginine (5p l/well), C1&C2: Overexpression of COVID-19 ORF1ab and RdRp+/treated by VS_ASO_1-FANA (oligo 1, 2, 5 and 6) without any reagents.

FIG. 32. Detection of SARS-CoV-2 ORF1ab and RdRp expressed in the human primary bronchial/tracheal epithelial cells (HBTEC) detected by qRT-PCR after treatment with inhibitory oligonucleotides. Significant down-regulation was observed: about 3 fold in the group treated by VS_DsiRNA oligo (purple/L: $p<0.01$) and about 2.6 fold in the presence of poly-Arginine only (yellow/A: $p<0.001$); about 6.4 fold in the group treated by VS_ASO_2 oligo (red/L: $p<0.001$) and about 4.5 fold in the presence of poly-Arginine only (orange/A: $p<0.001$); and about 11.9 fold in the group treated by the VS_ASO_1-FANA oligo (green/$p<0.001$); when compared with the group with SARS-CoV-2 ORF1ab and RdRp overexpression only. The cycle threshold of no-treatment is non-detectable, but in this case for calculation purposes, the number "40" was used as the cycle threshold for a base-line control.

FIG. 33. Experimental design for detection of SARS-CoV-2 N-protein expressed in the human primary bronchial/tracheal epithelial cells (HBTEC) by Western Blot after treatment. The human primary bronchial/tracheal epithelial cells (HBTEC) were cultured in a 6-well dish, and the cells were transfected with the genes encoding the viral protein (N-protein) of SARS-CoV-2. The inhibitory oligonucleotides were added into the cells for 24-48 hours before analysis with Western Blot. The VS_ASO_2 (oligo 4 & 8) is shown in the Table 2; and VS_DsiRNA (oligo 4 & 8) is shown in Table 4. A1: No treatment as control, A2: Overexpression of COVID-19 N-protein, A3: Overexpression of COVID-19 N-protein+/treated by VS_DsiRNA (oligo 4 and 8) with lipofectamine, B1: Overexpression of COVID-19 N-protein+/treated by VS_ASO_2 (oligo 4 and 8) with lipofectamine.

FIG. 34. Detection of SARS-CoV-2 N-protein expressed in the human primary bronchial/tracheal epithelial cells (HBTEC) by Western Blot after treatment with inhibitory oligonucleotides. Lane 1: no treatment, Lane 2: SARS-CoV-2 N-protein overexpression (OE); Lane 3: SARS-CoV-2 N-protein OE+VS_DsiRNA (oligo 4 & 8); Lane 4: SARS-CoV-2 N-protein OE+VS_ASO_2 (oligo 4 & 8). 10 μg total cell lysis were added into each well and blotted with primary antibody (1 μg/mL anti-SARS-CoV-2-N-protein antibody (ProSci, 3857)) or anti-GAPDH antibody (Novus Biologicals, NBP2-27103) (1:1000 dilution). The secondary antibodies were goat-anti-rabbit HRP-conjugated Antibody (R&D System, HAF008) (1:1000) dilution and goat-anti-mouse IgG HRP-conjugated Antibody (R&D System, HAF007) (1:1000) dilution. The detection was done using horseradish peroxidase-labeled secondary antibodies and an enhanced chemiluminescence detection reagent.

FIG. 35. Experiments designed for investigating cell penetration and therapeutic effects of ASO(s) and DsiRNA on human primary nasal epithelial cells (HNEpC) transfected with viral protein of SARS-CoV-2 after treatment. The human primary nasal epithelial cells (HNEpC) were cultured in a 24-well dish, and the cells were transfected with the genes encoding the viral proteins of SARS-CoV-2. The VS_ASO_1-FANA-FITC, VS_DsiRNA-Cy5 and VS_ASO_2-Cy3 were delivered into the cells for 24-48 hours before analysis with fluorescent microscope. The VS_ASO_1-FANA-FITC was FITC labeled (see Table 1), and VS_ASO_2-Cy3 was Cy3 labeled (See Table 2); and VS_DsiRNA-Cy5 was Cy5 labeled (see Table 3). A1&A2: No treatment as control, A3&A4: Overexpression of COVID-19 N-protein+/treated by VS_ASO_1-FANA without lipofectamine or arginine, B1&B2: No treatment as control, B3&B4: Overexpression of COVID-19 N-protein+/treated by VS_DsiRNA-Cy5 with lipofectamine, B5&B6: Overexpression of COVID-19 N-protein+/treated by VS_DsiRNA-Cy5 with poly-arginine (5 μl/well), C1&C2: No treatment as control, C3&C4: Overexpression of COVID-19 N-protein+/treated by VS_ASO_2-Cy3 with lipofectamine, C5&C6: Overexpression of COVID-19 N-protein+/treated by VS_ASO_2-Cy3 with poly-arginine (5 μl/well).

FIGS. 36A-36D. Microscopic analysis of Human Primary Nasal Epithelial Cells at 20×. This analysis showed that VS_ASO_1-FANA-FITC can enter epithelial cells (20×). FIGS. 36A and 36B were captured under FITC florescent filter, and FIGS. 36C and 36D were captured in the same view of bright fields (20×). FIGS. 36A and 36C were taken in well A3 & A4 (as shown in FIG. 35), FIGS. 36B and 36D were taken in well A1 & A2 (as shown in FIG. 35).

FIGS. 37A-37D. Microscopic analysis of Human Primary Nasal Epithelial Cells at 10×. This analysis showed that VS_ASO_1-FANA-FITC can enter epithelial cells (10×). FIGS. 37A and 37B were captured under FITC florescent filter, and FIGS. 37C and 37D were captured in the same view of bright fields (20×). FIGS. 37A and 37C were taken in well A3 & A4 (as shown in FIG. 35), FIGS. 37B and 37D were taken in well A1 & A2 (as shown in FIG. 35).

FIGS. 38A-38F. Microscopic analysis of Human Primary Nasal Epithelial Cells at 20×. This analysis showed that VS_DsiRNA-Cy5 can enter epithelial cells (20×). FIGS. 38A-38C were captured under the Cy5 florescent filter, and FIGS. 38D-38F were captured in the same view of bright fields (20×). FIGS. 38A and 38D were taken in well B3 & B4 (as shown in FIG. 35), FIGS. 38B and 38E were taken in well B5 & B6 (as shown in FIG. 35), FIGS. 38C and 38F were taken in well B1 & B2 (as shown in FIG. 35).

FIGS. 39A-39F. Microscopic analysis of Human Primary Nasal Epithelial Cells at 10×. This analysis showed that VS_DsiRNA-Cy5 can enter epithelial cells (10×). FIGS. 39A-39C were captured under the Cy5 florescent filter, and FIGS. 39D-39F were captured in the same view of bright fields (20×). FIGS. 39A and 39D were taken in well B3 & B4 (as shown in FIG. 35), FIGS. 39B and 39E were taken in well B5 & B6 (as shown in FIG. 35), FIGS. 39C and 39F were taken in well B1 & B2 (as shown in FIG. 35).

FIGS. 40A-40F. Microscopic analysis of Human Primary Nasal Epithelial Cells at 20×. This analysis showed that VS_ASO_2-Cy3 can enter epithelial cells (20×). FIGS.

40A-40C were captured under the Cy3 florescent filter, and FIGS. 40D-40F were captured in the same view of bright fields (20×). FIGS. 40A and 40D were taken in well B3 & B4 (as shown in FIG. 35), FIGS. 40B and 40E were taken in well B5 & B6 (as shown in FIG. 35), FIGS. 40C and 40F were taken in well B1 & B2 (as shown in FIG. 35).

Figure 41C:
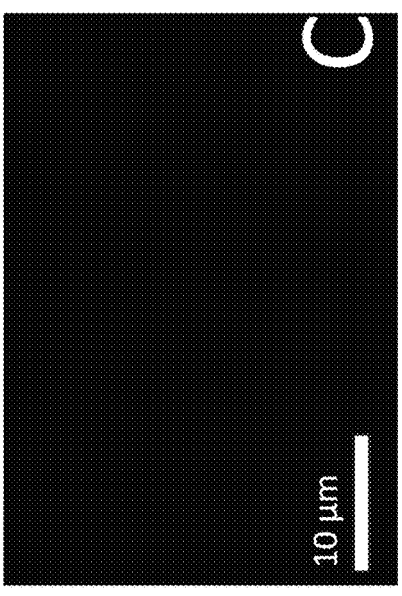
Figure 41B:
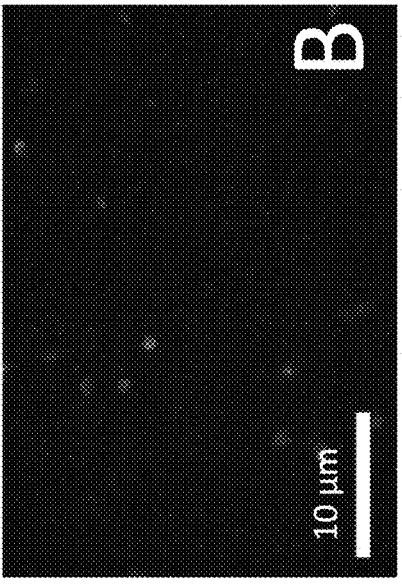
Figure 41A:
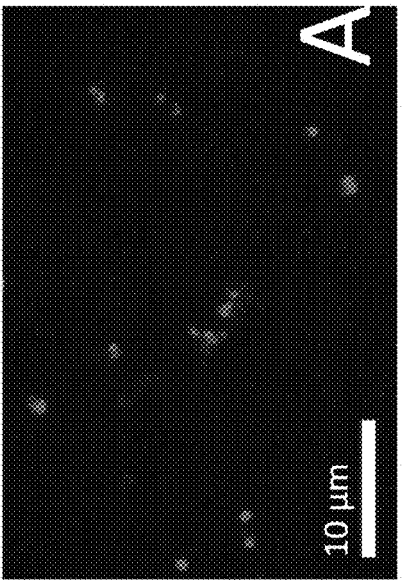
Figure 41F:
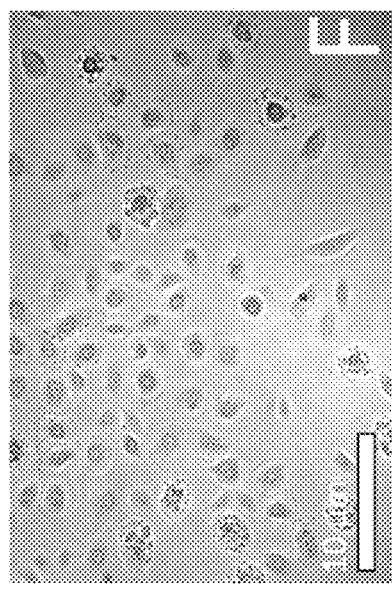
Figure 41E:
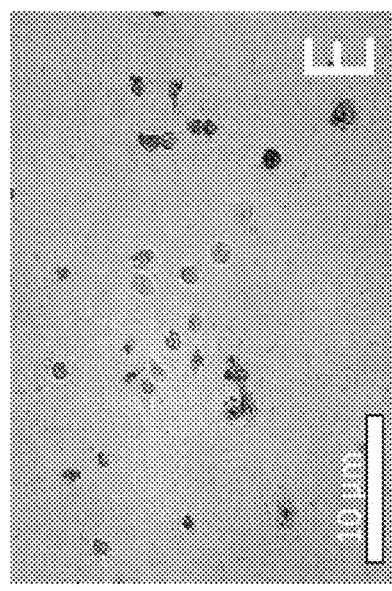
Figure 41D:
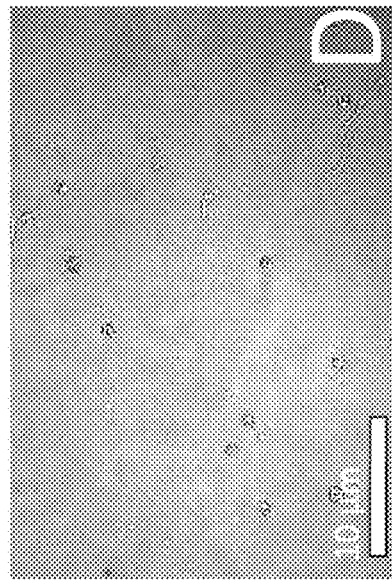

FIGS. 41A-41F. Microscopic analysis of Human Primary Nasal Epithelial Cells at 10×. This analysis showed that VS_ASO_2-Cy3 can enter epithelial cells (10×). FIGS. 41A-41C were captured under the Cy3 florescent filter, and FIGS. 41D-41F were captured in the same view of bright fields (10×). FIGS. 41A and 41D were taken in well B3 & B4 (as hown in FIG. 35), FIGS. 41B and 41E were taken in well B5 & B6 (as shown in FIG. 35), FIGS. 41C and 41F were taken in well B1 & B2 (as shown in FIG. 35).

Figure 42:
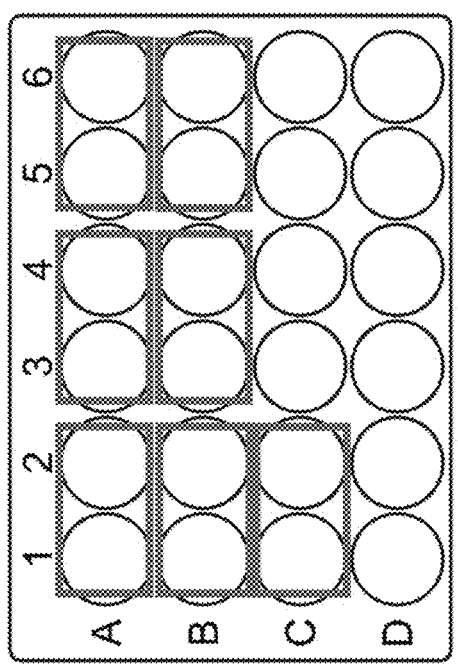

FIG. 42. Experimental design for detection of SARS-CoV-2 N-protein expressed on human primary nasal epithelial cells (HNEpC) by qRT-PCR. The human primary nasal epithelial cells (HNEpC) were cultured in a 24-well dish, and the cells were transfected with the genes encoding the viral protein (N-protein) of SARS-CoV-2. The inhibitory oligonucleotides were added into the cells for 24-48 hours before analysis with RT-PCR. VS_ASO_1-FANA-FITC was labeled with FITC as shown in the Table 1, and VS_ASO_2-Cy3 was labeled with Cy3 as shown in Table 2; and VS_DsiRNA-Cy5 was labeled with Cy5 as shown in Table 3. A1&A2: No treatment, A3&A4: Overexpression of COVID-19 N-protein, A5&A6: Overexpression of COVID-19 N-protein+/treated by VS_DsiRNA-Cy5 with lipofectamine, B1&B2: Overexpression of COVID-19 N-protein+/treated by VS_DsiRNA-Cy5 with Arginine (5 µl/well), B3&B4: Overexpression of COVID-19 N-protein+/treated by VS_ASO_2-Cy3 with lipofectamine, B5&B6: Overexpression of COVID-19 N-protein+/treated by VS_ASO_2-Cy3 with Arginine (5 µl/well), C1&C2: Overexpression of COVID-19 N-protein+/treated by VS_ASO_1-FANA-FITC without any reagents.

Figure 43:
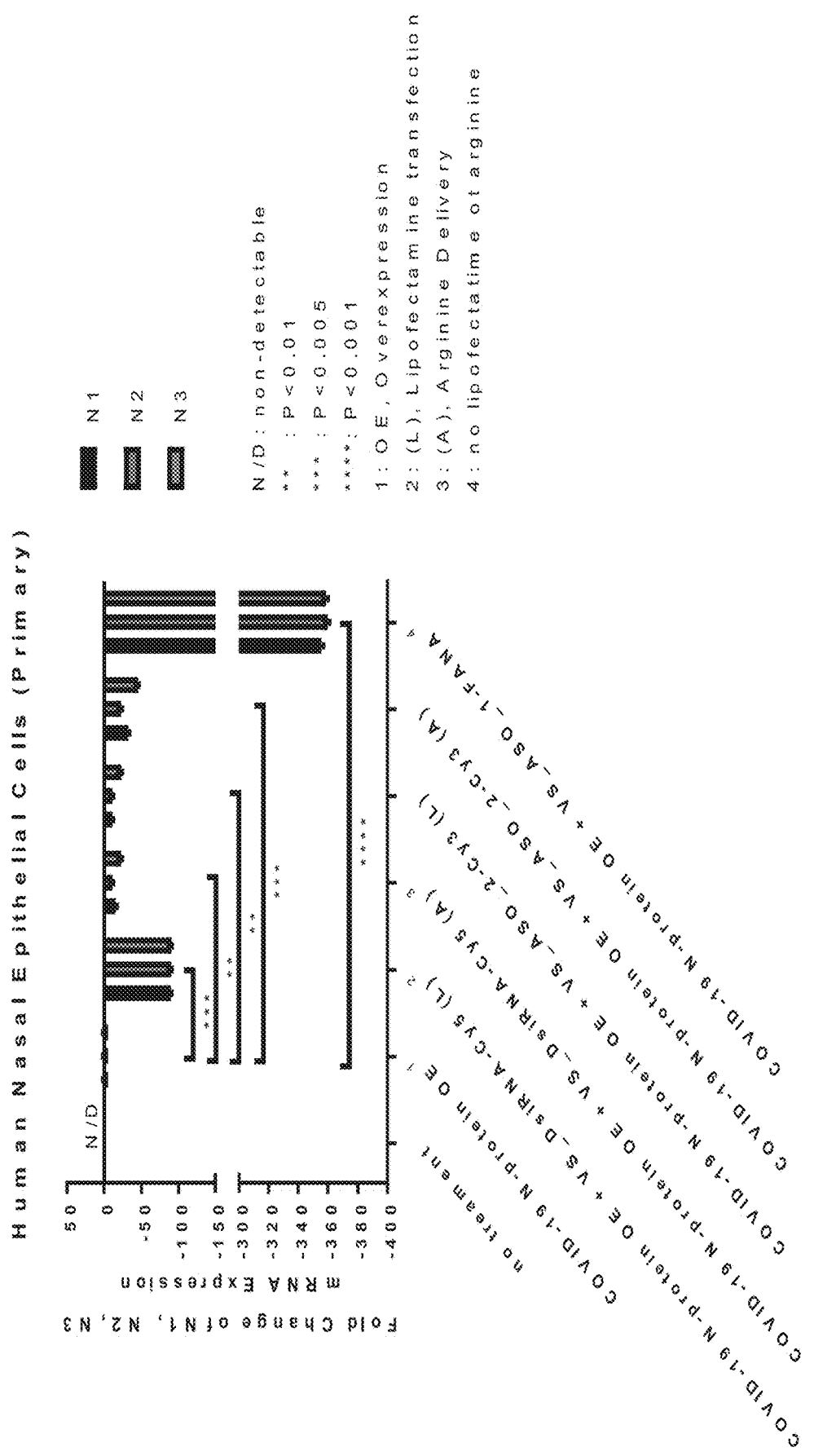

FIG. 43. Detection of SARS-CoV-2 N-protein expressed in the human primary nasal epithelial cells (HNEpC) by qRT-PCR after treatment with siRNA or ASO. Significant down-regulation was observed: about 90 fold in the group treated by VS_DsiRNA-Cy5 oligo (2: p<0.01); about 15 fold in the group treated by VS_ASO_2-Cy3 oligo (p<0.01), and about 350 fold of down-regulation in the group treated by the VS_ASO_1-FANA-FITC oligo (3: p<0.001); when compared with the group with COIVD-19 N-protein overexpression only. The cycle threshold of no-treatment is non-detectable, but in this case for calculation purposes, the number "40" was used as the cycle threshold for a base-line control.

Figure 44:
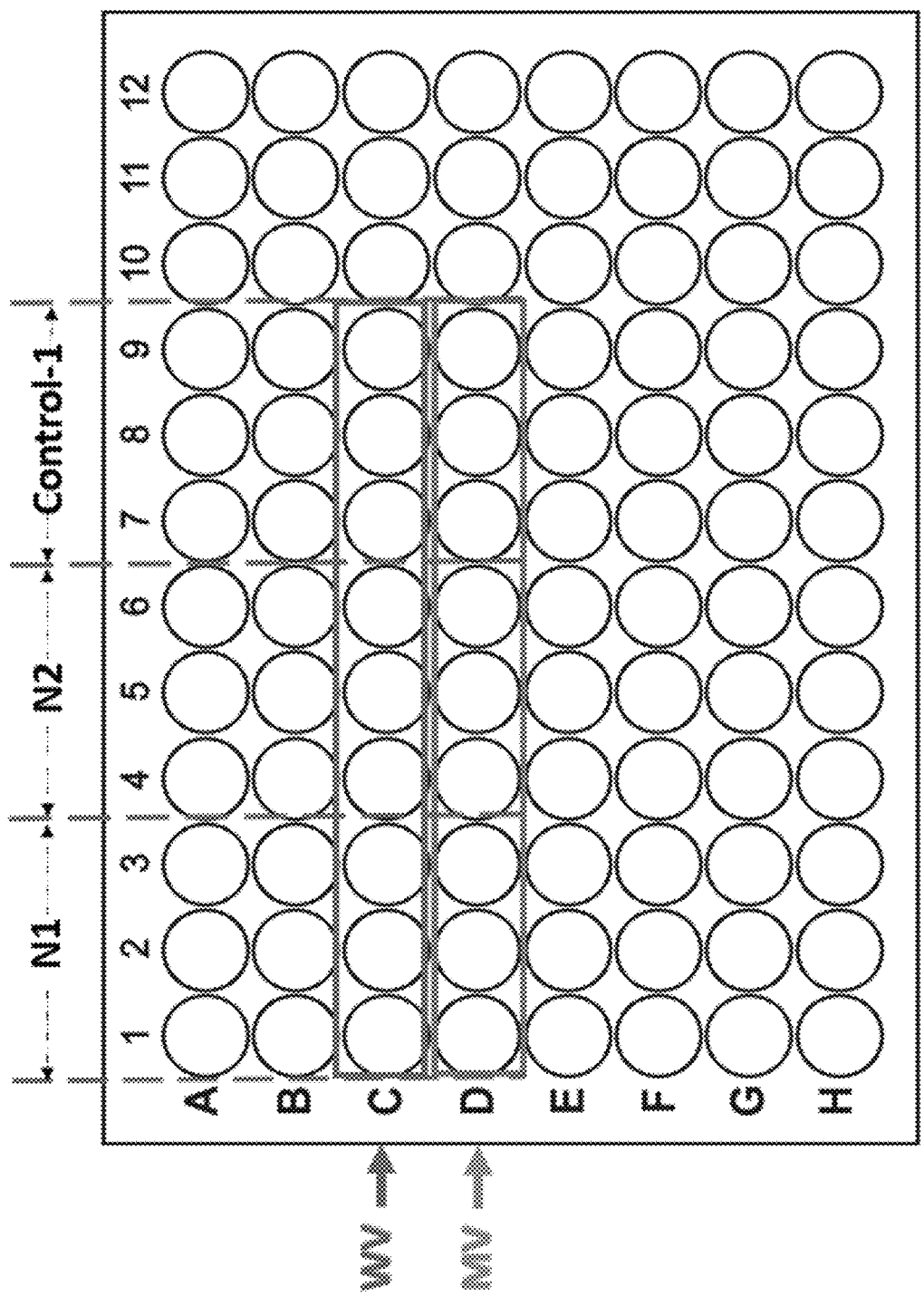

FIG. 44. Experimental design for inhibiting viral infections using inhibitory nucleotides. WV=Wild-type of pseud-COVID-19 virus, 5 µl (titer: $10^5$ TU/ml) of the virus added into each well (C1 to C9). MV=Mutant form of pseud-COVID-19 virus, 5 µl (titer: 105 TU/ml) of the virus added into each well (D1 to D9). N 1=VS_ASO_3 oligo (targeting on S-protein of COVID-19), N 2=VS_siRNA/RNAi_3 oligo (targeting on S-protein of COVID-19, Control-1=Scramble nucleotide oligo (SN) only.

FIGS. 45A-45F. Experimental data of inhibitions of wild-type viral infections by inhibitory nucleotides. FIG. 45A Brightfield image of VS_ASO_3-treated cells. FIG. 45B Brightfield image of VS_RNAi_3-treated cells. FIG. 45C Brightfield image of scramble-treated cells. FIG. 45D Fluorescence image of VS_ASO_3-treated cells. FIG. 45E Fluorescence image of VS_RNAi_3-treated cells. FIG. 45F Fluorescence image of scramble-treated cells. There were no significant GFP expressions found in those cells treated by VS_ASO_3 and VS_RNAi_3 oligos, detected under the confocal microscope; but the inventors were able to see the GFP expressions in the control group of the cells treated with the scramble nucleotide only. This data thus indicated that the VS_ASO_3 and VS_RNAi_3 have inhibited the wild-type of the viruses coupled with eGFP (WV) inside the cells; but not in the group treated with the scramble nucleotide.

Figure 46A:
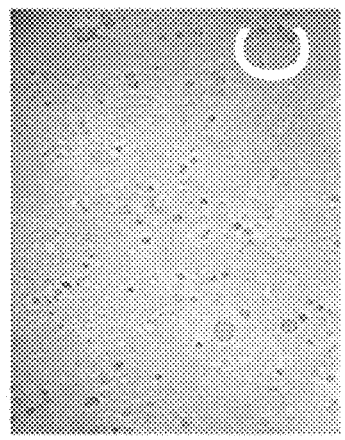
Figure 46B:
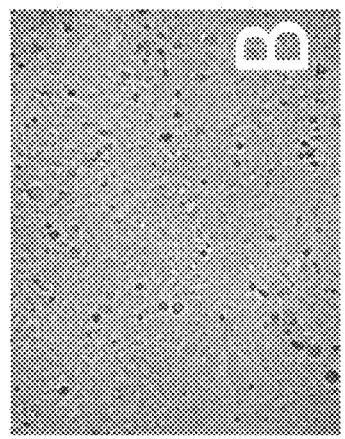
Figure 46C:
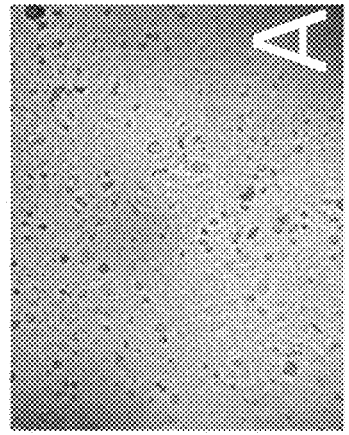
Figure 46D:
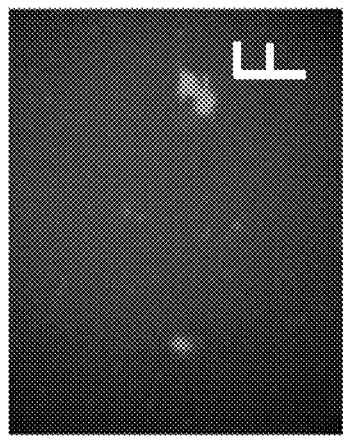
Figure 46E:
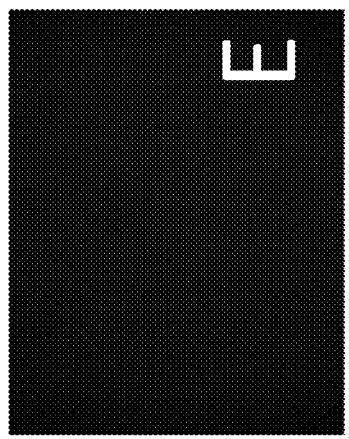
Figure 46F:
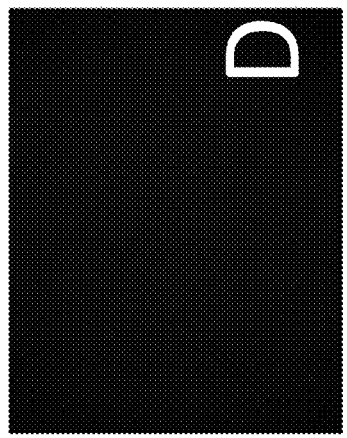

FIGS. 46A-46F. Experimental data of inhibitions of mutant viral infections by inhibitory nucleotides. FIG. 46A Brightfield image of VS_ASO_3-treated cells. FIG. 46B Brightfield image of VS_RNAi_3-treated cells. FIG. 46C Brightfield image of scramble-treated cells. FIG. 46D Fluorescence image of VS_ASO_3-treated cells. FIG. 46E Fluorescence image of VS_RNAi_3-treated cells. FIG. 46F Fluorescence image of scramble-treated cells. There was no significant GFP expressions found in those cells treated by VS_ASO_3 and VS_RNAi_3, detected under the confocal microscope; but the inventors were able to see the GFP expressions in the control group of the cells treated with the scramble nucleotide only. This data thus indicated that the VS_ASO_3 and VS_RNAi_3 have also inhibited the mutant viruses coupled with eGFP (MV) inside the cells; but not in the group treated with the scramble nucleotide.

FIG. 47. Analysis of the amino acid sequence of SARS-CoV-2 Spike protein (S-protein) (GenBank ID: QHD43416.1, SEQ ID NO: 61). The region of the sequence highlighted in red represents the predicted sequences of ACE2 binding sequences/motifs (aka. the Ligand binding Domain).

FIGS. 48A-48B. Analysis of the amino acid sequence of the BD motifs. FIG. 48A 3D interaction between the SARS-CoV-2 Spike protein and human ACE2. FIG. 48B Analysis of the amino acids of the RBD motifs in 3D structure between the SARS-CoV-2 Spike protein (B: K417 to Y505) and human ACE2 (B: Q24 to R393) was used to order to locate which regions of the sequences contribute to the protein-protein interaction, and to design peptides that mimic the RBD sequences (mimics act like a human ACE 2 and prevent or block the binding activities for the SARS-CoV-2 on the real ACE2 in the cells).

Figure 49:
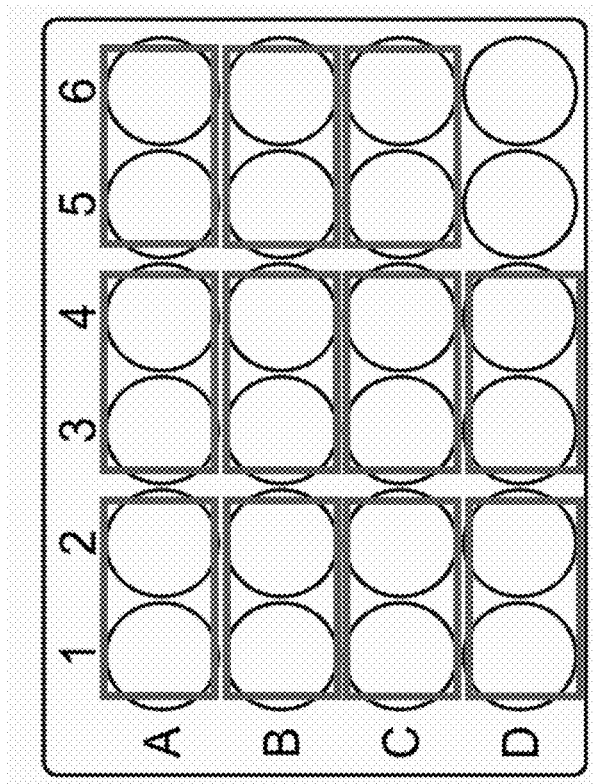

FIG. 49. Experimental design. A1&A2: No treatment as control, A3&A4: peptide 5-FITC, A5&A6: peptide 5-FITC+/treated by the peptide 1 (low dosage), B1&B2: peptide 5-FITC+/treated by the peptide 1 (high dosage), B3&B4: peptide 5-FITC+/treated by the peptide 2 (low dosage), B5&B6: peptide 5-FITC+/treated by the peptide 2 (high dosage), 1&C2: peptide 5-FITC+/treated by the peptide 3 (low dosage), C3&C4: peptide 5-FITC+/treated by the peptide 3 (high dosage), C5&C6: peptide 5-FITC+/treated by the peptide 4 (low dosage), D1&D2: peptide 5-FITC+/treated by the peptide 4 (high dosage), D3&D4: peptide 5-FITC+/treated by the peptide 1 (high dosage)+peptide 2 (high dosage)+peptide 3 (high dosage)+peptide 4 (high dosage), The dosage-1=1 µg per $10^5$ cells; and the dosage-2=10 µg per $10^5$ cells.

FIGS. 50A-50H. Cells infected with wild-type SARS-COV-2 virus (WV) in the presence of inhibitory peptides. FIG. 50A Brightfield image of cells treated with Peptide 1 (P1). FIG. 50B Brightfield image of cells treated with Peptide 2 (P2). FIG. 50C Brightfield image of cells treated with Peptide 3 (P3). FIG. 50D Brightfield image of cells treated with normal human serum (NHS). FIG. 50E Fluorescence (GFP) image cells treated with Peptide 1 (P1). FIG. 50F Fluorescence (GFP) image of cells treated with Peptide 2 (P2). FIG. 50G Fluorescence (GFP) image of cells treated with Peptide 3 (P3). FIG. 50H Fluorescence (GFP) image of cells treated with normal human serum (NHS).

FIGS. 51A-51H. Cells infected with mutant SARS-COV-2 virus (MV) in the presence of inhibitory peptides. FIG. 51A Brightfield image of cells treated with Peptide 1 (P1). FIG. 51B Brightfield image of cells treated with Peptide 2 (P2). FIG. 51C Brightfield image of cells treated with Peptide 3 (P3). FIG. 51D Brightfield image of cells treated with normal human serum (NHS). FIG. 51E Fluorescence (GFP) image cells treated with Peptide 1 (P1). FIG. 51F Fluorescence (GFP) image of cells treated with Peptide 2 (P2). FIG. 51G Fluorescence (GFP) image of cells treated with Peptide 3 (P3). FIG. 51H Fluorescence (GFP) image of cells treated with normal human serum (NHS).

FIG. 52A-52H. Microscope analysis of human primary small airway epithelial cells treated with inhibitory peptides (VS-peptides). FIGS. 52A, and 52E were captured under the FITC florescent filter, FIGS. 52B and 52E were captured in brightfield (20×). FIG. 52C shows the merge of FIGS. 52A and 52B. FIG. 52G is a merge photo of FIGS. 52E and 52F. The white dots indicate the box that was enlarged as shown in FIG. 52D. The yellow dots indicate the box that was enlarged as shown in FIG. 52H. White arrows suggested peptide 5-FITC internalized into cells cytoplasm and nucleus, while the yellow arrows suggested the VS-peptides combination can block the peptide 5-FITC from internalization, staying outside of cells.

Figure 53:
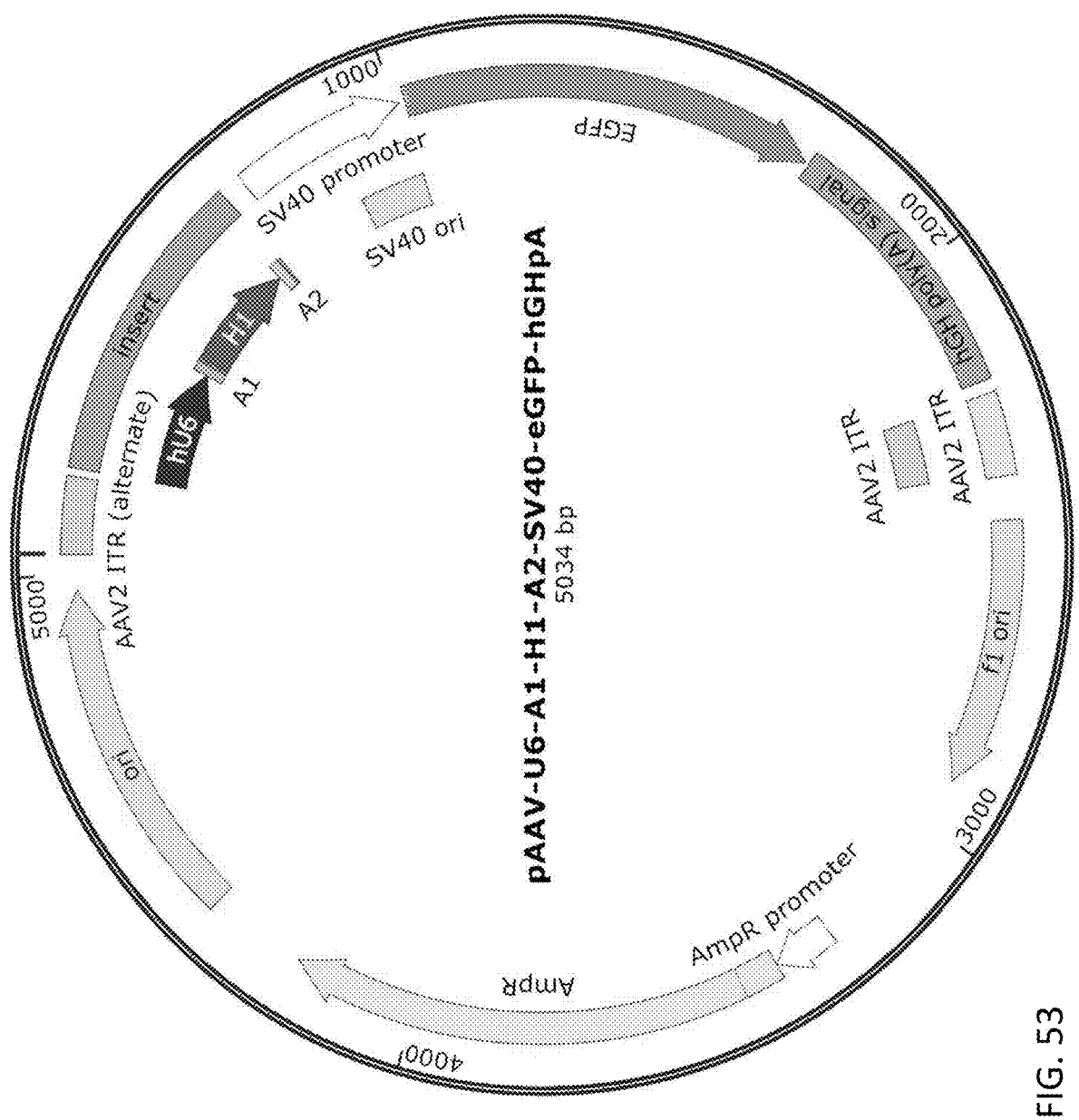

FIG. 53. Gene therapy vector AAV-U6-A1-H1-A2-SV40-eGFP. This AAV vector expresses two transgenes (namely ASO1 (A1) and ASO2 (A2)) simultaneously in one cell. U6=The 1st promoter that controls the expression of A1 gene in the mammalian cells, H1=The 2nd promoter that controls the expression of A2 gene in the mammalian cells, SV=The 3rd promoter that controls the expression of GFP gene in the mammalian cells. Full sequence of AAV-U6-A1-H1-A2-SV40-GFP is shown by SEQ ID NO: 46.

Figure 54:
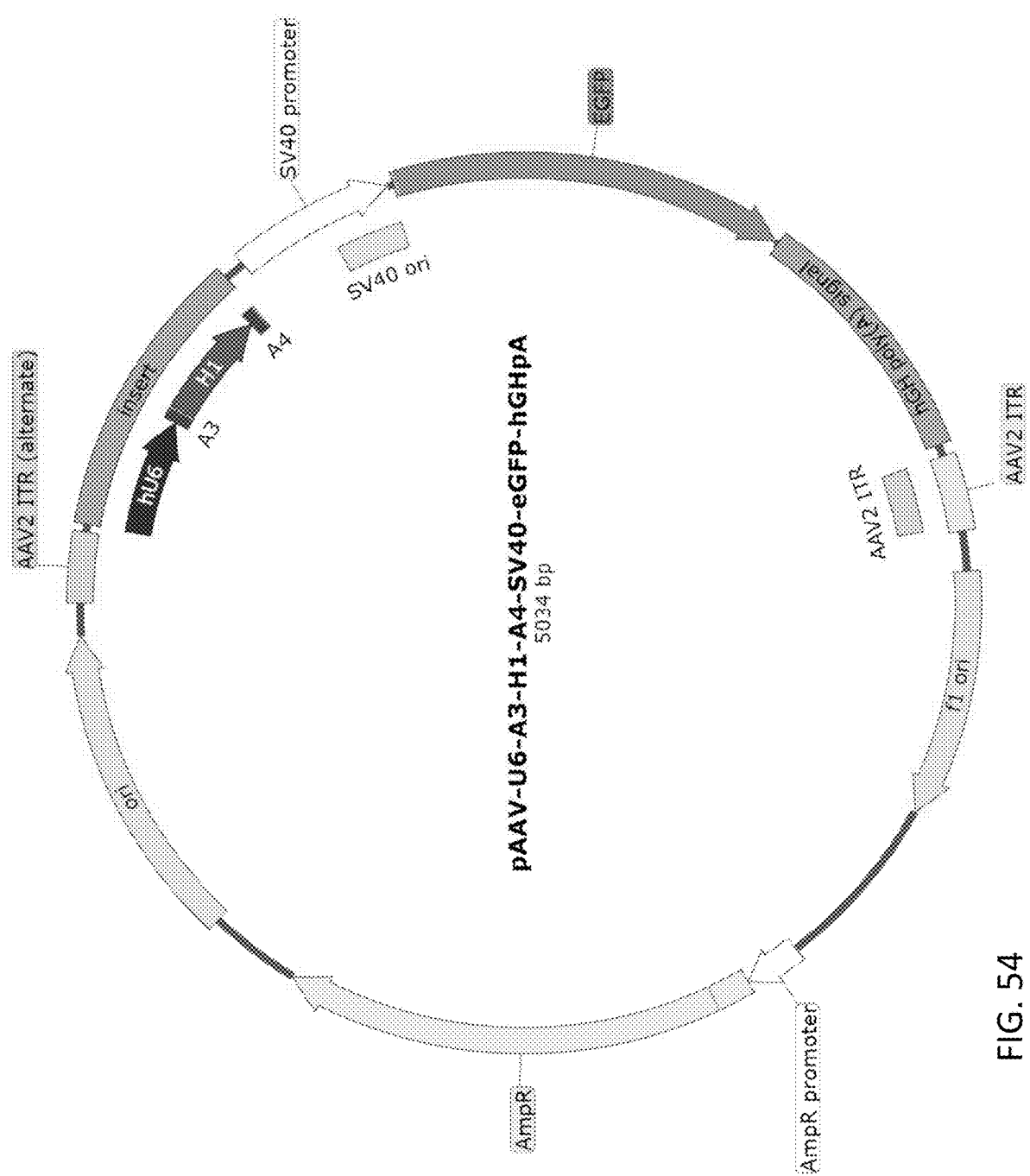

FIG. 54. Gene therapy vector AAV-U6-A3-H1-A4-SV40-eGFP. This AAV vector expresses two transgenes (namely ASO3 (A3) and ASO4 (A4)) simultaneously in one cell. U6=The 1st promoter that controls the expression of A3 gene in the mammalian cells, H1=The 2nd promoter that controls the expression of A4 gene in the mammalian cells SV40=The 3rd promoter that controls the expression of GFP gene in the mammalian cells. Full sequence of AAV-U6-A1-H1-A2-SV40-eGFP is shown by SEQ ID NO: 47.

Figure 55:
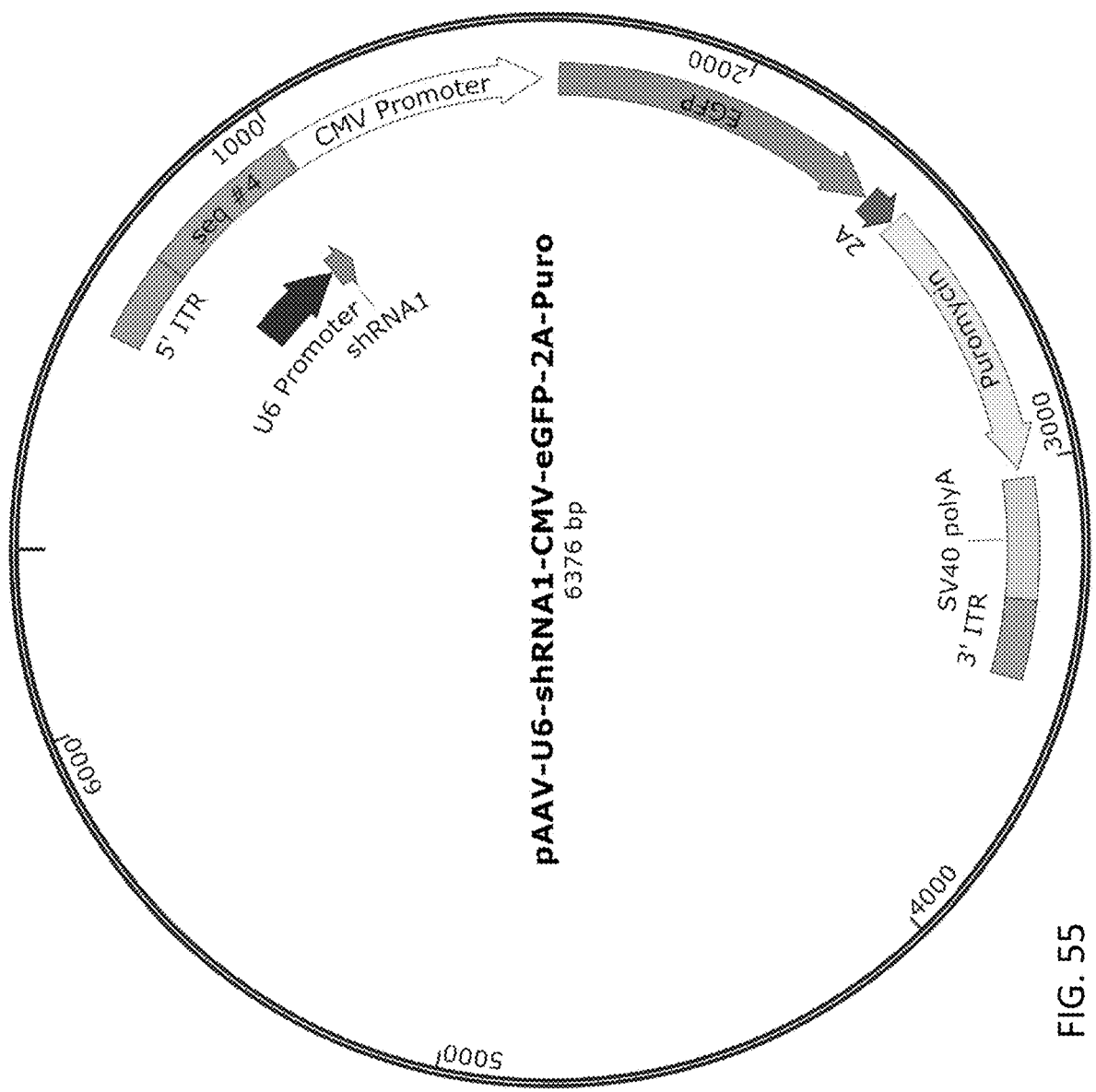

FIG. 55. Gene therapy vector AAV-U6-shRNA1-CMV-eGFP. This AAV vector expresses the transgene shRNA1. U6=The 1st promoter that controls the expression of shRNA1 gene in the mammalian cells, CMV=the 2nd promoter that controls the expression of eGFP gene in the mammalian cells. The full DNA sequence is shown by SEQ ID NO: 48 of AAV-U6-shRNA1-eGFP.

Figure 56:
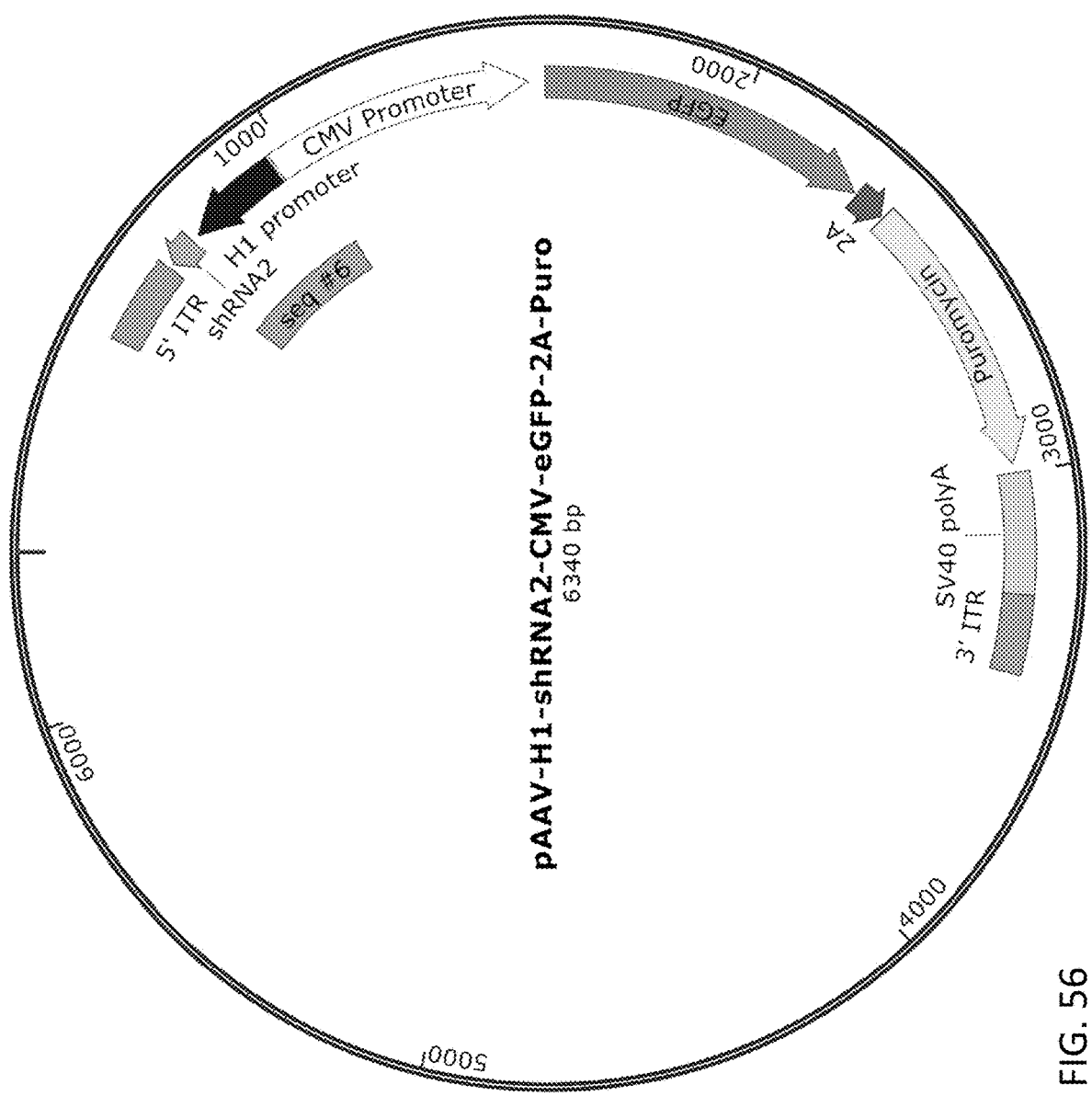

FIG. 56. Gene therapy vector AAV-U6-shRNA2-CMV-eGFP. This AAV vector expresses the transgene shRNA1 in one cell: U6=The 1st promoter that controls the expression of shRNA2 gene in the mammalian cells, CMV=the $2^{nd}$ promoter that controls the expression of eGFP gene in the mammalian cells. The sequence of AAV-U6-shRNA2-eGFP is shown by SEQ ID NO: 49.

Figure 57:
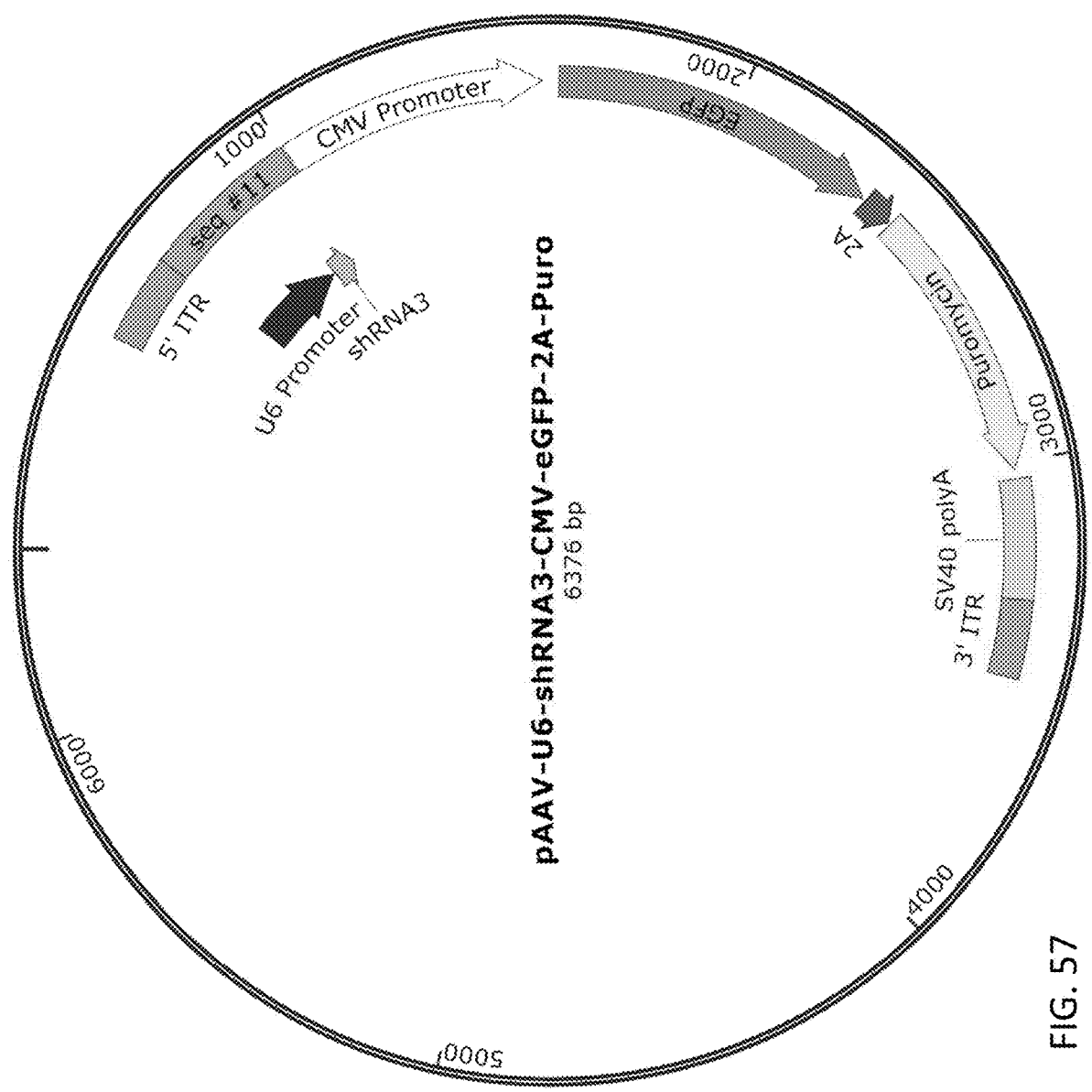

FIG. 57. Gene therapy vector AAV-U6-shRNA3-CMV-eGFP. A. This AAV vector expresses the transgene shRNA1. U6=The 1st promoter that controls the expression of shRNA3 gene in the mammalian cells, CMV=The 2nd promoter that controls the expression of eGFP gene in the mammalian cells. The full DNA sequence of AAV-U6-shRNA3-eGFP is shown by SEQ ID NO: 50.

Figure 58:
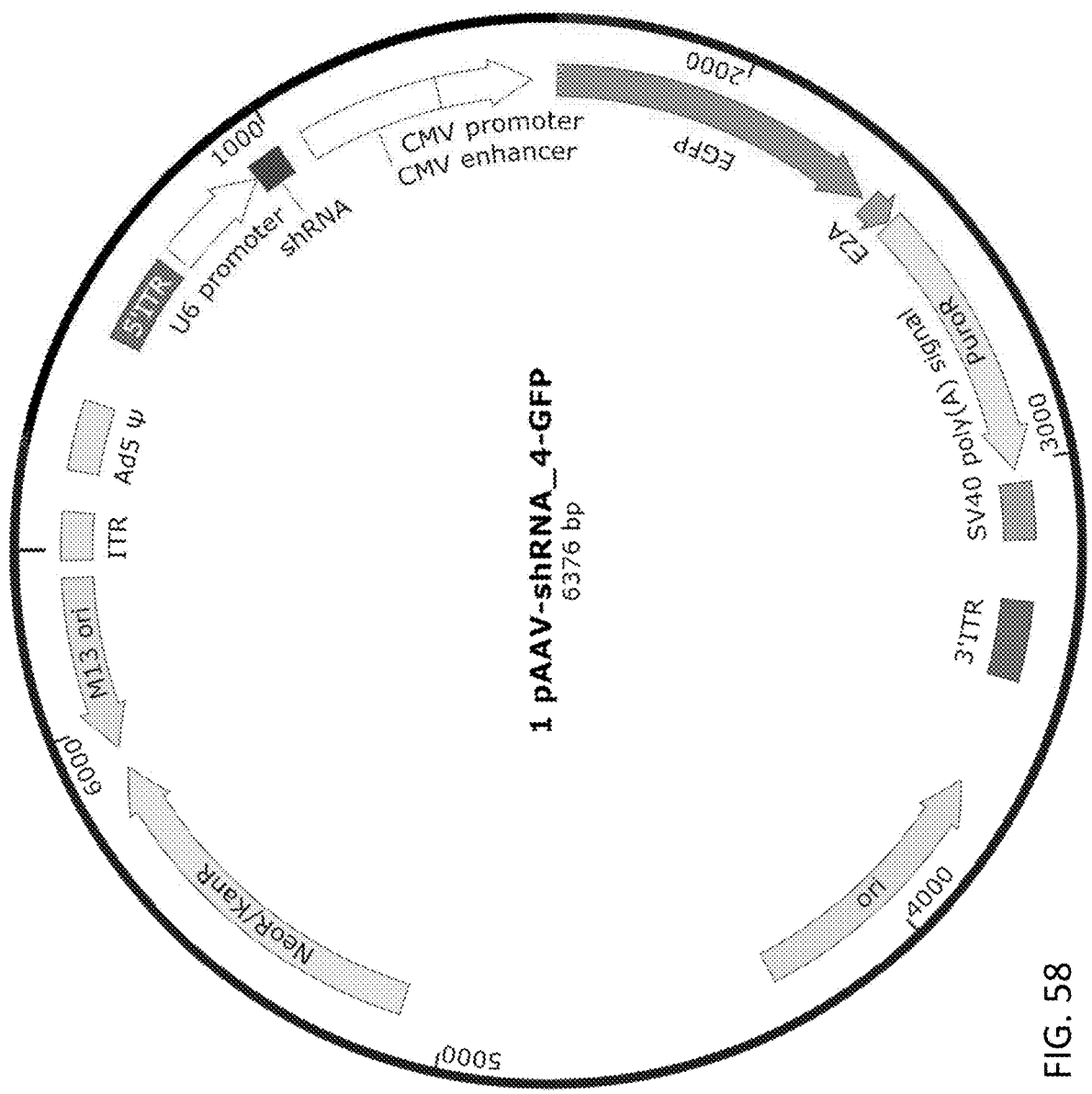

FIG. 58. Gene therapy vector AAV-U6-shRNA4-CMV-eGFP. A. This AAV vector expresses the transgene shRNA1. U6=The 1st promoter that controls the expression of shRNA4 gene in the mammalian cells, CMV=The 2nd promoter that controls the expression of eGFP gene in the mammalian cells. The full DNA sequence of AAV-U6-shRNA4-eGFP is shown by SEQ ID NO: 51.

FIGS. 59A-59B. These experiments were designed as plates A and B as follows: FIG. 59A Plate A: #1 vector: AAV-U6-shRNA1-GFP (ORF1ab), #2 vector: AAV-U6-shRNA2-GFP (RdRp), #3 vector: AAV-U6-shRNA3-GFP (S), #4 vector: AAV-U6-shRNA4-GFP (N), #5 vector: AAV-U6-ASO1-H1-ASO2-GFP (ORF1ab&RdRp), #6 vector: AAV-U6-ASO3-H1-ASO4-GFP (S & N). FIG. 59B Plate B: No treatment: Mock transfections, and Positive control: Cells transfected with COVID19 plasmids, but no gene therapy vectors.

Figure 60A:
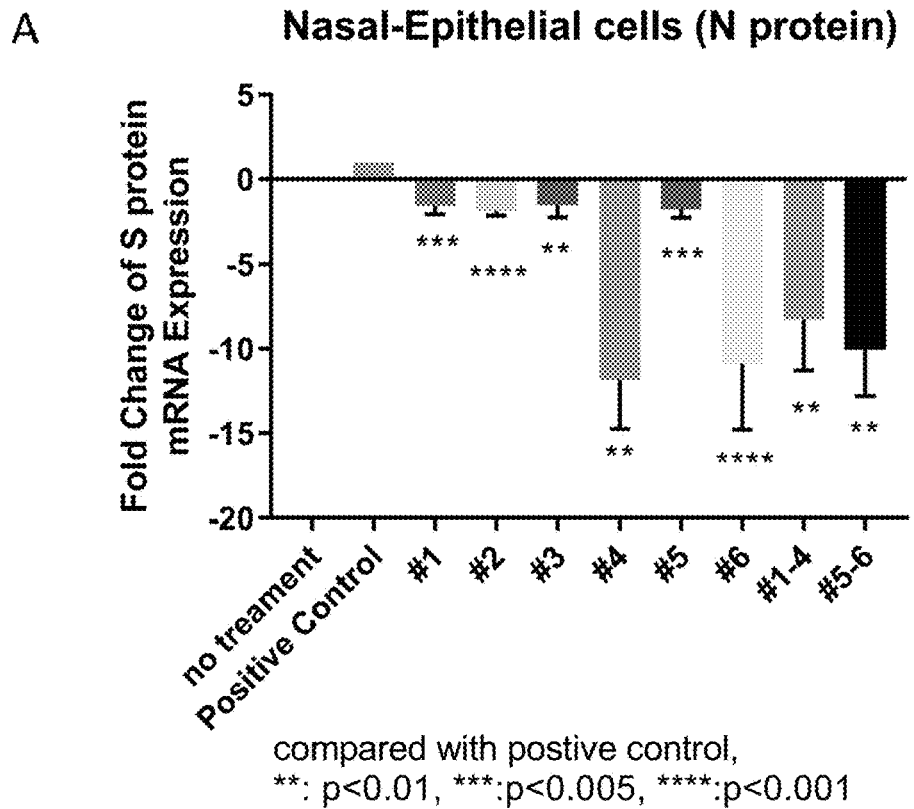
Figure 60B:
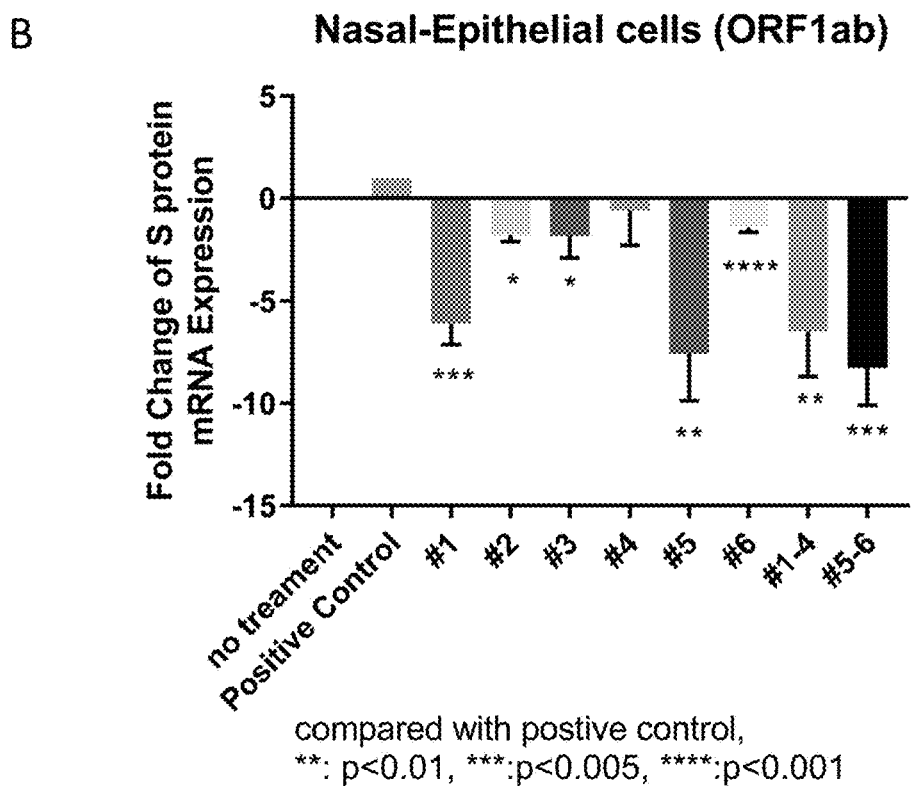

FIGS. 60A-60D. Data analysis by qRT-PCR. FIG. 60A Nasal-epithelial cells transfected with designed COVID-19 plasmid encoding N protein. FIG. 60B Nasal-epithelial cells transfected with designed COVID-19 plasmid encoding ORF1ab. FIG. 60C Nasal-epithelial cells transfected with designed COVID-19 plasmid encoding S protein. FIG. 60D Nasal-epithelial cells transfected with designed COVID-19 plasmid encoding RdRp. The cells were transfected with designed vectors with COVID-19 plasmids (S, N, RdRp and ORF1ab), and also the gene therapy vectors (#1 to #6) after 24 hours post-seeding. At the 48 hours post-transfection, the cells were then harvested, and their total RNA were extracted with including the DNase digestion before PCR assays. S proteins were conducted with TaqMan-probe assay kit (Thermofisher, A47532). The N protein, ORF1ab and RdRp proteins were determined by the GenScript kits (SARS-CoV-2PCR detection assay kit). The data indicated that the treatments by using the gene vectors have significant therapeutic effects to inhibit the expressions of the viral proteins. Synergic enhanced effects were observed when more than one peptide was used (see, #1 to 4 and #5 to 6).

FIGS. 61A-61B. FIG. 61A Western blot analysis of S-protein expression. FIG. 61B Quantification of (A). The cells were seed onto 6 well-plates. At 24 hours post-seeding, cells were transfected by the gene therapy vectors (#1 to #6) with including the plasmids encoding the COVID-19 S-proteins. After 48 hours post-transfection, cells were harvested and lysed. The primary antibody is SARS-CoV-2 Spike with 1 µg/mL (ProSc, Inc), and the secondary antibody is Goat-anti-Rabbit HRP conjugated antibody by 1:1000 dilution (R&D System). The data indicated that the treatments by using the gene vectors have significant therapeutic effects to block the expression of viral proteins. Synergic enhanced effects were observed when more than one peptide was used (see, #1 to 4 and #5 to 6).

Figure 62:
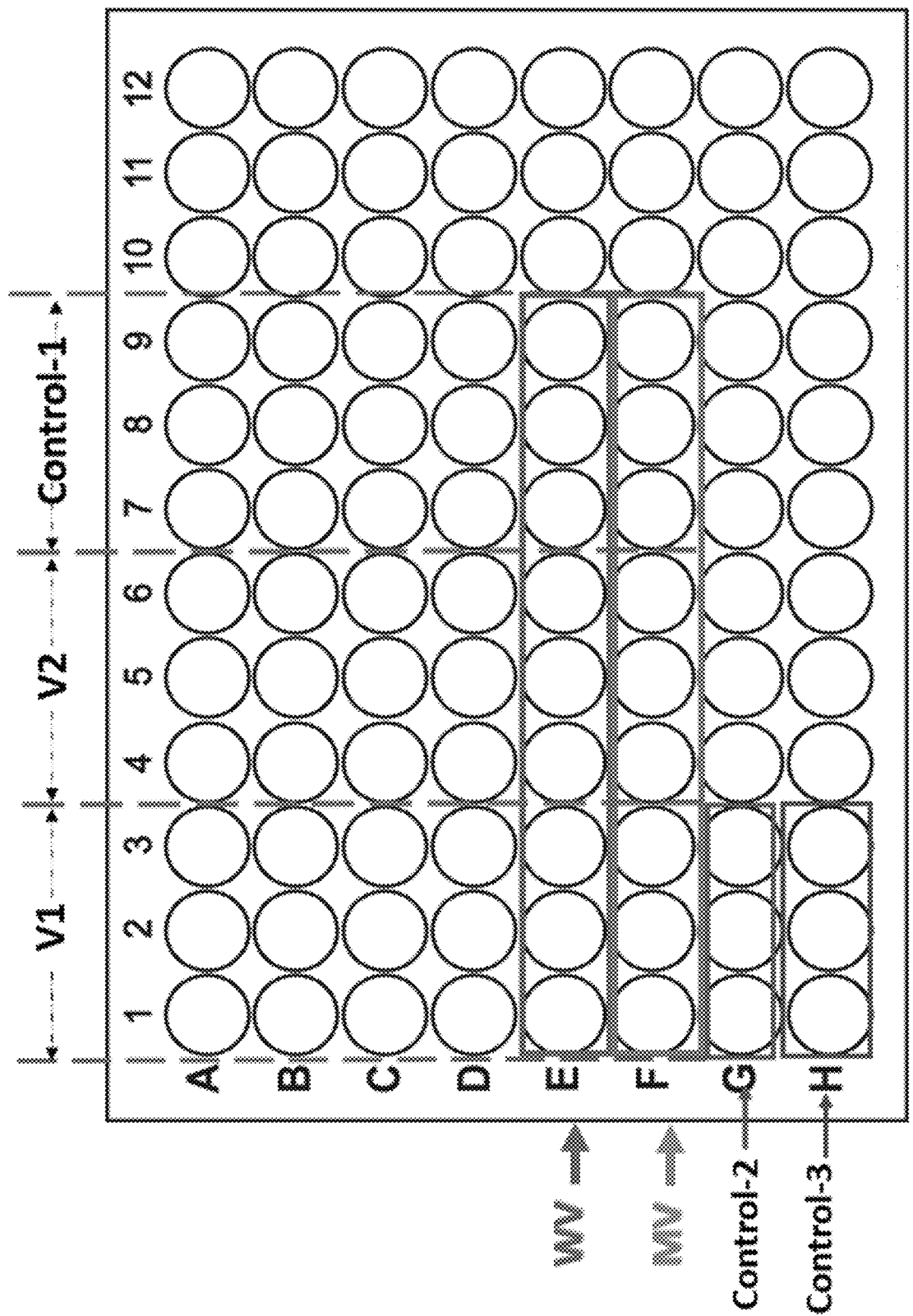

FIG. 62. Experimental design of in vitro gene therapy on inhibitions of the viral infections. WV=Wild-type of pseud-COVID-19 virus, 5 ul (titer: $10^5$ TU/ml) of the virus added into each well (E1 to E9). MV=Mutant form of pseud-COVID-19 virus, 5 ul (titer: $10^5$ TU/ml) of the virus added into each well (F1 to F9). V1=AAV-U6-A3_H1-A4-GFP, V2=AAV-U6-shRNA3-GFP, Control-1=irrelevant vector plasmid, Control-2=AAV-U6-A3_H1-A4-GFP (without virus added), Control-3=AAV-U6-shRNA3-GFP (without virus added).

FIGS. 63A-63F. In vitro gene therapy inhibits WV viral infections. ASO (V1) and RNAi (V2) were delivered by gene vectors into mammalian cells that express ACE2 proteins, in order to inhibit the WV viral infections (WV=wild-type pseudo-virus of COVID-19). FIG. 63A Brightfield image of cells treated with ASO (V1). FIG. 63B Brightfield image of cells treated with RNAi (V2). FIG. 63C Brightfield image of cells treated with control. FIG. 63D Fluorescence image of cells treated with ASO (V1). FIG. 63E Fluorescence image of cells treated with RNAi (V2). FIG. 63F Fluorescence image of cells treated with control.

Figure 64A:
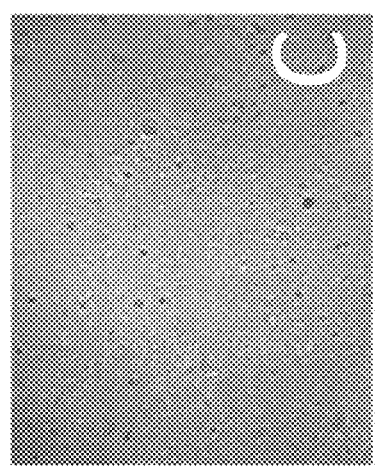
Figure 64B:
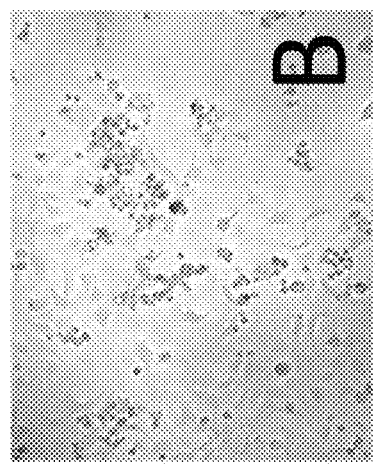
Figure 64C:
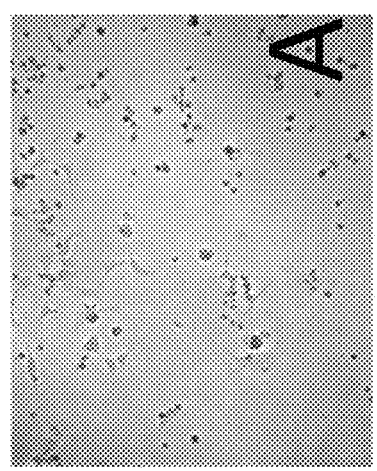
Figure 64D:
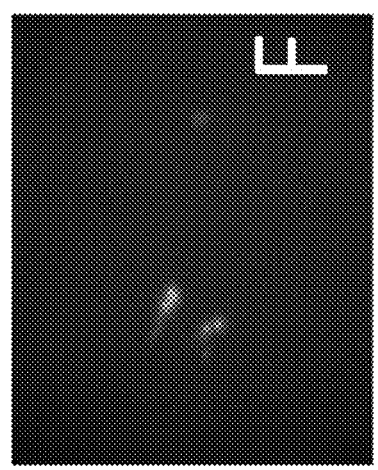
Figure 64E:
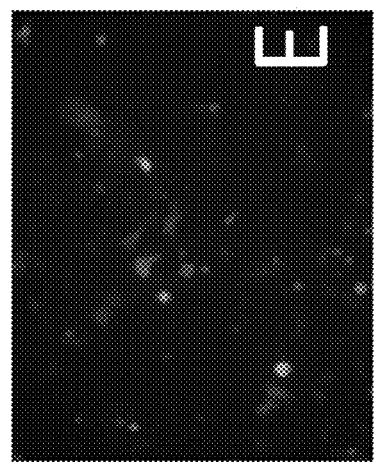
Figure 64F:
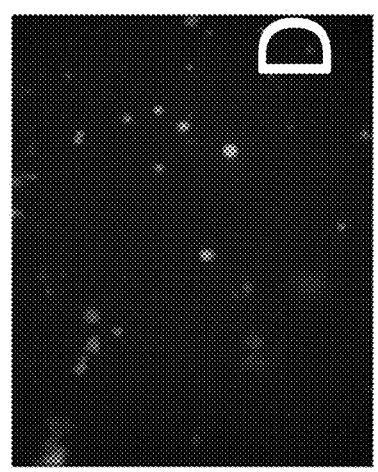

FIGS. 64A-64F. In vitro gene therapy inhibits MV viral infections. ASO (V1) and RNAi (V2) were delivered by gene vectors into mammalian cells that express ACE2 proteins, in order to inhibit the MV viral infections (MV=mutant pseudo-virus of COVID-19). FIG. 64A Brightfield image of cells treated with ASO (V1). FIG. 64B Brightfield image of cells treated with RNAi (V2). FIG. 64C Brightfield image of cells treated with control. FIG. 64D Fluorescence image of cells treated with ASO (V1). FIG. 64E Fluorescence image of cells treated with RNAi (V2). FIG. 64F Fluorescence image of cells treated with control.

FIGS. 65A-65D. In vitro delivery of gene vectors into living cells. ASO (V1) and RNAi (V2) were delivered by using the gene vectors into mammalian cells that express ACE2 proteins, the cells were not incubated with any viruses, which were served as background controls. The concentrations of the vectors encoding the ASO (control-2) or/and RNAi (control-3) were the same used in the FIGS. 61A-61B and 62. FIG. 65A Brightfield image of cells treated with ASO control. FIG. 65B Brightfield image of cells treated with RNAi control. FIG. 65C Fluorescence image of cells treated with ASO control. FIG. 65D Fluorescence image of cells treated with RNAi control.

Figure 66A:
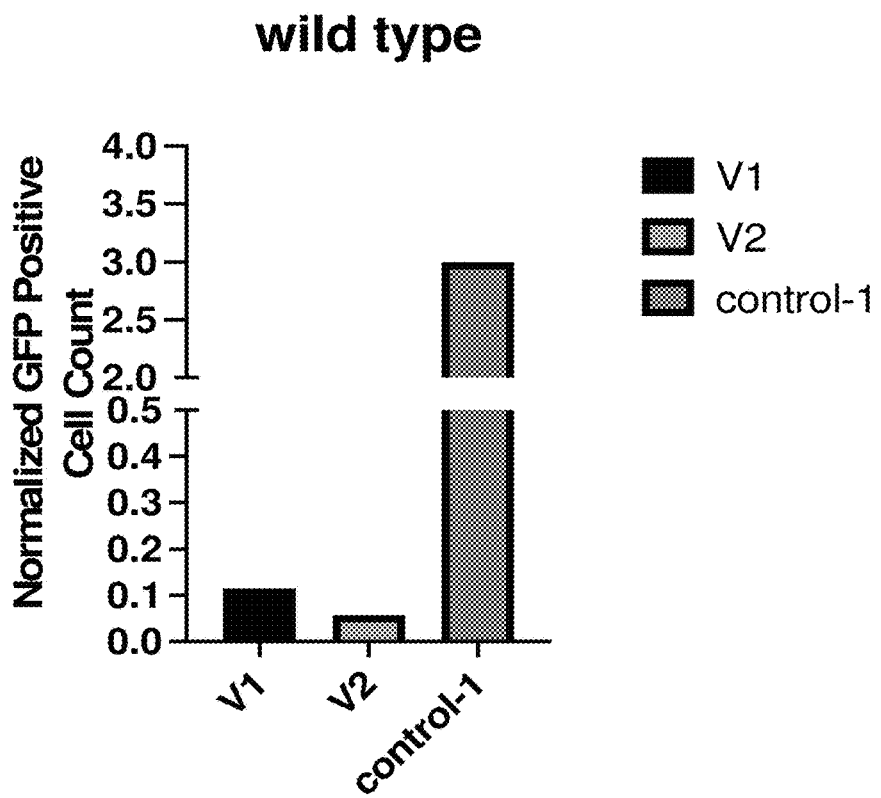
Figure 66B:
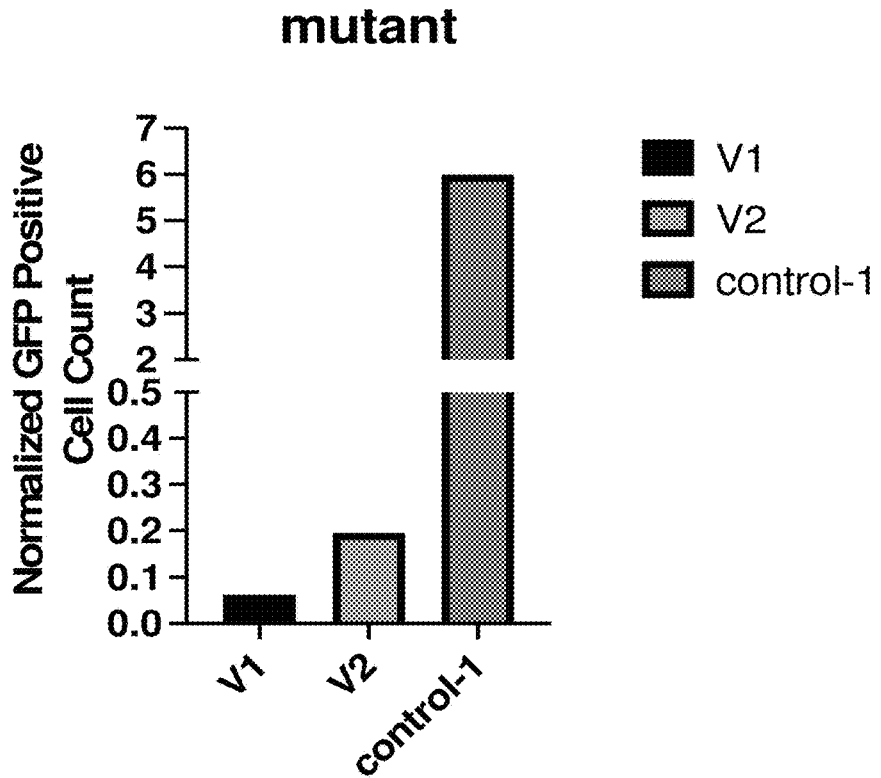

FIGS. 66A-66B. FIG. 66A Wild-type pseudo-virus experiment results and FIG. 66B mutant pseudo-virus experiment results. Since both gene vectors, encoding ASO and shRNA, also contain marker gene of GFP, normalized data was calculated based on control-2 and control-3 constructs (also see FIG. 62). The data analysis confirmed that ASO or shRNA vector expressing cells showed very little GFP signal, when compared with the control group-1. This data indicates that the gene vectors carrying either ASO or shRNA (inhibitory oligonucleotides) suppress viral infection and propagation in both wild-type and mutant viruses of COVID-19, pseudo-typed by lentiviruses.

Figure 67:
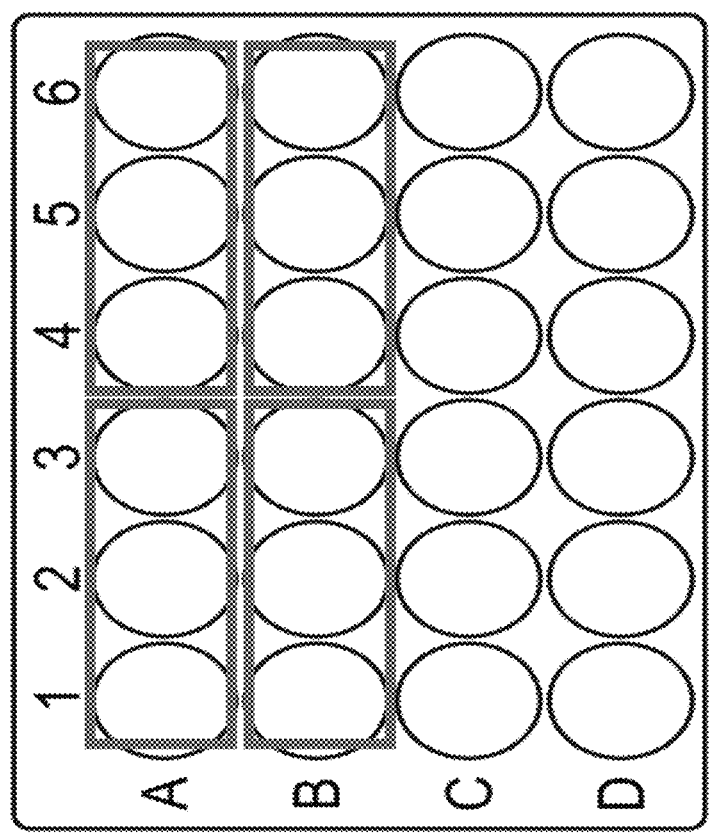

FIG. 67. Experimental design for detection of apoptosis/cytotoxicity of VS-nutrition in human bronchial/tracheal epithelial cells (HBTEC) by qRT-PCR. The human primary bronchial/tracheal epithelial cells (HBTEC) were cultured in the 24 well-dish, and the cells were treated with VS-nutrition with designated dilution (1:1, 1:300 and 1:500) for 5 days (in every day, refresh cell culture medium and added new VS-nutrition with same composition and ratio) before analysis by qRT-PCR.

Figure 68:
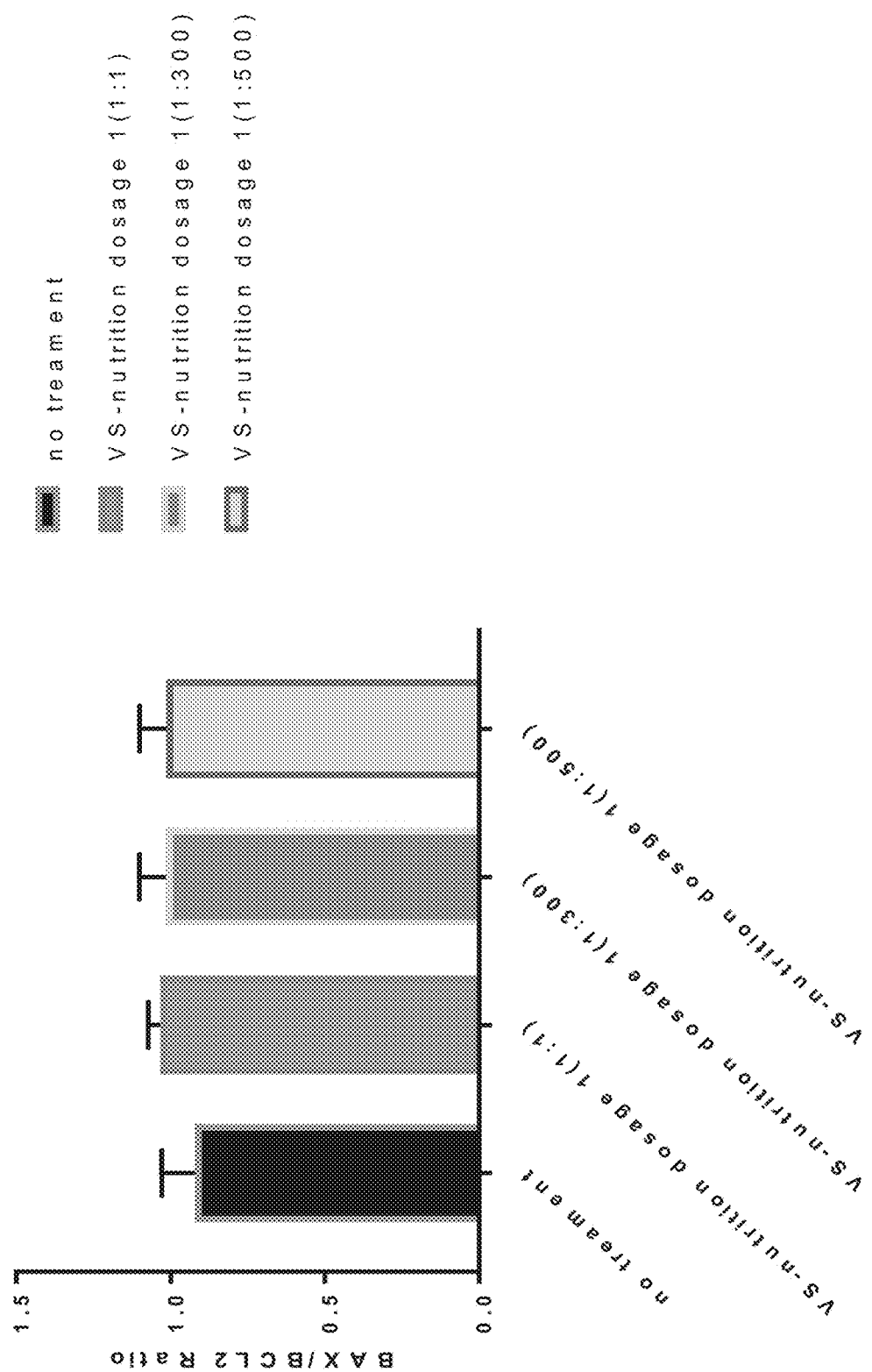

FIG. 68. Detection of on apoptosis/cytotoxicity of VS-nutrition in the human bronchial/tracheal epithelial cells (HBTEC) by qRT-PCR after treatment. Detection of apoptosis/cytotoxicity of VS-nutrition in the human primary bronchial/tracheal epithelial cells (HBTEC) by qRT-PCR after treatment with VS-nutrition. There are no significant up or down-regulation of BAX/BCL2 ratio in group treated by VS-nutrition when compared with the normal cells with no-treatment ($p>0.05$).

Figure 69:
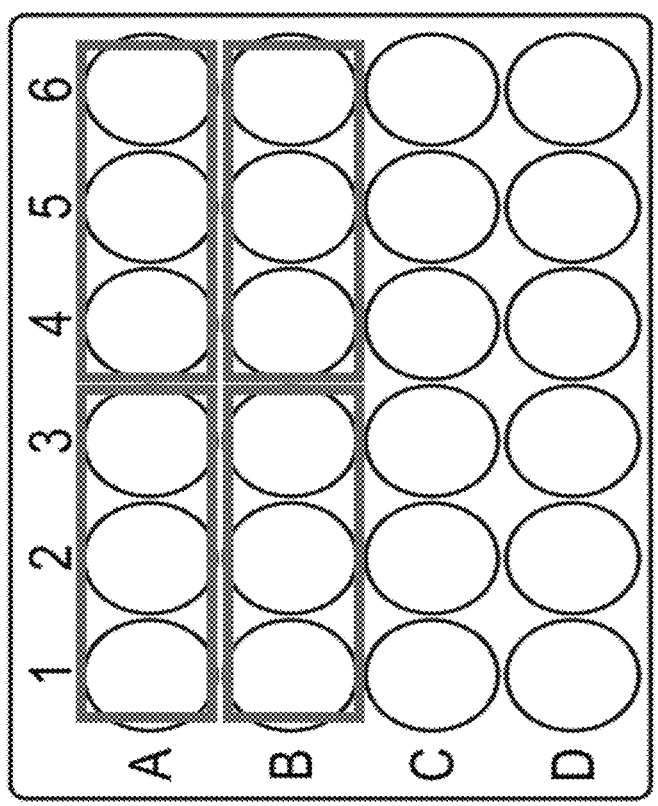

FIG. 69. Experimental design for detection of apoptosis/cytotoxicity of VS-nutrition in Human Primary Nasal Epithelial Cells (HNEpC) by qRT-PCR. The human primary nasal epithelial cells (HNEpC) were cultured in the 24 well-dish, and the cells were treated with VS-nutrition with designated dilution (1:1, 1:300 and 1:500) for 5 days (in every day, refresh cell culture medium and added new VS-nutrition with same composition and ratio) before analysis by qRT-PCR.

Figure 70:
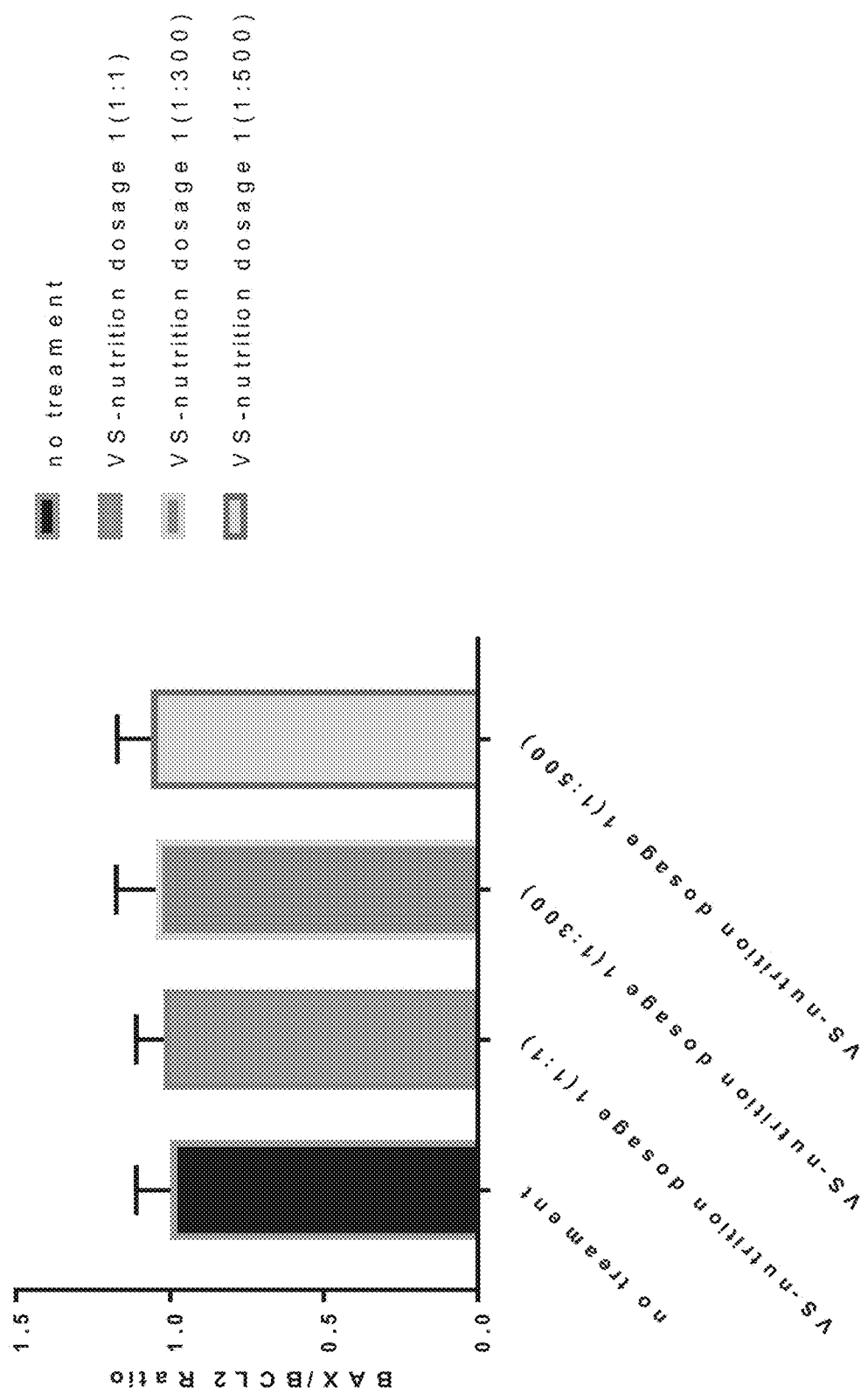

FIG. 70. Detection of on apoptosis/cytotoxicity of VS-nutrition in the human primary nasal epithelial cells (HNEpC) by qRT-PCR after treatment. Detection of apoptosis/cytotoxicity of VS-nutrition in the human primary nasal epithelial cells by RT-PCR after treatment with VS-nutrition. There are no significant up or down-regulation of BAX/BCL2 ratio in group treated by VS-nutrition when compared with the normal cells with no-treatment ($p>0.05$).

Figure 71A:
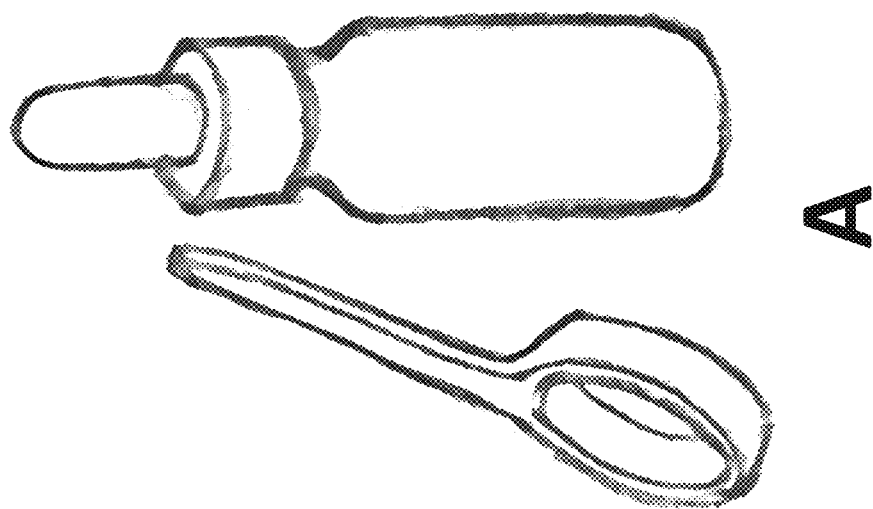
Figure 71B:
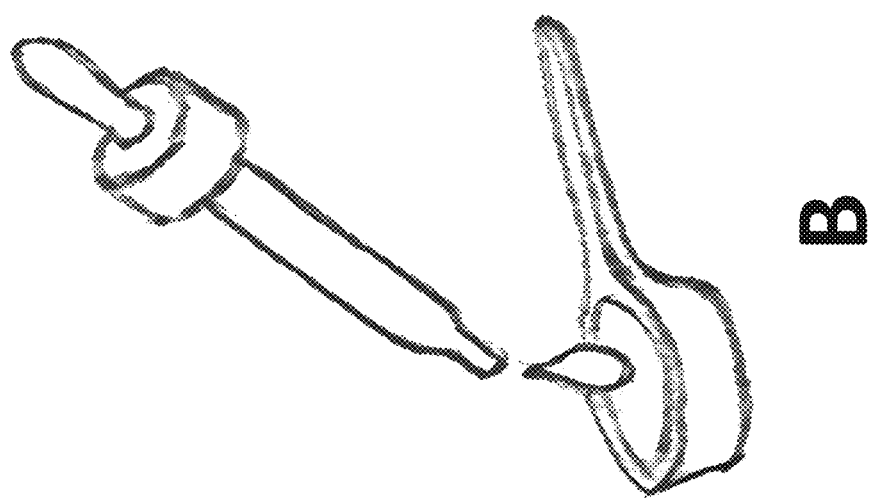

FIGS. 71A-71B. Oral intake formulations of VS product (nutritional supplement). Bottle product (10-15 ml) with FIG. 71A 1.5 ml spoon or FIG. 71B 1.0 ml drop.

FIGS. 72A-72C. Nasal (liquid) spray. Spray product with 10-15 ml bottle nasal spray. FIG. 72A composition and size of the product. FIGS. 72B & 72C usage example.

Figure 73A:
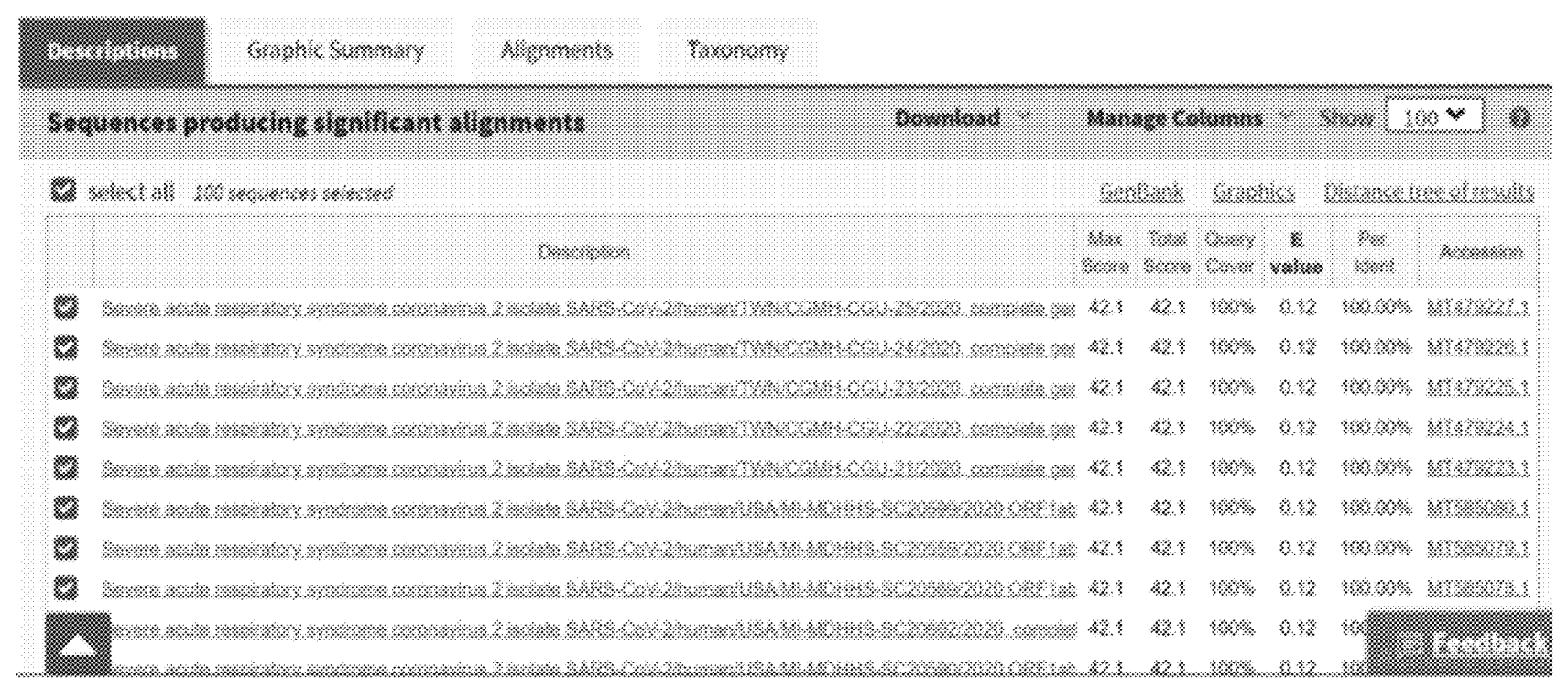
Figure 73B:
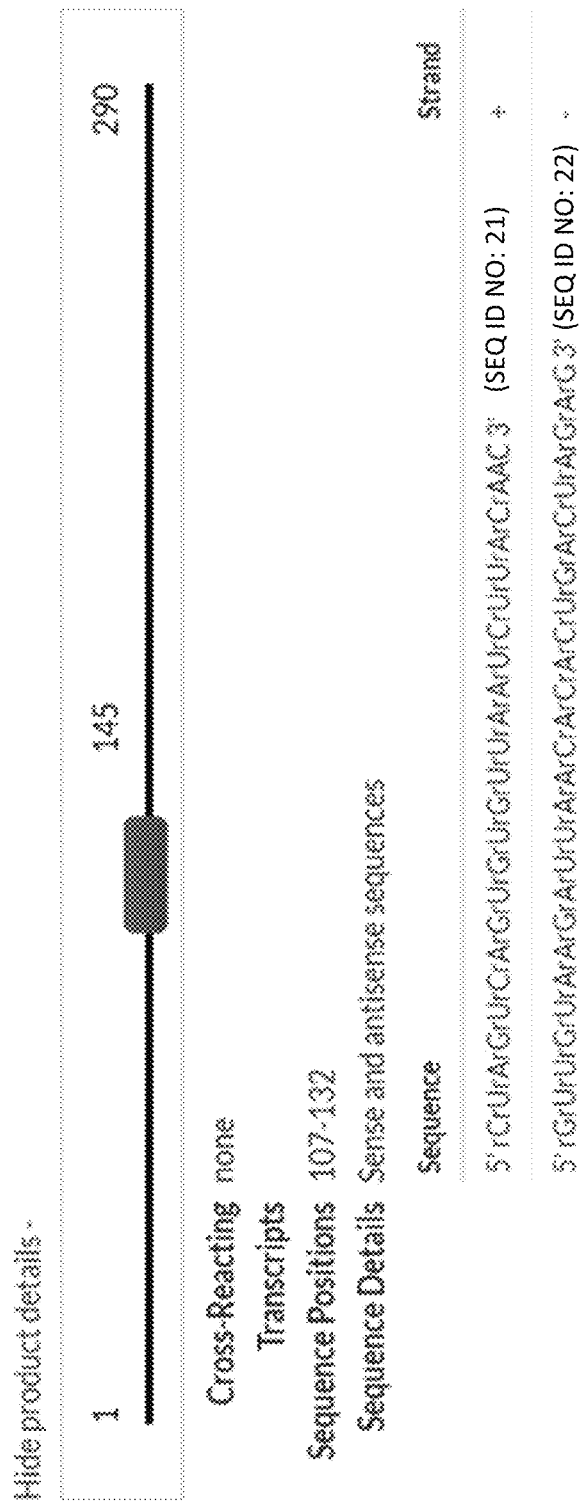

FIGS. 73A-73B. FIG. 73A The alignment of all ASO (ASO_1 and ASO_2) and all oligos in Tables 1, 2 and 4 showed that the designed inhibitory oligonucleotides specifically target the SARS-COV-2 virus genes. The alignment did not show any significant match to any human genes (thereby, avoiding potential side-effects when applied in human). FIG. 73B: The analysis of all DsiRNA indicated all oligos (in Tables 1, 2 and 4) specifically target the SARS-COV-2 virus genes. The alignment did not show any significant match to any human genes (thereby, avoiding potential side-effects when applied in human)

Figure 74A:
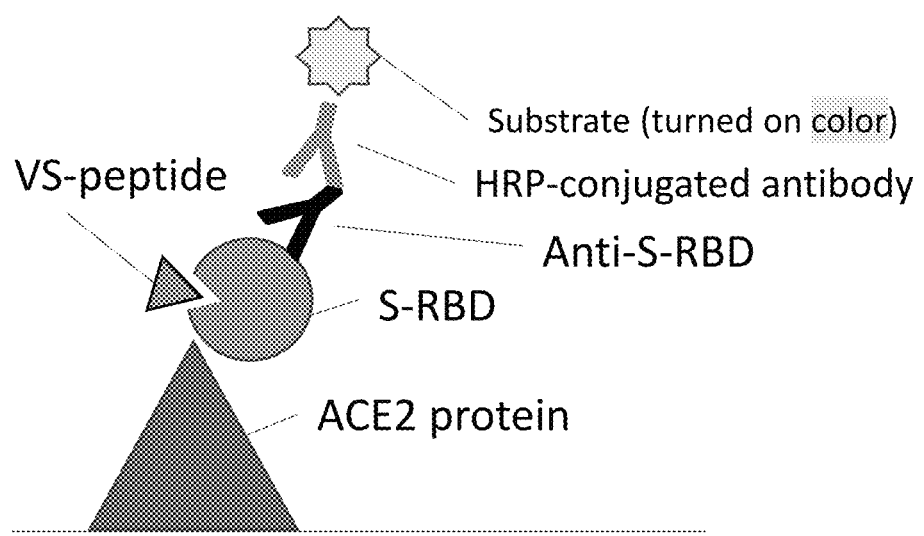
Figures 74B, 74C:
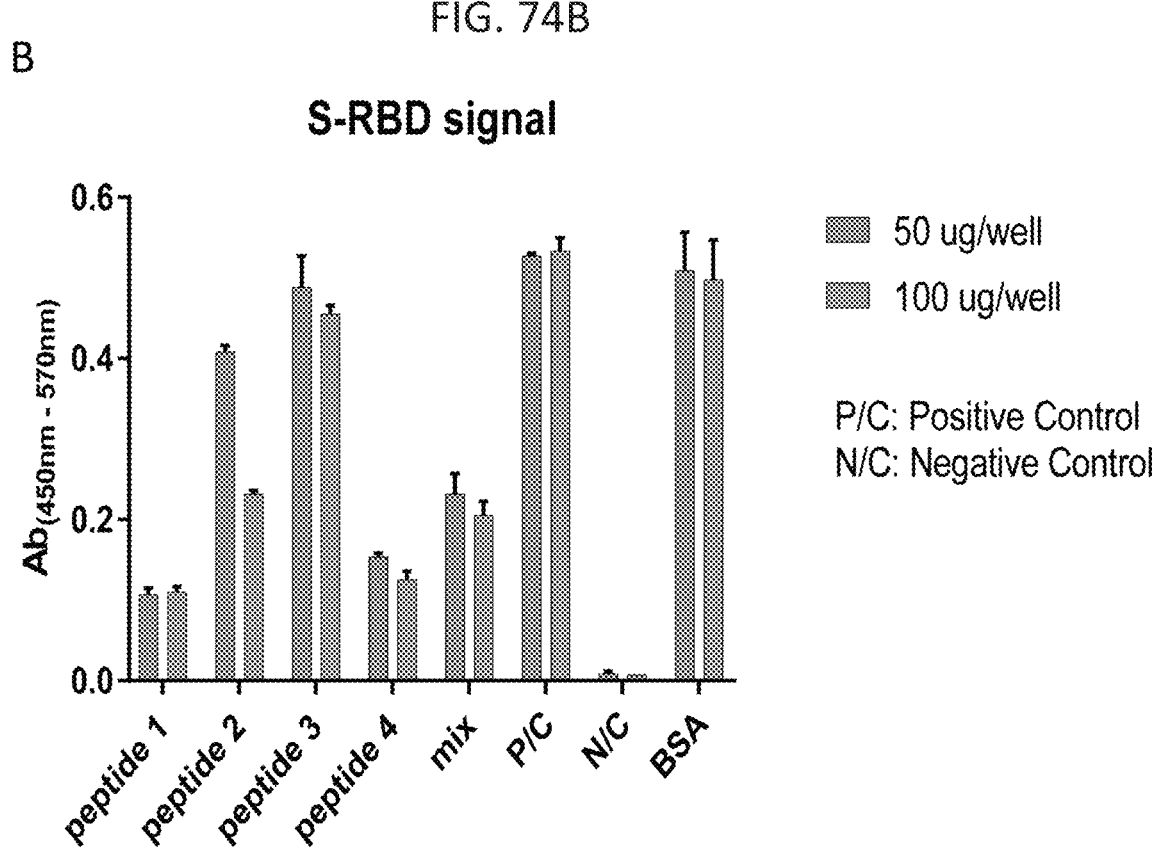

FIGS. 74A-74C. Peptide ELISA assays. FIG. 74A Schematic of ELISA assays. FIG. 74B Analysis of inhibitions of COVID-19 Spike Protein Receptor Binding Domain (S-RBD)-ACE2 binding by inhibitory peptides. FIG. 74C Table of p-values of the results in FIG. 74A and the number of amino acids participating in S-RBD/ACE2 interaction. These results indicated that the peptides could compete with ACE2 proteins and prevent S-RBD binding to ACE2. When the designed inhibitory peptides contained more amino acids interacting with S-RBD, stronger affinities were measured.

Figure 75A:
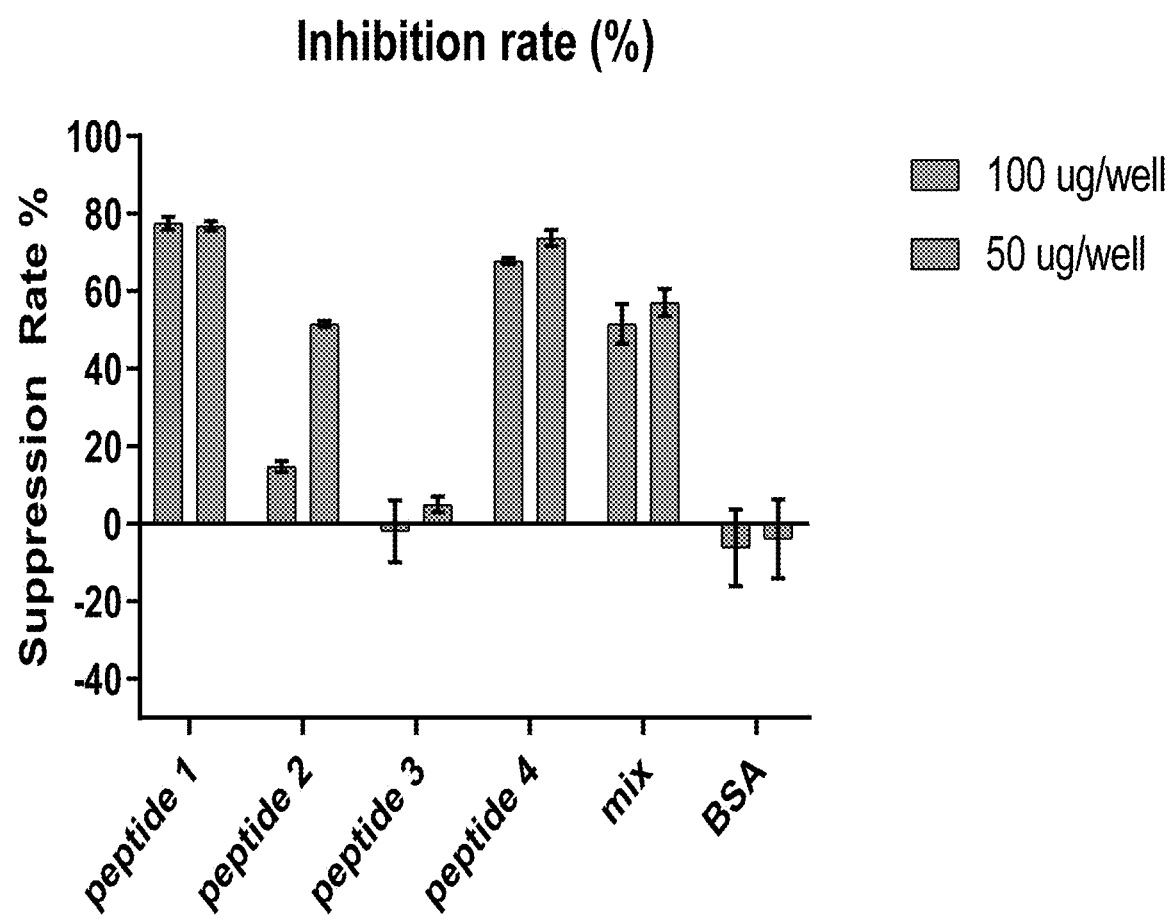
Figure 75B:
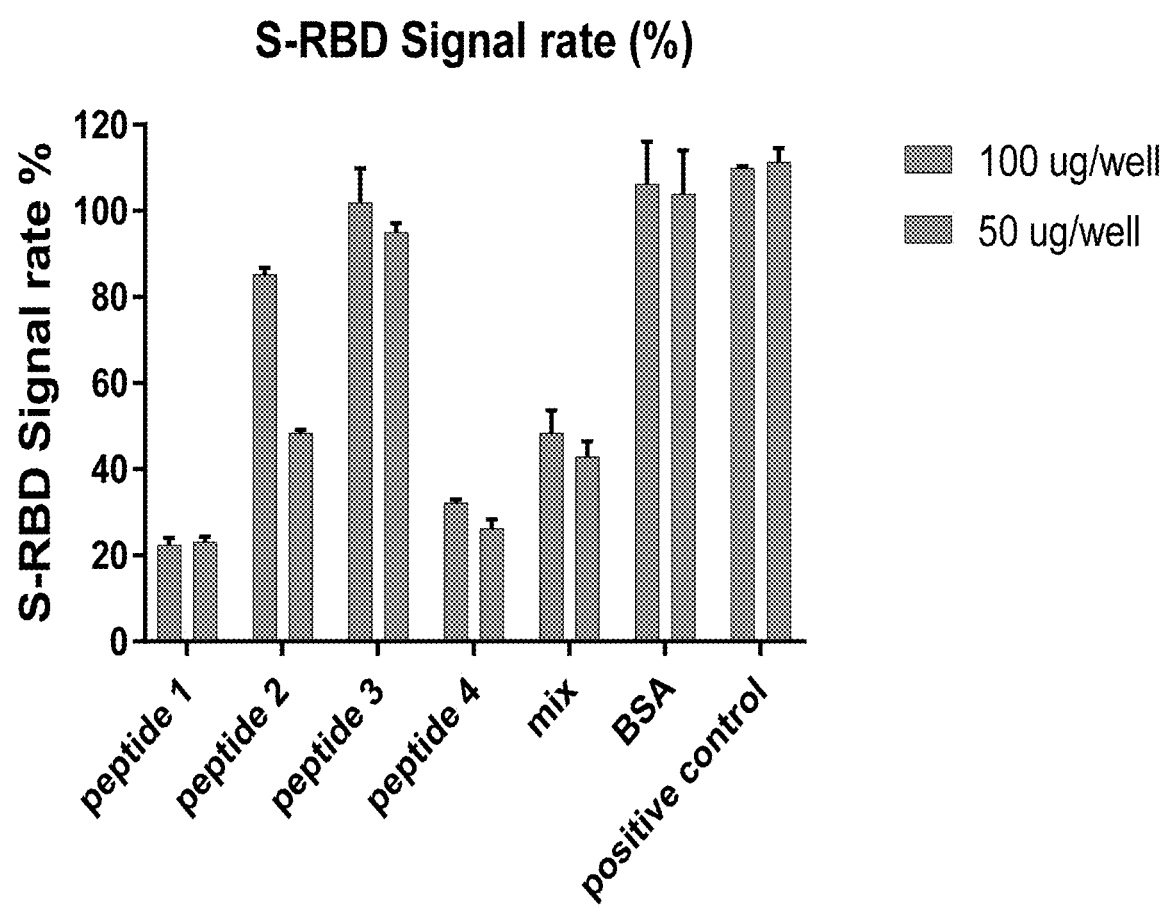

FIGS. 75A-75B. FIG. 75A Inhibition rate of S-RBD binding to ACE2 using VS peptides. FIG. 75B S-RBD signal rate. The data were converted and calculated as inhibition/suppression rates of the peptides based on the intensities of the S-RBD signals after treatment with the peptides compared with the control groups FIG. 75B. All peptides have shown their dosage-responses in the ELISA reactions, and indicated their strong biological affinities to bind with the S-RBD.

Figure 76A:
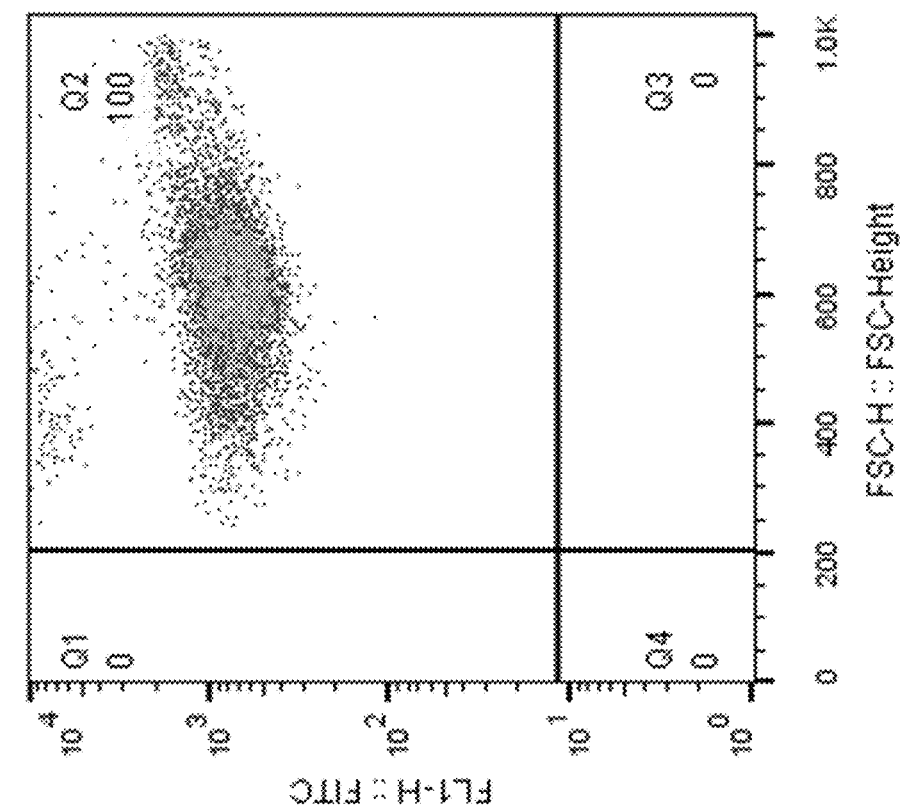
Figure 76B:
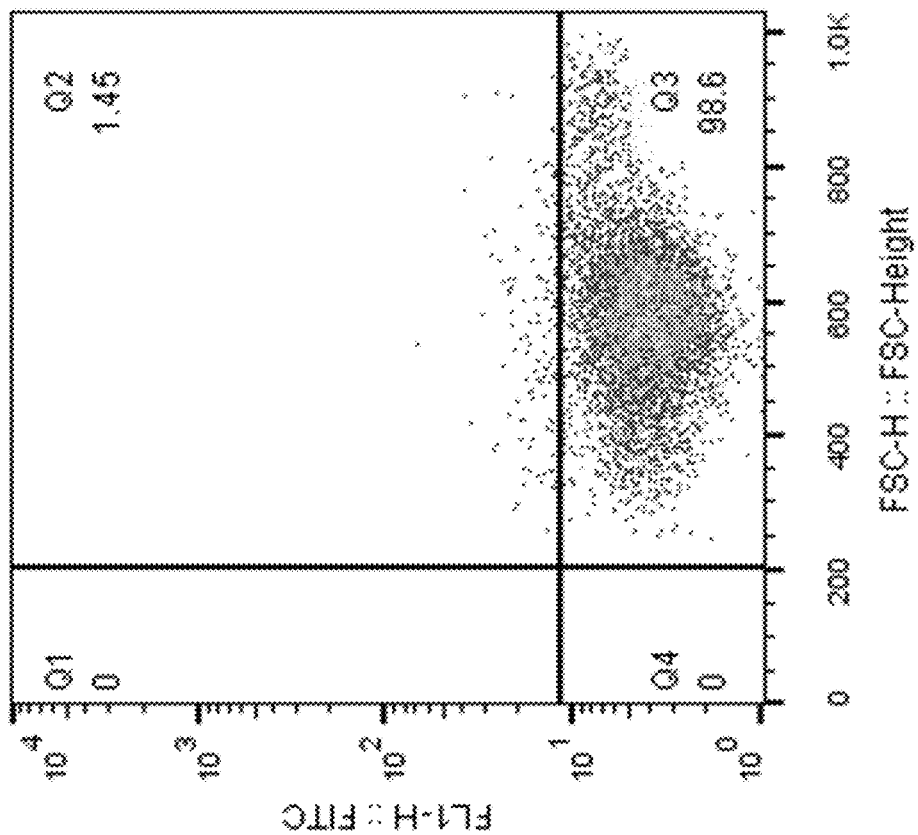
Figure 76E:
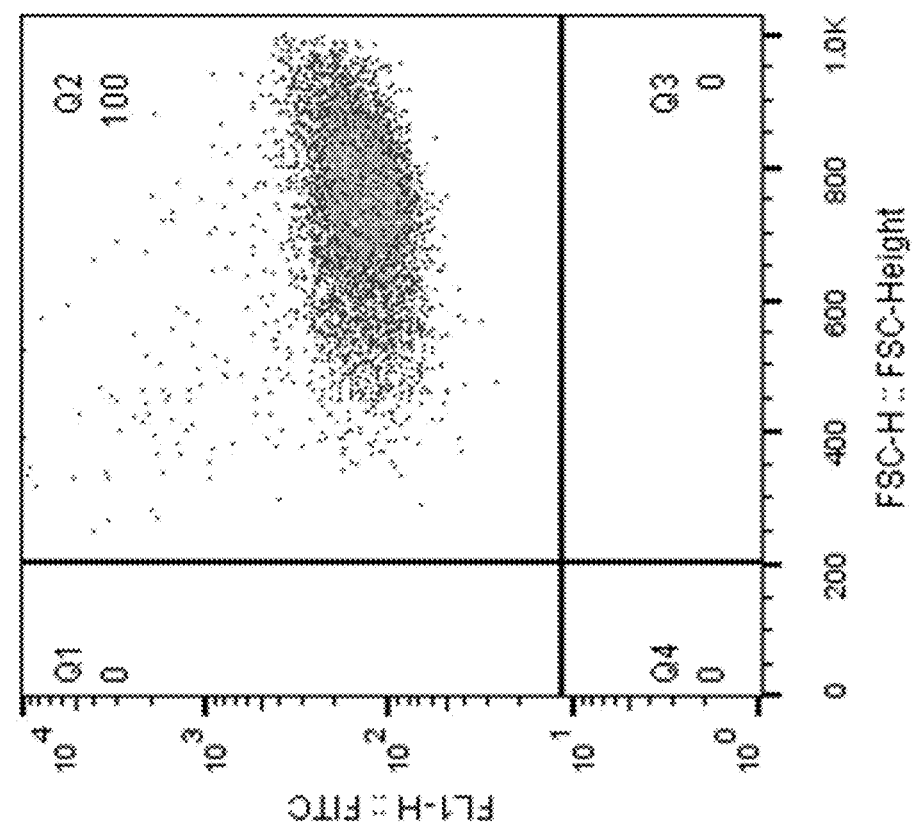
Figure 76F:
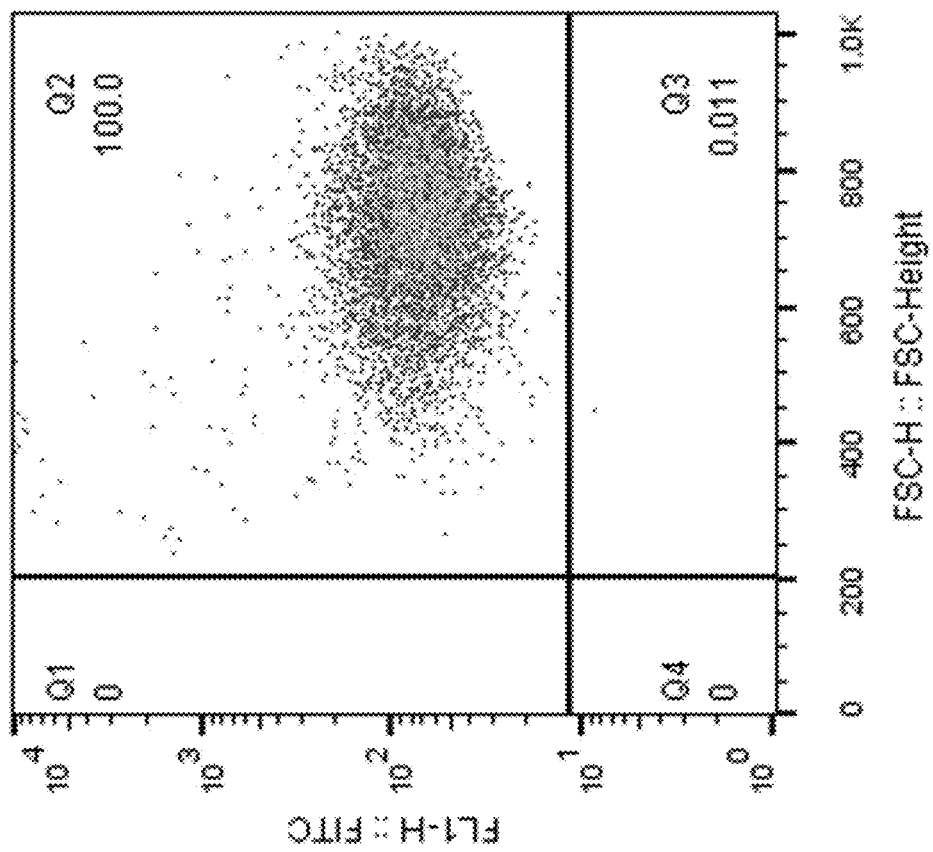
Figure 76I:
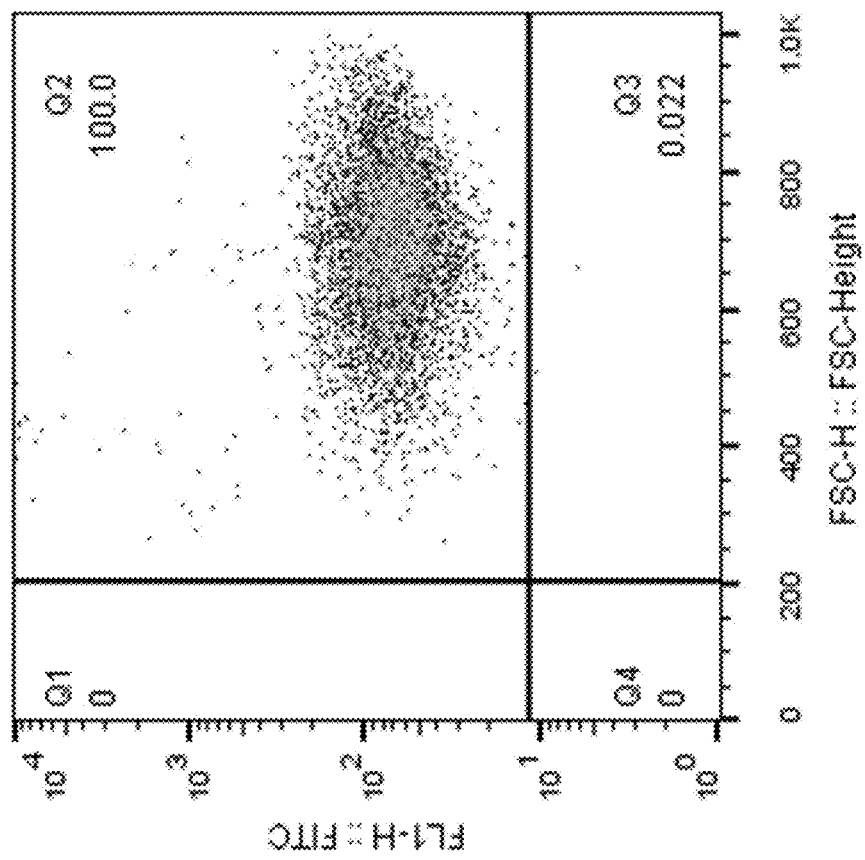
Figure 76J:
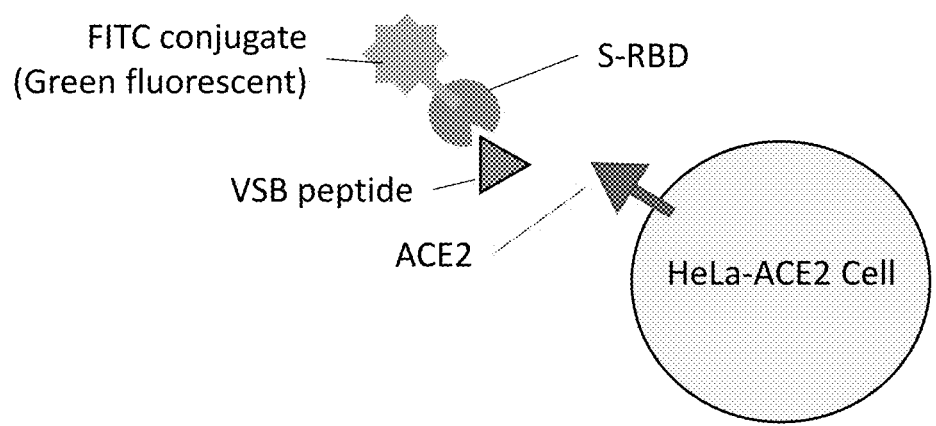

FIGS. 76A-76J. VS-peptides (VS-peptides 1, 2, 3, 4 and 5) block COVID-19 S-RBD-FITC from entering living mammalian cells expressing ACE2 receptors, as determined by FACS analysis. FIG. 76A Negative control (no peptide or FITC). FIG. 76B Positive control (FITC added, no peptide). FIG. 76C Human normal serum control (FITC added, no peptide). FIG. 76D VS-Peptide 1. FIG. 76E VS-Peptide 1. FIG. 76F VS-Peptide 1. FIG. 76G VS-Peptide 1. FIG. 76H VS-Peptide 1. FIG. 76I VS-Peptide 1. FIG. 76J Schematic of the experiment. Without a VS peptide, S-RBD (which is conjugated to FITC) binds to ACE2 and results the HeLa-ACE2 cells giving a FITC signal. When incubated with a VS peptide, S-RBD (conjugated to FITC) binds to VSB peptide instead of HeLa-ACE2 cells. In this case, HeLa-ACE2 cells have no FITC signal.

Figure 77:
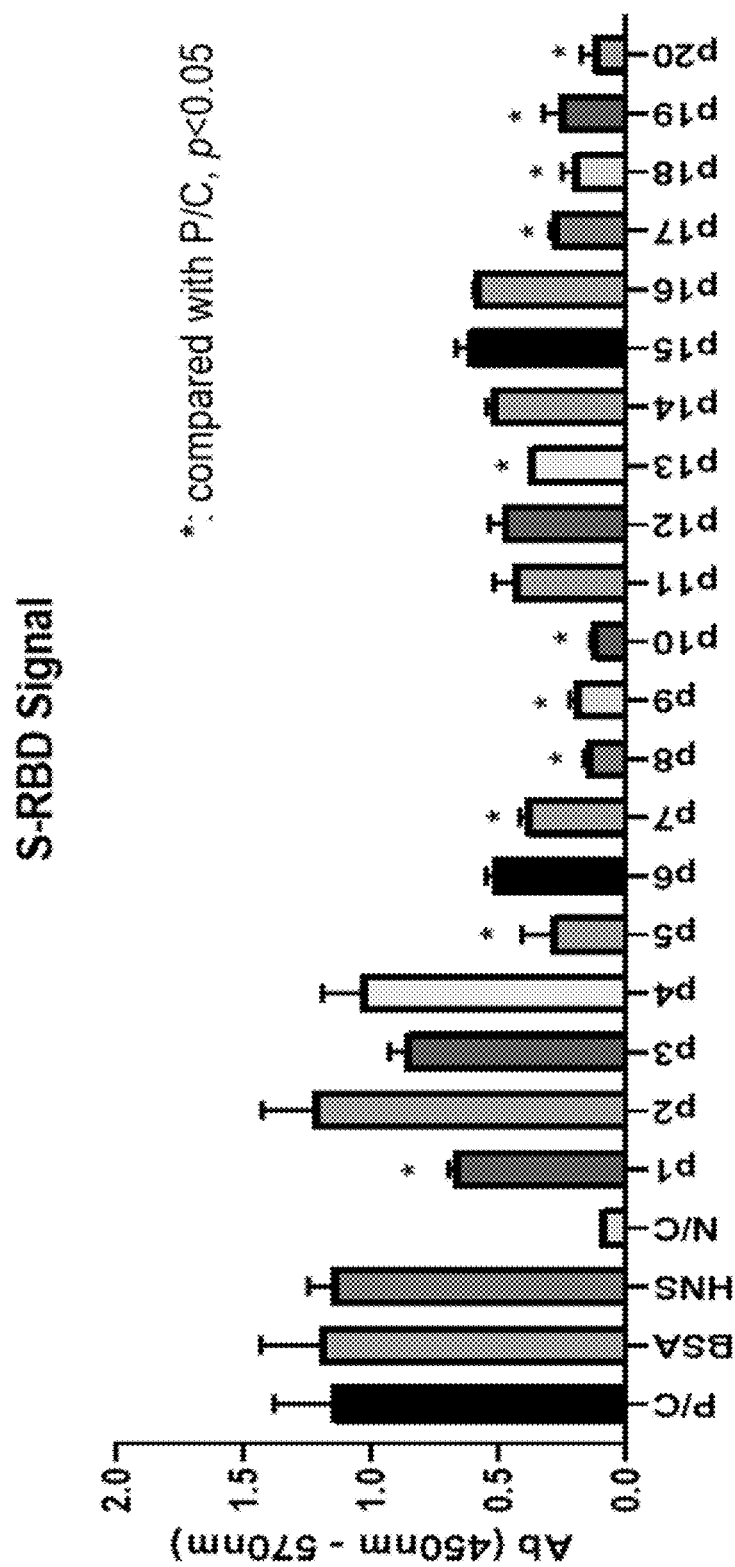

FIG. 77. ELISA results of S-RBD inhibition by inhibitory peptides derived from VS-Peptides 1-5 (P1 to P20—see Table 6 for sequences shown by SEQ ID NOS: 63-82). The competitive ELISA was performed as depicted in FIG. 74A. PL: VS-Peptide 1-a, P2: VS-Peptide 1-b, P3: VS-Peptide 1-c, P4: VS-Peptide 1-d, P5: VS-Peptide 2-a, P6: VS-Peptide 2-b, P7: VS-Peptide 2-c, P8: VS-Peptide 2-d, P9: VS-Peptide 3-a, P10: VS-Peptide 3-b, P11: VS-Peptide 3-c, P12: VS-Peptide 3-d, P13: VS-Peptide 4-a, P14: VS-Peptide 4-b, P15: VS-Peptide 4-c, P16: VS-Peptide 4-d, P17: VS-Peptide 5-a, P18: VS-Peptide 5-b, P19: VS-Peptide 5-c, P20: VS-Peptide 5-d. The data indicated that the derivative inhibitory peptides are capable of targeting the S-RBD of SARS-CoV-2 significantly to prevent viral binding on the human ACE2 receptors ($p<0.05$).

DETAILED DESCRIPTION

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

This disclosure is directed to compositions and methods for treating Coronavirus disease 2019 (COVID-19).

The term "COVID-19 treatment" (or "treating COVID-19"), refers to reduction, alleviation, or elimination of one or more of the COVID-19 disease symptoms, or prevention or inhibition of the onset of one or more COVID-19 disease or disease symptoms. Documented symptoms of include, for example, fever, dry cough, tiredness, aches and pains, sore throat, diarrhea, conjunctivitis, headache, loss of taste, loss of smell, a rash on skin, discoloration of fingers or toes, difficulty breathing, shortness of breath, chest pain or pressure, loss of speech, and loss of movement.

The compositions and methodologies described herein are effective to treat COVID-19 caused by infection of SARS-CoV2, including the originally or earlier isolated viral strains of SARS-CoV2, as well as variants of the original or earlier SARS-CoV2 viral isolates. In some embodiments, a SARS-CoV2 variant has a mutation in the spike protein. In some embodiments, the mutations comprise at least one amino acid deletion or substitution. In a specific embodiment, the SARS-CoV2 variant is the viral isolate known as B.1.1.7. In a specific embodiment, the B.1.1.7 has deletions of H69, V70 and Y144 of the spike protein as shown by SEQ ID NO: 61, and also has the following amino acid substitutions N501Y, A570D, D614G, P681H, T7161, S982A, and D118H of the spike protein as shown by SEQ ID NO: 61. All known variants of SARS-CoV2 cause similar and overlapping disease symptoms, as described above.

In one aspect, the compositions and the methods disclosed herein are directed towards targeting a plurality of selected target genes in the severe acute respiratory syndrome coronavirus 2 (SARS-CoV2) genome by employing a plurality of inhibitory oligonucleotides. In some embodiments, a selected target gene is targeted with a plurality of inhibitory oligonucleotides. The inhibitory oligonucleotides can be used directly in a composition formulated as a dietary supplement or a pharmaceutical composition (e.g., in the form of nanoparticles or liposomes) for administration to a subject; or alternatively, can be placed in one or more nucleic acid vectors which are administered to a subject.

This approach developed by the inventors has several advantages. RNA viruses have a tendency to mutate and a recent study suggests that mutations could make coronavirus more infectious. The genes selected to be targeted herein are essential to the function of the SARS-CoV-2 virus. Therefore, by providing a plurality of inhibitory oligonucleotides targeting multiple genes, inhibition of the viral function is accomplished even if one of the target genes has mutated. Further, the inhibitory oligonucleotides are small in size, which permits effective cell penetration including penetration of infected cells, an advantage not provided by vaccines or antibodies against SARS-CoV-2 proteins which are not effective once the virus has entered into host cells.

In another aspect, the compositions and the methods disclosed herein are directed towards inhibiting the interactions between the SARS-CoV-2 virus and the Angiotensin-converting enzyme 2 (ACE2) receptor by one or more inhibitory peptides that mimic either the binding surface of ACE2 ligand binding domain (LBD) or the binding surface of the SARS-CoV-2 S-protein receptor binding domain (RBD). The inhibitory peptides can be included in a composition formulated as a dietary supplement or a pharmaceutical composition (e.g., in the form of nanoparticles or liposomes) for administration to a subject.

In a further aspect, the compositions and the methods disclosed herein are based on a combination of a plurality of inhibitory oligonucleotides and inhibitory peptides.

In some embodiments, the gene vectors described herein, encoding the inhibitory oligonucleotides and peptides described herein, can target viral infective functional group genes that have been integrated into the host cell (e.g., a human cell) genome (see, Zhang, L., et al., *PNAS*, 118.21 (2021), incorporated herein in its entirety).

SARS-CoV-2 Genes

In some embodiments, the entire SARS-CoV-2 cDNA sequence is shown under GenBank Accession No: NC_045512.2 (SEQ ID NO: 52). The individual SARS-CoV-2 genes are as follows:

ORF1ab: The open reading frame for starting transcriptional genes of SARS-CoV-2, 1ab, and is between nucleotide numbers 266 and 21555 of SEQ ID NO: 52;

N-protein gene: encodes the Nucleocapsid Protein of SARS-CoV-2 (which is a structural protein that binds to the coronavirus RNA genome, thus creating a shell), and is between nucleotide numbers 28274 and 29533 of SEQ ID NO: 52;

S-protein gene: encodes the spike protein of SARS-CoV-2 (which binds to the host cell receptors, i.e., ACE2 to enter the host cells, and is between nucleotide numbers 21563 and 25384 of SEQ ID NO: 52;

E-protein gene: encodes envelope protein of SARS-CoV-2 (which is a small membrane protein that has an important role in the assembly of virions), and is between nucleotide numbers 26245 and 26472 of SEQ ID NO: 52;

RdRp: encodes the RNA-dependent RNA polymerase of SARS-CoV-2 (an enzyme that catalyzes the replication of RNA from a viral RNA template) and is between nucleotide numbers 13442 and 16236 of SEQ ID NO: 52.

Targeting/Target Site

As used herein, the term "targeting" refers to the action of an inhibitory oligonucleotide binding or hybridizing to a target site in a nucleic acid that results in inhibition of the expression of the nucleic acid.

As used herein, a "target site" refers to a stretch of nucleotides on an mRNA of a target gene to which an inhibitory oligonucleotide binds, which ultimately leads to inhibition of the function of the mRNA and thus the expression of the gene. In some embodiments, a target site comprises at least 15, 16, 17, 18, 19, 20, 21, 22, 23, 24, or 25 nucleotides. In some embodiments, a target site comprises not more than 50, 45, 40 or 35 nucleotides. In some embodiments, a target site comprises between 15-30, 18-28, 20-25, or 30-35 nucleotides. Selected target sites are unique to the virus with minimal or no overlap with mRNA sequences found in human, so that the oligonucleotides are specific in their inhibition of the viral mRNA, with minimal side effects/off-target effects. In specific embodiments, a target site comprises the nucleotide sequence of one of SEQ ID NOS: 1-8; for example, a target site may have a nucleotide sequence that includes one of SEQ ID NOS: 1-8 and additional nucleotide(s) (e.g., 1, 2, 3, 4, or 5 nucleotides) on either 5' or 3' of the selected sequence.

Inhibitory Oligonucleotides

As used herein, the phrase "inhibitory oligonucleotide" refers to an oligonucleotide that can inhibit expression of a target SARS-CoV-2 gene. In some embodiments, an inhibitory oligonucleotide binds to a target site in a nucleic acid (e.g., a selected SARS-CoV-2 mRNA). In some embodiments, an inhibitory oligonucleotide comprises the reverse complementary sequence of a target site. In some embodiments, an inhibitory oligonucleotide comprises a nucleotide sequence that is substantially complementary to the sequence of a target site and capable of binding to the target site. "Substantially complementary" means that the oligonucleotide may be identical to the reverse complementary sequence of a target site, or may differ from the reverse complementary sequence of a target site in one or more (e.g., 1, 2, or 3) nucleotide positions via substitution, addition or deletion of one or more nucleotides.

The inhibitory oligonucleotides disclosed herein have the following features:

(i) The inhibitory oligonucleotides can specifically target multiple target sites of SARS-CoV-2 RNA directly.

(ii) The inhibitory oligonucleotides can cross the cell membrane and interact with the viral RNA inside cellular cytoplasm.

(iii) Since the oligonucleotide compositions of the disclosure can target the multiple-target sites in the viral RNA, this approach is able to circumvent mutations which often occur in RNA viruses.

(iv) The inhibitory oligonucleotides can be easily, quickly and economically manipulated, and different kinds of viral infections (including, but not limited to, different strains of SARS-CoV-2) can be treated.

(v) Nucleotides provide nutrition for supporting on metabolism and health of the human body.

In some embodiments, the inhibitory oligonucleotides of this disclosure comprise at least 15, 16, 17, 18, 19, 20, 21, 22, 23, 24, or 25 nucleotides. In some embodiments, the inhibitory oligonucleotides comprise not more than 50, 49, 48, 47, 46, 45, 44, 43, 42, 41, 40, 39, 38, 37, 36, 35, 34, 33, 32, or 31 nucleotides. In some embodiments, the inhibitory oligonucleotides comprise between 15-20, 15-25, 15-30, 16-20, 16-25, 16-27, 16-30, 17-20, 17-25, 17-27, 17-30, 18-20, 18-25, 18-28, 18-30, 19-20, 19-25, 19-28, 19-30, 20-22, 20-25, 20-28, 20-30, 21-22, 21-25, 21-28, 21-30, 21-25, 21-28, 21-30, or 25-30 nucleotides.

In some embodiments, the inhibitory oligonucleotides are selected from the group consisting of an antisense oligonucleotide (ASO), a small interfering RNA (siRNA), a Dicer-substrate RNA (DsiRNA), and a microRNA.

In some embodiments, the inhibitory oligonucleotide is an ASO selected from SEQ ID NOS: 9-16, and 33-40. In some embodiments, the inhibitory oligonucleotide comprises a nucleotide sequence that is at least 80%, at least 85%, at least 90%, at least 95%, at least 99% identical to a nucleotide sequence selected from SEQ ID NOS: 9-16 and 33-40.

In some embodiments, the inhibitory oligonucleotide is an ASO targeting SARS-CoV2 ORF1ab gene. In a specific embodiment, the ASO comprises a sequence as shown in SEQ ID NO: 9 or SEQ ID NO: 33. In a specific embodiment, the ASO comprises a sequence as shown in SEQ ID NO: 13 or SEQ ID NO: 37.

In some embodiments, the inhibitory oligonucleotide is an ASO targeting SARS-CoV2 RdRp gene. In a specific embodiment, the ASO comprises a sequence as shown in SEQ ID NO: 10 or SEQ ID NO: 34. In a specific embodiment, the ASO comprises a sequence as shown in SEQ ID NO: 14 or SEQ ID NO: 38.

In some embodiments, the inhibitory oligonucleotide is an ASO targeting SARS-CoV2 S-protein gene. In a specific embodiment, the ASO comprises a sequence as shown in SEQ ID NO: 11 or SEQ ID NO: 35.

In some embodiments, the inhibitory oligonucleotide is an ASO targeting SARS-CoV2 N-protein gene. In a specific embodiment, the ASO comprises a sequence as shown in SEQ ID NO: 12 or SEQ ID NO: 36. In a specific embodiment, the ASO comprises a sequence as shown in SEQ ID NO: 16 or SEQ ID NO: 40.

In some embodiments, the inhibitory oligonucleotide is an ASO targeting SARS-CoV2 E-protein gene. In a specific embodiment, the ASO comprises a sequence as shown in SEQ ID NO: 15 or SEQ ID NO: 39.

In some embodiments, the inhibitory oligonucleotide comprises a pair of Dicer-substrate RNAs (DsiRNAs) selected from the group consisting of DsiRNA pair 1 (SEQ ID NOs: 17 & 18), DsiRNA pair 2 (SEQ ID NOs: 19 & 20), DsiRNA pair 3 (SEQ ID NOs: 21 & 22), DsiRNA pair 4 (SEQ ID NOs: 23 & 24), DsiRNA pair 5 (SEQ ID NOs: 25 & 26), DsiRNA pair 6 (SEQ ID NOs: 27 & 28), DsiRNA pair 7 (SEQ ID NOs: 29 & 30), and DsiRNA pair 8 (SEQ ID NOs: 31 & 32). In some embodiments, the plurality of inhibitory oligonucleotides comprise Dicer-substrate RNA (DsiRNA) pair 1 (SEQ ID NOs: 17 & 18), DsiRNA pair 2 (SEQ ID NOs: 19 & 20), DsiRNA pair 3 (SEQ ID NOs: 21 & 22), DsiRNA pair 4 (SEQ ID NOs: 23 & 24), DsiRNA pair 5 (SEQ ID NOs: 25 & 26), DsiRNA pair 6 (SEQ ID NOs: 27 & 28), DsiRNA pair 7 (SEQ ID NOs: 29 & 30), and DsiRNA pair 8 (SEQ ID NOs: 31 & 32).

In some embodiments, the inhibitory oligonucleotide is a pair of DsiRNAs targeting SARS-CoV2 ORF1ab gene. In a specific embodiment, the pair of DsiRNAs comprises SEQ ID NOs: 17 & 18 or SEQ ID NOs: 25 & 26.

In some embodiments, the inhibitory oligonucleotide is a pair of DsiRNAs targeting SARS-CoV2 RdRb gene. In some embodiments, the pair of DsiRNAs comprises a pair of nucleotide sequences that are at least 80%, at least 85%, at least 90%, at least 95%, at least 99% identical to SEQ ID NOs: 19 & 20 or SEQ ID NOs: 27 & 28. In a specific embodiment, the pair of DsiRNAs comprises SEQ ID NOs: 19 & 20 or SEQ ID NOs: 27 & 28.

In some embodiments, the inhibitory oligonucleotide is a pair of DsiRNAs targeting SARS-CoV2 S-protein gene. In some embodiments, the pair of DsiRNAs comprises a pair of nucleotide sequences that are at least 80%, at least 85%, at least 90%, at least 95%, at least 99% identical to SEQ ID NOs: 21 & 22. In a specific embodiment, the pair of DsiRNAs comprises SEQ ID NOs: 21 & 22.

In some embodiments, the inhibitory oligonucleotide is a pair of DsiRNAs targeting SARS-CoV2 N-protein gene. In some embodiments, the pair of DsiRNAs comprises a pair of nucleotide sequences that are at least 80%, at least 85%, at least 90%, at least 95%, at least 99% identical to SEQ ID NOs: 23 & 24 or SEQ ID NOs: 31 & 32. In a specific embodiment, the pair of DsiRNAs comprises SEQ ID NOs: 23 & 24 or SEQ ID NOs: 31 & 32.

In some embodiments, the inhibitory oligonucleotide is a pair of DsiRNAs targeting SARS-CoV2 E-protein gene. In some embodiments, the pair of DsiRNAs comprises a pair of nucleotide sequences that are at least 80%, at least 85%, at least 90%, at least 95%, at least 99% identical to SEQ ID NOs: 29 & 30. In a specific embodiment, the pair of DsiRNAs comprises SEQ ID NOs: 29 & 30.

In some embodiments, the inhibitory oligonucleotides are modified. As used herein the term "modified" or "modification" refers to a change in chemical structure of one or more nucleotides of an oligonucleotide, while leaving the sequence of the oligonucleotide unchanged as compared to the sequence before the modification. In some embodiments, the modification results in improved in vivo stability of the inhibitory oligonucleotides (e.g., by preventing degradation by cellular enzymes). In some embodiments, the modification results in improved entry of the inhibitory oligonucleotides into a cell (e.g., by improving cell membrane crossing properties). In a specific embodiment, the inhibitory oligonucleotides are 2'-Deoxy, 2'-Fluoroarabino Nucleic Acid (FANA)-modified antisense oligonucleotides. In a specific embodiment, the inhibitory oligonucleotides are 2' O-Methyl RNA modified antisense oligonucleotides.

In some embodiments, the inhibitory oligonucleotides of the disclosure comprise at least one detectable label. Non-limiting examples of detectable labels include, but are not limited to, Alexa 405, Pacific Blue, Pacific Green, Alexa 488, Alexa 532, Alexa 546, Rhodamine Red X, Alexa 610, Alexa 647, DyLight-510-LS, Hydroxycoumarin, methoxy-coumarin, Cy2, FAM, Flourescein FITC, Alexa 430, R-phy-coerythrin (PE), Tamara, Cy3.5 581, Rox, Alexa fluor 568, Red 613, Texas Red, Alexa fluor 594, Alexa fluor 633, Alexa fluor 660, Alexa fluor 680, Cy5, Cy 5.5, Cy 7, and Allo-phycocyanin.

Compositions Comprising Inhibitory Oligonucleotides

One aspect of the disclosure is directed to a composition comprising at least one inhibitory oligonucleotide as described herein, wherein the at least one inhibitory oligonucleotide targets a SARS-CoV-2 gene selected from the group consisting of ORF1ab, RdRp, the S-protein gene, the N-protein gene, and the E protein gene.

In some embodiments, the composition comprises at least one inhibitory oligonucleotide, wherein the at least one inhibitory oligonucleotide is selected from the group consisting of an antisense oligonucleotide (ASO), a small interfering RNA (siRNA), a Dicer-substrate RNA (DsiRNA), and a microRNA.

In some embodiments, the composition comprises at least one ASO selected from SEQ ID NOS: 9-16, and 33-40.

In some embodiments, the composition comprises at least one pair of Dicer-substrate RNAs (DsiRNAs) selected from the group consisting of DsiRNA pair 1 (SEQ ID NOs: 17 & 18), DsiRNA pair 2 (SEQ ID NOs: 19 & 20), DsiRNA pair 3 (SEQ ID NOs: 21 & 22), DsiRNA pair 4 (SEQ ID NOs: 23 & 24), DsiRNA pair 5 (SEQ ID NOs: 25 & 26), DsiRNA pair 6 (SEQ ID NOs: 27 & 28), DsiRNA pair 7 (SEQ ID NOs: 29 & 30), and DsiRNA pair 8 (SEQ ID NOs: 31 & 32). In some embodiments, the plurality of inhibitory oligonucleotides comprise Dicer-substrate RNA (DsiRNA) pair 1 (SEQ ID NOs: 17 & 18), DsiRNA pair 2 (SEQ ID NOs: 19 & 20), DsiRNA pair 3 (SEQ ID NOs: 21 & 22), DsiRNA pair 4 (SEQ ID NOs: 23 & 24), DsiRNA pair 5 (SEQ ID NOs: 25 & 26), DsiRNA pair 6 (SEQ ID NOs: 27 & 28), DsiRNA pair 7 (SEQ ID NOs: 29 & 30), and DsiRNA pair 8 (SEQ ID NOs: 31 & 32).

In one aspect, the disclosure is directed to a composition comprising a plurality of inhibitory oligonucleotides, wherein the plurality of inhibitory oligonucleotides targets at least two SARS-CoV-2 genes selected from the group consisting of ORF1ab, RdRp, the S-protein gene, the N-protein gene, and the E protein gene. In some embodiments, the plurality of inhibitory oligonucleotides targets all of the ORF1ab, RdRp, S-protein, N-protein and E protein genes.

In some embodiments, a selected SARS-CoV-2 gene is targeted by at least two inhibitory oligonucleotides. In some embodiments, a selected SARS-CoV-2 gene is targeted by two, three, four, five, or six different, e.g., non-overlapping, inhibitory oligonucleotides. In some embodiments, the at least two inhibitory oligonucleotides simultaneously target at least two different sites on at least two SARS-CoV-2 genes.

In some embodiments, the plurality of inhibitory oligonucleotides comprises at least two, at least three, at least four, at least five, at least six, at least seven, or more oligonucleotides which comprise a nucleotide sequence selected from the group consisting of SEQ ID NOS: 9-16 and modified forms of SEQ ID NOS: 9-16 (e.g., SEQ ID NOS: 33-40). In some embodiments, the plurality of inhibitory oligonucleotides comprises all eight oligonucleotides as shown in SEQ ID NOS: 9-16 or modified forms of SEQ ID NOS: 9-16 (e.g., SEQ ID NOS: 33-40), respectively.

In some embodiments, the plurality of inhibitory oligonucleotides comprise at least two, at least three, at least four, at least five, at least six, at least seven, or more pairs of Dicer-substrate RNAs (DsiRNAs) selected from the group consisting of DsiRNA pair 1 (SEQ ID NOs: 17 & 18), DsiRNA pair 2 (SEQ ID NOs: 19 & 20), DsiRNA pair 3 (SEQ ID NOs: 21 & 22), DsiRNA pair 4 (SEQ ID NOs: 23 & 24), DsiRNA pair 5 (SEQ ID NOs: 25 & 26), DsiRNA pair 6 (SEQ ID NOs: 27 & 28), DsiRNA pair 7 (SEQ ID NOs: 29 & 30), and DsiRNA pair 8 (SEQ ID NOs: 31 & 32). In some embodiments, the plurality of inhibitory oligonucleotides comprise Dicer-substrate RNA (DsiRNA) pair 1 (SEQ ID NOs: 17 & 18), DsiRNA pair 2 (SEQ ID NOs: 19 & 20), DsiRNA pair 3 (SEQ ID NOs: 21 & 22), DsiRNA pair 4 (SEQ ID NOs: 23 & 24), DsiRNA pair 5 (SEQ ID NOs: 25 & 26), DsiRNA pair 6 (SEQ ID NOs: 27 & 28), DsiRNA pair 7 (SEQ ID NOs: 29 & 30), and DsiRNA pair 8 (SEQ ID NOs: 31 & 32).

In some embodiments, the plurality of inhibitory oligonucleotides are expressed from at least one nucleic acid vector (i.e., one or more vectors). In some embodiments, the at least one nucleic acid vector is selected from a viral vector, a non-viral vector, an integrative vector, or a non-integrative vector. In some embodiments, the plurality of inhibitory oligonucleotides are expressed from one nucleic acid vector.

In some embodiments, the inhibitory oligonucleotides are 2' O-Methyl RNA modified antisense oligonucleotides and have a nucleotide sequence selected from the group consisting of SEQ ID NO: 33, SEQ ID NO: 34, SEQ ID NO: 35, SEQ ID NO: 36, SEQ ID NO: 37, SEQ ID NO: 38, SEQ ID NO: 39, and SEQ ID NO: 40.

In some embodiments, the inhibitory oligonucleotides are in modified forms that comprise phosphorothioate bonds that render them resistant to nucleases.

In some embodiment, the inhibitory oligonucleotides comprise a 5-methyl dC modification at the in 5' ends.

In some embodiments, the composition comprises a pharmaceutically acceptable carrier. In some embodiments, the pharmaceutically acceptable carrier comprises nanoparticles or other delivery vehicles (e.g., lipid-based delivery vehicles such as lipofectamine and oligofectamine) to which the plurality of inhibitory oligonucleotides is conjugated.

Compositions Comprising Inhibitory Peptides

ACE2 is an enzyme that plays a critical role in human biology and metabolism. ACE2 also functions as the receptor for the SARS-CoV-2 for its cellular entry. Disclosed herein are peptides designed to block SARS-CoV-2 S-protein receptor binding domain (RBD) from interacting with ACE2 ligand binding domain (LBD), thereby preventing viral entry.

The inventors recognized that if a peptide that is too long is used to treat the disease, that peptide's effect would be limited because of folding of the 3D structure during the binding on SARS-CoV-2. Therefore, the inventors designed peptides that are long enough to prevent ACE2 LBD and SARS-CoV-2 RBD interaction, but short enough to not require secondary structures to work. In some embodiments, the length of a peptide is about 15 amino acids, about 16 amino acids, about 17 amino acids, about 18 amino acids, about 19 amino acids, about 20 amino acids, about 21 amino acids, about 22 amino acids, about 23 amino acids, about 24 amino acids, about 25 amino acids, about 26 amino acids, about 27 amino acids, about 28 amino acids, about 29 amino acids, about 30 amino acids, about 31 amino acids, about 32 amino acids, about 33 amino acids, about 34 amino acids, or about 35 amino acids. In some embodiments, the length of a peptide is not more than 50 amino acids, not more than 49 amino acids, not more than 48 amino acids, not more than 47 amino acids, not more than 46 amino acids, not more than 45 amino acids, not more than 44 amino acids, not more than 43 amino acids, not more than 42 amino acids, not more than 41 amino acids, not more than 40 amino acids, not more than 39 amino acids, not more than 38 amino acids, not more than 37 amino acids, not more than 36 amino acids, not more than 37 amino acids, not more than 36 amino acids, not more than 35 amino acids, not more than 34 amino acids, not more than 33 amino acids, not more than 32 amino acids, not more than 31 amino acids, or not more than 30 amino acids in length. As used herein, the term "about" refers to ±10% of any given value. The inhibitory peptides bind to ACE2 LBD or SARS-CoV-2 RBD by mimicking a portion of ACE2 LBD or a portion of SARS-CoV-2 RBD. A "portion" means a contiguous peptide sequence of at least 15, 16, 17, 18, 19, 20, 21, 22, 23, 24, 25, 26, 27, 28, 29, 30, 31, 32, 33, 34 or 35 amino acids.

In some embodiments, the inhibitory peptides of the instant disclosure comprise modifications to a peptide of a naturally occurring protein, e.g., by adding, substituting or removing one or more amino acids in a peptide of a naturally occurring protein (e.g., at the N-terminus, the C-terminus or within the peptide) such that the modified peptide differs in sequence from the peptide of a naturally occurring protein; by including one or more non-natural amino acids in the peptide, by making a modification (e.g., a label or a tag) to the side chain of an amino acid in the peptide.

The inhibitory peptides disclosed herein can also serve as antigens for generation of antibodies against these peptides. The generated antibodies can bind to the RBD domain of the S protein of SARS-CoV-2, or to the LBD of human ACE2, thereby blocking the interaction between the S protein and human ACE receptor. Thus, the inhibitory peptides can be administered to a subject and antibodies can be generated in the subject; or alternatively, the inhibitory peptides, especially peptides that mimic the binding surface of the RBD domain of the S protein of SARS-CoV-2 (such as peptide 6 in Table 5, SEQ ID NO: 45), can be used to produce antibodies in vitro or in a host animal, which antibodies are then administered to a subject.

In one aspect, the disclosure is directed to a composition comprising at least one peptide mimicking the ligand binding domain (LBD) of human Angiotensin-converting Enzyme 2 (ACE2) protein, wherein the at least one peptide prevents binding of the S-protein of SARS-CoV-2 to the human ACE2 protein. The amino acid sequence of the human ACE2 protein is shown in SEQ ID NO: 55. The nucleotide sequence of the human ACE2 gene is shown in GenBank Accession Number: AB046569.1. The amino acids in the ACE2 protein that directly interact with SARS-CoV-2 S-protein are as follows: Q24, T27, F28, D30, K31, H34, E35, E37, D38, Y41, Q42, L79, M82, Y83, N330, K353, G354, D355, R357 and R393 of SEQ ID NO: 55.

In some embodiments, the LBD of human ACE2 is as defined in Lan, Jun et al. (*Nature*, vol. 581, 7807 (2020): 215-220, Extended Data Table 2|Contact residues of the SARS-CoV-2 RBD-ACE2 and SARS-CoV RBD-ACE2 interfaces), which is incorporated herein in its entirety. In some embodiments, the LBD of human ACE2 comprises the amino acid sequence of any one of SEQ ID NOS: 41-44, 54, and 63-82. In some embodiments, the LBD of human ACE2 comprises the amino acid sequence shown by SEQ ID NO: 56, or an amino acid sequence that is at least 80%, at least 85%, at least 90%, at least 95%, at least 99% identical to SEQ ID NO: 56.

In some embodiments, the composition comprises at least one peptide. In some embodiments, the at least one peptide is between 15 and 30 amino acids in length (e.g., about 15, 16, 17, 18, 19, 20, 21, 22, 23, 24, 25, 26, 27, 28, 29, or 30 amino acids in length).

In some embodiments, the peptide is an LBD mimic peptide (e.g., a peptide that correspond to a region/segment of the LBD).

In some embodiments, the LBD mimic peptide comprises a core amino acid sequence as shown in SEQ ID NO: 63, or an amino acid sequence that is at least 80%, at least 85%, at least 90%, at least 95%, at least 99% identical to SEQ ID NO: 63. In some embodiments, the LBD mimic peptide comprises an amino acid sequence as shown in SEQ ID NO: 63 and has a length of at least 15, 16, 17, 18, 19, 20, 21, 22, 23, 24, 25, 26, 27, 28, 29, or 30 amino acids. In a specific embodiment, the LBD mimic peptide comprises an amino acid sequence as shown in SEQ ID NO: 64, or an amino acid sequence that is at least 80%, at least 85%, at least 90%, at least 95%, at least 99% identical to SEQ ID NO: 64. In a specific embodiment, the LBD mimic peptide comprises an amino acid sequence as shown in SEQ ID NO: 41, or an amino acid sequence that is at least 80%, at least 85%, at least 90%, at least 95%, at least 99% identical to SEQ ID NO: 41. In a specific embodiment, the LBD mimic peptide comprises an amino acid sequence as shown in SEQ ID NO: 65, or an amino acid sequence that is at least 80%, at least 85%, at least 90%, at least 95%, at least 99% identical to SEQ ID NO: 65. In a specific embodiment, the LBD mimic peptide comprises an amino acid sequence as shown in SEQ ID NO: 66, or an amino acid sequence that is at least 80%, at least 85%, at least 90%, at least 95%, at least 99% identical to SEQ ID NO: 66.

In some embodiments, the LBD mimic peptide comprises a core amino acid sequence as shown in SEQ ID NO: 67, or an amino acid sequence that is at least 80%, at least 85%, at least 90%, at least 95%, at least 99% identical to SEQ ID NO: 67. In some embodiments, the LBD mimic peptide comprises an amino acid sequence as shown in SEQ ID NO: 67 and has a length of at least 15, 16, 17, 18, 19, 20, 21, 22, 23, 24, 25, 26, 27, 28, 29, or 30 amino acids. In a specific embodiment, the LBD mimic peptide comprises an amino acid sequence as shown in SEQ ID NO: 42, or an amino acid sequence that is at least 80%, at least 85%, at least 90%, at least 95%, at least 99% identical to SEQ ID NO: 42. In a specific embodiment, the LBD mimic peptide comprises an amino acid sequence as shown in SEQ ID NO: 68, or an amino acid sequence that is at least 80%, at least 85%, at least 90%, at least 95%, at least 99% identical to SEQ ID NO: 68. In a specific embodiment, the LBD mimic peptide comprises an amino acid sequence as shown in SEQ ID NO: 69, or an amino acid sequence that is at least 80%, at least 85%, at least 90%, at least 95%, at least 99% identical to SEQ ID NO: 69. In a specific embodiment, the LBD mimic peptide comprises an amino acid sequence as shown in SEQ ID NO: 70, or an amino acid sequence that is at least 80%, at least 85%, at least 90%, at least 95%, at least 99% identical to SEQ ID NO: 70.

In some embodiments, the LBD mimic peptide comprises a core amino acid sequence as shown in SEQ ID NO: 71, or an amino acid sequence that is at least 80%, at least 85%, at least 90%, at least 95%, at least 99% identical to SEQ ID NO: 71. In some embodiments, the LBD mimic peptide comprises an amino acid sequence as shown in SEQ ID NO: 71 and has a length of at least 15, 16, 17, 18, 19, 20, 21, 22, 23, 24, 25, 26, 27, 28, 29, or 30 amino acids. In a specific embodiment, the LBD mimic peptide comprises an amino acid sequence as shown in SEQ ID NO: 43, or an amino acid sequence that is at least 80%, at least 85%, at least 90%, at least 95%, at least 99% identical to SEQ ID NO: 43. In a specific embodiment, the LBD mimic peptide comprises an amino acid sequence as shown in SEQ ID NO: 72, or an amino acid sequence that is at least 80%, at least 85%, at least 90%, at least 95%, at least 99% identical to SEQ ID NO: 72. In a specific embodiment, the LBD mimic peptide comprises an amino acid sequence as shown in SEQ ID NO: 73, or an amino acid sequence that is at least 80%, at least 85%, at least 90%, at least 95%, at least 99% identical to SEQ ID NO: 73. In a specific embodiment, the LBD mimic peptide comprises an amino acid sequence as shown in SEQ ID NO: 74, or an amino acid sequence that is at least 80%, at least 85%, at least 90%, at least 95%, at least 99% identical to SEQ ID NO: 74.

In some embodiments, the LBD mimic peptide comprises a core amino acid sequence as shown in SEQ ID NO: 75, or an amino acid sequence that is at least 80%, at least 85%, at least 90%, at least 95%, at least 99% identical to SEQ ID NO: 75. In some embodiments, the LBD mimic peptide comprises an amino acid sequence as shown in SEQ ID NO: 75 and has a length of at least 15, 16, 17, 18, 19, 20, 21, 22, 23, 24, 25, 26, 27, 28, 29, or 30 amino acids. In a specific embodiment, the LBD mimic peptide comprises an amino acid sequence as shown in SEQ ID NO: 44, or an amino acid sequence that is at least 80%, at least 85%, at least 90%, at least 95%, at least 99% identical to SEQ ID NO: 44. In a specific embodiment, the LBD mimic peptide comprises an amino acid sequence as shown in SEQ ID NO: 76, or an amino acid sequence that is at least 80%, at least 85%, at least 90%, at least 95%, at least 99% identical to SEQ ID NO: 76. In a specific embodiment, the LBD mimic peptide comprises an amino acid sequence as shown in SEQ ID NO: 77, or an amino acid sequence that is at least 80%, at least 85%, at least 90%, at least 95%, at least 99% identical to SEQ ID NO: 77. In a specific embodiment, the LBD mimic peptide comprises an amino acid sequence as shown in SEQ ID NO: 78, or an amino acid sequence that is at least 80%, at least 85%, at least 90%, at least 95%, at least 99% identical to SEQ ID NO: 78.

In some embodiments, the LBD mimic peptide comprises a core amino acid sequence as shown in SEQ ID NO: 79, or an amino acid sequence that is at least 80%, at least 85%, at least 90%, at least 95%, at least 99% identical to SEQ ID NO: 79. In some embodiments, the LBD mimic peptide comprises an amino acid sequence as shown in SEQ ID NO: 79 and has a length of at least 15, 16, 17, 18, 19, 20, 21, 22, 23, 24, 25, 26, 27, 28, 29, or 30 amino acids. In a specific embodiment, the LBD mimic peptide comprises an amino acid sequence as shown in SEQ ID NO: 54, or an amino acid sequence that is at least 80%, at least 85%, at least 90%, at least 95%, at least 99% identical to SEQ ID NO: 54. In a specific embodiment, the LBD mimic peptide comprises an amino acid sequence as shown in SEQ ID NO: 80, or an amino acid sequence that is at least 80%, at least 85%, at least 90%, at least 95%, at least 99% identical to SEQ ID NO: 80. In a specific embodiment, the LBD mimic peptide comprises an amino acid sequence as shown in SEQ ID NO: 81, or an amino acid sequence that is at least 80%, at least 85%, at least 90%, at least 95%, at least 99% identical to SEQ ID NO: 81. In a specific embodiment, the LBD mimic peptide comprises an amino acid sequence as shown in SEQ ID NO: 82, or an amino acid sequence that is at least 80%, at least 85%, at least 90%, at least 95%, at least 99% identical to SEQ ID NO: 82.

In a specific embodiment, the composition comprises a plurality of LBD mimic peptides (e.g., peptides that correspond to different regions/segments of the LBD). In some embodiments, the composition comprises LBD mimic peptides that comprise an amino acid sequence selected from the group consisting of SEQ ID NOs: 41-44, 54, and 63-82, or an amino acid sequence that is at least 80%, at least 85%, at least 90%, at least 95%, at least 99% identical to an amino acid sequence selected from the group consisting of SEQ ID NOs: 41-44, 54, and 63-82. In some embodiments, the composition comprises a plurality of peptides comprising an amino acid sequence selected from the group consisting of SEQ ID NOs: 41-44, 54, and 63-82. In some embodiments, the composition comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24 or 25 peptides, and each peptide in the composition is selected from the group of peptides comprising an amino acid sequence as shown in SEQ ID NOS: 41-44, 54, and 63-82, or an amino acid sequence that is at least 80%, at least 85%, at least 90%, at least 95%, at least 99% identical to an amino acid sequence selected from the group consisting of SEQ ID NOs: 41-44, 54, and 63-82.

Another aspect of the disclosure is directed to a composition comprising a peptide mimicking the receptor binding domain (RBD) of the S-Protein of SARS-CoV-2 (an RBD mimic peptide), wherein the peptide prevents binding of the S-protein of SARS-CoV-2 to the human ACE2 protein. In some embodiments, the full-length S-protein of SARS-CoV-2 comprises an amino acid sequence as shown in SEQ ID NO: 62 (GenBank Accession No: QHD43416.1), or an amino acid sequence that is at least 80%, at least 85%, at least 90%, at least 95%, at least 99% identical to SEQ ID NO: 62.

In some embodiments, the RBD-mimic peptide comprises a core amino acid sequence as shown in SEQ ID NO: 45, or an amino acid sequence that is at least 80%, at least 85%, at least 90%, at least 95%, at least 99% identical to SEQ ID NO: 45. In a specific embodiment, the RBD-mimic peptide comprises an amino acid sequence as shown in SEQ ID NO: 45 and has a length of at least 23, 24, 25, 26, 27, 28, 29, or 30 amino acids, wherein the additional amino acids are selected from the amino acids immediate N or C terminal of the SEQ ID NO: 45 core sequence in the full length S-protein as shown by SEQ ID NO: 62. SEQ ID NO: 45 corresponds to amino acids 17-39 of SEQ ID NO: 69. In some embodiments, the RBD-mimic peptide comprises a sequence between amino acids 10-39 and 17-46 of SEQ ID NO: 62, and has a length of at least 23, 24, 25, 26, 27, 28, 29, or 30 amino acids (e.g., amino acids 10-39, 11-39, 11-40, 12-39, 12-40, 12-41, 13-39, 13-40, 13-41, 13-42, 14-39, 14-40, 14-41, 14-42, 14-43, 15-39, 15-40, 15-41, 15-42, 15-43, 15-44, 16-39, 16-40, 16-41, 16-42, 16-43, 16-44, 16-45, 17-39 (SEQ ID NO:42), 17-40, 17-41, 17-42, 17-43, 17-44, 17-45, or 17-46 of SEQ ID NO: 62).

In some embodiments, the composition comprises a plurality of LBD and/or RBD mimic peptides (e.g., peptides that correspond to different regions/segments of the LBD and/or at least one peptide that corresponds to different regions/segments of the RBD).

In some embodiments, the at least one peptide is labeled. In some embodiment the label is a fluorescent label. In some exemplary embodiments, the fluorescent label is selected from the group consisting of Alexa 405, Pacific Blue, Pacific Green, Alexa 488, Alexa 532, Alexa 546, Rhodamine Red X, Alexa 610, Alexa 647, DyLight-510-LS, Hydroxycoumarin, methoxycoumarin, Cy2, FAM, Flourescein FITC, Alexa 430, R-phycoerythrin (PE), Tamara, Cy3.5 581, Rox, Alexa fluor 568, Red 613, Texas Red, Alexa fluor 594, Alexa fluor 633, Alexa fluor 660, Alexa fluor 680, FAM (6-carboxyfluorescein), Cy 5.5, Cy 7, and Allophycocyanin In some embodiments, the composition comprises a pharmaceutically acceptable carrier as described herein. In some embodiments, the pharmaceutically acceptable carrier comprises nanoparticles or other delivery vehicles (e.g., lipid-based carriers such as lipofectamine, oligofectamine, etc.) to which the at least one peptide is conjugated.

Dietary Supplements

The instant disclosure is also directed to dietary supplements compositions that are capable of supporting the immune system and helping with viral infection, such as SARS-CoV-2.

Inventors of the instant disclosure have formulated dietary supplements that comprise at least one of the compositions (comprising inhibitory oligonucleotides, inhibitory peptides, or a combination thereof) described above.

In some embodiments, a dietary supplement comprises inhibitory oligonucleotides at an amount between about 0.1 microgram (mcg) and about 1 milligram (mg) per serving of the dietary supplement. In some embodiments, a dietary supplement comprises about 0.1 mcg, 0.5 mcg, 1 mcg, 1.5 mcg, 2 mcg, 2.5 mcg, 5 mcg, 8 mcg, 9 mcg, 10 mcg, 15 mcg, 20 mcg, 25 mcg, 30 mcg, 50, mcg, 100 mcg, 150 mcg, 200 mcg, 250 mcg, 300 mcg, 350 mcg, 400 mcg, 450 mcg, 500 mcg, 550 mcg, 600 mcg, 650 mcg, 700 mcg, 750 mcg, 800 mcg, 850 mcg, 900 mcg, 950 mcg or 1000 mcg (1 mg) of inhibitory oligonucleotides per serving of the dietary supplement. As used herein, a "serving of a dietary supplement" refers to the maximum amount recommended, as appropriate, for consumption per eating occasion, or in the absence of recommendations, 1 unit (e.g., tablet, capsule, packet, teaspoonful, etc.). For example, if the directions on the label say to take 1-3 tablets with breakfast, the serving size would be 3 tablets. If the dietary supplement is a liquid, a serving may be measured in milliliters (ml) (e.g., 0.5 ml, 1 ml, 2 ml, etc.) or teaspoons.

In some embodiments, a dietary supplement comprises inhibitory peptides at an amount between about 0.1 microgram (mcg) and about 10 milligram (mg) per serving of the dietary supplement. In some embodiments, a dietary supplement comprises about 0.1 mcg, 0.5 mcg, 1 mcg, 1.5 mcg, 2 mcg, 2.5 mcg, 5 mcg, 8 mcg, 9 mcg, 10 mcg, 15 mcg, 20 mcg, 25 mcg, 30 mcg, 50, mcg, 100 mcg, 150 mcg, 200 mcg, 250 mcg, 300 mcg, 350 mcg, 400 mcg, 450 mcg, 500 mcg, 550 mcg, 600 mcg, 650 mcg, 700 mcg, 750 mcg, 800 mcg, 850 mcg, 900 mcg, 950 mcg, 1000 mcg (1 mg), 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg or 10 mg of inhibitory peptides per serving of the dietary supplement.

In some embodiments, the dietary supplement comprises a composition comprising a plurality of inhibitory oligonucleotides as described herein, wherein the plurality of inhibitory oligonucleotides targets at least two SARS-CoV-2 genes selected from the group consisting of ORF1ab, RdRp, the S-protein gene, the N-protein gene, and the E protein gene.

In some embodiments, the dietary supplement comprises a composition as described herein comprising at least one peptide mimicking the ligand binding domain (LBD) of human ACE2 protein, wherein the at least one peptide prevents binding of the S-protein of SARS-CoV-2 to the human ACE2 protein.

In some embodiments, the dietary supplement comprises both a composition comprising a plurality of inhibitory oligonucleotides and a composition comprising at least one peptide, as described herein. In some embodiments, the dietary supplement comprises a composition comprising a plurality of inhibitory oligonucleotides and at least one peptide, as described herein.

In some embodiments, the dietary supplement the disclosure further comprises at least one additional nutrient selected from Vitamin C, Vitamin B6, Vitamin B12, Vitamin D, Zinc, polypeptides, nucleotide, L-arginine or peppermint oil.

In some embodiments, the dietary supplement of the disclosure is formulated for oral (e.g., pills, tablets, capsules, inhalers, liquid formulations), nasal (e.g., nasal sprays), ocular (e.g. eye drops), ear (e.g. ear drops), or topical (e.g., cream, lotion, shampoo, paper towels, wet wipes) application.

In some embodiments, in addition to at least one of the compositions (comprising inhibitory oligonucleotides, inhibitory peptides, or a combination thereof) described herein, an oral tablet comprises:
1) Vitamin C, 1-1000 mg
2) Vitamin B-mix (B6 and B12), 0.1-0.6 mg B6/1-2.4 mcg B12
3) Vitamin D, 1-800 IU
4) Zinc supplement, 1-50 mg
5) Polypeptides, 1-1000 mcg
6) L-Arginine, 1-10 mg
7) Peppermint oil, 1-2 mg.

In some embodiments, an oral drop/spray/tablet formula comprises Inhibitory Polypeptides (0.1 mcg-10 mg) and/or Inhibitory Nucleotides (0.1 mcg-1 mg) and one or more of: N-Acetyl Cysteine (1-100 mg), L-Arginine (1-10 mg), Glutathione (0.1-10 mg), Vitamin D3 (1-5000 IU), Vitamin C (1-1000 mg), Zinc (1 mcg-50 mg), Vitamin B6 (1 mcg-800 mcg), Vitamin B12 (0.1-10 mcg), Peppermint (leaf powder or oil) (10 mcg-5 mg), DHA (Docosahexaenoic acid) or EPA (Eicosapentaenoic acid) (5 mg) and other ingredients such as sweeteners (e.g., sugar, stevia), preservatives (e.g., potassium sorbate), glycerin and/or sorbic acid (amounts in parentheses are per serving (e.g., 0.5 ml Droplet for liquid)).

In a specific embodiment, an oral drop/spray/tablet formula comprises Inhibitory Polypeptides (50 mcg) and/or Inhibitory Nucleotides (2.5 mcg), and one or more of: N-Acetyl Cysteine (25 mg), L-Arginine (2.5 mg), Glutathione (2.5 mg), Vitamin D3 (500 IU), Vitamin C (50 mg), Zinc (65 mcg), Vitamin B6 (30 mcg), Vitamin B12 (0.5 mcg), Peppermint (leaf powder or oil) (0.1 mg), DHA (Docosahexaenoic acid) or EPA (Eicosapentaenoic acid) (5 mg) and other ingredients such as sweeteners (e.g., sugar, stevia), preservatives (e.g., potassium sorbate), glycerin and/or sorbic acid (amounts in parentheses are per serving (e.g., 0.5 ml droplet)).

In some embodiments, a nasal spray formula comprises: N-Acetyl Cysteine (1-100 mg), Glutathione (0.1-10 mg), Vitamin C (1-1000 mg), Vitamin B6 (1 mcg-800 mcg), Vitamin B12 (0.1-10 mcg), Inhibitory Polypeptides (0.1 mcg-10 mg), Inhibitory Nucleotides (0.1 mcg-1 mg), Xylitol (0.1 mg-50 mg) and saline (amounts in parentheses are per serving (e.g., 0.5 ml Droplet for liquid)).

In a specific embodiment, a nasal spray formula comprises: N-Acetyl Cysteine (2.5 mg), Glutathione (1 mg), Vitamin C (5 mg), Vitamin B6 (5 mcg), Vitamin B12 (0.5 mcg), Inhibitory Polypeptides (20 mcg), Inhibitory Nucleotides (5 mcg), Xylitol (0.25 mg) and saline (amounts in parentheses are per serving (e.g., 0.5 ml Droplet for liquid)).

In some embodiments, a nasal spray formula comprises:
1) Vitamin C, 1-1000 mg
2) Vitamin B-mix (B6 and B12), 0.1-0.6 mg/1-2.4 ug
3) Vitamin D, 1-800 IU
4) Zinc supplement, 1-50 mg
5) Polypeptides, 1-1000 ug
6) L-Arginine, 1-10 mg
7) Peppermint oil, 1-2 mg In some embodiments, a dietary supplement is formulated for kids (ages between 5-12) or teens (ages between 13-19). In some embodiments, a kid/teen formula comprises Inhibitory Polypeptides (0.1 mcg-10 mg) and/or Inhibitory Nucleotides (0.1 mcg-1 mg) and one or more of Vitamin A (0.1-10 mg), Vitamin C (1-1000 mg), Vitamin D (0.1 mcg, 1 mg), Vitamin E (1 mg-100 mg), Vitamin K (0.1 mcg-1 mg), Vitamin B6 (1 mcg-5 mg), Vitamin B12 (0.1 mcg-10 meg), Zinc (0.1 mg-50 mg) and other ingredients (calcium (1 mg-500 mg), Iron (0.1 mg-15 mg), sweetener (sugar or stevia—0.1 g-3 g) (amounts in parentheses are per serving (e.g., 1 pellet or gummy per day)). It is understood that In a specific embodiment, a teen formula comprises: Vitamin A (1.5 mg), Vitamin C (80 mg), Vitamin D (20 mcg), Vitamin E (27 mg), Vitamin K (20 mg), Vitamin B6 (1.4 mg), Vitamin B12 (3 mcg), Inhibitory Polypeptides (200 mcg), Inhibitory Nucleotides (5 mcg), Zinc (0.5 mg) and other ingredients (calcium (120 mg), Iron (9 mg), sweetener (sugar or stevia—0.5 g) (amounts in parentheses are per serving (e.g., 1 pellet or gummy per day)).

In a specific embodiment, a kid formula comprises: Vitamin A (0.3 mg), Vitamin C (40 mg), Vitamin D (10 mcg), Vitamin E (6 mg), Vitamin K (10 mg), Vitamin B6 (0.7 mg), Vitamin B112 (2 mcg), Inhibitory Polypeptides (50 mcg), Inhibitory Nucleotides (2.5 mcg), Zinc (0.1 mg) and other ingredients (calcium (25 mg), Iron (1 mg), sweetener (sugar or stevia—0.5 g) (amounts in parentheses are per serving (e.g., 1 pellet or gummy per day)).

In some embodiments, the dietary supplement is formulated for oral (e.g., pills, tablets, capsules, inhalers, liquid formulations), nasal (e.g., nasal sprays), eye (eye drop or ointment), ear (ear drop), or topical (e.g., cream, lotion, shampoo, paper towels, wet wipes) application.

Nucleic Acid Vectors

Another aspect of the disclosure is directed to a nucleic acid vector encoding at least one inhibitory oligonucleotides disclosed herein. In some embodiments, the disclosure is directed to a nucleic acid vector encoding a plurality of inhibitory oligonucleotides disclosed herein.

In some embodiments, a nucleic acid vector encodes at least two inhibitory oligonucleotides. In some embodiments, a nucleic acid vector encodes for at least two inhibitory oligonucleotides of different types (e.g., at least two inhibitory oligonucleotides selected from an antisense oligonucleotide, a small interfering RNA (siRNA), a Dicer-substrate RNA (DsiRNA), and a microRNA).

In some embodiments, each nucleic acid vector encodes only one inhibitory oligonucleotide, and a combination of such nucleic acid vectors are provided.

In some embodiments, the nucleic acid vectors are suitable for delivery to a subject and capable of expression of the encoded inhibitory oligonucleotides in the subject.

In some embodiments, the nucleic acid vector is an integrative vector, i.e., a vector that integrates into the genome of a host cell. In some embodiments, the nucleic acid vector is a non-integrative vector. In some embodiments, the nucleic acid vector is viral vector, e.g., an Adeno-Associated Virus (AAV)-based vector, or a lentiviral vector. In some embodiments, the nucleic acid vector is a non-viral vector.

In some embodiments, the AAV-based vector is selected from AAV1, AAV2, AAV3, VAAV4, AAV5, AAV6, AAV7, AAV8, AAV9, AAV10, AAV 11, AAV12, and AAV13 and AAV14. In some embodiments, the AAV-derived vector is one of the vectors described in Lykken, Erik Allen, et al., *Journal of Neurodevelopmental Disorders* 10.1 (2018): 16, incorporated herein in its entirety.

In some embodiments, the nucleic acid vector has the ability to integrate into the genome of a cell (i.e., is an integrative vector). In some embodiments, the nucleic acid vector does not have the ability to integrate into the genome of a cell (i.e., is a non-integrative vector).

In some embodiments, the nucleic acid vector is a lentiviral vector. In some embodiments, lentiviral vector has the ability to integrate into the genome of a cell. In some embodiments, the lentiviral vector does not have the ability to integrate into the genome of a cell (e.g., as described in Philippe, Stéphanie, et al. *PNAS,* 103.47 (2006): 17684-17689, and Lai et al., *PNAS* 97 (21), (2000): 11297-11302, both of which are incorporated herein in their entirety). In some embodiments, the lentiviral vector has a defective (i.e., nonfunctional) integrase (which prevents its genome integration).

Methods for Gene Therapy

Another aspect of the disclosure is directed at a method of treating or preventing a SARS-CoV-2 infection comprising expressing a plurality of inhibitory oligonucleotides in a target cell, wherein the plurality of inhibitory oligonucleotides are those disclosed herein.

In some embodiments, the target cell is a mammalian cell expressing an ACE2 receptor. In some embodiments, the target cell is a human cell. In some embodiments, the target cell is a lung epithelial cell. In some embodiments, the target cell is selected from the group consisting of a small airway epithelial cell, a bronchial/tracheal epithelial cell, and a nasal epithelial cell.

In some embodiments, the plurality of inhibitory oligonucleotides are expressed from at least one nucleic acid vector (i.e., one or more vectors) disclosed herein.

In some embodiments, the at least one vector is administered to a subject in need via oral (e.g., pills, tablets, capsules, inhalers, liquid formulations), nasal (e.g., nasal sprays), ocular (e.g., eye drops), ear (e.g., ear drops), intravenous (i.v.) injection or topical (e.g., cream, lotion, shampoo) routes.

In some embodiments, the at least one vector is selected from a viral vector, (e.g., an Adeno-Associated Virus (AAV)-based vector, or a lentiviral vector), or a non-viral vector (e.g., lipid, carbon, metal, or polymer nanoparticles), an integrative vector, or a non-integrative vector (e.g., a lentiviral vector with a defective integrase).

In some embodiments, combinations of gene therapy application include the following gene therapy vectors described herein:
1) AAV-ASO (A1 to A8): 1) AAV-U6-A1_H1-A2_CMV/EF-A3-E2A-A4; 2) AAV-U6-A5_H1-A6 CMV/EF-A7-E2A-A8.
2) AAV-shRNA (siRNA1 to siRNA8): 1) AAV-US-shRNA1_H1-shRNA2 CMV-shRNA3_EF-shRNA4; 2) AAV-US-shRNA5_H1-shRNA6_CMV-shRNA7_EF-shRNA8.

Methods for Treatment

Another aspect of the disclosure is directed to a method for treating a SARS-CoV-2 infection comprising administering to a subject an effective amount of; 1) a composition; 2) a nucleic acid vector; 3) combination of nucleic acid vectors; or 4) a combination thereof. The compositions (comprising inhibitory oligonucleotides, peptides, or a combination thereof), nucleic acid vectors, and combination of nucleic acid vectors are described above.

Pharmaceutical Carriers and Administration

A "pharmaceutically-acceptable carrier" includes any of the standard pharmaceutical carriers. Examples of suitable carriers are well known in the art and may include, but are not limited to, any of the standard pharmaceutical carriers such as a phosphate buffered saline solution and various wetting agents. Other carriers may include additives used in tablets, granules and capsules, and the like. Typically, such carriers contain excipients such as starch, milk, sugar, certain types of clay, gelatin, stearic acid or salts thereof, magnesium or calcium stearate, talc, vegetable fats or oils, gum, glycols or other known excipients. Such carriers may also include flavor and color additives or other ingredients. Compositions comprising such carriers are formulated by well-known conventional methods.

In some embodiments, the pharmaceutically acceptable carrier of the present disclosure comprises non-viral delivery vehicles such as nanoparticles (as described in Jin, Sha, and Kaiming Ye., (2007), *Biotechnology Progress,* 23.1: 3241; Z. Liu, et al., *Advanced Drug Delivery Reviews*, vol. 60, no. 15, 2008, pp. 1650-1662; and Saravanakumar G. et al., *Curr. Med. Chem.,* 19(19), 2012, pp. 3212-3229, all of which are herein incorporated by reference in their entirety). In some embodiments, the nanoparticles are lipid nanoparticles (as described in WO2017218704A1, which is incorporated by reference in its entirety). In some embodiments, the nanoparticles are lipid nanoparticles, carbon nanoparticles, metal nanoparticles (e.g., iron nanoparticles), or polymer nanoparticles.

In some embodiments, the pharmaceutically acceptable carrier of the present disclosure comprises lipid-based delivery vehicles such as liposomes (as described in U.S. Ser. No. 10/258,629B2; Gabizon, A. et al. *J Control Release* 1998, 53 (1-3), 275-9; Bomgaars, L. et al., *J Clin. Oncol.* 2004, 22 (19), 3916-21; Drummond, D. C. et al, *Pharmacol. Rev.* 1999, 51 (4), 691-743; Allen, T. M.; Cullis, P. R., Science 2004, 303 (5665), 1818-22, which are incorporated by reference in their entirety).

The pharmaceutical preparations of the present disclosure can be made up in any conventional form including, inter alia, (a) a solid form for oral administration such as tablets, capsules (e.g., hard or soft gelatin capsules), pills, cachets, powders, granules, and the like; (b) preparations for topical administrations such as solutions, suspensions, ointments, creams, gels, micronized powders, sprays, aerosols and the like. The pharmaceutical preparations may be sterilized and/or may contain adjuvants such as preservatives, stabilizers, wetting agents, emulsifiers, salts for varying the osmotic pressure and/or buffers.

The pharmaceutical compositions of the present disclosure can be used in liquid, solid, tablet, capsule, pill, ointment, cream, nebulized or other forms as explained below. In some embodiments, the composition of the present disclosure can be administered by different routes of administration such as oral, oronasal, parenteral or topical.

"Oral" or "peroral" administration refers to the introduction of a substance into a subject's body through or by way of the mouth and involves swallowing or transport through the oral mucosa (e.g., sublingual or buccal absorption) or both.

"Oronasal" administration refers to the introduction of a substance into a subject's body through or by way of the nose and the mouth, as would occur, for example, by placing one or more droplets in the nose. Oronasal administration involves transport processes associated with oral and intranasal administration.

"Parenteral administration" refers to the introduction of a substance into a subject's body through or by way of a route that does not include the digestive tract. Parenteral administration includes subcutaneous administration, intramuscular administration, transcutaneous administration, intradermal administration, intraperitoneal administration, intraocular administration, and intravenous administration. For the purposes of this disclosure, parenteral administration excludes administration routes that primarily involve transport of the substance through mucosal tissue in the mouth, nose, trachea, and lungs.

Abbreviations Used in this Disclosure

ASO/Antisense Oligos: A sequence of nucleotides complementary to (and hence capable of binding to) a coding sequence of a messenger RNA molecule.
FANA: 2'-deoxy-2'-fluoroarabinonucleotide (FANA) modified, a technology to induce oligos self delivery
siRNA: Small interfering RNA/Short interfering RNA or Silencing RNA,
siRNA therapy: The siRNA interferes with specific genes. This may be used to turn off overactive genes within the human body or turn off genes from foreign invaders, such as virtues in the body to cure disease.
Antisense therapy is a form of treatment for genetic disorders or infections. When the genetic sequence of a particular gene is known to cause a particular disease, it is possible to synthesize a strand of nucleic acid (DNA, RNA or a chemical analogue) that will bind to the messenger RNA (mRNA) produced by that gene and inactivate.

VS_ASO_1-FANA: ASO designed by the inventors with 2'-deoxy-2'-fluoroarabinonucleotide (FANA) modified, including Table 1: oligos 1, 2, 3, 4, 5, 6, 7 and 8

VS_ASO_1-FANA-FITC: VS_ASO_1-FANA oligo 9 (FITC labeled) (Table 1)

VS_ASO_2: ASO designed by the inventors including Table 2: oligo 1, 2, 3, 4, 5, 6, 7, 8 and 9 1, 2, 3, 4, 5, 6, 7 and 8

VS_ASO_2-Cy3: VS_ASO_2 oligo 9 (Cy3 labeled) (Table 2)

VS_DsiRNA: siRNA designed by the inventors with DsiRNA technology including table 3: oligo 1, 2, 3, 4, 5, 6, 7 and 8

VS_DsiRNA-Cy5: VS_DsiRNA oligo 9 (Cy5 labeled) (Table 3)

N-Protein: Nucleocapsid Protein of SARS-CoV-2, which is a structural protein that binds to the coronavirus RNA genome, thus creating a capsid.

S-Protein: The spike protein of SARS-CoV-2, which bind to the host cell receptors, i.e., ACE2, to enter the host cells.

RdRp: The RNA-dependent RNA polymerase (RdRp) of SARS-CoV-2, which is an enzyme that catalyzes the replication of RNA from a viral RNA template.

E-Protein: The envelope protein of SARS-CoV-2, which is a small membrane protein that has an important role in the assembly of virions.

ORF1ab: The open reading frame for starting transcriptional genes of SARS-CoV-2, 1ab.

VS-nutrition: The inventors designed nutrition with Inhibitory oligonucleotides and poly-peptides.

FACS: Fluorescence-activated cell sorting (a cell-based fluorescent analysis technique used in biological experiment to detect and analyze fluorescent signal in every single cell).

Cycle threshold: Real-Time PCR calculation parameter used to quantify specific gene expression level. Cycle threshold refers to the cycle number in an RT-PCR reaction when the specific amplification signal rises above a predetermined level (e.g., above the background noise). As used herein, cycle threshold is a value that ranges from 0 to 40. Genes with high expression have lower cycle thresholds (e.g., between 0 and 20), and genes with low expression have high cycle thresholds (e.g., between 21 and 40).

Inhibitory oligonucleotides: ASO (VS_ASO_1-FANA and VS_ASO_2), and siRNA (VS_DsiRNA) designed and produced by VS qRT-PCR: Real-Time Quantitative Reverse Transcription PCR AAV: Adeno-associated viral vector U6: Human U6 promoter H1: Human H1 promoter SV40: Simian Virus 40 promoter A1: The gene encoding the Antisense 1 (ASO1) which binds to a target sequence on the SARS-CoV-2 ORF1ab protein.

A2: The gene encoding the Antisense 2 (ASO2) which binds to a target sequence on the SARS-CoV-2 RdRp protein A3: The gene encoding the Antisense 3 (ASO3) which binds to a target sequence on the SARS-CoV-2 S-protein A4: The gene encoding the Antisense 4 (ASO4) which binds to a target sequence on the SARS-CoV-2 N-protein A5: The gene encoding the Antisense 5 (ASO5) which binds to a target sequence on the SARS-CoV-2 ORF1ab protein (but in a different region from the region that ASO1 binds)

A6: The gene encoding the Antisense 6 (ASO6) which binds to a target sequence on the SARS-CoV-2 RdRp protein (but in a different region from the region that ASO2 binds)

A7: The gene encoding the Antisense 7 (ASO7) which binds to a target sequence on the SARS-CoV-2 E-protein A8: The gene encoding the Antisense 8 (ASO8) which binds to a target sequence on the SARS-CoV-2 N-proteins (but in a different region from the region that ASO4 binds)

eGFP: Enhanced green fluorescent protein hGHpA: Human grown hormone poly-A

ITR: The inverted terminal repeat (ITR)

CMV promoter: Human cytomegalovirus (CMV) promoter

EF promoter: Human elongation factor promoter

E2A: 2A peptide with 19 amino acids derived from equine rhinitis A virus

TABLE 1

The VS_ASO_1-FANA designed, and all the ASO sequences are included in the Table; but the sequence of oligo 4 is same as olgo 9 with its fluorescent probe labeled for studying on its intercellular delivering capacity. The FANA: 2'-deoxy-2'-fluoroarabinonucleotide (FANA) modified, a technology to make the oligos with self-delivery into the mammalian cells.

| VS_ASO_1-FANA oligos numbers | ASO_1 Sequences (from 5' to 3') | Target on SARS-COV-2 | SEQ ID NO | Fluorescence |
|---|---|---|---|---|
| 1 | AAGAACCTTGCGGTAAGCCAC | ORF1ab | 9 | None |
| 2 | ATACGACATCAGTACTAGTGC | RdRp | 10 | None |
| 3 | ATAAGTAGGGACTGGGTCTTC | S-protein | 11 | None |
| 4 | TGTTAATTGGAACGCCTTGTC | N-protein | 12 | None |
| 5 | AGTTGTGCGTAATATCGTGCC | ORF1ab | 13 | None |
| 6 | AAGTCTAGAGCTATGTAAGTT | RdRp | 14 | None |
| 7 | TATTAACGTACCTGTCTCTTC | E-protein | 15 | None |
| 8 | TGTCTGATTAGTTCCTGGTCC | N-protein | 16 | None |
| 9 | TGTTAATTGGAACGCCTTGTC | N-protein | 12 | FITC |

TABLE 2

The VS_ASO_2 designed, and all the ASO sequences are included in the Table, which are the same DNA sequences as VS_ASO_1, but their structures were modified by another different technique (see Table 3). The sequence of oligo 4 is same as oligo 9 with its fluorescent probe labeled for studying on its intercellular delivering capacity.

| VS_ASO_2 oligos numbers | ASO_2 sequences (from 5' to 3') | Target on SARS-COV-2 | SEQ ID NO | Fluorescence |
|---|---|---|---|---|
| 1 | AAGAACCTTGCGGTAAGCCAC | ORF1ab | 9 | None |
| 2 | ATACGACATCAGTACTAGTGC | RdRp | 10 | None |
| 3 | ATAAGTAGGGACTGGGTCTTC | S-protein | 11 | None |
| 4 | TGTTAATTGGAACGCCTTGTC | N-protein | 12 | None |
| 5 | AGTTGTGCGTAATATCGTGCC | ORF1ab | 13 | None |
| 6 | AAGTCTAGAGCTATGTAAGTT | RdRp | 14 | None |
| 7 | TATTAACGTACCTGTCTCTTC | E-protein | 15 | None |
| 8 | TGTCTGATTAGTTCCTGGTCC | N-protein | 16 | None |
| 9 | TGTTAATTGGAACGCCTTGTC | N-protein | 12 | Cy3 |

TABLE 3

The structure of VS_ASO_2 molecules modified: The ASO molecules modified as shown: (1) *: Phosphorothioate-bond in all base pairs to provide resistance to exonuclease degradation; (2) m: 2' O-Methyl RNA modified in those pb, to increases both 5' end nuclease stability and affinity of the antisense oligo to the target RNA; (3) 5-methyl dC in 5' end of the oligos (ASO), it can also reduce the chance of adverse immune response to Toll-like receptor 9 (TLR9). The middle region is a "gapmer" designed.

/5Me-dC/mA*mA*mG*mA*mA*C*C*T*T*G*C*G*G*T*A*mA*mG*mC*mC*mA*C
(SEQ ID NO: 33) Oligo-1 (Table 2)

/5Me-dC/mA*mU*mA*mC*mG*A*C*A*T*C*A*G*T*A*C*mU*mA*mG*mU*mG*C
(SEQ ID NO: 34) Oligo-2 (Table 2)

/5Me-dC/mA*mU*mA*mA*mG*T*A*G*G*G*A*C*T*G*G*mG*mU*mC*mU*mU*C
(SEQ ID NO: 35) Oligo-3 (Table 2)

/5Me-dC/mU*mG*mU*mU*mA*A*T*T*G*G*A*A*C*G*C*mC*mU*mU*mG*T*C
(SEQ ID NO: 36) Oligo-4 (Table 2)

/5Me-dC/mA*mG*mU*mU*mG*T*G*C*G*T*A*A*T*A*T*mC*mG*mU*mG*mC*C
(SEQ ID NO: 37) Oligo-5 (Table 2)

/5Me-dC/mA*mA*mG*mU*mC*T*A*G*A*G*C*T*A*T*G*mU*mA*mA*mG*mU*T
(SEQ ID NO: 38) Oligo-6 (Table 2)

/5Me-dC/ mU*mA*mU*mU*mA*A*C*G*T*A*C*C*T*G*T*mC*mU*mC*mU*mU*C
(SEQ ID NO: 39) Oligo-7 (Table 2)

/5Me-dC/ mU*mG*mU*mC*mU*G*A*T*T*A*G*T*T*C*C*mU*mG*mG*mU*mC*C
(SEQ ID NO: 40) Oligo-8 (Table 2)

TABLE 4

The VS_DsiRNA- Cy5 designed, all their sequences shown in the table. The sequence of oligo 4 is same as oligo 9 with its fluorescent probe labeled for studying on its intercellular delivering capacity. The 'r's in SEQ ID NOS: 17-32 in the table below denote "ribonucleic acid" nucleotides in the sequences. If there is no "r" before a nucleotide, that nucleotide is a deoxyribonucleic acid.

| VS_DsiRNA oligos # | Sequences (from 5' to 3') | Target | SEQ ID NO: | Tag |
|---|---|---|---|---|
| 1 | 5' rGrCrCrUrUrGrUrCrCrUrGrGrUrUrUrCrArArCrGrArGAA 3'<br>5' rUrUrCrUrCrGrUrGrUrGrArArArArCrCrArGrGrGrArCrArArGrGrCrUrC3' | ORF1ab | 17<br>18 | None |
| 2 | 5' rCrArGrCrUrGrArUrGrCrArCrArArUrCrGrUrUrUrUrAAA 3'<br>5' rUrUrUrArArArArArCrGrArUrUrGrUrGrCrArUrCrArGrCrUrGrArC3' | RdRp | 19<br>20 | None |
| 3 | 5' rCrUrArGrUrCrArGrUrGrUrGrUrUrArArUrCrUrUrArCrAAC 3'<br>5' rGrUrUrGrUrArArGrArUrUrArArCrArCrArCrUrGrArCrUrArGrArG3' | S-protein | 21<br>22 | None |
| 4 | 5' rArArArCrUrArArArArUrGrUrCrUrGrArUrArArUrGrGrACC 3'<br>5' rGrGrUrCrCrArUrUrArUrCrArGrArCrArUrUrUrUrArGrUrUrUrGrU3' | N-protein | 23<br>24 | None |
| 5 | 5' rGrGrUrArGrUrUrArUrArCrUrArArUrGrArCrArArArGrCTT 3'<br>5' rArArGrCrUrUrUrGrUrCrArUrUrArGrUrArUrArArCrUrArCrCrArC3' | ORF1ab | 25<br>26 | None |
| 6 | 5' rCrUrUrCrUrGrGrUrArArUrCrUrArUrUrArCrUrArGrArUAA 3'<br>5' rUrUrArUrCrUrArGrUrArArUrArGrArUrUrArCrCrArGrArArGrCrA3' | RdRp | 27<br>28 | None |
| 7 | 5' rGrGrArArGrArGrArCrArGrGrUrArCrGrUrUrArArArUrArGTT 3'<br>5' rArArCrUrArUrUrUrArArCrGrUrArCrCrUrGrUrCrUrCrUrCrCrGrA3' | E-protein | 29<br>30 | None |
| 8 | 5' rGrGrCrCrArArArArCrUrGrUrCrArCrUrArArGrArArArUrCTG 3'<br>5' rCrArGrArUrUrUrCrUrUrArGrUrGrArCrArGrUrUrUrGrGrCrCrUrU3' | N-protein | 31<br>32 | None |
| 9 | 5' rArArArCrUrArArArArUrGrUrCrUrGrArUrArArUrGrGrACC 3'<br>5' rGrGrUrCrCrArUrUrArUrCrArGrArCrArUrUrUrUrArGrUrUrUrGrU3' | N-protein | 23<br>24 | Cy5 |

TABLE 5

Sequences of VS-Peptides 1-6.

| Name | Sequence | SEQ ID NO |
|---|---|---|
| Peptide 1 | EEQAKTFLDKFNHEAEDLFYQSS | 41 |
| Peptide 2 | FLKEQSTLAQMYPLQEIQNL | 42 |
| Peptide 3 | LPNMTQGFWENSMLTDPGNVQ | 43 |
| Peptide 4 | HPTAWDLGKGDFRILMCTKV | 44 |
| Peptide 5 | MAYAAQPFLLRNGANEGFHEA | 54 |
| Peptide 6 | GNYNYLYRLFRKSNLKPFERDIS | 45 |

The sequences for the peptides of 1, 2, 3, 4 and 5 were designed based on the RBD amino acids of human ACE2, a receptor for COVID-19 entering the cells (see FIGS. 47 through FIGS. 52A-52H); which are capable to bind on the S-protein of COVID-19, in order to protect the human ACE 2 receptors by blocking the binding sites of the S-protein to elicit their therapeutic effects. However, the AA sequences of peptide 6 was designed to mimic the BD of S-Protein (see, FIG. 49), which was labelled by FITC; this peptide 5 could also be served as a pre-blocker on the RBD of ACE2 to prevent the COVID-19 infection as well.

TABLE 6

Alternative peptides based on VS Peptide 1-5

| Name | Length | Sequence | SEQ ID NO |
|---|---|---|---|
| VS-Peptide 1 | 23 | EEQAKTFLDKFNHEAEDLFYQSS | 41 |
| VS-Peptide 1-a | 15 | TFLDKFNHEAEDLFY | 63 |

TABLE 6-continued

Alternative peptides based on VS Peptide 1-5

| Name | Length | Sequence | SEQ ID NO |
|---|---|---|---|
| VS-Peptide 1-b | 20 | QAKTFLDKFNHEAEDLFYQS | 64 |
| VS-Peptide 1-c | 25 | TIEEQAKTFLDKFNHEAEDLFYQSSL | 65 |
| VS-Peptide 1-d | 30 | QSTIEEQAKTFLDKFNHEAEDLFYQSSLAS | 66 |
| VS-Peptide 2 | 20 | FLKEQSTLAQMYPLQEIQNL | 42 |
| VS-Peptide 2-a | 15 | EQSTLAQMYPLQEIQ | 67 |
| VS-Peptide 2-b | 20 | LKEQSTLAQMYPLQEIQNLT | 68 |
| VS-Peptide 2-c | 25 | WSAFLKEQSTLAQMYPLQEIQNLTV | 69 |
| VS-Peptide 2-d | 30 | DKWSAFLKEQSTLAQMYPLQEIQNLTVKLQ | 70 |
| VS-Peptide 3 | 21 | LPNMTQGFWENSMLTDPGNVQ | 43 |
| VS-Peptide 3-a | 15 | TQGFW ENSML TDPGN | 71 |
| VS-Peptide 3-b | 20 | LPNMT QGFWE NSMLT DPGNV | 72 |
| VS-Peptide 3-c | 25 | VGLPN MTQGF WENSM LTDPG NVQKA | 73 |
| VS-Peptide 3-d | 30 | VSVGL PNMTQ GFWEN SMLTD PGNVQ KAVCH | 74 |
| VS-Peptide 4 | 20 | HPTAWDLGKGDFRILMCTKV | 44 |
| VS-Peptide 4-a | 15 | WDLGKGDFRILMCTK | 75 |
| VS-Peptide 4-b | 20 | PTAWDLGKGDFRILMCTKVT | 76 |
| VS-Peptide 4-c | 25 | VCHPTAWDLGKGDFRILMCTKVTMD | 77 |
| VS-Peptide 4-d | 30 | KAVCHPTAWDLGKGDFRILMCTKVTMDDFL | 78 |
| VS-Peptide 5 | 21 | MAYAAQPFLLRNGANEGFHEA | 54 |
| VS-Peptide 5-a | 15 | AQPFLLRNGANEGFH | 79 |
| VS-Peptide 5-b | 20 | AYAAQPFLLRNGANEGFHEA | 80 |
| VS-Peptide 5-c | 25 | YDMAYAAQPFLLRNGANEGFHEAVG | 81 |
| VS-Peptide 5-d | 30 | IQYDMAYAAQPFLLRNGANEGFHEAVGEIMS | 82 |

Unless defined otherwise, all technical and scientific terms used herein have the same meaning as commonly understood by one skilled in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The present disclosure is further illustrated by the following non-limiting examples.

EXAMPLES

Example 1: Materials and Methods

Tissue Culture

Human Normal Primary Small Airway Epithelial Cells (HSAEC) (ATCC Number: PCS-301-010) and Human Normal Primary Bronchial/Tracheal Epithelial Cells (HBTEC) (ATCC Number: PCS-300-010) were purchased from American Type Culture Collection (ATCC) (Manassas, Va.). Human Nasal Epithelial Cells (HNEpC) were purchased from PromoCell (Catalog Number: C-12621) (Heidelberg, Germany). HSAEC and HBTEC were grown Airway Epithelial Cell Basal Medium supplement with Bronchial Epithelial Cell Growth Kit (ATCC, PCS-300-030 and PCS-300-040). HNEpC were grown in Airway/Nasal Epithelial Cell Grow Medium (PromoCell, C-21060)). Cells were maintained in a humidified atmosphere with 5% $CO_2$ at 37° C.

RNAi, ASO Delivery

Transfection

HSAEC, HBTEC and HNEpC were seeded into 6-well tissue-culture plate (VWR-USA, 10062-892), and transfected with lipofectamine 3000 (Thermo Fisher Scientific, L3000001) per manufacturer's protocol.

"Untreated": medium

"Treated": SARS-CoV-2 viral protein expression vectors (S-protein, E-protein, N-protein, RdRp and ORF1ab) or SARS-CoV-2 viral protein expression vectors (S-protein, E-protein, N-protein, RdRp and ORF1ab)+VS-vector.

"Overexpression vector": N-protein: MC_0101137, GenScript, S-protein: MC_0101080, GenScript E-protein: MC_0101135, GenScript
ORF1ab: MC_0101079, GenScript
RdRP: MC_0101076, GenScript"

Arginine Delivery

HSAEC, HBTEC and HNEpC were seeded into tissue-culture plate (VWR-USA, 10062-892). The cells were either left untreated, or treated with the following mixture: 10 μL arginine (200 mg/mL), SARS-CoV-2 N, S and E protein overexpression vector, and VS-vector (VS-RNAi or VS-ASO).

"Untreated": medium

"Treated": COVID-19 viral protein expression vectors (S-protein, E-protein, N-protein, RdRp and ORF1ab) or COVID-19 viral protein expression vectors (S-protein, E-protein, N-protein, RdRp and ORF1ab)+VS-vector.

"Overexpression vector": N-protein: MC_0101137, GenScript; S-protein: MC_0101080, GenScript; E-protein: MC_0101135, GenScript; ORF1ab: MC_0101079, GenScript; RdRP: MC_0101076, GenScript.

Confocal Microscopy

Untreated or VS-vector treated HSAEC, HBTEC and HNEpC were washed twice in phosphate buffered solution (PBS, pH 7.4). The cells were then observed under confocal microscope (BD pathway 855) with four channels: transmitted, FITC (excitation filter: 488/10, emission: 515LP), Cy3 (excitation filter: 548/20, emission filter: 84101) and Cy5 (excitation filter: 635/20, emission filter: 84101) respectively.

Western Blot Analysis

Untreated or VS-vector treated HSAEC, HBTEC and HNEpC were washed twice in phosphate buffered solution (PBS, pH 7.4), scraped into 15-mL conical tubes, and centrifuged at 1,000×g at 4° C. for 5 minutes. Cell extracts were prepared by lysis in NET buffer [50 mmol/L Tris-HCl, (pH 7.4), 150 mmol/L NaCl, 0.1% NP40, 1 mmol/L EDTA, 0.25% gelatin, 0.02% sodium azide, 1 mmol/L phenylmethylsulfonyl fluoride, and 1% aprotinin]. The lysates were centrifuged at 15,000×g for 30 minutes at 4° C. The protein concentrations in the supernatant fractions were determined by Bicinchoninic Acid assay (Thermo Fisher Scientific, 23255).

Ten micrograms of total HSAEC protein extracts were resolved by 10% SDS-PAGE and transferred to nitrocellulose membranes. Membranes were blocked with 5% nonfat dry milk in PBS/Tween 20 (0.05%) for 1 hour, followed by overnight incubation with 1p g/mL anti-COVID19-Spike-protein antibody (ProSci, 3223) in 10% milk/PBS-T and 1 μg/mL anti-COVID19-N-protein antibody (ProSci, 3857) in 10% milk/PBS-T. Loading control antibody used rabbit anti-GAPDH antibody (Novus Biologicals, NB100-56875) with 1:1000 dilution or mouse anti-GAPDH antibody (Novus Biologicals, NBP2-27103). Secondary antibody: rabbit IgG HRP-conjugated Antibody (R&D System, HAF008) with 1:1000 dilution and mouse IgG HRP-conjugated Antibody (R&D System, HAF007) with 1:1000 dilution. The detection was done using horseradish peroxidase-labeled secondary antibodies and enhanced chemiluminescence detection reagent.

S-Protein, N-Protein, E-Protein, ORF1ab and RdRP Detection by Quantitative Real-Time PCR (qRT-PCR)

Untreated or treated HSAEC, HBTEC and HNEpC were washed twice in PBS. RNA was extracted from cells per manufacturer's protocol using Qiagen RNA extraction kit (Qiagen, 74104). One-step RT-PCR was conducted by StepOne Real-Time PCR System (Thermo Fisher Scientific, CA): 5 μl extracted RNA (300 ng/μl) samples were added to a mixture of 6.25 μl Taqman-Master-Mix (Thermo Fisher Scientific, 4444432), 11.25 μl PCR-grade water (Thermo Fisher Scientific, AM9916) and 1.25 FAM Probe (information as following):

For SARS-CoV-2 S-protein: Thermo Fisher Scientific, A47532
For SARS-CoV-2 N-protein: Thermo Fisher Scientific, A47532
For SARS-CoV-2 ORF1ab: Thermo Fisher Scientific, A47532
For RNAse P (internal control): Thermo Fisher Scientific, A47532
For SARS-CoV-2 E protein: GenScript, E_Sarbeco_P1

(SEQ ID NO: 53)
(ACACTAGCCATCCTTACTGCGCTTCG).

Apoptosis Analysis by qRT-PCR

Untreated or treated HSAEC, HBTEC and HNEpC were washed twice in PBS. RNA was extracted from cells per manufacturer's protocol using Qiagen RNA extraction kit (Qiagen, 74104). Total RNA was reverse-transcribed to cDNA according to manufacturer's protocol (Thermo Fisher Scientific, 18091050). The cDNA concentration was determined by NanoDrop 1000 (Thermo Scientific). Real-Time PCR was conducted by StepOne Real-Time PCR System (Thermo Fisher Scientific, CA): 3 μl cDNA (300 ng/ul) samples were added to a mixture of 10 μl Taqman-Master-Mix (Thermo Fisher Scientific, 4444557), 5 μl of PCR-grade water (Thermo Fisher Scientific, AM9916) and 2 μl FAM Probe (information as following):

For BCL2: Thermo Fisher Scientific, Hs04986394_s1
For BAX: Thermo Fisher Scientific, Hs00180269_m1
For GAPDH (internal control): Hs02786624_g1

Fluorescence Signal Detection by Flow Cytometry

Untreated or treated HSAEC, HBTEC and HNEpC were washed twice in PBS (pH 7.4), scraped into 15-mL conical tubes, and centrifuged at 1,000×g at 4° C. for 5 minutes. Cells were resuspended into 0.5 mL PBS/BSA (0.5%). Fluorescence signal detection was carried out on BD FacsCalibur (BD Biosciences) with excitation laser (485 nm, 635 nm) and emission channel (530/30, 585/42, 670/LP and 661/16). 10,000 cells (or event) were collected for analysis.

Cytotoxicity by MTT Assay

Cells were seeded in 96-well plates (100 μL per well of $1\times10^5$ cells/mL). The cells were left undisturbed until they adhered to the plate. The cells were then treated with culture medium (control) or VS-vectors. After the cells were incubated with MTT dye (Sigma) for another 4 h at 37° C., the medium was removed and the crystal formazan dye was solubilized in 150 μL dimethyl sulphoxide (DMSO; Sigma). Absorbance was measured at 570 nm by using the Bio-Tek Powerwave X microplate reader (BioTek Instruments).

Cell Cycle and Cell Apoptosis Rate Analysis

HSAEC, HTBEC and HNEpC were seeded in 25-mL culture flasks at a density of $5\times10^5$ cell/mL and cultured in recommended medium until the cells adhered to the flasks. The cells were then treated with culture medium (control) or VS-vector for 24 h. Cells were harvested by scrapping, and aliquots of $1\times10^6$ cell/mL were prepared for analysis. The cells were washed with PBS twice (centrifuged at 300 g with 5 min and resuspended in PBS), fixed with ice-chilled 70% ethanol for 24 h, and then treated with 20 mg/L RNase for 30 min. Propidium iodide (Sigma) was added to a final concentration of 20 mg/L. DNA contents of the samples were analyzed on a BD FacsCalibur (BD Biosciences), and the number of cells in every phase was calculated using FlowJo.

VS-Peptide In Vitro Fluorescent Observation and Detection

HSAEC, HBTEC and HNEpC were seeded into 24-well tissue-culture plate (VWR-USA, 10062-896), and transfected (Thermo Fisher Scientific, L3000001) with CMV-human ACE2-vector by lipofectamine 3000 (Thermo Fisher Scientific, L3000001) per manufacturer's protocol. After 24 hours, peptides were added into 24-well tissue-culture plate as follows:

Untreated: SARS-CoV-2-S-Protein-peptide-FITC (final concentration: 1 ug per $1 \times 10^5$ cells)
VS-peptide-1-dosage-1: SARS-CoV-2-S-Protein-peptide-FITC (final concentration: 1 ug per $1 \times 10^5$ cells)+VS-peptide-1 (final concentration: 1 ug per $1 \times 10^5$ cells)
VS-peptide-1-dosage-2: SARS-CoV-2-S-Protein-peptide-FITC (final concentration: 1 ug per $1 \times 10^5$ cells)+VS-peptide-1 (final concentration: 1 ug per $1 \times 10^5$ cells)
VS-peptide-2-dosage-1: SARS-CoV-2-S-Protein-peptide-FITC (final concentration: 1 ug per $1 \times 10^5$ cells)+VS-peptide-2 (final concentration: 1 ug per $1 \times 10^5$ cells)
VS-peptide-2-dosage-2: SARS-CoV-2-S-Protein-peptide-FITC (final concentration: 1 ug per $1 \times 10^5$ cells)+VS-peptide-2 (final concentration: 1 ug per $1 \times 10^5$ cells)
VS-peptide-3-dosage-1: SARS-CoV-2-S-Protein-peptide-FITC (final concentration: 1 ug per $1 \times 10^5$ cells)+VS-peptide-3 (final concentration: 1 ug per $1 \times 10^5$ cells)
VS-peptide-3-dosage-2: SARS-CoV-2-S-Protein-peptide-FITC (final concentration: 1 ug per $1 \times 10^5$ cells)+VS-peptide-3 (final concentration: 1 ug per $1 \times 10^5$ cells)
VS-peptide-4-dosage-1: SARS-CoV-2-S-Protein-peptide-FITC (final concentration: 1 ug per $1 \times 10^5$ cells)+VS-peptide-4 (final concentration: 1 ug per $1 \times 10^5$ cells)
VS-peptide-4-dosage-2: SARS-CoV-2-S-Protein-peptide-FITC (final concentration: 1 ug per $1 \times 10^5$ cells)+VS-peptide-4 (final concentration: 1 ug per $1 \times 10^5$ cells)
VS-peptide-combination: SARS-CoV-2-S-Protein-peptide-FITC (final concentration: 1 ug per $1 \times 10^5$ cells)+VS-peptide-1+VS-peptide-2+VS-peptide-3+VS-peptide-4 (final concentration: 1 ug per $1 \times 10^5$ cells)

Observed under confocal microscope (BD pathway 855) with channel: transmitted, FITC (excitation: 488/10, emission: 515LP) and detected FITC intensity via fluorescent microplate reader (BIO-TEK Synergy HT) in each well.

Inhibitions of Nucleotides on the Viral Infections from Both Pseudo-Viruses of Wild-Type and Mutant Forms of the COVID-19

5000 HELA cells were seeded per well in 96-well-plate. Co-transfections of ACE-2 (50 ng) and nucleosides (500 nM). For control-1, transfection of ACE-2 (50 ng) in the cells, and the scramble nucleotides (500 nM) was added.

24 hr-post transfection, add 4 ul of the wild-type virus of SARS-CoV-2 Spike pseudo-typed in the lentivirus, (WV: titer $10^5$ TU/ml, eGFP reporter with catalog: 79981, BPS Bioscience) or/and 4 ul of the mutant virus of SARS-CoV-2 Spike (MV: B.1.1.7 mutant variant virus from UK/England) pseudo-typed in the lentivirus (titer $10^5$ TU/ml, eGFP reporter with catalog: 78158, BPS Bioscience), and the polybrene was added into each well, as its final concentration of 5 ug/ml.

Observation on the GFP expression in the transduced cells under the confocal microscope in 48-72 hrs after viruses added into the wells.

ELISA Assays

A 96 well dish was coated with the ACE2 protein (Cat #: 10-014, ProSci, Inc) at the concentration of 10 ng/well at 4° C. overnight. After overnight, washed 3 times (400 ul/well/time) by 1× washing buffer (Cat #: DY008, R&D System). Later, it was blocked by 3% BSA for 1 hr RT, and washing 3 times (400 ul/well/time) by 1× washing buffer (Cat #: DY008, R&D System). VS Peptides of 1 to 4 (see Table 1) were diluted into two concentrations of 100 ug/well and 50 ug/well, and then mixed with the Receptor-Binding Domain (RBD) of Covid-19 viral Spike recombinant protein (S-RBD) (Cat #: 10-303, ProSci, Inc) at the concentration of 3000 ng/well for 30 min at 37° C. before adding onto each well. After adding the mixture solution of peptides and S-RBD, the specific anti-S-RBD antibody (Cat #: 9087, ProSci, Inc) was added onto each well at a concentration of 1000 ng/well at 37° C. for 30 min at a tissue-culture incubator. After the incubation, wells were washed by 1× washing buffer for 3 times (300 ul/well/time). The secondary HRP (Horseradish Peroxidase) antibody (Cat #: HAF008, R&D System), that binds to the primary antibody, was then added onto each well (1:30000) 100 ul/well for 30 min in RT. After the incubation, the well was washed by 1× washing buffer for 3 times (300 ul/well/time) (Cat #: DY008, R&D System). 100 ul color substrate (Cat #: DY008, R&D System) was added to each well for 20 min at RT to show the color. Finally, 50 ul of stop solution was added to each well (Cat #: DY008, R&D System). The 96-well plate was placed inside the Microplate Reader (Model: Bio-TEK Synergy HT) and read the wavelength signal autumnally by the computer program. The signals of intensities from the "yellow-like" color, called as TMB signals, were scanned and read at a wave-length of 450 nm by the Microplate Reader, and recorded and calculated by its computer software automatedly (see the FIG. 1S: the table at the left-bottom), the 570 nm was measured as the background signals that was subtracted out from the final data analysis.

Example 2: VS-Nucleotide Treatment of Human Primary Small Airway Epithelial Cells (HSAEC) Transfected with COVID-19 Viral Proteins FIG. 1 shows experimental designs of investigating on delivery capable and therapeutic effects of ASO(s) and siRNA on human primary small airway epithelial cells transfected with viral protein of SARS-CoV-2. The human lung small airway epithelial cells were cultured in the 24 well-dish, and the cells were transfected with the genes encoding the viral proteins of SARS-CoV-2. The VS_ASO_1-FANA-FITC, VS_DsiRNA-Cy5 and VS_ASO_2-Cy3 were into the cells for 24-48 hours before analysis with fluorescent microscope. The VS_ASO_1-FANA-FITC designed with FITC labeled shown in the Table 1, and VS_ASO_2-Cy3 with Cy3 label shown in the Table 2; and VS_DsiRNA-Cy5 with Cy5 label shown in Table 3. A1&A2: No treatment as control, A3&A4: Overexpression of both COVID-19 N-protein and the VS_ASO_1-FANA using lipofectamine reagent, A5&A6: Overexpression of both COVID-19 N-protein and the VS_ASO_1-FANA without any regents; B1&B2: No treatment as control, B3&B4: Overexpression of both COVID-19 N-protein and the VS_DsiRNA-Cy5 using lipofectamine reagent, B5&B6: Overexpression of both COVID-19 N-protein and the VS_DsiRNA-Cy5 using Poly-arginine (5 μl/well) only; C1&C2: No treatment as control, C3&C4: Overexpression of both COVID-19 N-protein and the VS_ASO_2-Cy3 using lipofectamine reagent, C5&C6: Overexpression of both COVID-19 N-protein and the VS_ASO_2-Cy3 using Poly-arginine (5 μl/well) only.

FIGS. 2A-2F show microscopic analysis showing entry of VS_ASO_1-FANA-FITC into the primary human lung small airway epithermal cells (20×). FIGS. 2A-2C were captured under the FITC florescent filter, and FIGS. 2D-2F were captured in the same view of bright fields (20×). FIGS. 2A and 2D were taken in well A3 & A4 (as shown in FIG. 1), FIGS. 2B and 2E were taken in well A5 & A6 (as shown in FIG. 1), and FIGS. 2C and 2F were taken in well A 1 & A2 (as shown in FIG. 1).

FIGS. 3A-3F show microscopic analysis showing entry of VS_ASO_1-FANA-FITC into primary human lung small airway epithermal cells (10×). FIGS. 3A-3C were captured under the FITC florescent filter, and FIGS. 3D-3F were captured in the same view of bright fields (20×). FIGS. 3A and 3D were taken in well A3 & A4 (as shown in FIG. 1), FIGS. 3B and 3E were taken in well A5 & A6 (as shown in FIG. 1), and FIGS. 3C and 3F were taken in well A1 & A2 (as shown in FIG. 1).

FIGS. 4A-4F show microscopic analysis showing entry of VS_DsiRNA-Cy5 into primary human lung small airway epithermal cells (20×). FIGS. 4A-4C were captured under the Cy5 florescent filter, and FIGS. 4D-4F were captured in the same view of bright fields (20×). FIGS. 4A and 4D were taken in well B3 & B4 (as shown in FIG. 1), FIGS. 4B and 4E were taken in well B5 & B6 (as shown in FIG. 1), and FIGS. 4C and 4F were taken in well B1 & B2 (as shown in FIG. 1).

FIGS. 5A-5F show microscopic analysis entry of VS_D-siRNA-Cy5 into primary human lung small airway epithermal cells (10×). FIGS. 5A-5C were captured under the Cy5 florescent filter, and FIGS. 5D-5F were captured in the same view of bright field images (10×). FIGS. 5A and 5D were taken in well B3 & B4 (as shown in FIG. 1), FIGS. 5B and 5E were taken in well B5 & B6 (as shown in FIG. 1), and FIGS. 5C and SF were taken in well B1 & B2 (as shown in FIG. 1).

FIGS. 6A-6F show microscopic analysis entry of VS_ASO_2-Cy3 into primary human lung small airway epithermal cells (20×). FIGS. 6A-6C were captured under the Cy3 florescent filter, and FIGS. 6D-6F were captured in the same view of bright fields (20×). FIGS. 6A and 6D were taken in well C3 & C4 (as shown in FIG. 1), FIGS. 6B and 6E were taken in well C5 & C6 (as shown in FIG. 1), and FIGS. 6C and 6F were taken in well C1 & C2 (as shown in FIG. 1).

FIGS. 7A-7F show microscopic analysis showing entry of VS_ASO_2-Cy3 into primary human lung small airway epithermal cells (10×). The FIGS. 7A-7C were captured under the Cy3 florescent filter, and FIGS. 7D-7F were captured in the same view of bright fields (10×). FIGS. 7A and 7D were taken in well C3 & C4 (as shown in FIG. 1), FIGS. 7B and 7E were taken in well C5 & C6 (as shown in FIG. 1), and FIGS. 7C and 7F were taken in well C1 & C2 (as shown in FIG. 1).

Example 3: Intercellular Delivery of Inhibitory Oligonucleotides in Human Primary Lung Small Airway Epithelial Cells (HSAEC)

FIG. 8 shows experimental design for FACS detection of intercellular delivery of oligos in the human primary lung small airway epithelial cells (HSAEC). The human lung small airway epithelial cells were cultured in the 6-well dish, and the genes encoding the viral proteins of SARS-CoV-2 were delivered by transfection or arginine delivery. The siRNA or ASO were added into the cells for 24-48 hours before analysis with FACS. The VS_ASO_1-FANA-FITC designed with labeled with FITC shown in the Table 1, and VS_ASO_2-Cy3 with modification shown in the Table 2; and VS_DsiRNA-Cy5 shown in Table 3. A1: No treatment as control; A2: Overexpression of N-protein+VS_ASO_1-FANA-FITC without lipofectamine or arginine; A3: Overexpression of N-protein+VS_DsiRNA-Cy5 with lipofectamine; B1: Overexpression of N-protein+VS_DsiRNA-Cy5 with Arginine (10 µl/well); B2: Overexpression of N-protein+VS_ASO_2-Cy3 with lipofectamine; B3: Overexpression of N-protein+VS_ASO_2-Cy3 with Arginine (10 µl/well).

FIGS. 9A-9C show FACS analysis of in vitro treatment with VS_ASO_1-FANA-FITC without lipofectamine or Arginine in human primary lung small airway epithelial cells (HSAEC). FACS analysis of HSAEC treated by VS_ASO_1-FANA-FITC (excitation: 488 nm, emission band pass filter: 530/30, Total event: 20,000). FIG. 9A no-treatment control, FIG. 9B VS_ASO_1-FANA-FITC and FIG. 9C Merge. The FACS data indicate that the intensities of FITC signals were significantly stronger with shifting to the right (B: FL1-H:FITC) when compared with the control FIG. 9A in the cells after treated with the VS_ASO_1-FANA-FITC without lipofectamine or Arginine reagents FIG. 9B. The FIG. 9C is the merged figures of FIGS. 9A and 9B.

FIGS. 10A-10B show FACS analysis of in vitro treatment with VS_DsiRNA-Cy5 with lipofectamine FIG. 10A or Arginine only FIG. 10B in human primary lung small airway epithelial cells (HSAEC). FACS analysis of HSAEC treated by VS_DsiRNA-Cy5 (excitation: 635 nm, emission band pass filter: 661/16, Total event: 20,000). Left to right panel: no-treatment control, VS_DsiRNA-Cy5 and merge. The FACS data indicates that the intensities of Cy5 signals were significantly higher with shifting to the right (middle panel: FL4-H:Cy5) in both of panel (FIG. 10A) and (FIG. 10B), it also shown that there are more cells with intercellular signals of the oligos in the presence of 10 µl/well Arginine (panel FIG. 10B) when compared with the lipofectamine (panel FIG. 10A).

FIGS. 11A-11B show FACS analysis of in vitro treatment with VS_ASO_2-Cy3 with lipofectamine FIG. 11A or Arginine only FIG. 11B in human primary lung small airway epithelial cells (HSAEC). FACS analysis of HSAEC treated by VS_VS_ASO-Cy3 (excitation: 488 nm, emission band pass filter: 585/42, Total event: 20,000). Left to right panel: no-treatment control, VS_ASO_2-Cy3 and merge. The FACS data indicates that the intensities of Cy3 signals were significantly higher with shifting to the right (middle panel: FL2-H:Cy3) in both of (FIG. 11A) and (FIG. 11B), it also shown that there are more cells with intercellular signals of the oligos in the presence of 10 µl/well Arginine (panel FIG. 11B) when compared with the lipofectamine (panel FIG. 11A).

Example 4: SARS-CoV-2 N-Protein Expression is Reduced in Human Primary Lung Small Airway Epithelial Cells (HSAEC) after Treatment by VS-Oligonucleotides FIG. 12 shows the experimental design for detecting SARS-CoV-2 N-protein expressed in the human primary lung small airway epithelial cells (HSAEC) by qRT-PCR after treatment. The human lung small airway epithelial cells were cultured in a 24-well dish, and the cells were transfected with the genes encoding the viral protein (N-protein) of SARS-CoV-2. The inhibitory oligonucleotides were added into the cells for 24-48 hours before analysis with RT-PCR. The VS_ASO_1-FANA-FITC designed with FITC labeled shown in the Table 1, and VS_ASO_2-Cy3 with Cy3 modification shown in the Table 2; and VS_DsiRNA-Cy5 with Cy5 modification shown in Table 3. A1&A2: No treatment as control, A3&A4: Overexpression of COVID-19 N-protein, A5&A6: Overexpression of COVID-19 N-protein+/treated by VS_DsiRNA_Cy5 with lipofectamine, B1&B2: Overexpression of COVID-19 N-protein+/treated by VS_ASO_2-Cy3 with lipofectamine, B3&B4: Overexpression of COVID-19 N-protein+/treated by VS_ASO_1-FANA without any reagents.

FIG. 13 shows detection of SARS-CoV-2 N-protein expressed in the human primary lung small airway epithelial cells (HSAEC) by qRT-PCR after treatment with VS-Nucleotides. Significant down-regulation was observed: about 5-fold in group treated by VS_DsiRNA-Cy5 oligos ($p<0.005$); about 1.5 fold in the group treated by VS_ASO_2-cy3 oligo ($p<0.01$), and about 6 fold in the group treated by the VS_ASO_1-FANA-FITC oligo ($p<0.005$); when compared with the group with SARS-CoV-2 N-protein overexpression only. The cycle threshold of no-treatment is non-detectable, but in this case for calculation purposes, the number "40" was used as the cycle threshold for a base-line control.

FIG. 14 shows experimental design for detection of SARS-CoV-2 S-protein expressed in the primary human lung small airway epithelial cells (HSAEC) by qRT-PCR after treatment. The human primary lung small airway epithelial cells (HSAEC) were cultured in the 24 well-dish, and the cells were transfected with the genes encoding the viral protein (S-protein) of SARS-CoV-2. The inhibitory oligonucleotides were added into the cells for 24-48 hours before analysis with RT-PCR. The VS_ASO_1-FANA (oligo 3) designed shown in the Table 1, and VS_ASO_2 (oligo 3) shown in the Table 2; and VS_DsiRNA (oligo 3) shown in Table 3. A1&A2: No treatment as control, A3&A4: Overexpression of COVID-19 S-protein, A5&A6: Overexpression of COVID-19 S-protein+/treated by VS_DsiRNA (oligo 3) with lipofectamine, B1&B2: Overexpression of COVID-19 S-protein+/treated by VS_DsiRNA (oligo 3) with Arginine (5 μl/well), B3&B4: Overexpression of COVID-19 S-protein+/treated by VS_ASO_2 (oligo 3) with lipofectamine, B5&B6: Overexpression of COVID-19 S-protein+/treated by VS ASO_2 (oligo 3) with Arginine (5 μl/well), C1&C2: Overexpression of COVID-19 S-protein+/treated by VS_ASO_1-FANA (oligo 3) without any reagents.

FIG. 15 shows detection of SARS-CoV-2 S-protein expressed in the human primary lung small airway epithelial cells (HSAEC) by qRT-PCR after treatment with VS-Nucleotides. Significant down-regulation was observed: about 4 fold in group treated by VS_DsiRNA oligo (purple/L: $p<0.01$) and about 2.8 fold in the presence of poly-Arginine only (yellow/A: $p<0.001$); about 4 fold in the group treated by VS_ASO_2 oligo (red/L: $p<0.001$) and about 4 fold in the in the presence of poly-Arginine only (orange/A: $p<0.001$); and about 11.5 fold in the group treated by the VS_ASO_1-FANA oligo (green/$p<0.001$); when compared with the group with SARS-CoV-2 S-protein overexpression only. The cycle threshold of no-treatment is non-detectable, but in this case for calculation purposes, the number "40" was used as the cycle threshold for a base-line control.

FIG. 16 shows the experimental design for detection of both of SARS-CoV-2 ORF1ab and RdRp expressed in the primary human lung small airway epithelial cells (HSAEC) by qRT-PCR after treatment. The human primary lung small airway epithelial cells (HSAEC) were cultured in the 24-well dish, and the cells were transfected with the genes encoding both ORF1ab and RdRp of SARS-CoV-2 viral protein. The inhibitory oligonucleotides were added into the cells for 24-48 hours before analysis with RT-PCR. The VS_ASO_1-FANA (oligo 1, 2, 5 and 6) designed shown in the Table 1, and VS_ASO_2 (oligo 1, 2, 5 and 6) shown in the Table 2; and the VS_DsiRNA (oligo 1, 2, 5 and 6) shown in Table 4. A1&A2: No treatment as control, A3&A4: Overexpression of COVID-19 viral genes encoding both ORF1ab and RdRp, A5&A6: Overexpression of both ORF1ab and RdRp+/treated by VS_DsiRNA (oligo 1, 2, 5 and 6) with lipofectamine, B1&B2: Overexpression of both ORF1ab and RdRp+/treated by VS_DsiRNA (oligo 1, 2, 5 and 6) with Arginine (5 μl/well), B3&B4: Overexpression of both ORF1ab and RdRp+/treated by VS_ASO_2 (oligo 1, 2, 5 and 6) with lipofectamine, B5&B6: Overexpression of both ORF1ab and RdRp+/treated by VS_ASO_2 (oligo 1, 2, 5 and 6) with Arginine (5 μl/well), C1&C2: Overexpression of both ORF1ab and RdRp+/treated by VS_ASO_1-FANA (oligo 1, 2, 5 and 6) without any reagents.

FIG. 17 shows detection of SARS-CoV-2 ORF1ab and RdRp expressed in the human primary lung small airway epithelial cells (HSAEC) by qRT-PCR after treatment with inhibitory oligonucleotides. Significant down-regulation was observed: about 3.5 fold in group treated by VS_DsiRNA oligo (purple/L: $p<0.01$) and about 2.2 fold in the presence of poly-Arginine only (yellow/A: $p<0.001$); about 4.5 fold in the group treated by VS_ASO_2 oligo (red/L: $p<0.001$) and about 2.1 fold in the in the presence of poly-Arginine only (orange/A: $p<0.001$); and about 11.8 fold in the group treated by the VS_ASO_1-FANA oligo (green/$p<0.001$); when compared with the group with SARS-CoV-2 ORF1ab and RdRp overexpression only. The cycle threshold of no-treatment is non-detectable, but in this case for calculation purposes, the number "40" was used as the cycle threshold for a base-line control.

Example 5: SARS-CoV-2 N-Protein Levels are Decreased in Human Primary Lung Small Airway Epithelial Cells (HSAEC) after Treatment by Inhibitory Oligonucleotides FIG. 18 shows the experimental design for detection of SARS-CoV-2 N-protein expressed in the primary human lung small airway epithelial cells (HSAEC) by Western Blot after treatment. The human primary lung small airway epithelial cells (HSAEC) were cultured in the 6-well dish, and the cells were transfected with the genes encoding the viral protein (N-protein) of SARS-CoV-2. The inhibitory oligonucleotides were added into the cells for 24-48 hours before analysis with Western Blot. The VS_ASO_2 (oligo 4 & 8) shown in the Table 2; and VS_DsiRNA (oligo 4 & 8) shown in Table 4. A1: No treatment as control, A2: Overexpression of COVID-19 N-protein, A3: Overexpression of COVID-19 N-protein+/treated by VS_DsiRNA (oligo 4 and 8) with lipofectamine, B1: Overexpression of COVID-19 N-protein+/treated by VS_ASO_2 (oligo 4 and 8) with lipofectamine.

FIG. 19 shows detection of SARS-CoV-2 N-protein expressed in the human primary lung small airway epithelial cells (HSAEC) by Western Blot after treatment with inhibitory oligonucleotides: Lane-1: no treatment; Lane-2: SARS-CoV-2 N-protein overexpression (OE); Lane-3: SARS-CoV-2 N-protein OE+/treated by VS_DsiRNA (oligo 4 & 8); Lane-4: SARS-CoV-2 N-protein OE+/treated by the VS_ASO_2 (oligo 4 & 8). The 10 ug total cell-lysis were added into each well. primary antibody: 1p g/mL anti-SARS-CoV-2-N-protein antibody (ProSci, 3857) and anti-GAPDH antibody (Novus Biologicals, NBP2-27103) with 1:1000 dilution. The secondary antibody: goat-anti-rabbit HRP-conjugated Antibody (R&D System, HAF008) with 1:1000 dilution and goat-anti-mouse IgG HRP-conjugated Antibody (R&D System, HAF007) with 1:1000 dilution. The detection was done using horseradish peroxidase-labeled secondary antibodies and enhanced chemiluminescence detection reagent.

Example 6: Inhibitory Oligonucleotide Treatment of Human Primary Bronchial/Tracheal Epithelial (HBTEC) Cells Transfected with Viral Proteins of SARS-CoV-2

FIG. 20 shows experiments designed for investigating cell penetration and therapeutic effects of VS-Nucleotides (inhibitory oligonucleotides) on human primary bronchial/tracheal epithelial cells (HBTEC) transfected with viral protein of SARS-CoV-2 after treatment. The primary human bronchial/tracheal epithelial cells (HBTEC) were cultured in a 24-well dish, and the cells were transfected with the genes encoding the viral proteins of SARS-CoV-2. The VS_ASO_1-FANA-FITC, VS_DsiRNA-Cy5 and VS_ASO_2-Cy3 were added into the cells for 24-48 hours before analysis with fluorescent microscope. VS_ASO_1-FANA-FITC designed with FITC labeled shown in the Table 1, and VS_ASO_2-Cy3 with Cy3 label shown in the Table 2; and VS_DsiRNA-Cy5 with Cy5 label shown in Table 3. A1&A2: No treatment as control, A3&A4: Overexpression of COVID-19 N-protein+/treated by VS_ASO_1-FANA-FITC without lipofectamine or/and Poly-arginine, B1&B2: No treatment as control, B3&B4: Overexpression of COVID-19 N-protein+/treated by VS_DsiRNA-Cy5 with lipofectamine, B5&B6: Overexpression of COVID-19 N-protein+/treated by VS_DsiRNAi-Cy5 with arginine (5 µl/well), C1&C2: No treatment as control, C3&C4: Overexpression of COVID-19 N-protein+/treated by VS_ASO_2-Cy3 with lipofectamine, C5&C6: Overexpression of COVID-19 N-protein+/treated by VS_ASO_2-Cy3 with arginine (5 µl/well).

FIGS. 21A-21D shows microscopic analysis showing entry of VS_ASO_1-FANA-FITC into primary human lung bronchial/tracheal epithelial cells (20×). FIGS. 21A-21B were captured under FITC florescent filter, and FIGS. 21C and 21D were captured in the same view of bright fields (20×). FIGS. 21A and 21C were taken in well A1 & A2 (as shown in FIG. 20), and FIGS. 21B and 21D were taken in well A3 & A4 (as shown in FIG. 20).

FIGS. 22A-22D shows microscopic analysis showing entry of VS_ASO_1-FANA-FITC into primary human lung bronchial/tracheal epithelial cells (10×). FIG. 22A-22B were captured under FITC florescent filter, and FIGS. 22C and 22D were captured in the same view of bright fields (10×). FIGS. 22A and 22C were taken in well A1 & A2 (as shown in FIG. 20), and FIGS. 22B and 22D were taken in well A3 & A4 (as shown in FIG. 20).

FIGS. 23A-23F shows microscopic analysis showing entry of VS_DsiRNA-Cy5 into primary human lung bronchial/tracheal epithermal cells (20×). FIG. 23A-23C were captured under the Cy5 florescent filter, and FIGS. 23D-23F were captured in the same view of bright fields (20×). FIGS. 23A and 23D were taken in well B3 & B4 (as shown in FIG. 20), FIGS. 23B and 23E were taken in well B5 & B6 (as shown in FIG. 20), and FIGS. 23C and 23F were taken in well B1 & B2 (as shown in FIG. 20).

FIGS. 24A-24F shows microscopic analysis showing entry of VS_DsiRNA-Cy5 into primary human lung bronchial/tracheal epithermal cells (10×). FIGS. 24A-24C were captured under the Cy5 florescent filter, and FIGS. 24D-24F were captured in the same view of bright fields (20×). FIGS. 24A and 24D were taken in well B3 & B4 (as shown in FIG. 20), FIGS. 24B and 24E were taken in well B5 & B6 (as shown in FIG. 20), and FIGS. 24C and 24F were taken in well B1 & B2 (as shown in FIG. 20).

FIGS. 25A-25F shows microscopic analysis showing entry of VS_ASO_2-Cy3 into primary human lung bronchial/tracheal epithermal cells (20×). FIGS. 25A-25C were captured under the Cy3 florescent filter, and FIGS. 25D-25F were captured in the same view of bright fields (20×). FIGS. 25A and 25D were taken in well B3 & B4 (as shown in FIG. 20), FIGS. 25B and 25E were taken in well B5 & B6 (as shown in FIG. 20), and FIGS. 25C and 25F were taken in well B1 & B2 (as shown in FIG. 20).

FIGS. 26A-26F shows microscopic analysis showing entry of VS_ASO_2-Cy3 into primary human lung bronchial/tracheal epithermal cells (10×). FIGS. 26A-26C were captured under the Cy3 florescent filter, and FIGS. 26D-26F were captured in the same view of bright fields (20×). FIGS. 26A and 26D were taken in well B3 & B4 (as shown in FIG. 20), FIGS. 26B and 26E were taken in well B5 & B6 (as shown in FIG. 20), and FIGS. 26C and 26F were taken in well B1 & B2 (as shown in FIG. 20).

Example 7: SARS-CoV-2 N-Protein Expression is Decreased Upon Treatment by the Inhibitory Oligonucleotides FIG. 27 shows the experimental design for detection of SARS-CoV-2 N-protein expressed on human primary bronchial/tracheal epithelial cells (HBTEC) by qRT-PCR. The human primary bronchial/tracheal epithelial cells (HBTEC) were cultured in a 24-well dish, and the cells were transfected with the genes encoding the viral protein (N-protein) of SARS-CoV-2. The inhibitory oligonucleotides were added into the cells for 24-48 hours before analysis with RT-PCR. The VS_ASO_1-FANA-FITC designed with FITC labeled shown in the Table 1, and VS_ASO_2-Cy3 with Cy3 modification shown in the Table 2; and VS_DsiRNA-Cy5 with Cy5 modification shown in Table 3. A1&A2: No treatment as control, A3&A4: Overexpression of COVID-19 N-protein, A5&A6: Overexpression of COVID-19 N-protein+/treated by VS_DsiRNA-Cy5 with lipofectamine, B1&B2: Overexpression of COVID-19 N-protein+/treated by VS_Dsi RNA-Cy3 with lipofectamine, B3&B4: Overexpression of COVID-19 N-protein+/treated by VS_ASO_1-FANA without any reagents.

FIG. 28 shows detection of SARS-CoV-2 N-protein expressed in the human primary bronchial/tracheal epithelial cells (HBTEC) by qRT-PCR after treatment with inhibitory oligonucleotides. Significant down-regulation was observed: about 4 fold in the group treated by VS_DsiRNA-Cy5 oligos ($p<0.005$); about 6 fold in the group treated by VS_ASO_2-cy3 oligo ($p<0.01$), and about 8 fold in the group treated by the VS_ASO_1-FANA-FITC oligo ($p<0.005$); when compared with the group with SARS-CoV-2 N-protein overexpression only. The cycle threshold of no-treatment is non-detectable, but in this case for calculation purposes, the number "40" was used as the cycle threshold for a base-line control.

FIG. 29 shows the experimental design for detection of SARS-CoV-2 S-protein expressed in human primary bronchial/tracheal epithelial cells (HBTEC) by qRT-PCR. The human primary bronchial/tracheal epithelial cells (HBTEC) were cultured in a 24-well dish, and the cells were transfected with the genes encoding the viral protein (S-protein) of SARS-CoV-2. The siRNA or ASO were added into the cells for 24-48 hours before analysis with RT-PCR. The VS_ASO_1-FANA (oligo 3) designed is shown in the Table 1, VS_ASO_2 (oligo 3) is shown in the Table 2; and VS_DsiRNA (oligo 3) is shown in Table 3. A1&A2: No treatment, A3&A4: Overexpression of COVID-19 S-protein, A5&A6: Overexpression of COVID-19 S-protein+/treated by DsiRNA-Cy5 with lipofectamine, B1&B2: Overexpression of COVID-19 S-protein+/treated by VS_DsiRNA-Cy5 with Arginine (5 µl/well), B3&B4: Overexpression of COVID-19 S-protein+/treated by the VS_ASO_2-Cy3 with lipofectamine, B5&B6: Overexpression of COVID-19 S-protein+/treated by VS_ASO_2-Cy3 with Arginine (5 µl/well), C1&C2: Overexpression of COVID-19 S-protein+/treated by VS_ASO_1-FANA without any reagents.

FIG. 30 shows detection of SARS-CoV-2 S-protein expression in the human bronchial/tracheal epithelial cells (HBTEC) by qRT-PCR after treatment with inhibitory oligonucleotides. Significant down-regulation was observed: about 8 fold in the group treated by VS-DsiRNA oligo (purple/L: $p<0.01$), but about 16.3 fold in presence of Poly-arginine only (yellow/$p<0.001$); about 15.8 fold in the group treated by VS_ASO_2 oligo (red/L: $p<0.001$), but about 16.6 fold in presence of Poly-arginine only (orange/A: $p<0.001$); about 11.7 fold in the group treated by the VS_ASO_1 oligo (green/$p<0.001$); when compared with the group with SARS-CoV-2 S-protein overexpression only (1). The cycle threshold of no-treatment is non-detectable, but in this case for calculation purposes, the number "40" was used as the cycle threshold for a base-line control.

Inhibitory Peptide—ACE2 Protein Competition Assays

Inhibitory peptide (VS-peptide)—ACE2 protein Competition Assays prove the VSB peptides' therapeutic efficiency (blocking/interfere S-RBD binding to ACE2) in live cell condition. HeLa cells were transfected with ACE2 plasmid to express ACE2 (HeLa cells do not have endogenous ACE2 expression). Without VSB peptide, S-RBD (conjugated with FITC) will bind to ACE2 and resulting the HeLa-ACE2 cell with FITC (green) signal. In the presence of a VSB peptide, the S-RBD (conjugated with FITC) binds to VSB peptide instead of HeLa-ACE2 cells. In this case, HeLa-ACE2 cells has no FITC signal.

Example 8: SARS-CoV-2 ORF1ab and RdRp Expression is Decreased Upon Treatment by Inhibitory Oligonucleotides

FIG. 31 shows the experimental design for detection of SARS-CoV-2 ORF1ab and RdRp expressed in the human primary bronchial/tracheal epithelial cells (HBTEC) detected by qRT-PCR after treatment. The human primary bronchial/tracheal epithelial cells (HBTEC) were cultured in the 24-well dish, and the cells were transfected with the genes encoding the viral protein (ORF1ab and RdRp) of SARS-CoV-2. The inhibitory oligonucleotides were added into the cells for 24-48 hours before analysis with RT-PCR. VS_ASO_1-FANA (oligo 1, 2, 5 and 6) designed is shown in the Table 1, VS_ASO_2 (oligo 1, 2, 5 and 6) is shown in the Table 2; and the VS_DsiRNA (oligo 1, 2, 5 and 6) is shown in Table 4. A1&A2: No treatment as control, A3&A4: Overexpression of COVID-19 viral genes encoding both ORF1ab and RdRp, A5&A6: Overexpression of COVID-19 ORF1ab and RdRp+/treated by VS_DsiRNA (oligo 1, 2, 5 and 6) with lipofectamine, B1&B2: Overexpression of COVID-19 ORF1ab and RdRp+/treated by VS_DsiRNA (oligo 1, 2, 5 and 6) with Arginine (5 μl/well), B3&B4: Overexpression of COVID-19 ORF1ab and RdRp+/treated by VS_ASO_2 (oligo 1, 2, 5 and 6) with lipofectamine, B5&B6: Overexpression of COVID-19 ORF1ab and RdRp+/treated by VS_ASO_2 (oligo 1, 2, 5 and 6) with Arginine (5 μl/well), C1&C2: Overexpression of COVID-19 ORF1ab and RdRp+/treated by VS_ASO_1-FANA (oligo 1, 2, 5 and 6) without any reagents.

FIG. 32 shows detection of SARS-CoV-2 ORF1ab and RdRp expressed in the human primary bronchial/tracheal epithelial cells (HBTEC) detected by qRT-PCR after treatment with inhibitory oligonucleotides. Significant down-regulation was observed: about 3 fold in the group treated by VS_DsiRNA oligo (purple/L: $p<0.01$) and about 2.6 fold in the presence of poly-Arginine only (yellow/A: $p<0.001$); about 6.4 fold in the group treated by VS_ASO_2 oligo (red/L: $p<0.001$) and about 4.5 fold in the presence of poly-Arginine only (orange/A: $p<0.001$); and about 11.9 fold in the group treated by the VS_ASO_1-FANA oligo (green/$p<0.001$); when compared with the group with SARS-CoV-2 ORF1ab and RdRp overexpression only. The cycle threshold of no-treatment is non-detectable, but in this case for calculation purposes, the number "40" was used as the cycle threshold for a base-line control.

Example 9: SARS-CoV-2 N-Protein Levels are Down after Treatment by the Inhibitory Oligonucleotides FIG. 33 shows the experimental design for detection of SARS-CoV-2 N-protein expressed in the human primary bronchial/tracheal epithelial cells (HBTEC) by Western Blot after treatment. The human primary bronchial/tracheal epithelial cells (HBTEC) were cultured in a 6-well dish, and the cells were transfected with the genes encoding the viral protein (N-protein) of SARS-CoV-2. The inhibitory oligonucleotides were added into the cells for 24-48 hours before analysis with Western Blot. The VS_ASO_02 (oligo 4 & 8) is shown in the Table 2; and VS_DsiRNA (oligo 4 & 8) is shown in Table 4. A1: No treatment as control, A2: Overexpression of COVID-19 N-protein, A3: Overexpression of COVID-19 N-protein+/treated by VS_DsiRNA (oligo 4 and 8) with lipofectamine, B1: Overexpression of COVID-19 N-protein+/treated by VS_ASO_2 (oligo 4 and 8) with lipofectamine.

FIG. 34 shows detection of SARS-CoV-2 N-protein expressed in the human primary bronchial/tracheal epithelial cells (HBTEC) by Western Blot after treatment with inhibitory oligonucleotides. Lane 1: no treatment, Lane 2: SARS-CoV-2 N-protein overexpression (OE); Lane 3: SARS-CoV-2 N-protein OE+VS_DsiRNA (oligo 4 & 8); Lane 4: SARS-CoV-2 N-protein OE+VS_ASO_2 (oligo 4 & 8). 10 μg total cell lysis were added into each well and blotted with primary antibody (1 μg/mL anti-SARS-CoV-2-N-protein antibody (ProSci, 3857)) or anti-GAPDH antibody (Novus Biologicals, NBP2-27103) (1:1000 dilution). The secondary antibodies were goat-anti-rabbit HRP-conjugated Antibody (R&D System, HAF008) (1:1000) dilution and goat-anti-mouse IgG HRP-conjugated Antibody (R&D System, HAF007) (1:1000) dilution. The detection was done using horseradish peroxidase-labeled secondary antibodies and an enhanced chemiluminescence detection reagent.

FIG. 35 shows the experimental designs for investigating cell penetration and therapeutic effects of ASO(s) and DsiRNA on human primary nasal epithelial cells (HNEpC)

transfected with viral protein of SARS-CoV-2 after treatment. The human primary nasal epithelial cells (HNEpC) were cultured in a 24-well dish, and the cells were transfected with the genes encoding the viral proteins of SARS-CoV-2. The VS_ASO_1-FANA-FITC, VS_DsiRNA-Cy5 and VS_ASO_2-Cy3 were delivered into the cells for 24-48 hours before analysis with fluorescent microscope. The VS_ASO_1-FANA-FITC was FITC labeled (see Table 1), and VS_ASO_2-Cy3 was Cy3 labeled (See Table 2); and VS_DsiRNA-Cy5 was Cy5 labeled (see Table 3). A1&A2: No treatment as control, A3&A4: Overexpression of COVID-19 N-protein+/treated by VS_ASO_1-FANA without lipofectamine or arginine, B1&B2: No treatment as control, B3&B4: Overexpression of COVID-19 N-protein+/treated by VS_DsiRNA-Cy5 with lipofectamine, B5&B6: Overexpression of COVID-19 N-protein+/treated by VS_DsiRNA-Cy5 with poly-arginine (5 μl/well), C1&C2: No treatment as control, C3&C4: Overexpression of COVID-19 N-protein+/treated by VS_ASO_2-Cy3 with lipofectamine, C5&C6: Overexpression of COVID-19 N-protein+/treated by VS_ASO_2-Cy3 with poly-arginine (5 μl/well).

Figure 36A:
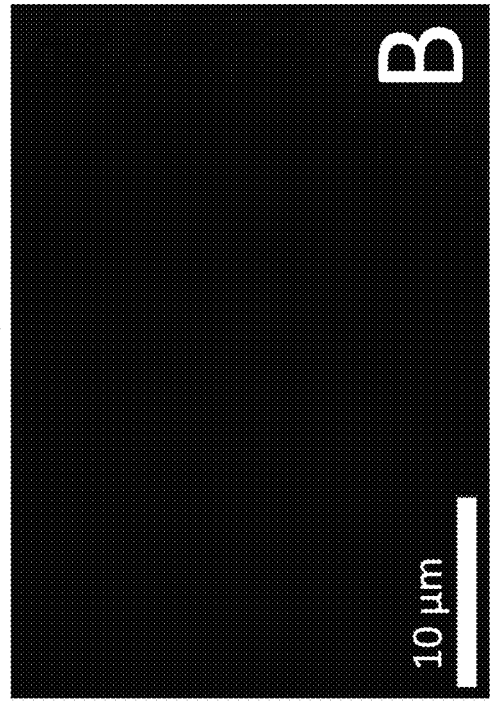
Figure 36B:
Figure 36C:
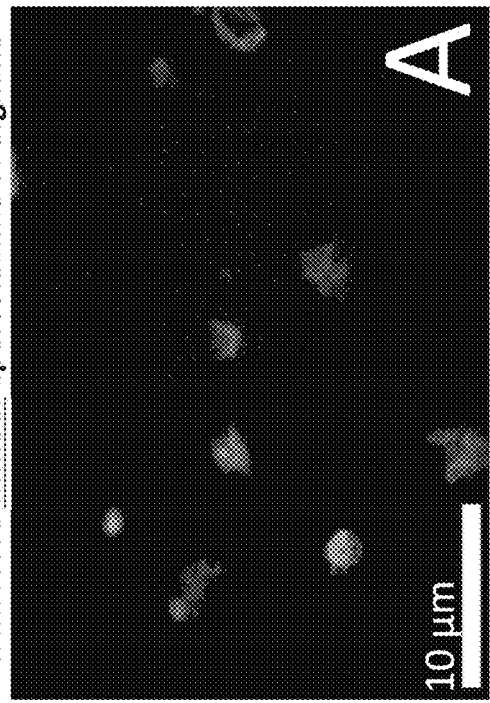
Figure 36D:
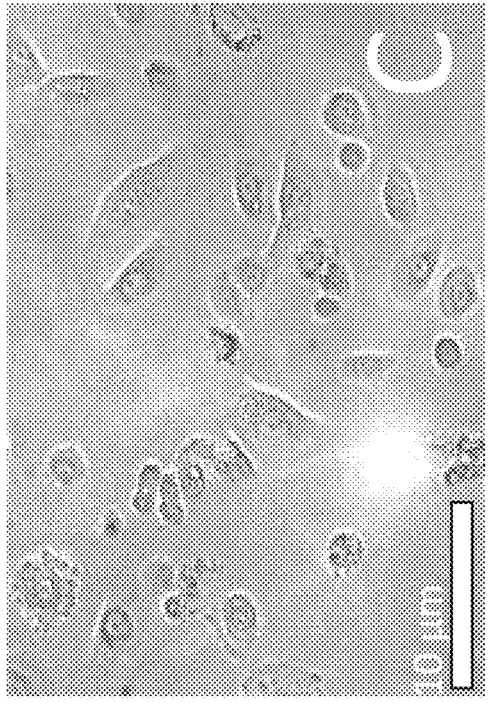

FIGS. 36A-36D show the microscopic analysis of Human Primary Nasal Epithelial Cells at 20×. This analysis showed that VS_ASO_1-FANA-FITC can enter epithelial cells (20×). FIGS. 36A and 36B were captured under FITC florescent filter, and FIGS. 36C and 36D were captured in the same view of bright fields (20×). FIGS. 36A and 36C were taken in well A3 & A4 (as shown in FIG. 35), FIGS. 36B and 36D were taken in well A1 & A2 (as shown in FIG. 35).

Figure 37B:
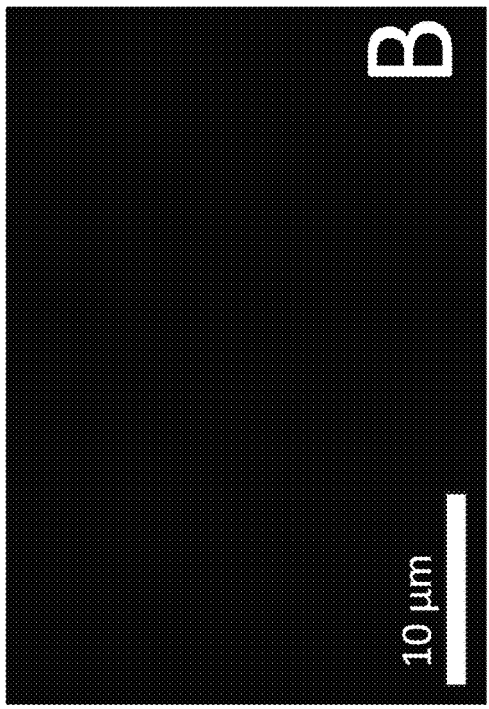
Figure 37D:
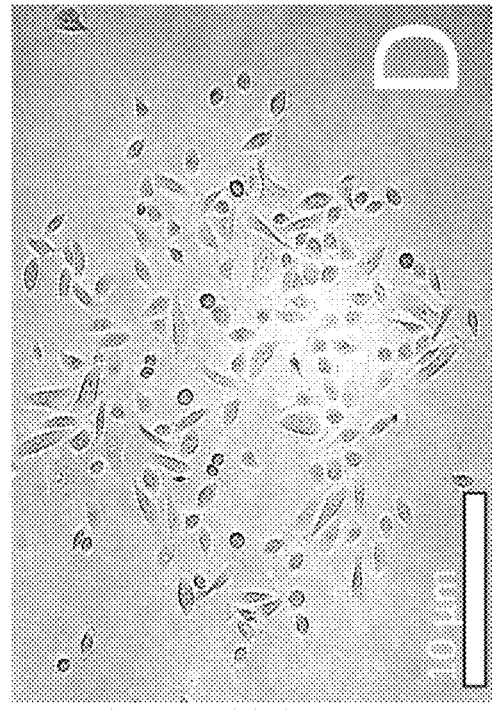
Figure 37A:
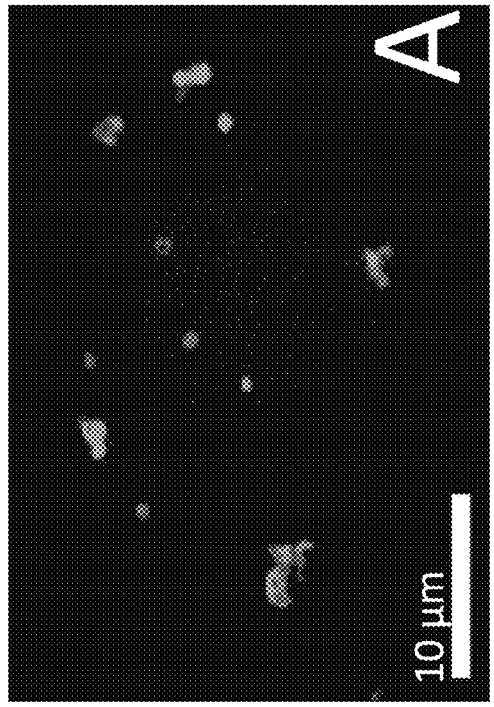
Figure 37C:
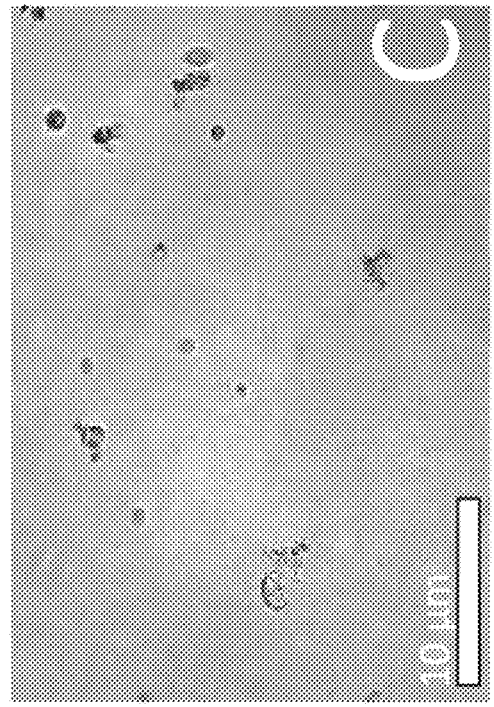

FIGS. 37A-37D show the microscopic analysis of Human Primary Nasal Epithelial Cells at 20×. This analysis showed that VS_ASO_1-FANA-FITC can enter epithelial cells (10×). FIGS. 37A and 37B were captured under FITC florescent filter, and FIGS. 37C and 37D were captured in the same view of bright fields (20×). FIGS. 37A and 37C were taken in well A3 & A4 (as shown in FIG. 35), FIGS. 37B and 37D were taken in well A1 & A2 (as shown in FIG. 35).

FIGS. 38A-38F show the microscopic analysis of Human Primary Nasal Epithelial Cells at 20×. This analysis showed that VS_DsiRNA-Cy5 can enter epithelial cells (20×). FIGS. 38A-38C were captured under the Cy5 florescent filter, and FIGS. 38D-38F were captured in the same view of bright fields (20×). FIGS. 38A and 38D were taken in well B3 & B4 (as shown in FIG. 35), FIGS. 38B and 38E were taken in well B5 & B6 (as shown in FIG. 35), FIGS. 38C and 38F were taken in well B1 & B2 (as shown in FIG. 35).

Figure 39C:
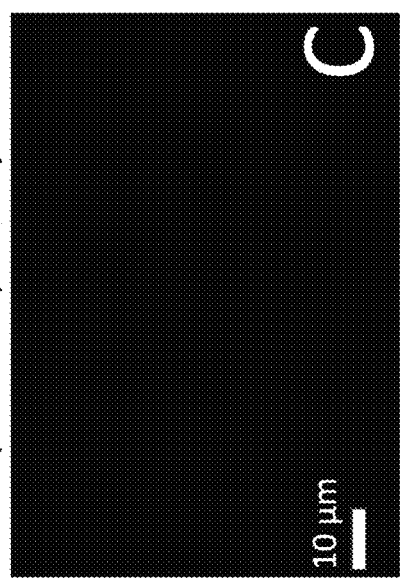
Figure 39B:
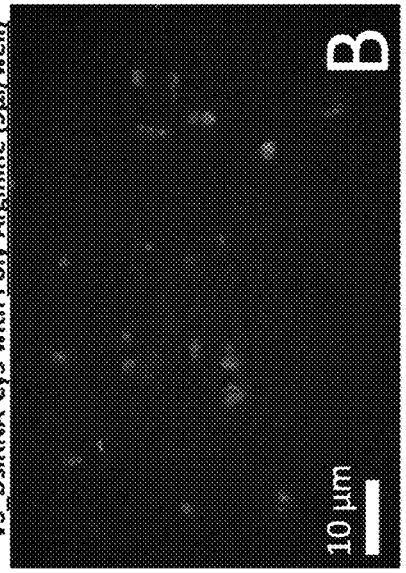
Figure 39A:
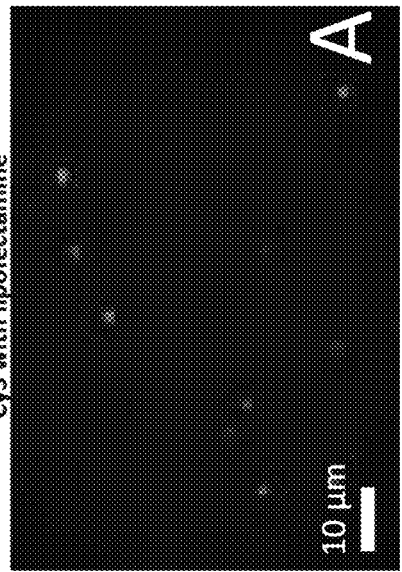
Figure 39F:
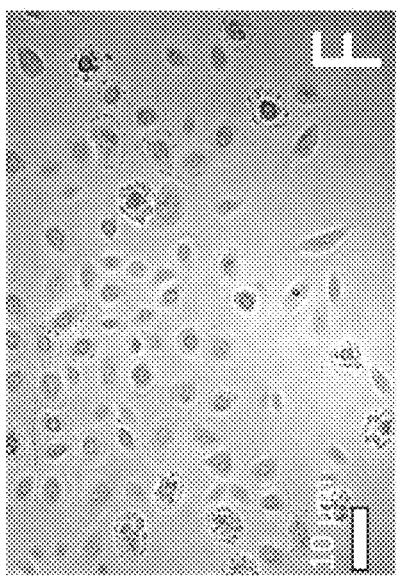
Figure 39E:
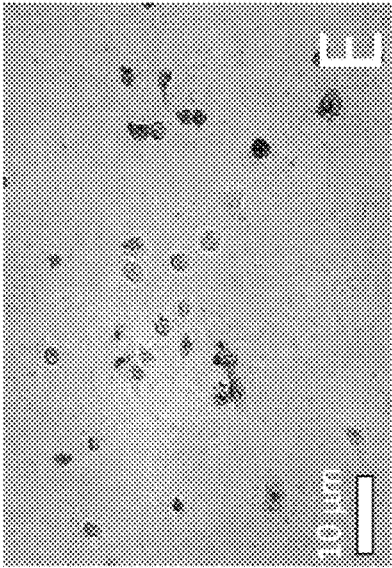
Figure 39D:
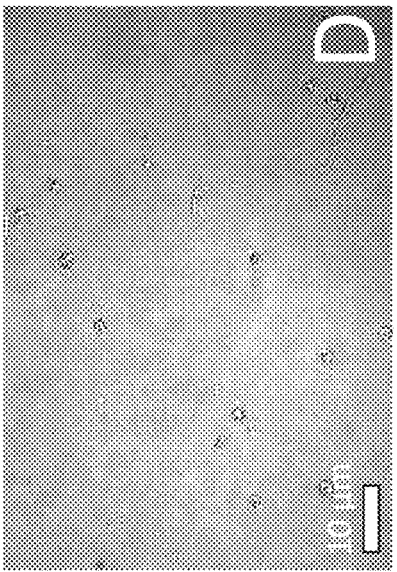

FIGS. 39A-39F show the microscopic analysis of Human Primary Nasal Epithelial Cells at 10×. This analysis showed that VS_DsiRNA-Cy5 can enter epithelial cells (10×). FIGS. 39A-39C were captured under the Cy5 florescent filter, and FIGS. 39D-39F were captured in the same view of bright fields (20×). FIGS. 39A and 39D were taken in well B3 & B4 (as shown in FIG. 35), FIGS. 39B and 39E were taken in well B5 & B6 (as shown in FIG. 35), FIGS. 39C and 39F were taken in well B1 & B2 (as shown in FIG. 35).

FIGS. 40A-40F show the microscopic analysis of Human Primary Nasal Epithelial Cells at 20×. This analysis showed that VS_ASO_2-Cy3 can enter epithelial cells (20×). FIGS. 40A-40C were captured under the Cy3 florescent filter, and FIGS. 40D-40F were captured in the same view of bright fields (20×). FIGS. 40A and 40D were taken in well B3 & B4 (as shown in FIG. 35), FIGS. 40B and 40E were taken in well B5 & B6 (as shown in FIG. 35), FIGS. 40C and 40F were taken in well B1 & B2 (as shown in FIG. 35).

FIGS. 41A-41F show the microscopic analysis of Human Primary Nasal Epithelial Cells at 10×. This analysis showed that VS_ASO_2-Cy3 can enter epithelial cells (10×). FIGS. 41A-41C were captured under the Cy3 florescent filter, and FIGS. 41D-41F were captured in the same view of bright fields (10×). FIGS. 41A and 41D were taken in well B3 & B4 (as shown in FIG. 35), FIGS. 41B and 41E were taken in well B5 & B6 (as shown in FIG. 35), FIGS. 41C and 41F were taken in well B1 & B2 (as shown in FIG. 35).

Example 10: SARS-CoV-2 N-Gene Expression is Reduced after Treatment by the Inhibitory Oligonucleotides in HNEpCs FIG. 42. show the experimental design for detection of SARS-CoV-2 N-protein expressed on human primary nasal epithelial cells (HNEpC) by qRT-PCR. The human primary nasal epithelial cells (HNEpC) were cultured in a 24-well dish, and the cells were transfected with the genes encoding the viral protein (N-protein) of SARS-CoV-2. The inhibitory oligonucleotides were added into the cells for 24-48 hours before analysis with RT-PCR. VS_ASO_1-FANA-FITC was labeled with FITC as shown in the Table 1, and VS_ASO_2-Cy3 was labeled with Cy3 as shown in Table 2; and VS_DsiRNA-Cy5 was labeled with Cy5 as shown in Table 3. A1&A2: No treatment, A3&A4: Overexpression of COVID-19 N-protein, A5&A6: Overexpression of COVID-19 N-protein+/treated by VS_DsiRNA-Cy5 with lipofectamine, B1&B2: Overexpression of COVID-19 N-protein+/treated by VS_DsiRNA-Cy5 with Arginine (5 μl/well), B3&B4: Overexpression of COVID-19 N-protein+/treated by VS_ASO_2-Cy3 with lipofectamine, B5&B6: Overexpression of COVID-19 N-protein+/treated by VS_ASO_2-Cy3 with Arginine (5 μl/well), C1&C2: Overexpression of COVID-19 N-protein+/treated by VS_ASO_1-FANA-FITC without any reagents.

FIG. 43 shows detection of SARS-CoV-2 N-protein expressed in the human primary nasal epithelial cells (HNEpC) by qRT-PCR after treatment with siRNA or ASO. Significant down-regulation was observed: about 90 fold in the group treated by VS_DsiRNA-Cy5 oligo (2: p<0.01); about 15 fold in the group treated by VS_ASO_2-Cy3 oligo (p<0.01), and about 350 fold of down-regulation in the group treated by the VS_ASO_1-FANA-FITC oligo (3: p<0.001); when compared with the group with COIVD-19 N-protein overexpression only. The cycle threshold of no-treatment is non-detectable, but in this case for calculation purposes, the number "40" was used as the cycle threshold for a base-line control.

FIG. 44 shows experimental design for inhibiting viral infections using inhibitory nucleotides. WV=Wild-type of pseud-COVID-19 virus, 5 μl (titer: $10^5$ TU/ml) of the virus added into each well (C1 to C9). MV=Mutant form of pseud-COVID-19 virus, 5 μl (titer: $10^5$ TU/ml) of the virus added into each well (D1 to D9). N 1=VS_ASO_3 oligo (targeting on S-protein of COVID-19), N 2=VS_siRNA/RNAi_3 oligo (targeting on S-protein of COVID-19, Control-1=Scramble nucleotide oligo (SN) only.

FIGS. 45A-45F show experimental data of inhibitions of wild-type viral infections by inhibitory nucleotides. FIG. 45A Brightfield image of VS_ASO_3-treated cells. FIG. 45B Brightfield image of VS_RNAi_3-treated cells. FIG. 45C Brightfield image of scramble-treated cells. FIG. 45D Fluorescence image of VS_ASO_3-treated cells. FIG. 45E Fluorescence image of VS_RNAi_3-treated cells. FIG. 45F Fluorescence image of scramble-treated cells. There were no significant GFP expressions found in those cells treated by VS_ASO_3 and VS_RNAi_3 oligos, detected under the confocal microscope; but the inventors were able to see the GFP expressions in the control group of the cells treated with the scramble nucleotide only. This data thus indicated that the VS_ASO_3 and VS_RNAi_3 have inhibited the wild-type pseudoviruses coupled with eGFP (WV) inside the cells; but not in the group treated with the scramble nucleotide. The pseudo-type of COVID-19 virus (both the wild-type virus (WV) and the mutant virus (MV)) used in these experiments is an RNA virus like SARS-CoV-2. Without being bound to a particular theory, the inhibitory nucleotides of the disclosure are believed to inhibit viral infection by blocking the transcription of the spike protein; and also by disrupting the RNA transcription of the pseudo-type of COVID-19 viral genes.

FIGS. 46A-46F show experimental data of inhibitions of mutant viral infections by inhibitory nucleotides. FIG. 46A Brightfield image of VS_ASO_3-treated cells. FIG. 46B Brightfield image of VS_RNAi_3-treated cells. FIG. 46C Brightfield image of scramble-treated cells. FIG. 46D Fluorescence image of VS_ASO_3-treated cells. FIG. 46E Fluorescence image of VS_RNAi_3-treated cells. FIG. 46F Fluorescence image of scramble-treated cells. There was no significant GFP expressions found in those cells treated by VS_ASO_3 and VS_RNAi_3, detected under the confocal microscope; but the inventors were able to see the GFP expressions in the control group of the cells treated with the scramble nucleotide only. This data thus indicated that the VS_ASO_3 and VS_RNAi_3 have also inhibited the mutant pseudo viruses coupled with eGFP (MV) inside the cells; but not in the group treated with the scramble nucleotide. The pseudo-type of COVID-19 virus (both the wild-type virus (WV) and the mutant virus (MV)) used in these experiments is an RNA virus like SARS-CoV-2. Without being bound to a particular theory, the inhibitory nucleotides of the disclosure are believed to inhibit viral infection by blocking the transcription of the spike protein; and also by disrupting the RNA transcription of the pseudo-type of COVID-19 viral genes.

The designed nucleotides of VS_ASO and VS_RNAi (see Table 1) were able to inhibit viral infections and propagations with both the wild-type (WV) and mutant (MV) viruses of the pseudo COVID-19 in the living mammalian cells expressed ACE2 proteins.

Example 11: Inhibitory Peptides Block RBD Derived from the S-Protein of SARS-CoV-2

FIG. 47 shows the analysis of the amino acid sequence of SARS-CoV-2 Spike protein (S-protein) (GenBank ID: QHD43416.1, SEQ ID NO: 61). The region of the sequence highlighted in red represents the predicted sequences of ACE2 binding sequences/motifs (aka. the Ligand binding Domain).

FIGS. 48A-48B show the analysis of the amino acid sequence of the BD motifs. FIG. 48A 3D interaction between the SARS-CoV-2 Spike protein and human ACE2. FIG. 48B Analysis of the amino acids of the RBD motifs in 3D structure between the SARS-CoV-2 Spike protein (B: K417 to Y505) and human ACE2 (B: Q24 to R393) was used to order to locate which regions of the sequences contribute to the protein-protein interaction, and to design peptides that mimic the RBD sequences (mimics act like a human ACE 2 and prevent or block the binding activities for the SARS-CoV-2 on the real ACE2 in the cells).

FIG. 49 shows the experimental design. A1&A2: No treatment as control, A3&A4: peptide 5-FITC, A5&A6: peptide 5-FITC+/treated by the peptide 1 (low dosage), B1&B2: peptide 5-FITC+/treated by the peptide 1 (high dosage), B3&B4: peptide 5-FITC+/treated by the peptide 2 (low dosage), B5&B6: peptide 5-FITC+/treated by the peptide 2 (high dosage), 1&C2: peptide 5-FITC+/treated by the peptide 3 (low dosage), C3&C4: peptide 5-FITC+/treated by the peptide 3 (high dosage), C5&C6: peptide 5-FITC+/treated by the peptide 4 (low dosage), D1&D2: peptide 5-FITC+/treated by the peptide 4 (high dosage), D3&D4: peptide 5-FITC+/treated by the peptide 1 (high dosage)+peptide 2 (high dosage)+peptide 3 (high dosage)+peptide 4 (high dosage), The dosage-1=1 µg per $10^5$ cells; and the dosage-2=10 µg per $10^5$ cells.

FIGS. 50A-50H show cells infected with wild-type SARS-COV-2 virus (WV) in the presence of inhibitory peptides. FIG. 50A Brightfield image of cells treated with Peptide 1 (P1). FIG. 50B Brightfield image of cells treated with Peptide 2 (P2). FIG. 50C Brightfield image of cells treated with Peptide 3 (P3). FIG. 50D Brightfield image of cells treated with normal human serum (NHS). FIG. 50E Fluorescence (GFP) image cells treated with Peptide 1 (P1). FIG. 50F Fluorescence (GFP) image of cells treated with Peptide 2 (P2). FIG. 50G Fluorescence (GFP) image of cells treated with Peptide 3 (P3). FIG. 50H Fluorescence (GFP) image of cells treated with normal human serum (NHS).

FIGS. 51A-51H show cells infected with mutant SARS-COV-2 virus (MV) in the presence of inhibitory peptides. FIG. 51A Brightfield image of cells treated with Peptide 1 (P1). FIG. 51B Brightfield image of cells treated with Peptide 2 (P2). FIG. 51C Brightfield image of cells treated with Peptide 3 (P3). FIG. 51D Brightfield image of cells treated with normal human serum (NHS). FIG. 51E Fluorescence (GFP) image cells treated with Peptide 1 (P1). FIG. 51F Fluorescence (GFP) image of cells treated with Peptide 2 (P2). FIG. 51G Fluorescence (GFP) image of cells treated with Peptide 3 (P3). FIG. 51H Fluorescence (GFP) image of cells treated with normal human serum (NHS).

FIGS. 52A-52H show microscopic analysis of human primary small airway epithelial cells treated with inhibitory peptides (VS-peptides). FIGS. 52A, and 52E were captured under the FITC florescent filter, FIGS. 52B and 52E were captured in brightfield (20×). FIG. 52C shows the merge of FIGS. 52A and 52B. FIG. 52G is a merge photo of FIGS. 52E and 52F. The white dots indicate the box that was enlarged as shown in (D). The yellow dots indicate the box that was enlarged as shown in FIG. 52H. White arrows suggested peptide 5-FITC internalized into cells cytoplasm and nucleus, while the yellow arrows suggested the VS-peptides combination can block the peptide 5-FITC from internalization, staying outside of cells.

FIGS. 73A-73B. show alignments of inhibitory oligonucleotides. FIG. 73A The alignment of all ASO (ASO_1 and ASO_2) and all oligos in Tables 1, 2 and 4 showed that the designed inhibitory oligonucleotides specifically target the SARS-COV-2 virus genes. The alignment did not show any significant match to any human genes (thereby, avoiding potential side-effects when applied in human). FIG. 73B: The analysis of all DsiRNA indicated all oligos (in Tables 1, 2 and 4) specifically target the SARS-COV-2 virus genes. The alignment did not show any significant match to any human genes (thereby, avoiding potential side-effects when applied in human).

Inhibitory Peptides Block COVID-19 Spike Protein In Vitro

FIGS. 74A-74C show peptide ELISA assays. FIG. 74A Schematic of ELISA assays. FIG. 74B Analysis of inhibitions of COVID-19 Spike Protein Receptor Binding Domain (S-RBD)-ACE2 binding by inhibitory peptides. FIG. 74C Table of p-values of the results in FIG. 74A and the number of amino acids participating in S-RBD/ACE2 interaction. These results indicated that the peptides could compete with ACE2 proteins and prevent S-RBD binding to ACE2. When the designed inhibitory peptides contained more amino acids interacting with S-RBD, stronger affinities were measured.

FIGS. 75A-75B show peptide inhibition data. FIG. 75A Inhibition rate of S-RBD binding to ACE2 using VS peptides. FIG. 75B S-RBD signal rate. The data were converted and calculated as inhibition/suppression rates of the peptides based on the intensities of the S-RBD signals after treatment with the peptides compared with the control groups FIG. 75B. All peptides have shown their dosage-responses in the ELISA reactions, and indicated their strong biological affinities to bind with the S-RBD.

Inhibitory Peptides Block COVID-19 S-RBD-FITC Entry to Living Mammalian Cells

The HeLa-ACE2 cell were harvested after 48 hr post-transfection when ACE2 receptors were expressed on the cell membranes; and suspended in FACS running buffer (0.1% BSA in PBS) with final concentration in 1×106 cells/mL. Divided into 9 tubes (each tube has about 1 million cells). The above cells in each tube were incubated at RT in the dark for 30 min and subsequently subjected to run the FACS analysis BD FACSCalibur (total event: 10 k). The figures were generated and analyzed by a computer program of FlowJo, which were shown as the format of "Scatter-plot." The data indicated that all peptides could target/bind on the S-RBD-FITC to prevent viral RBD entry the cells expressed the ACE2 receptors. See FIGS. 76A-76I. The peptides 1 (FIG. 76D), 2 (FIG. 76E), 4 (FIG. 76G), 5 (FIG. 76H) and mixture showed significant strongest therapeutic effects, but peptides 3 (FIG. 76F) was weak; when compared with the control groups of "HNS/Tube-9" (FIG. 76C), "Positive control/Tube-8" (FIG. 76B) and "Negative control/Tube-7" (FIG. 76A).

Derivatives of Inhibitory Peptides can Also Inhibit S-RBD as Measured by ELISA Assays Inventors have developed variants of original inhibitory peptides VS-Peptides 1-5 (see Table 6). FIG. 77 shows ELISA results of S-RBD inhibition by inhibitory peptides derived from VS-Peptides 1-5 (P1 to P20—corresponding to SEQ ID NOS: 63-82, respectively). The data indicated that the derivative inhibitory peptides are also capable of targeting the S-RBD of SARS-CoV-2 significantly to prevent viral binding on the human ACE2 receptors ($p<0.05$) (FIG. 77).

Example 12: Gene Therapy

FIG. 53 shows the gene therapy vector AAV-U6-A1-H1-A2-SV40-eGFP. This AAV vector expresses two transgenes (namely ASO1 (A1) and ASO2 (A2)) simultaneously in one cell. U6=The 1st promoter that controls the expression of A1 gene in the mammalian cells, H 1=The 2nd promoter that controls the expression of A2 gene in the mammalian cells, SV=The 3rd promoter that controls the expression of GFP gene in the mammalian cells. Full sequence of AAV-U6-A1-H1-A2-SV40-GFP is shown by SEQ ID NO: 46.

FIG. 54 shows the gene therapy vector AAV-U6-A3-H1-A4-SV40-eGFP. This AAV vector expresses two transgenes (namely ASO3 (A3) and ASO4 (A4)) simultaneously in one cell. U6=The 1st promoter that controls the expression of A3 gene in the mammalian cells, H1=The 2nd promoter that controls the expression of A4 gene in the mammalian cells SV40=The 3rd promoter that controls the expression of GFP gene in the mammalian cells. Full sequence of AAV-U6-A1-H1-A2-SV40-eGFP is shown by SEQ ID NO: 47.

FIG. 55 shows the gene therapy vector AAV-U6-shRNA1-CMV-eGFP. This AAV vector expresses the transgene shRNA1. U6=The 1st promoter that controls the expression of shRNA1 gene in the mammalian cells, CMV=the 2nd promoter that controls the expression of eGFP gene in the mammalian cells. The full DNA sequence is shown by SEQ ID NO: 48 of AAV-U6-shRNA1-eGFP.

FIG. 56 shows the gene therapy vector AAV-U6-shRNA2-CMV-eGFP. This AAV vector expresses the transgene shRNA1 in one cell: U6=The 1st promoter that controls the expression of shRNA2 gene in the mammalian cells, CMV=the 2$^{nd}$ promoter that controls the expression of eGFP gene in the mammalian cells. The sequence of AAV-U6-shRNA2-eGFP is shown by SEQ ID NO: 49.

FIG. 57 shows the gene therapy vector AAV-U6-shRNA3-CMV-eGFP. A. This AAV vector expresses the transgene shRNA1. U6=The 1st promoter that controls the expression of shRNA3 gene in the mammalian cells, CMV=The 2nd promoter that controls the expression of eGFP gene in the mammalian cells. The full DNA sequence of AAV-U6-shRNA3-eGFP is shown by SEQ ID NO: 50.

FIG. 58 shows the gene therapy vector AAV-U6-shRNA4-CMV-eGFP. A. This AAV vector expresses the transgene shRNA1. U6=The 1st promoter that controls the expression of shRNA4 gene in the mammalian cells, CMV=The 2nd promoter that controls the expression of eGFP gene in the mammalian cells. The full DNA sequence of AAV-U6-shRNA4-eGFP is shown by SEQ ID NO: 51.

FIGS. 59A-59B show the experimental design of plates FIGS. 59A and 59B.

FIGS. 60A-60D show fold change of exogenously-expressed COVID-19 proteins with gene therapy treatment. The cells were transfected with designed vectors with COVID-19 plasmids (S, N, RdRp and ORF1ab), and also the gene therapy vectors (#1 to #6) after 24 hours post-seeding. At the 48 hours post-transfection, the cells were then harvested, and their total RNA were extracted with including the DNase digestion before PCR assays. S proteins were conducted with TaqMan-probe assay kit (Thermofisher, A47532). The N protein, ORF1ab and RdRp proteins were determined by the GenScript kits (SARS-CoV-2PCR detection assay kit). The data indicated that the treatments by using the gene vectors have significant therapeutic effects to inhibit the expressions of the viral proteins. Synergic enhanced effects were observed when more than one peptide was used (see, #1 to 4 and #5 to 6)

FIGS. 61A-61B show western blot analysis of S-protein expression. FIG. 61B shows quantification of FIG. 61A. The cells were seed onto 6 well-plates. At 24 hours post-seeding, cells were transfected by the gene therapy vectors (#1 to #6) with including the plasmids encoding the COVID-19 S-proteins. After 48 hours post-transfection, cells were harvested and lysed. The primary antibody is SARS-CoV-2 Spike with 1 μg/mL (ProSc, Inc), and the secondary antibody is Goat-anti-Rabbit HRP conjugated antibody by 1:1000 dilution (R&D System). The data indicated that the treatments by using the gene vectors have significant therapeutic effects to block the expression of viral proteins. Synergic enhanced effects were observed when more than one peptide was used (see, #1 to 4 and #5 to 6).

FIG. 62 shows the experimental design of in vitro gene therapy on inhibitions of the viral infections.

FIGS. 63A-63F show in vitro gene therapy inhibits WV viral infections. ASO (V1) and RNAi (V2) were delivered by gene vectors into mammalian cells that express ACE2 proteins, in order to inhibit the WV viral infections (WV=wild-type pseudo-virus of COVID-19). FIG. 63A Brightfield image of cells treated with ASO (V1). FIG. 63B Brightfield image of cells treated with RNAi (V2). FIG. 63C Brightfield image of cells treated with control. FIG. 63D Fluorescence image of cells treated with ASO (V1). FIG. 63E Fluorescence image of cells treated with RNAi (V2). FIG. 63F Fluorescence image of cells treated with control.

FIGS. 64A-64F show in vitro gene therapy inhibits MV viral infections. ASO (V1) and RNAi (V2) were delivered by gene vectors into mammalian cells that express ACE2 proteins, in order to inhibit the MV viral infections (MV=mutant pseudo-virus of COVID-19). FIG. 64A Brightfield image of cells treated with ASO (V1). FIG. 64B Brightfield image of cells treated with RNAi (V2). FIG. 64C Brightfield image of cells treated with control. FIG. 64D Fluorescence image of cells treated with ASO (V1). FIG. 64E Fluorescence image of cells treated with RNAi (V2). FIG. 64F Fluorescence image of cells treated with control.

FIG. 65A-65D show in vitro delivery of gene vectors into living cells. ASO (V1) and RNAi (V2) were delivered by using the gene vectors into mammalian cells that express ACE2 proteins, the cells were not incubated with any viruses, which were served as background controls. The concentrations of the vectors encoding the ASO (control-2) or/and RNAi (control-3) were the same used in the FIGS. 61A-61B and 62. FIG. 65A Brightfield image of cells treated with ASO control. FIG. 65B Brightfield image of cells treated with RNAi control. FIG. 65C Fluorescence image of cells treated with ASO control. FIG. 65D Fluorescence image of cells treated with RNAi control.

FIGS. 66A-66B show analysis of FIG. 66A Wild-type pseudovirus experiment results and FIG. 66B mutant pseudovirus experiment results. Since both gene vectors, encoding ASO and shRNA, also contain marker gene of GFP, normalized data was calculated based on control-2 and control-3 constructs (also see FIG. 62). The data analysis confirmed that ASO or shRNA vector expressing cells showed very little GFP signal, when compared with the control group-1. This data indicates that the gene vectors carrying either ASO or shRNA (inhibitory oligonucleotides) suppress viral infection and propagation in both wild-type and mutant pseudoviruses of COVID-19, pseudo-typed by lentiviruses. The pseudo-type of COVID-19 virus (both the wild-type virus (WV) and the mutant virus (MV)) used in these experiments is an RNA virus like SARS-CoV-2. Without being bound to a particular theory, the inhibitory nucleotides expressed by the genes vectors of the instant disclosure are believed to inhibit viral infection by blocking the transcription of the spike protein; and also by disrupting the RNA transcription of the pseudo-type of COVID-19 viral genes.

Example 13: Nutrition/Dietary Supplements

FIG. 67 shows experimental design for detection of apoptosis/cytotoxicity of VS-nutrition in human bronchial/tracheal epithelial cells (HBTEC) by qRT-PCR. The human primary bronchial/tracheal epithelial cells (HBTEC) were cultured in the 24 well-dish, and the cells were treated with VS-nutrition with designated dilution (1:1, 1:300 and 1:500) for 5 days (in every day, refresh cell culture medium and added new VS-nutrition with same composition and ratio) before analysis by qRT-PCR.

FIG. 68 shows detection of on apoptosis/cytotoxicity of VS-nutrition in the human bronchial/tracheal epithelial cells (HBTEC) by qRT-PCR after treatment. Detection of apoptosis/cytotoxicity of VS-nutrition in the human primary bronchial/tracheal epithelial cells (HBTEC) by qRT-PCR after treatment with VS-nutrition. There are no significant up or down-regulation of BAX/BCL2 ratio in group treated by VS-nutrition when compared with the normal cells with no-treatment ($p>0.05$).

FIG. 69 shows the experimental design for detection of apoptosis/cytotoxicity of VS-nutrition in Human Primary Nasal Epithelial Cells (HNEpC) by qRT-PCR. The human primary nasal epithelial cells (HNEpC) were cultured in the 24 well-dish, and the cells were treated with VS-nutrition with designated dilution (1:1, 1:300 and 1:500) for 5 days (in every day, refresh cell culture medium and added new VS-nutrition with same composition and ratio) before analysis by qRT-PCR.

FIG. 70 shows detection on apoptosis/cytotoxicity of VS-nutrition in the human primary nasal epithelial cells (HNEpC) by qRT-PCR after treatment. Detection of apoptosis/cytotoxicity of VS-nutrition in the human primary nasal epithelial cells by RT-PCR after treatment with VS-nutrition. There are no significant up or down-regulation of BAX/BCL2 ratio in group treated by VS-nutrition when compared with the normal cells with no-treatment ($p>0.05$).

FIGS. 71A-71B show oral intake formulations of VS product (nutritional supplement). Bottle product (10-15 ml) with FIG. 71A 1.5 ml spoon or FIG. 71B 1.0 ml drop.

FIGS. 72A-72C show an exemplary nasal (liquid) spray. Spray product with 10-15 ml bottle nasal spray. FIG. 72A composition and size of the product. FIGS. 72B & 72C usage example.

What is claimed is:

1. A composition comprising
a plurality of peptides each mimicking a different portion of the ligand binding domain (LBD) of human ACE2 protein, wherein each of the peptides is of a length of 15-31 amino acids and prevents binding of the S-protein of SARS-CoV-2 to the human ACE2 protein; wherein the plurality of peptides each comprise an amino acid sequence selected from the group consisting of SEQ ID NOs: 42-44, 54, and 68-82; and
a plurality of inhibitory oligonucleotides or a combination of nucleic acid vectors encoding said plurality of inhibitory oligonucleotides, wherein the plurality of inhibitory oligonucleotides targets at least two SARS-CoV-2 genes selected from the group consisting of ORF1ab, RdRp, the S-protein gene, the N-protein gene, and the E protein gene.

2. The composition of claim 1, wherein the composition comprises at least five peptides each comprising an amino acid sequence as shown in SEQ ID NOS: 42-44, 54, and 68-82.

3. A dietary supplement comprising a composition according to claim 1, comprising at least one additional nutrient selected from Vitamin C, Vitamin B6, Vitamin B12, Vitamin D, Zinc, polypeptides, nucleotide, L-arginine, peppermint oil, N-Acetyl Cysteine, glutathione, eicosapentaenoic acid (EPA), or docosahexaenoic acid (DHA).

4. A method for treating a SARS-CoV-2 infection comprising administering to a subject an effective amount of a composition according to claim 1.

5. The composition of claim 1, wherein the inhibitory oligonucleotides are antisense oligonucleotides of 20-22 nucleotides in length.

6. The composition of claim 1, wherein the plurality of inhibitory oligonucleotides are antisense oligonucleotides comprising at least two oligonucleotides selected from the group consisting of SEQ ID NOS: 9-16 and modified forms of SEQ ID NOS: 9-16.

7. The composition of claim 1, wherein the plurality of inhibitory oligonucleotides comprises eight oligonucleotides as shown in SEQ ID NOS: 9-16 or modified forms of SEQ ID NOS: 9-16.

8. The composition of claim 1, wherein the plurality of inhibitory oligonucleotides comprises at least two pairs of Dicer-substrate RNAs (DsiRNAs) selected from the group consisting of DsiRNA pair 1 (SEQ ID NOs: 17 & 18), DsiRNA pair 2 (SEQ ID NOs: 19 & 20), DsiRNA pair 3 (SEQ ID NOs: 21 & 22), DsiRNA pair 4 (SEQ ID NOs: 23 & 24), DsiRNA pair 5 (SEQ ID NOs: 25 & 26), DsiRNA pair 6 (SEQ ID NOs: 27 & 28), DsiRNA pair 7 (SEQ ID NOs: 29 & 30), and DsiRNA pair 8 (SEQ ID NOs: 31 & 32).

9. The composition of claim 1, wherein the plurality of inhibitory oligonucleotides comprises Dicer-substrate RNA (DsiRNA) pair 1 (SEQ ID NOs: 17 & 18), DsiRNA pair 2 (SEQ ID NOs: 19 & 20), DsiRNA pair 3 (SEQ ID NOs: 21 & 22), DsiRNA pair 4 (SEQ ID NOs: 23 & 24), DsiRNA pair 5 (SEQ ID NOs: 25 & 26), DsiRNA pair 6 (SEQ ID NOs: 27 & 28), DsiRNA pair 7 (SEQ ID NOs: 29 & 30), and DsiRNA pair 8 (SEQ ID NOs: 31 & 32).

10. The composition of claim 1, wherein the inhibitory oligonucleotides are modified antisense oligonucleotides.

11. The composition of claim 10, wherein the modified antisense oligonucleotides are 2'-Deoxy, 2'-Fluoroarabino Nucleic Acid (FANA)-modified, and 2' O-Methyl RNA modified antisense oligonucleotides that comprise phosphorothioate bonds and a 5-methyl dC modification at the 5' end.

12. The composition of claim 10, wherein the modified antisense oligonucleotides are 2' O-Methyl RNA modified antisense oligonucleotides selected from the group consisting of SEQ ID NO: 33, SEQ ID NO: 34, SEQ ID NO: 35, SEQ ID NO: 36, SEQ ID NO: 37, SEQ ID NO: 38, SEQ ID NO: 39, and SEQ ID NO: 40.

13. The method of claim 4, wherein the composition comprises at least five peptides each comprising an amino acid sequence as shown in SEQ ID NOS: 42-44, 54, and 68-82.

14. The method of claim 4, wherein the plurality of inhibitory oligonucleotides are antisense oligonucleotides comprising at least two oligonucleotides selected from the group consisting of SEQ ID NOS: 9-16 and modified forms of SEQ ID NOS: 9-16.

15. The method of claim 4, wherein the plurality of inhibitory oligonucleotides comprises eight oligonucleotides as shown in SEQ ID NOS: 9-16 or modified forms of SEQ ID NOS: 9-16.

16. The method of claim 4, wherein the inhibitory oligonucleotides are 2' O-Methyl RNA modified antisense oligonucleotides selected from the group consisting of SEQ ID NO: 33, SEQ ID NO: 34, SEQ ID NO: 35, SEQ ID NO: 36, SEQ ID NO: 37, SEQ ID NO: 38, SEQ ID NO: 39, and SEQ ID NO: 40.

* * * * *

SEQUENCE LISTING

```
<160> NUMBER OF SEQ ID NOS: 82

<210> SEQ ID NO 1
<211> LENGTH: 21
<212> TYPE: RNA
<213> ORGANISM: Artificial Sequence
<220> FEATURE:
<223> OTHER INFORMATION: Oligonucleotide

<400> SEQUENCE: 1
guggcuuacc gcaagguucu u                                             21

<210> SEQ ID NO 2
<211> LENGTH: 21
<212> TYPE: RNA
<213> ORGANISM: Artificial Sequence
```

<220> FEATURE:
<223> OTHER INFORMATION: Oligonucleotide

<400> SEQUENCE: 2
gcacuaguac ugaugucgua u                                              21

<210> SEQ ID NO 3
<211> LENGTH: 21
<212> TYPE: RNA
<213> ORGANISM: Artificial Sequence
<220> FEATURE:
<223> OTHER INFORMATION: Oligonucleotide

<400> SEQUENCE: 3
gaagacccag ucccuacuua u                                              21

<210> SEQ ID NO 4
<211> LENGTH: 21
<212> TYPE: RNA
<213> ORGANISM: Artificial Sequence
<220> FEATURE:
<223> OTHER INFORMATION: Oligonucleotide

<400> SEQUENCE: 4
gacaaggcgu uccaauuaac a                                              21

<210> SEQ ID NO 5
<211> LENGTH: 21
<212> TYPE: RNA
<213> ORGANISM: Artificial Sequence
<220> FEATURE:
<223> OTHER INFORMATION: Oligonucleotide

<400> SEQUENCE: 5
ggcacgauau uacgcacaac u                                              21

<210> SEQ ID NO 6
<211> LENGTH: 21
<212> TYPE: RNA
<213> ORGANISM: Artificial Sequence
<220> FEATURE:
<223> OTHER INFORMATION: Oligonucleotide

<400> SEQUENCE: 6
aacuuacaua gcucuagacu u                                              21

<210> SEQ ID NO 7
<211> LENGTH: 21
<212> TYPE: RNA
<213> ORGANISM: Artificial Sequence
<220> FEATURE:
<223> OTHER INFORMATION: Oligonucleotide

<400> SEQUENCE: 7
gaagagacag guacguuaau a                                              21

<210> SEQ ID NO 8
<211> LENGTH: 21
<212> TYPE: RNA
<213> ORGANISM: Artificial Sequence
<220> FEATURE:
<223> OTHER INFORMATION: Oligonucleotide

<400> SEQUENCE: 8
ggaccaggaa cuaaucagac a                                              21

<210> SEQ ID NO 9
<211> LENGTH: 21
<212> TYPE: DNA
<213> ORGANISM: Artificial Sequence
<220> FEATURE:
<223> OTHER INFORMATION: Oligonucleotide

<400> SEQUENCE: 9
aagaaccttg cggtaagcca c                                              21

<210> SEQ ID NO 10
<211> LENGTH: 21
<212> TYPE: DNA
<213> ORGANISM: Artificial Sequence
<220> FEATURE:
<223> OTHER INFORMATION: Oligonucleotide

<400> SEQUENCE: 10
atacgacatc agtactagtg c                                              21

<210> SEQ ID NO 11
<211> LENGTH: 21
<212> TYPE: DNA
<213> ORGANISM: Artificial Sequence
<220> FEATURE:
<223> OTHER INFORMATION: Oligonucleotide

<400> SEQUENCE: 11
ataagtaggg actgggtctt c                                              21

<210> SEQ ID NO 12
<211> LENGTH: 21
<212> TYPE: DNA
<213> ORGANISM: Artificial Sequence
<220> FEATURE:
<223> OTHER INFORMATION: Oligonucleotide

<400> SEQUENCE: 12
tgttaattgg aacgccttgt c                                              21

<210> SEQ ID NO 13
<211> LENGTH: 21
<212> TYPE: DNA
<213> ORGANISM: Artificial Sequence
<220> FEATURE:
<223> OTHER INFORMATION: Oligonucleotide

<400> SEQUENCE: 13
agttgtgcgt aatatcgtgc c                                              21

<210> SEQ ID NO 14
<211> LENGTH: 21
<212> TYPE: DNA
<213> ORGANISM: Artificial Sequence
<220> FEATURE:
<223> OTHER INFORMATION: Oligonucleotide

<400> SEQUENCE: 14
aagtctagag ctatgtaagt t                                              21

<210> SEQ ID NO 15
<211> LENGTH: 21
<212> TYPE: DNA
<213> ORGANISM: Artificial Sequence
<220> FEATURE:
<223> OTHER INFORMATION: Oligonucleotide

```
<400> SEQUENCE: 15
tattaacgta cctgtctctt c                                          21

<210> SEQ ID NO 16
<211> LENGTH: 21
<212> TYPE: DNA
<213> ORGANISM: Artificial Sequence
<220> FEATURE:
<223> OTHER INFORMATION: Oligonucleotide

<400> SEQUENCE: 16
tgtctgatta gttcctggtc c                                          21

<210> SEQ ID NO 17
<211> LENGTH: 25
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (1)..(23)
<223> OTHER INFORMATION: ribonucleotide
<220> FEATURE:
<221> NAME/KEY: misc_feature
<222> LOCATION: (24)..(25)
<223> OTHER INFORMATION: Deoxyribonucleotide

<400> SEQUENCE: 17
gccuuguccc ugguuucaac gagaa                                      25

<210> SEQ ID NO 18
<211> LENGTH: 27
<212> TYPE: RNA
<213> ORGANISM: Artificial Sequence
<220> FEATURE:
<223> OTHER INFORMATION: Oligonucleotide

<400> SEQUENCE: 18
uucucguuga aaccagggac aaggcuc                                    27

<210> SEQ ID NO 19
<211> LENGTH: 25
<212> TYPE: RNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (1)..(23)
<223> OTHER INFORMATION: ribonucleotide
<220> FEATURE:
<221> NAME/KEY: misc_feature
<222> LOCATION: (24)..(25)
<223> OTHER INFORMATION: Deoxyribonucleotide

<400> SEQUENCE: 19
cagcugaugc acaaucguuu uuaaa                                      25

<210> SEQ ID NO 20
<211> LENGTH: 27
<212> TYPE: RNA
<213> ORGANISM: Artificial Sequence
<220> FEATURE:
<223> OTHER INFORMATION: Oligonucleotide

<400> SEQUENCE: 20
```
uuuaaaaacg auugugcauc agcugac 27

<210> SEQ ID NO 21
<211> LENGTH: 25
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (1)..(23)
<223> OTHER INFORMATION: ribonucleotide
<220> FEATURE:
<221> NAME/KEY: misc_feature
<222> LOCATION: (24)..(25)
<223> OTHER INFORMATION: Deoxyribonucleotide

<400> SEQUENCE: 21
cuagucagug uguuaaucuu acaac 25

<210> SEQ ID NO 22
<211> LENGTH: 27
<212> TYPE: RNA
<213> ORGANISM: Artificial Sequence
<220> FEATURE:
<223> OTHER INFORMATION: Oligonucleotide

<400> SEQUENCE: 22
guuguaagau uaacacacug acuagag 27

<210> SEQ ID NO 23
<211> LENGTH: 25
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (1)..(23)
<223> OTHER INFORMATION: ribonucleotide
<220> FEATURE:
<221> NAME/KEY: misc_feature
<222> LOCATION: (24)..(25)
<223> OTHER INFORMATION: Deoxyribonucleotide

<400> SEQUENCE: 23
aaacuaaaau gucugauaau ggacc 25

<210> SEQ ID NO 24
<211> LENGTH: 27
<212> TYPE: RNA
<213> ORGANISM: Artificial Sequence
<220> FEATURE:
<223> OTHER INFORMATION: Oligonucleotide

<400> SEQUENCE: 24
gguccauuau cagacauuuu aguuugu 27

<210> SEQ ID NO 25
<211> LENGTH: 25
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (1)..(23)
<223> OTHER INFORMATION: ribonucleotide
<220> FEATURE:
<221> NAME/KEY: misc_feature
<222> LOCATION: (24)..(25)
<223> OTHER INFORMATION: Deoxyribonucleotide

<400> SEQUENCE: 25
gguaguuaua cuaaugacaa agctt                                              25

<210> SEQ ID NO 26
<211> LENGTH: 27
<212> TYPE: RNA
<213> ORGANISM: Artificial Sequence
<220> FEATURE:
<223> OTHER INFORMATION: Oligonucleotide

<400> SEQUENCE: 26
aagcuuuguc auuaguauaa cuaccac                                            27

<210> SEQ ID NO 27
<211> LENGTH: 25
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (1)..(23)
<223> OTHER INFORMATION: ribonucleotide
<220> FEATURE:
<221> NAME/KEY: misc_feature
<222> LOCATION: (24)..(25)
<223> OTHER INFORMATION: Deoxyribonucleotide

<400> SEQUENCE: 27
cuucugguaa ucuauuacua gauaa                                              25

<210> SEQ ID NO 28
<211> LENGTH: 27
<212> TYPE: RNA
<213> ORGANISM: Artificial Sequence
<220> FEATURE:
<223> OTHER INFORMATION: Oligonucleotide

<400> SEQUENCE: 28
uuaucuagua auagauuacc agaagca                                            27

<210> SEQ ID NO 29
<211> LENGTH: 25
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (1)..(23)
<223> OTHER INFORMATION: ribonucleotide
<220> FEATURE:
<221> NAME/KEY: misc_feature
<222> LOCATION: (24)..(25)
<223> OTHER INFORMATION: Deoxyribonucleotide

<400> SEQUENCE: 29
ggaagagaca gguacguuaa uagtt                                              25

<210> SEQ ID NO 30
<211> LENGTH: 27
<212> TYPE: RNA
<213> ORGANISM: Artificial Sequence
<220> FEATURE:
<223> OTHER INFORMATION: Oligonucleotide

```
<400> SEQUENCE: 30
aacuauuaac guaccugucu cuuccga                                        27

<210> SEQ ID NO 31
<211> LENGTH: 25
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (1)..(24)
<223> OTHER INFORMATION: ribonucleotide
<220> FEATURE:
<221> NAME/KEY: misc_feature
<222> LOCATION: (24)..(25)
<223> OTHER INFORMATION: Deoxyribonucleotide

<400> SEQUENCE: 31
ggccaaacug ucacuaagaa auctg                                          25

<210> SEQ ID NO 32
<211> LENGTH: 27
<212> TYPE: RNA
<213> ORGANISM: Artificial Sequence
<220> FEATURE:
<223> OTHER INFORMATION: Oligonucleotide

<400> SEQUENCE: 32
cagauuucuu agugacaguu uggccuu                                        27

<210> SEQ ID NO 33
<211> LENGTH: 21
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (1)..(5)
<223> OTHER INFORMATION: 2' O-Methyl RNA
<220> FEATURE:
<221> NAME/KEY: misc_feature
<222> LOCATION: (6)..(15)
<223> OTHER INFORMATION: Deoxyribonucleotide
<220> FEATURE:
<221> NAME/KEY: misc_feature
<222> LOCATION: (16)..(20)
<223> OTHER INFORMATION: 2' O-Methyl RNA
<220> FEATURE:
<221> NAME/KEY: misc_feature
<222> LOCATION: (21)..(21)
<223> OTHER INFORMATION: Deoxyribonucleotide

<400> SEQUENCE: 33
aagaaccttg cggtaagcca c                                              21

<210> SEQ ID NO 34
<211> LENGTH: 21
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (1)..(5)
<223> OTHER INFORMATION: 2' O-Methyl RNA
<220> FEATURE:
<221> NAME/KEY: misc_feature
<222> LOCATION: (6)..(15)
<223> OTHER INFORMATION: Deoxyribonucleotide
```

```
<220> FEATURE:
<221> NAME/KEY: misc_feature
<222> LOCATION: (16)..(20)
<223> OTHER INFORMATION: 2' O-Methyl RNA
<220> FEATURE:
<221> NAME/KEY: misc_feature
<222> LOCATION: (21)..(21)
<223> OTHER INFORMATION: Deoxyribonucleotide

<400> SEQUENCE: 34
auacgacatc agtacuagug c                                              21

<210> SEQ ID NO 35
<211> LENGTH: 21
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (1)..(5)
<223> OTHER INFORMATION: 2' O-Methyl RNA
<220> FEATURE:
<221> NAME/KEY: misc_feature
<222> LOCATION: (6)..(15)
<223> OTHER INFORMATION: Deoxyribonucleotide
<220> FEATURE:
<221> NAME/KEY: misc_feature
<222> LOCATION: (16)..(20)
<223> OTHER INFORMATION: 2' O-Methyl RNA
<220> FEATURE:
<221> NAME/KEY: misc_feature
<222> LOCATION: (21)..(21)
<223> OTHER INFORMATION: Deoxyribonucleotide

<400> SEQUENCE: 35
auaagtaggg actgggucuu c                                              21

<210> SEQ ID NO 36
<211> LENGTH: 21
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (1)..(5)
<223> OTHER INFORMATION: 2' O-Methyl RNA
<220> FEATURE:
<221> NAME/KEY: misc_feature
<222> LOCATION: (6)..(15)
<223> OTHER INFORMATION: Deoxyribonucleotide
<220> FEATURE:
<221> NAME/KEY: misc_feature
<222> LOCATION: (16)..(20)
<223> OTHER INFORMATION: 2' O-Methyl RNA
<220> FEATURE:
<221> NAME/KEY: misc_feature
<222> LOCATION: (21)..(21)
<223> OTHER INFORMATION: Deoxyribonucleotide

<400> SEQUENCE: 36
uguuaattgg aacgccuugt c                                              21

<210> SEQ ID NO 37
<211> LENGTH: 21
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (1)..(5)
```

<223> OTHER INFORMATION: 2' O-Methyl RNA
<220> FEATURE:
<221> NAME/KEY: misc_feature
<222> LOCATION: (6)..(15)
<223> OTHER INFORMATION: Deoxyribonucleotide
<220> FEATURE:
<221> NAME/KEY: misc_feature
<222> LOCATION: (16)..(20)
<223> OTHER INFORMATION: 2' O-Methyl RNA
<220> FEATURE:
<221> NAME/KEY: misc_feature
<222> LOCATION: (21)..(21)
<223> OTHER INFORMATION: Deoxyribonucleotide

<400> SEQUENCE: 37
aguugtgcgt aatatcgugc c                                              21

<210> SEQ ID NO 38
<211> LENGTH: 21
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (1)..(5)
<223> OTHER INFORMATION: 2' O-Methyl RNA
<220> FEATURE:
<221> NAME/KEY: misc_feature
<222> LOCATION: (6)..(15)
<223> OTHER INFORMATION: Deoxyribonucleotide
<220> FEATURE:
<221> NAME/KEY: misc_feature
<222> LOCATION: (16)..(20)
<223> OTHER INFORMATION: 2' O-Methyl RNA
<220> FEATURE:
<221> NAME/KEY: misc_feature
<222> LOCATION: (21)..(21)
<223> OTHER INFORMATION: Deoxyribonucleotide

<400> SEQUENCE: 38
aaguctagag ctatguaagu t                                              21

<210> SEQ ID NO 39
<211> LENGTH: 21
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (1)..(5)
<223> OTHER INFORMATION: 2' O-Methyl RNA
<220> FEATURE:
<221> NAME/KEY: misc_feature
<222> LOCATION: (6)..(15)
<223> OTHER INFORMATION: Deoxyribonucleotide
<220> FEATURE:
<221> NAME/KEY: misc_feature
<222> LOCATION: (16)..(20)
<223> OTHER INFORMATION: 2' O-Methyl RNA
<220> FEATURE:
<221> NAME/KEY: misc_feature
<222> LOCATION: (21)..(21)
<223> OTHER INFORMATION: Deoxyribonucleotide

<400> SEQUENCE: 39
uauuaacgta cctgtcucuu c                                              21

<210> SEQ ID NO 40
<211> LENGTH: 21
<212> TYPE: DNA
<213> ORGANISM: Artificial Sequence

```
<220> FEATURE:
<223> OTHER INFORMATION: Oligonucleotide
<220> FEATURE:
<221> NAME/KEY: misc_feature
<222> LOCATION: (1)..(5)
<223> OTHER INFORMATION: 2' O-Methyl RNA
<220> FEATURE:
<221> NAME/KEY: misc_feature
<222> LOCATION: (6)..(15)
<223> OTHER INFORMATION: Deoxyribonucleotide
<220> FEATURE:
<221> NAME/KEY: misc_feature
<222> LOCATION: (16)..(20)
<223> OTHER INFORMATION: 2' O-Methyl RNA
<220> FEATURE:
<221> NAME/KEY: misc_feature
<222> LOCATION: (21)..(21)
<223> OTHER INFORMATION: Deoxyribonucleotide

<400> SEQUENCE: 40
ugucugatta gttccugguc c                                              21

<210> SEQ ID NO 41
<211> LENGTH: 23
<212> TYPE: PRT
<213> ORGANISM: Artificial Sequence
<220> FEATURE:
<223> OTHER INFORMATION: Oligopeptide

<400> SEQUENCE: 41

Glu Glu Gln Ala Lys Thr Phe Leu Asp Lys Phe Asn His Glu Ala Glu
1               5                   10                  15

Asp Leu Phe Tyr Gln Ser Ser
            20

<210> SEQ ID NO 42
<211> LENGTH: 20
<212> TYPE: PRT
<213> ORGANISM: Artificial Sequence
<220> FEATURE:
<223> OTHER INFORMATION: Oligopeptide

<400> SEQUENCE: 42

Phe Leu Lys Glu Gln Ser Thr Leu Ala Gln Met Tyr Pro Leu Gln Glu
1               5                   10                  15

Ile Gln Asn Leu
            20

<210> SEQ ID NO 43
<211> LENGTH: 21
<212> TYPE: PRT
<213> ORGANISM: Artificial Sequence
<220> FEATURE:
<223> OTHER INFORMATION: Oligopeptide

<400> SEQUENCE: 43

Leu Pro Asn Met Thr Gln Gly Phe Trp Glu Asn Ser Met Leu Thr Asp
1               5                   10                  15

Pro Gly Asn Val Gln
            20

<210> SEQ ID NO 44
<211> LENGTH: 20
<212> TYPE: PRT
<213> ORGANISM: Artificial Sequence
<220> FEATURE:
<223> OTHER INFORMATION: Oligopeptide
```

<400> SEQUENCE: 44

His Pro Thr Ala Trp Asp Leu Gly Lys Gly Asp Phe Arg Ile Leu Met
1               5                   10                  15

Cys Thr Lys Val
            20

<210> SEQ ID NO 45
<211> LENGTH: 23
<212> TYPE: PRT
<213> ORGANISM: Artificial Sequence
<220> FEATURE:
<223> OTHER INFORMATION: Oligopeptide

<400> SEQUENCE: 45

Gly Asn Tyr Asn Tyr Leu Tyr Arg Leu Phe Arg Lys Ser Asn Leu Lys
1               5                   10                  15

Pro Phe Glu Arg Asp Ile Ser
            20

<210> SEQ ID NO 46
<211> LENGTH: 5034
<212> TYPE: DNA
<213> ORGANISM: Artificial Sequence
<220> FEATURE:
<223> OTHER INFORMATION: Oligonucleotide

<400> SEQUENCE: 46
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact    120 agggggttcct gcggccgccc tagggagggc ctatttccca tgattccttc atatttgcat    180
atacgataca aggctgttag agagataatt agaattaatt tgactgtaaa cacaaagata    240
ttagtacaaa atacgtgacg tagaaagtaa taatttcttg ggtagtttgc agttttaaaa    300
ttatgtttta aaatggacta tcatatgctt accgtaactt gaaagtattt cgatttcttg    360
ggtttatata tcttgtggaa aggacgaaga accttgcggt aagccacttt tttcgcaatt    420
cgaacgctga cgtcatcaac ccgctccaag gaatcgcggg cccagtgtca ctaggcggga    480
acacccagcg cgcgtgcgcc ctggcaggaa gatggctgtg agggacaggg gagtggcgcc    540
ctgcaatatt tgcatgtcgc tatgtgttct gggaaatcac cataaacgtg aaatgtcttt    600
ggatttggga atcttataag ttctgtatga gaccacagat ctagatacga catcagtact    660 agtgctttt tctcgagcgt cccagactac gcttgagttt aaacacgcgt ggtgtggaaa     720
gtccccaggc tccccagcag gcagaagtat gcaaagcatg catctcaatt agtcagcaac    780
caggtgtgga aagtcccag gctccccagc aggcagaagt atgcaaagca tgcatctcaa     840
ttagtcagca accatagtcc cgcccctaac tccgcccatc ccgccctaa ctccgcccag     900 ttccgcccat tctccgcccc atggctgact aattttttt atttatgcag aggccgaggc    960
cgcctcggcc tctgagctat tccagaagta gtgaggaggc ttttttggag gccgccacca  1020
tggtgagcaa gggcgaggag ctgttcaccg gggtggtgcc catcctggtc gagctggacg  1080
gcgacgtaaa cggccacaag ttcagcgtgt ccggcgaggg cgagggcgat gccacctacg  1140
gcaagctgac cctgaagttc atctgcacca ccggcaagct gcccgtgccc tggcccaccc  1200
tcgtgaccac cctgacctac ggcgtgcagt gcttcagccg ctaccccgac cacatgaagc  1260
agcacgactt cttcaagtcc gccatgcccg aaggctacgt ccaggagcgc accatcttct  1320
tcaaggacga cggcaactac aagacccgcg ccgaggtgaa gttcgagggc gacaccctgg  1380

```
tgaaccgcat cgagctgaag ggcatcgact tcaaggagga cggcaacatc ctggggcaca    1440
agctggagta caactacaac agccacaacg tctatatcat ggccgacaag cagaagaacg    1500
gcatcaaggt gaacttcaag atccgccaca acatcgagga cggcagcgtg cagctcgccg    1560
accactacca gcagaacacc cccatcggcg acggccccgt gctgctgccc gacaaccact    1620
acctgagcac ccagtccgcc ctgagcaaag accccaacga aagcgcgat cacatggtcc    1680 tgctggagtt cgtgaccgcc gccgggatca ctctcggcat ggacgagctg tacaagtgac    1740
ttaaggggtg catccctgt gaccccctccc cagtgcctct cctggccctg aagttgcca     1800 ctccagtgcc caccagcctt gtcctaataa aattaagttg catcattttg tctgactagg    1860
tgtccttcta taatattatg gggtggaggg gggtggtatg gagcaagggg caagttggga    1920
agacaacctg tagggcctgc ggggtctatt gggaaccaag ctggagtgca gtggcacaat    1980
cttggctcac tgcaatctcc gcctcctggg ttcaagcgat tctcctgcct cagcctcccg    2040
agttgttggg attccaggca tgcatgacca ggctcagcta ttttgttt ttttggtaga      2100 gacggggttt caccatattg gccaggctgg tctccaactc ctaatctcag gtgatctacc    2160
caccttggcc tcccaaattg ctgggattac aggcgtgaac cactgctccc ttccctgtcc    2220
ttcacgtgcg gaccgagcgg ccgcaggaac ccctagtgat ggagttggcc actccctctc    2280
tgcgcgctcg ctcgctcact gaggccgggc gaccaaaggt cgcccgacgc ccgggctttg    2340
cccgggcggc ctcagtgagc gagcgagcgc gcagctgcct gcaggggcgc ctgatgcggt    2400
attttctcct tacgcatctg tgcggtattt cacaccgcat acgtcaaagc aaccatagta    2460
cgcgccctgt agcggcgcat taagcgcggc gggtgtggtg gttacgcgca gcgtgaccgc    2520
tacacttgcc agcgccttag cgcccgctcc tttcgctttc ttcccttcct ttctcgccac    2580
gttcgccggc tttccccgtc aagctctaaa tcggggctc cctttagggt tccgatttag    2640
tgctttacgg cacctcgacc ccaaaaaact tgatttgggt gatggttcac gtagtgggcc    2700
atcgccctga tagacggttt ttcgcccttt gacgttggag tccacgttct ttaatagtgg    2760
actcttgttc caaactggaa caacactcaa ctctatctcg gctattctt ttgatttata    2820 agggattttg ccgatttcgg tctattggtt aaaaaatgag ctgatttaac aaaaatttaa    2880
cgcgaatttt aacaaaatat taacgtttac aatttatgg tgcactctca gtacaatctg     2940
ctctgatgcc gcatagttaa gccagccccg acacccgcca acacccgctg acgcgccctg    3000
acgggcttgt ctgctcccgg catccgctta cagacaagct gtgaccgtct ccgggagctg    3060
catgtgtcag aggttttcac cgtcatcacc gaaacgcgcg agcccgggagc tgcatgtgtc    3120 agaggttttc accgtcatca ccgaaacgcg cgagacgaaa gggcctcgtg atacgcctat    3180
ttttataggt taatgtcatg ataataatgg tttcttagac gtcaggtggc acttttcggg    3240
gaaatgtgcg cggaaccct atttgtttat ttttctaaat acattcaaat atgtatccgc     3300
tcatgagaca ataaccctga taaatgcttc aataatattg aaaaggaag agtatgagta     3360 ttcaacattt ccgtgtcgcc cttattccct tttttgcggc attttgcctt cctgtttttg    3420
ctcacccaga aacgctggtg aaagtaaaag atgctgaaga tcagttgggt gcacgagtgg    3480
gttacatcga actggatctc aacagcggta agatccttga gttttcgc cccgaagaac      3540 gttttccaat gatgagcact tttaaagttc tgctatgtgg cgcggtatta tcccgtattg    3600
acgccgggca agagcaactc ggtcgccgca tacactattc tcagaatgac ttggttgagt    3660
actcaccagt cacagaaaag catcttacgg atggcatgac agtaagagaa ttatgcagtg    3720
```

```
ctgccataac catgagtgat aacactgcgg ccaacttact tctgacaacg atcggaggac     3780
cgaaggagct aaccgctttt ttgcacaaca tggggatca tgtaactcgc cttgatcgtt      3840
gggaaccgga gctgaatgaa gccataccaa acgacgagcg tgacaccacg atgcctgtag     3900
caatggcaac aacgttgcgc aaactattaa ctggcgaact acttactcta gcttcccggc     3960
aacaattaat agactggatg gaggcggata agttgcagg accacttctg cgctcggccc      4020
ttccggctgg ctggtttatt gctgataaat ctggagccgg tgagcgtggg tctcgcggta    4080
tcattgcagc actggggcca gatggtaagc cctcccgtat cgtagttatc tacacgacgg    4140
ggagtcaggc aactatggat gaacgaaata gacagatcgc tgagataggt gcctcactga    4200
ttaagcattg gtaactgtca gaccaagttt actcatatat actttagatt gatttaaaac    4260 ttcatttta atttaaaagg atctaggtga agatccttt tgataatctc atgaccaaaa      4320
tcccttaacg tgagttttcg ttccactgag cgtcagaccc cgtagaaaag atcaaaggat    4380
cttcttgaga tccttttttt ctgcgcgtaa tctgctgctt gcaaacaaaa aaaccaccgc    4440
taccagcggt ggtttgtttg ccggatcaag agctaccaac tctttttccg aaggtaactg    4500
gcttcagcag agcgcagata ccaaatactg ttcttctagt gtagccgtag ttaggccacc    4560
acttcaagaa ctctgtagca ccgcctacat acctcgctct gctaatcctg ttaccagtgg    4620
ctgctgccag tggcgataag tcgtgtctta ccgggttgga ctcaagacga tagttaccgg    4680
ataaggcgca gcggtcgggc tgaacggggg gttcgtgcac acagcccagc ttggagcgaa    4740
cgacctacac cgaactgaga tacctacagc gtgagctatg agaaagcgcc acgcttcccg    4800
aagggagaaa ggcggacagg tatccggtaa gcggcagggt cggaacagga gagcgcacga    4860
gggagcttcc agggggaaac gcctggtatc tttatagtcc tgtcgggttt cgccacctct    4920
gacttgagcg tcgatttttg tgatgctcgt caggggggcg gagcctatgg aaaaacgcca    4980
gcaacgcggc cttttacgg ttcctggcct tttgctggcc ttttgctcac atgt           5034
```

<210> SEQ ID NO 47
<211> LENGTH: 5034
<212> TYPE: DNA
<213> ORGANISM: Artificial Sequence
<220> FEATURE:
<223> OTHER INFORMATION: Oligonucleotide

<400> SEQUENCE: 47

```
cctgcaggca gctgcgcgct cgctcgctca ctgaggccgc ccgggcgtcg ggcgaccttt       60
ggtcgcccgg cctcagtgag cgagcgagcg cgcagagagg gagtggccaa ctccatcact     120
aggggttcct gcggccgccc tagggagggc ctatttccca tgattccttc atatttgcat     180
atacgataca aggctgttag agagataatt agaattaatt tgactgtaaa cacaaagata    240
ttagtacaaa atacgtgacg tagaaagtaa taatttcttg ggtagtttgc agttttaaaa    300
ttatgtttta aaatggacta tcatatgctt accgtaactt gaaagtattt cgatttcttg    360
ggtttatata tcttgtggaa aggacgataa gtagggacta ggtcttcttt tttcgcaatt    420
cgaacgctga cgtcatcaac ccgctccaag gaatcgcggg cccagtgtca ctaggcggga    480
acacccagcg cgcgtgcgcc ctggcaggaa gatggctgtg agggacaggg gagtggcgcc    540
ctgcaatatt tgcatgtcgc tatgtgttct gggaaatcac cataaacgtg aaatgtcttt    600
ggatttggga atcttataag ttctgtatga gccacagat ctagtgttaa ttggaacgcc    660
ttgtcttttt tctcgagcgt cccagactac gcttgagttt aaacacgcgt ggtgtggaaa   720
gtccccaggc tccccagcag gcagaagtat gcaaagcatg catctcaatt agtcagcaac   780
```

```
caggtgtgga aagtccccag gctccccagc aggcagaagt atgcaaagca tgcatctcaa    840
ttagtcagca accatagtcc cgcccctaac tccgcccatc ccgcccctaa ctccgcccag    900
ttccgcccat tctccgcccc atggctgact aattttttttt atttatgcag aggccgaggc   960
cgcctcggcc tctgagctat tccagaagta gtgaggaggc ttttttggag gccgccacca  1020
tggtgagcaa gggcgaggag ctgttcaccg gggtggtgcc catcctggtc gagctggacg  1080
gcgacgtaaa cggccacaag ttcagcgtgt ccggcgaggg cgagggcgat gccacctacg  1140
gcaagctgac cctgaagttc atctgcacca ccggcaagct gcccgtgccc tggcccaccc  1200
tcgtgaccac cctgacctac ggcgtgcagt gcttcagccg ctaccccgac cacatgaagc  1260
agcacgactt cttcaagtcc gccatgcccg aaggctacgt ccaggagcgc accatcttct  1320
tcaaggacga cggcaactac aagacccgcg ccgaggtgaa gttcgagggc gacaccctgg  1380
tgaaccgcat cgagctgaag ggcatcgact tcaaggagga cggcaacatc ctggggcaca  1440
agctggagta caactacaac agccacaacg tctatatcat ggccgacaag cagaagaacg  1500
gcatcaaggt gaacttcaag atccgccaca acatcgagga cggcagcgtg cagctcgccg  1560
accactacca gcagaacacc cccatcggcg acggccccgt gctgctgccc gacaaccact  1620
acctgagcac ccagtccgcc ctgagcaaag accccaacga aaagcgcgat cacatggtcc  1680
tgctggagtt cgtgaccgcc gccgggatca ctctcggcat ggacgagctg tacaagtgac  1740
ttaaggggtg catccctgt gaccctccc cagtgcctct cctggccctg aagttgcca   1800
ctccagtgcc caccagcctt gtcctaataa aattaagttg catcattttg tctgactagg  1860
tgtccttcta taatattatg gggtggaggg gggtggtatg gagcaagggg caagttggga  1920
agacaacctg tagggcctgc ggggtctatt gggaaccaag ctggagtgca gtggcacaat  1980
cttggctcac tgcaatctcc gcctcctggg ttcaagcgat tctcctgcct cagcctcccg  2040
agttgttggg attccaggca tgcatgacca ggctcagcta ttttttgttt tttttggtaga 2100
gacggggttt caccatattg gccaggctgg tctccaactc ctaatctcag gtgatctacc  2160
caccttggcc tcccaaattg ctgggattac aggcgtgaac cactgctccc ttccctgtcc  2220
ttcacgtgcg gaccgagcgg ccgcaggaac ccctagtgat ggagttggcc actccctctc  2280
tgcgcgctcg ctcgctcact gaggccgggc gaccaaaggt cgcccgacgc ccgggctttg  2340
cccgggcggc ctcagtgagc gagcgagcgc gcagctgcct gcaggggcgc ctgatgcggt  2400
attttctcct tacgcatctg tgcggtattt cacaccgcat acgtcaaagc aaccatagta  2460
cgcgccctgt agcggcgcat taagcgcggc gggtgtggtg gttacgcgca gcgtgaccgc  2520
tacacttgcc agcgccttag cgcccgctcc tttcgctttc ttcccttcct ttctcgccac  2580
gttcgccggc tttccccgtc aagctctaaa tcggggggctc cctttagggt tccgatttag  2640
tgctttacgg cacctcgacc ccaaaaaact tgatttgggt gatggttcac gtagtgggcc  2700
atcgccctga tagacggttt ttcgcccttt gacgttggag tccacgttct ttaatagtgg  2760
actcttgttc caaactggaa caacactcaa ctctatctcg gctattcttt tgatttata   2820
agggattttg ccgatttcgg tctattggtt aaaaaatgag ctgatttaac aaaaatttaa  2880
cgcgaatttt aacaaaatat taacgtttac aattttatgg tgcactctca gtacaatctg  2940
ctctgatgcc gcatagttaa gccagccccg acacccgcca acacccgctg acgcgccctg  3000
acggcttgt ctgctcccgg catccgctta cagacaagct gtgaccgtct ccgggagctg  3060
catgtgtcag aggttttcac cgtcatcacc gaaacgcgcg agccgggagc tgcatgtgtc  3120
```

```
agaggttttc accgtcatca ccgaaacgcg cgagacgaaa gggcctcgtg atacgcctat    3180
ttttataggt taatgtcatg ataataatgg tttcttagac gtcaggtggc acttttcggg    3240
gaaatgtgcg cggaacccct atttgtttat ttttctaaat acattcaaat atgtatccgc    3300
tcatgagaca ataaccctga taaatgcttc aataatattg aaaaggaag agtatgagta    3360 ttcaacattt ccgtgtcgcc cttattccct tttttgcggc attttgcctt cctgtttttg    3420
ctcacccaga aacgctggtg aaagtaaaag atgctgaaga tcagttgggt gcacgagtgg    3480
gttacatcga actggatctc aacagcggta agatccttga gagttttcgc cccgaagaac    3540
gttttccaat gatgagcact tttaaagttc tgctatgtgg cgcggtatta tcccgtattg    3600
acgccgggca agagcaactc ggtcgccgca tacactattc tcagaatgac ttggttgagt    3660
actcaccagt cacagaaaag catcttacgg atggcatgac agtaagagaa ttatgcagtg    3720
ctgccataac catgagtgat aacactgcgg ccaacttact tctgacaacg atcggaggac    3780
cgaaggagct aaccgctttt ttgcacaaca tgggggatca tgtaactcgc cttgatcgtt    3840
gggaaccgga gctgaatgaa gccataccaa acgacgagcg tgacaccacg atgcctgtag    3900
caatggcaac aacgttgcgc aaactattaa ctggcgaact acttactcta gcttcccggc    3960
aacaattaat agactggatg gaggcggata aagttgcagg accacttctg cgctcggccc    4020
ttccggctgg ctggtttatt gctgataaat ctggagccgg tgagcgtggg tctcgcggta    4080
tcattgcagc actggggcca gatggtaagc cctcccgtat cgtagttatc tacacgacgg    4140
ggagtcaggc aactatggat gaacgaaata gacagatcgc tgagataggt gcctcactga    4200
ttaagcattg gtaactgtca gaccaagttt actcatatat actttagatt gatttaaaac    4260 ttcatttta atttaaaagg atctaggtga agatcctttt tgataatctc atgaccaaaa    4320
tcccttaacg tgagttttcg ttccactgag cgtcagaccc cgtagaaaag atcaaaggat    4380
cttcttgaga tcctttttt ctgcgcgtaa tctgctgctt gcaaacaaaa aaaccaccgc    4440
taccagcggt ggtttgtttg ccggatcaag agctaccaac tctttttccg aaggtaactg    4500
gcttcagcag agcgcagata ccaaatactg ttcttctagt gtagccgtag ttaggccacc    4560
acttcaagaa ctctgtagca ccgcctacat acctcgctct gctaatcctg ttaccagtgg    4620
ctgctgccag tggcgataag tcgtgtctta ccgggttgga ctcaagacga tagttaccgg    4680
ataaggcgca gcggtcgggc tgaacggggg gttcgtgcac acagcccagc ttggagcgaa    4740
cgacctacac cgaactgaga tacctacagc gtgagctatg agaaagcgcc acgcttcccg    4800
aagggagaaa ggcggacagg tatccggtaa gcggcagggt cggaacagga gagcgcacga    4860
gggagcttcc agggggaaac gcctggtatc tttatagtcc tgtcgggttt cgccacctct    4920
gacttgagcg tcgatttttg tgatgctcgt caggggggcg gagcctatgg aaaaacgcca    4980
gcaacgcggc ctttttacgg ttcctggcct tttgctggcc ttttgctcac atgt          5034
```

<210> SEQ ID NO 48
<211> LENGTH: 4104
<212> TYPE: DNA
<213> ORGANISM: Artificial Sequence
<220> FEATURE:
<223> OTHER INFORMATION: Oligonucleotide

<400> SEQUENCE: 48

```
ttttggattg aagccaatat gataatgagg gggtggagtt tgtgacgtgg cgcggggcgt      60
gggaacgggg cgggtgacgt agtagtgtgg cggaagtgtg atgttgcaag tgtggcggaa     120
cacatgtaag cgacggatgt ggcaaaagtg acgttttgg tgtgcgccgg tgtacacagg     180
```

```
aagtgacaat tttcgcgcgg ttttaggcgg atgttgtagt aaatttgggc gtaaccgagt    240
aagatttggc cattttcgcg ggaaaactga ataagaggaa gtgaaatctg aataattttg    300
tgttactcat agcgcgtaat acggcagacc tcagcgctag attattgaag catttatcag    360
ggttattgtc tcatgagcgg atacatattt gaatgtattt agaaaaataa acaaataggg    420
gttccgcgca catttccccg aaaagtgcca cctgacgtta acctgcgcgc tcgctcgctc    480
actgaggccg cccgggcaaa gcccgggcgt cgggcgacct ttggtcgccc ggcctcagtg    540
agcgagcgag cgcgcagaga gggagtggcc aactccatca ctaggggttc cttgtagtta    600
atgattaacc cgccatgcta cttatctacg tagccatgct ctaggaagat cgcctaggta    660
cgtccaaggt cgggcaggaa gagggcctat ttcccatgat tccttcatat ttgcatatac    720
gatacaaggc tgttagagag ataattagaa ttaatttgac tgtaaacaca agatattag    780 tacaaaatac gtgacgtaga aagtaataat ttcttgggta gtttgcagtt ttaaaattat    840
gttttaaaat ggactatcat atgcttaccg taacttgaaa gtatttcgat ttcttggctt    900
tatatatctt gtggaaagga caaaaagcct tgtccctggt ttcaacgaga attcaagaga    960
ttctcgttga aaccagggac aaggcttttt tggtaccaat tgtagtaatc aattacgggg   1020
tcattagttc atagcccata tatggagttc cgcgttacat aacttacggt aaatggcccg   1080
cctggctgac cgcccaacga cccccgccca ttgacgtcaa taatgacgta tgttcccata   1140
gtaacgccaa tagggacttt ccattgacgt caatgggtgg agtatttacg gtaaactgcc   1200
cacttggcag tacatcaagt gtatcatatg ccaagtacgc cccctattga cgtcaatgac   1260
ggtaaatggc ccgcctggca ttatgcccag tacatgacct tatgggactt tcctacttgg   1320
cagtacatct acgtattagt catcgctatt accatggtga tgcggttttg gcagtacatc   1380
aatgggcgtg gatagcggtt tgactcacgg ggatttccaa gtctccaccc cattgacgtc   1440
aatgggagtt tgttttggca ccaaaatcaa cgggactttc caaaatgtcg taacaactcc   1500
gccccattga cgcaaatggg cggtaggcgt gtacggtggg aggtctatat aagcagagct   1560
ggtttagtga accgtcaggg taccggatcc cttaagtgaa caactagtgc caccatggtg   1620
agcaagggcg aggagctgtt caccggggtg gtgcccatcc tggtcgagct ggacggcgac   1680
gtaaacggcc acaagttcag cgtgtccggc gagggcgagg gcgatgccac ctacggcaag   1740
ctgaccctga agttcatctg caccaccggc aagctgcccg tgccctggcc caccctcgtg   1800
accaccctga cctacggcgt gcagtgcttc agccgctacc ccgaccacat gaagcagcac   1860
gacttcttca gtccgccat gcccgaaggc tacgtccagg agcgcaccat cttcttcaag   1920
gacgacggca actacaagac ccgcgccgag gtgaagttcg agggcgacac cctggtgaac   1980
cgcatcgagc tgaagggcat cgacttcaag gaggacggca acatcctggg gcacaagctg   2040
gagtacaact acaacagcca caacgtctat atcatggccg acaagcagaa gaacggcatc   2100
aaggtgaact tcaagatccg ccacaacatc gaggacggca gcgtgcagct cgccgaccac   2160
taccagcaga acacccccat cggcgacggc cccgtgctgc tgcccgacaa ccactacctg   2220
agcacccagt ccgccctgag caaagacccc aacgagaagc gcgatcacat ggtcctgctg   2280
gagttcgtga ccgccgccgg gatcactctc ggcatggacg agctgtacaa ggaattcgga   2340
agcgggcagt gcaccaacta cgccctgctg aagctggccg gcgacgtgga gagcaacccc   2400
ggccccggat ccatggccac cgagtacaag cccacggtgc gcctcgccac cgcgacgac   2460 gtcccccggg ccgtacgcac cctcgccgcc gcgttcgccg actaccccgc cacgcgccac   2520
```

```
accgtcgacc cggaccgcca catcgagcgg gtcaccgagc tgcaagaact cttcctcacg    2580
cgcgtcgggc tcgacatcgg caaggtgtgg gtcgcggacg acggcgccgc ggtggcggtc    2640
tggaccacgc cggagagcgt cgaagcgggg gcggtgttcg ccgagatcgg ctcgcgcatg    2700
gccgagttga gcggttcccg gctggccgcg cagcaacaga tggaaggcct cctggcgccg    2760
caccggccca aggagcccgc gtggttcctg gccaccgtcg gcgtctcgcc cgaccaccag    2820
ggcaagggtc tggcagcgc cgtcgtgctc cccggagtgg aggcggccga gcgcgctggg    2880
gtgcccgcct tcctggagac ctccgcgccc cgcaacctcc ccttctacga gcggctcggc    2940
ttcaccgtca ccgccgacgt cgaggtgccc gaaggaccgc gcacctggtg catgacccgc    3000
aagcccggtg cctgaacgcg tcttaaggcg atcgcagaca tgataagata cattgatgag    3060
tttggacaaa ccacaactag aatgcagtga aaaaaatgct ttatttgtga aatttgtgat    3120
gctattgctt tatttgtaac cattataagc tgcaataaac aagttaataa caacaattcc    3180
attcatttta tgtttcaggt tcaggggag atgtgggagg ttttttaaag caagtaaaac    3240
ctctacaaat gtggtagtcg aaattcccga taaggatctt cctagagcat ggctacgtag    3300
ataagtagca tggcgggtta atcattaact acaaggaacc cctagtgatg gagttggcca    3360
ctccctctct gcgcgctcgc tcgctcactg aggccgggcg accaaaggtc gcccgacgcc    3420
cgggctttgc ccgggcggcc tcagtgagcg agcgagcgcg cagggatccc ggtgtgaaat    3480
accgcacaga tgcgtaagga gaaaataccg catcaggcgc tcttccgctt cctcgctcac    3540
tgactcgctg cgctcggtcg ttcggctgcg gcgagcggta tcagctcact caaaggcggt    3600
aatacggtta tccacagaat caggggataa cgcaggaaag aacatgtgag caaaaggcca    3660
gcaaaaggcc aggaaccgta aaaaggccgc gttgctggcg ttttccata ggctccgccc    3720
ccctgacgag catcacaaaa atcgacgctc aagtcagagg tggcgaaacc cgacaggact    3780
ataaagatac caggcgtttc ccctggaag ctccctcgtg cgctctcctg ttccgaccct    3840
gccgcttacc ggatacctgt ccgcctttct cccttcggga agcgtggcgc tttctcatag    3900
ctcacgctgt aggtatctca gttcggtgta ggtcgttcgc tccaagctgg gctgtgtgca    3960
cgaacccccc gttcagcccg accgctgcgc cttatccggt aactatcgtc ttgagtccaa    4020
cccggtaaga cacgacttat cgccactggc agcagccact ggtaacagga ttagcagagc    4080
gaggtatgta ggcggtgcta caga                                           4104

<210> SEQ ID NO 49
<211> LENGTH: 4118
<212> TYPE: DNA
<213> ORGANISM: Artificial Sequence
<220> FEATURE:
<223> OTHER INFORMATION: Oligonucleotide

<400> SEQUENCE: 49
ttttggattg aagccaatat gataatgagg gggtggagtt tgtgacgtgg cgcggggcgt      60
gggaacgggg cgggtgacgt agtagtgtgg cggaagtgtg atgttgcaag tgtggcggaa     120
cacatgtaag cgacggatgt ggcaaaagtg acgttttttgg tgtgcgccgg tgtacacagg    180
aagtgacaat tttcgcgcgg ttttaggcgg atgttgtagt aaatttgggc gtaaccgagt    240
aagatttggc cattttcgcg ggaaaactga ataagaggaa gtgaaatctg ataaattttg    300
tgttactcat agcgcgtaat acggcagacc tcagcgctag attattgaag catttatcag    360
ggttattgtc tcatgagcgg atacatattt gaatgtattt agaaaaataa acaatagggt    420
gttccgcgca catttccccg aaaagtgcca cctgacgtta acctgcgcgc tcgctcgctc    480
```

-continued

```
actgaggccg cccgggcaaa gcccgggcgt cgggcgacct ttggtcgccc ggcctcagtg    540
agcgagcgag cgcgcagaga gggagtggcc aactccatca ctaggggttc cttgtagtta    600
atgattaacc cgccatgcta cttatctacg tagccatgct ctaggaagat cgcctagggt    660
accaaaaaat atcagaggca cgtcaacatc ttaatctctt gaattaagat gttgacgtgc    720
ctctgatact ttttttggtg tttcgtggtc tcatacagaa cttataagat tcccaaatcc    780
aaagacattt cacgtttatg gtgatttccc agaacacata gcgacatgca aatattgcag    840
ggcgccactc ccctgtccct cacagccatc ttcctgccag ggcgcacgcg cgctgggtgt    900
tcccgcctag tgacactggg cccgcgattc cttggagcgg gttgatgacg tcagcgttct    960
caattgtagt aatcaattac ggggtcatta gttcatagcc catatatgga gttccgcgtt   1020
acataactta cggtaaatgg cccgcctggc tgaccgccca cgacccccg cccattgacg   1080
tcaataatga cgtatgttcc catagtaacg ccaataggga cttccattg acgtcaatgg   1140
gtggagtatt tacggtaaac tgcccacttg gcagtacatc aagtgtatca tatgccaagt   1200
acgcccccta ttgacgtcaa tgacggtaaa tggcccgcct ggcattatgc ccagtacatg   1260
accttatggg actttcctac ttggcagtac atctacgtat tagtcatcgc tattaccatg   1320
gtgatgcggt tttggcagta catcaatggg cgtggatagc ggtttgactc acggggattt   1380
ccaagtctcc accccattga cgtcaatggg agtttgtttt ggcaccaaaa tcaacgggac   1440
tttccaaaat gtcgtaacaa ctccgcccca ttgacgcaaa tgggcggtag cgtgtacgg   1500
tgggaggtct atataagcag agctggttta gtgaaccgtc agggtaccgg atcccttaag   1560
tgaacaacta gtgccaccat ggtgagcaag ggcgaggagc tgttcaccgg ggtggtgccc   1620
atcctggtcg agctgacgg cgacgtaaac ggccacaagt tcagcgtgtc cggcgagggc   1680
gagggcgatg ccacctacgg caagctgacc ctgaagttca tctgcaccac cggcaagctg   1740
cccgtgccct ggcccaccct cgtgaccacc ctgacctacg gcgtgcagtg cttcagccgc   1800
taccccgacc acatgaagca gcacgacttc ttcaagtccg ccatgcccga aggctacgtc   1860
caggagcgca ccatcttctt caaggacgac ggcaactaca agacccgcgc cgaggtgaag   1920
ttcgagggcg acaccctggt gaaccgcatc gagctgaagg gcatcgactt caaggaggac   1980
ggcaacatcc tggggcacaa gctggagtac aactacaaca gccacaacgt ctatatcatg   2040
gccgacaagc agaagaacgg catcaaggtg aacttcaaga tccgccacaa catcgaggac   2100
ggcagcgtgc agctcgccga ccactaccag cagaacaccc ccatcggcga cggccccgtg   2160
ctgctgcccg acaaccacta cctgagcacc cagtccgccc tgagcaaaga ccccaacgag   2220
aagcgcgatc acatggtcct gctggagttc gtgaccgccg ccgggatcac tctcggcatg   2280
gacgagctgt acaaggaatt cggaagcggg cagtgcacca actacgccct gctgaagctg   2340
gccggcgacg tggagagcaa ccccggcccc ggatccatgg ccaccgagta caagcccacg   2400
gtgcgcctcg ccacccgcga cgacgtcccc cgggccgtac gcaccctcgc cgccgcgttc   2460
gccgactacc ccgccacgcg ccacaccgtc gacccggacc gccacatcga gcgggtcacc   2520
gagctgcaag aactcttcct cacgcgcgtc gggctcgaca tcggcaaggt gtgggtcgcg   2580
gacgacggcg ccgcggtggc ggtctggacc acgccggaga gcgtcgaagc gggggcggtg   2640
ttcgccgaga tcggctcgcg catggccgag ttgagcggtt cccggctggc cgcgcagcaa   2700
cagatggaag gcctcctggc gccgcaccgg cccaaggagc ccgcgtggtt cctggccacc   2760
gtcggcgtct cgcccgacca ccagggcaag ggtctgggca gcgccgtcgt gctccccgga   2820
```

```
gtggaggcgg ccgagcgcgc tggggtgccc gccttcctgg agacctccgc gccccgcaac    2880
ctccccttct acgagcggct cggcttcacc gtcaccgccg acgtcgaggt gcccgaagga    2940
ccgcgcacct ggtgcatgac ccgcaagccc ggtgcctgaa cgcgtcttaa ggcgatcgca    3000
gacatgataa gatacattga tgagtttgga caaaccacaa ctagaatgca gtgaaaaaaa    3060
tgctttattt gtgaaatttg tgatgctatt gctttatttg taaccattat aagctgcaat    3120
aaacaagtta ataacaacaa ttccattcat tttatgtttc aggttcaggg ggagatgtgg    3180 gaggttttt aaagcaagta aaacctctac aaatgtggta gtcgaaattc ccgataagga    3240
tcttcctaga gcatggctac gtagataagt agcatggcgg gttaatcatt aactacaagg    3300 aaccctagt gatggagttg ccactccct ctctgcgcgc tcgctcgctc actgaggccg    3360
ggcgaccaaa ggtcgcccga cgcccgggct ttgcccgggc ggcctcagtg agcgagcgag    3420
cgcgcaggga tcccggtgtg aaataccgca cagatgcgta aggagaaaat accgcatcag    3480
gcgctcttcc gcttcctcgc tcactgactc gctgcgctcg gtcgttcggc tgcggcgagc    3540
ggtatcagct cactcaaagg cggtaatacg gttatccaca gaatcagggg ataacgcagg    3600
aaagaacatg tgagcaaaag gccagcaaaa ggccaggaac cgtaaaaagg ccgcgttgct    3660 ggcgttttc cataggctcc gcccccctga cgagcatcac aaaaatcgac gctcaagtca    3720
gaggtggcga aacccgacag gactataaag ataccaggcg tttccccctg gaagctccct    3780
cgtgcgctct cctgttccga ccctgccgct taccggatac ctgtccgcct ttctcccttc    3840
gggaagcgtg gcgctttctc atagctcacg ctgtaggtat ctcagttcgg tgtaggtcgt    3900
tcgctccaag ctgggctgtg tgcacgaacc cccgttcag cccgaccgct gcgccttatc    3960
cggtaactat cgtcttgagt ccaacccggt aagacacgac ttatcgccac tggcagcagc    4020
cactggtaac aggattagca gagcgaggta tgtaggcggt gctacagagt tcttgaagtg    4080
gtggcctaac tacggctaca ctagaaggac agtatttg                            4118
```

<210> SEQ ID NO 50
<211> LENGTH: 4121
<212> TYPE: DNA
<213> ORGANISM: Artificial Sequence
<220> FEATURE:
<223> OTHER INFORMATION: Oligonucleotide

<400> SEQUENCE: 50

```
ttttggattg aagccaatat gataatgagg gggtggagtt tgtgacgtgg cgcggggcgt      60
gggaacgggg cgggtgacgt agtagtgtgg cggaagtgtg atgttgcaag tgtggcggaa     120
cacatgtaag cgacggatgt ggcaaaagtg acgttttgg tgtgcgccgg tgtacacagg     180
aagtgacaat tttcgcgcgg ttttaggcgg atgttgtagt aaatttgggc gtaaccgagt     240
aagatttggc cattttcgcg ggaaaactga ataagaggaa gtgaaatctg ataatttttg     300
tgttactcat agcgcgtaat acggcagacc tcagcgctag attattgaag catttatcag     360
ggttattgtc tcatgagcgg atacatattt gaatgtattt agaaaaataa acaaataggg     420
gttccgcgca catttccccg aaaagtgcca cctgacgtta acctgcgcgc tcgctcgctc     480
actgaggccg cccgggcaaa gcccgggcgt cgggcgacct ttggtcgccc ggcctcagtg     540
agcgagcgag cgcgcagaga gggagtggcc aactccatca ctaggggttc cttgtagtta     600
atgattaacc cgccatgcta cttatctacg tagccatgct ctaggaagat cgcctaggta     660
cgtccaaggt cgggcaggaa gagggcctat ttccccatgat tccttcatat ttgcatatac     720
gatacaaggc tgttagagag ataattagaa ttaatttgac tgtaaacaca agatattag     780
```

```
tacaaaatac gtgacgtaga aagtaataat ttcttgggta gtttgcagtt ttaaaattat    840
gttttaaaat ggactatcat atgcttaccg taacttgaaa gtatttcgat ttcttggctt    900
tatatatctt gtggaaagga caaaaacagg cactagtact gatgtcgtat attcaagaga    960
tatacgacat cagtactagt gcctgttttt tggtaccaat tgtagtaatc aattacgggg   1020
tcattagttc atagcccata tatggagttc cgcgttacat aacttacggt aaatggcccg   1080
cctggctgac cgcccaacga cccccgccca ttgacgtcaa taatgacgta tgttcccata   1140
gtaacgccaa tagggacttt ccattgacgt caatgggtgg agtatttacg gtaaactgcc   1200
cacttggcag tacatcaagt gtatcatatg ccaagtacgc cccctattga cgtcaatgac   1260
ggtaaatggc ccgcctggca ttatgcccag tacatgacct tatgggactt tcctacttgg   1320
cagtacatct acgtattagt catcgctatt accatggtga tgcggttttg gcagtacatc   1380
aatgggcgtg gatagcggtt tgactcacgg ggatttccaa gtctccaccc cattgacgtc   1440
aatgggagtt tgttttggca ccaaaatcaa cgggactttc caaaatgtcg taacaactcc   1500
gccccattga cgcaaatggg cggtaggcgt gtacggtggg aggtctatat aagcagagct   1560
ggtttagtga accgtcaggg taccggatcc cttaagtgaa caactagtgc caccatggtg   1620
agcaagggcg aggagctgtt caccggggtg gtgcccatcc tggtcgagct ggacggcgac   1680
gtaaacggcc acaagttcag cgtgtccggc gagggcgagg gcgatgccac ctacggcaag   1740
ctgaccctga agttcatctg caccaccggc aagctgcccg tgccctggcc caccctcgtg   1800
accaccctga cctacggcgt gcagtgcttc agccgctacc ccgaccacat gaagcagcac   1860
gacttcttca gtccgccat gcccgaaggc tacgtccagg agcgcaccat cttcttcaag   1920
gacgacggca actacaagac ccgcgccgag gtgaagttcg agggcgacac cctggtgaac   1980
cgcatcgagc tgaagggcat cgacttcaag gaggacggca acatcctggg gcacaagctg   2040
gagtacaact acaacagcca caacgtctat atcatggccg acaagcagaa gaacggcatc   2100
aaggtgaact tcaagatccg ccacaacatc gaggacggca gcgtgcagct cgccgaccac   2160
taccagcaga acacccccat cggcgacggc cccgtgctgc tgcccgacaa ccactacctg   2220
agcacccagt ccgccctgag caaagacccc aacgagaagc gcgatcacat ggtcctgctg   2280
gagttcgtga ccgccgccgg gatcactctc ggcatggacg agctgtacaa ggaattcgga   2340
agcgggcagt gcaccaacta cgccctgctg aagctggccg cgacgtggaa gagcaaccccc   2400 ggccccggat ccatggccac cgagtacaag cccacggtgc cctcgccac ccgcgacgac   2460 gtcccccggg ccgtacgcac cctcgccgcc gcgttcgccg actacccgc cacgcgccac   2520 accgtcgacc cggaccgcca catcgagcgg gtcaccgagc tgcaagaact cttcctcacg   2580
cgcgtcgggc tcgacatcgg caaggtgtgg gtcgcggacc acggcgccgc ggtggcggtc   2640
tggaccacgc cggagagcgt cgaagcgggg gcggtgttcg ccgagatcgg ctcgcgcatg   2700
gccgagttga gcggttccc gctggccgcg cagcaacaga tggaaggcct cctggcgccg   2760
caccggccca aggagcccgc gtggttcctg gccaccgtcg gcgtctcgcc cgaccaccag   2820
ggcaagggtc tgggcagcgc cgtcgtgctc cccggagtgg aggcggccga gcgcgctggg   2880 gtgccccgcct tcctggagac ctccgcgccc cgcaacctcc ccttctacga gcggtcggc   2940 ttcaccgtca ccgccgacgt cgaggtgccc gaaggaccgc gcacctggtg catgacccgc   3000
aagcccggtg cctgaacgcg tcttaaggcg atcgcagaca tgataagata cattgatgag   3060
tttggacaaa ccacaactag aatgcagtga aaaaaatgct ttatttgtga aatttgtgat   3120
```

```
gctattgctt tatttgtaac cattataagc tgcaataaac aagttaataa caacaattcc    3180
attcatttta tgtttcaggt tcaggggag atgtgggagg ttttttaaag caagtaaaac     3240
ctctacaaat gtggtagtcg aaattcccga taaggatctt cctagagcat ggctacgtag    3300
ataagtagca tggcgggtta atcattaact acaaggaacc cctagtgatg gagttggcca    3360
ctccctctct gcgcgctcgc tcgctcactg aggccgggcg accaaaggtc gcccgacgcc    3420
cgggctttgc ccgggcggcc tcagtgagcg agcgagcgcg cagggatccc ggtgtgaaat    3480
accgcacaga tgcgtaagga gaaaataccg catcaggcgc tcttccgctt cctcgctcac    3540
tgactcgctg cgctcggtcg ttcggctgcg gcgagcggta tcagctcact caaaggcggt    3600
aatacggtta tccacagaat cagggataa cgcaggaaag aacatgtgag caaaaggcca    3660
gcaaaaggcc aggaaccgta aaaaggccgc gttgctggcg ttttcccata ggctccgccc    3720
ccctgacgag catcacaaaa atcgacgctc aagtcagagg tggcgaaacc cgacaggact    3780
ataaagatac caggcgtttc ccctggaag ctccctcgtg cgctctcctg ttccgacccct   3840 gccgcttacc ggatacctgt ccgcctttct cccttcggga agcgtggcgc tttctcatag    3900
ctcacgctgt aggtatctca gttcggtgta ggtcgttcgc tccaagctgg gctgtgtgca    3960
cgaacccccc gttcagcccg accgctgcgc cttatccggt aactatcgtc ttgagtccaa    4020
cccggtaaga cacgacttat cgccactggc agcagccact ggtaacagga ttagcagagc    4080
gaggtatgta ggcggtgcta cagagttctt gaagtggtgg c                       4121
```

<210> SEQ ID NO 51
<211> LENGTH: 4104
<212> TYPE: DNA
<213> ORGANISM: Artificial Sequence
<220> FEATURE:
<223> OTHER INFORMATION: Oligonucleotide

<400> SEQUENCE: 51

```
ttttggattg aagccaatat gataatgagg gggtggagtt tgtgacgtgg cgcggggcgt     60
gggaacgggg cgggtgacgt agtagtgtgg cggaagtgtg atgttgcaag tgtggcggaa   120
cacatgtaag cgacggatgt ggcaaaagtg acgttttgg tgtgcgccgg tgtacacagg    180
aagtgacaat tttcgcgcgg ttttaggcgg atgttgtagt aaatttgggc gtaaccgagt    240
aagatttggc cattttcgcg ggaaaactga ataagaggaa gtgaaatctg ataattttg    300 tgttactcat agcgcgtaat acggcagacc tcagcgctag attattgaag catttatcag    360
ggttattgtc tcatgagcgg atacatattt gaatgtattt agaaaaataa acaaataggg    420
gttccgcgca catttccccg aaaagtgcca cctgacgtta acctgcgcgc tcgctcgctc    480
actgaggccg cccgggcaaa gcccgggcgt cgggcgacct ttggtcgccc ggcctcagtg    540
agcgagcgag cgcgcagaga gggagtggcc aactccatca ctaggggttc cttgtagtta    600
atgattaacc cgccatgcta cttatctacg tagccatgct ctaggaagat cgcctaggta    660
cgtccaaggt cgggcaggaa gagggcctat ttcccatgat tccttcatat ttgcatatac    720
gatacaaggc tgttagagag ataattagaa ttaatttgac tgtaaacaca agatattag    780 tacaaaatac gtgacgtaga aagtaataat tccttgggta gtttgcagtt ttaaaattat    840
gttttaaaat ggactatcat atgcttaccg taacttgaaa gtatttcgat ttcttggctt    900
tatatatctt gtggaaagga caaaaaaaac taaaatgtct gataatggac cttcaagaga    960
ggtccattat cagacatttt agttttttttt tggtaccaat tgtagtaatc aattacgggg   1020
tcattagttc atagcccata tatggagttc cgcgttacat aacttacggt aaatggcccg    1080
```

-continued

```
cctggctgac cgcccaacga cccccgccca ttgacgtcaa taatgacgta tgttcccata   1140
gtaacgccaa tagggacttt ccattgacgt caatgggtgg agtatttacg gtaaactgcc   1200
cacttggcag tacatcaagt gtatcatatg ccaagtacgc ccctattga cgtcaatgac    1260
ggtaaatggc ccgcctggca ttatgcccag tacatgacct tatgggactt tcctacttgg   1320
cagtacatct acgtattagt catcgctatt accatggtga tgcggttttg gcagtacatc   1380
aatgggcgtg gatagcggtt tgactcacgg ggatttccaa gtctccaccc cattgacgtc   1440
aatgggagtt tgttttggca ccaaaatcaa cgggactttc caaaatgtcg taacaactcc   1500
gccccattga cgcaaatggg cggtaggcgt gtacggtggg aggtctatat aagcagagct   1560
ggtttagtga accgtcaggg taccggatcc cttaagtgaa caactagtgc caccatggtg   1620
agcaagggcg aggagctgtt caccggggtg gtgcccatcc tggtcgagct ggacggcgac   1680
gtaaacggcc acaagttcag cgtgtccggc gagggcgagg gcgatgccac ctacggcaag   1740
ctgaccctga agttcatctg caccaccggc aagctgcccg tgccctggcc caccctcgtg   1800
accaccctga cctacggcgt gcagtgcttc agccgctacc ccgaccacat gaagcagcac   1860
gacttcttca gtccgccat gcccgaaggc tacgtccagg agcgcaccat cttcttcaag    1920
gacgacggca actacaagac ccgcgccgag gtgaagttcg agggcgacac cctggtgaac   1980
cgcatcgagc tgaagggcat cgacttcaag gaggacggca acatcctggg gcacaagctg   2040
gagtacaact acaacagcca caacgtctat atcatggccg acaagcagaa gaacggcatc   2100
aaggtgaact tcaagatccg ccacaacatc gaggacggca gcgtgcagct cgccgaccac   2160
taccagcaga acacccccat cggcgacggc cccgtgctgc tgcccgacaa ccactacctg   2220
agcacccagt ccgccctgag caaagacccc aacgagaagc gcgatcacat ggtcctgctg   2280
gagttcgtga ccgccgccgg gatcactctc ggcatggacg agctgtacaa ggaattcgga   2340
agcgggcagt gcaccaacta cgccctgctg aagctggccg cgacgtgga gagcaacccc    2400
ggccccggat ccatggccac cgagtacaag cccacggtgc gcctcgccac ccgcgacgac   2460
gtccccgggg ccgtacgcac cctcgccgcc gcgttcgccg actacccgc cacgcgccac    2520
accgtcgacc cggaccgcca catcgagcgg gtcaccgagc tgcaagaact cttcctcacg   2580
cgcgtcgggc tcgacatcgg caaggtgtgg gtcgcggacg acggcgccgc ggtggcggtc   2640
tggaccacgc cggagagcgt cgaagcgggg gcggtgttcg ccgagatcgg ctcgcgcatg   2700
gccgagttga gcggttcccg gctggccgcg cagcaacaga tggaaggcct cctggcgccg   2760
caccggccca aggagcccgc gtggttcctg gccaccgtcg gcgtctcgcc cgaccaccag   2820
ggcaagggtc tgggcagcgc cgtcgtgctc cccggagtgg aggcggccga gcgcgctggg   2880
gtgcccgcct cctggagac ctccgcgccc cgcaacctcc ccttctacga gcggctcggc    2940
ttcaccgtca ccgccgacgt cgaggtgccc gaaggaccgc gcacctggtg catgacccgc   3000
aagcccggtg cctgaacgcg tcttaaggcg atcgcagaca tgataagata cattgatgag   3060
tttggacaaa ccacaactag aatgcagtga aaaaaatgct ttatttgtga aatttgtgat   3120
gctattgctt tatttgtaac cattataagc tgcaataaac aagttaataa caacaattcc   3180
attcatttta tgttttcaggt tcaggggggag atgtgggagg ttttttaaag caagtaaaac   3240
ctctacaaat gtggtagtcg aaattcccga taaggatctt cctagagcat ggctacgtag   3300
ataagtagca tggcgggtta atcattaact acaaggaacc cctagtgatg gagttggcca   3360
ctccctctct gcgcgctcgc tcgctcactg aggccgggcg accaaaggtc gcccgacgcc   3420
```

| | |
|---|---|
| cgggctttgc ccgggcggcc tcagtgagcg agcgagcgcg cagggatccc ggtgtgaaat | 3480 |
| accgcacaga tgcgtaagga gaaaataccg catcaggcgc tcttccgctt cctcgctcac | 3540 |
| tgactcgctg cgctcggtcg ttcggctgcg gcgagcggta tcagctcact caaaggcggt | 3600 |
| aatacggtta tccacagaat caggggataa cgcaggaaag aacatgtgag caaaaggcca | 3660 |
| gcaaaaggcc aggaaccgta aaaaggccgc gttgctggcg ttttccata ggctccgccc | 3720 |
| ccctgacgag catcacaaaa atcgacgctc aagtcagagg tggcgaaacc cgacaggact | 3780 |
| ataaagatac caggcgtttc cccctggaag ctccctcgtg cgctctcctg ttccgaccct | 3840 |
| gccgcttacc ggatacctgt ccgcctttct cccttcggga agcgtggcgc tttctcatag | 3900 |
| ctcacgctgt aggtatctca gttcggtgta ggtcgttcgc tccaagctgg gctgtgtgca | 3960 |
| cgaacccccc gttcagcccg accgctgcgc cttatccggt aactatcgtc ttgagtccaa | 4020 |
| cccggtaaga cacgacttat cgccactggc agcagccact ggtaacagga ttagcagagc | 4080 |
| gaggtatgta ggcggtgcta caga | 4104 |

<210> SEQ ID NO 52
<211> LENGTH: 29903
<212> TYPE: DNA
<213> ORGANISM: Artificial Sequence
<220> FEATURE:
<223> OTHER INFORMATION: SARS-COV-2

<400> SEQUENCE: 52

| | |
|---|---|
| attaaaggtt tataccttcc caggtaacaa accaaccaac tttcgatctc ttgtagatct | 60 |
| gttctctaaa cgaactttaa aatctgtgtg gctgtcactc ggctgcatgc ttagtgcact | 120 |
| cacgcagtat aattaataac taattactgt cgttgacagg acacgagtaa ctcgtctatc | 180 |
| ttctgcaggc tgcttacggt ttcgtccgtg ttgcagccga tcatcagcac atctaggttt | 240 |
| cgtccgggtg tgaccgaaag gtaagatgga gagccttgtc cctggtttca acgagaaaac | 300 |
| acacgtccaa ctcagtttgc ctgttttaca ggttcgcgac gtgctcgtac gtggctttgg | 360 |
| agactccgtg gaggaggtct tatcagaggc acgtcaacat cttaaagatg gcacttgtgg | 420 |
| cttagtagaa gttgaaaaag gcgttttgcc tcaacttgaa cagccctatg tgttcatcaa | 480 |
| acgttcggat gctcgaactg cacctcatgg tcatgttatg gttgagctgg tagcagaact | 540 |
| cgaaggcatt cagtacggtc gtagtggtga cacttggt gtccttgtcc ctcatgtggg | 600 |
| cgaaatacca gtggcttacc gcaaggttct tcttcgtaag aacggtaata aaggagctgg | 660 |
| tggccatagt tacggcgccg atctaaagtc atttgactta ggcgacgagc ttggcactga | 720 |
| tccttatgaa gattttcaag aaaactggaa cactaaacat agcagtggtg ttacccgtga | 780 |
| actcatgcgt gagcttaacg gaggggcata cactcgctat gtcgataaca acttctgtgg | 840 |
| ccctgatggc taccctcttg agtgcattaa agaccttcta gcacgtgctg gtaaagcttc | 900 |
| atgcactttg tccgaacaac tggactttat tgacactaag aggggtgtat actgctgccg | 960 |
| tgaacatgag catgaaattg cttggtacac ggaacgttct gaaagagct atgaattgca | 1020 |
| gacaccttt gaaattaaat tggcaagaa atttgacacc ttcaatgggg aatgtccaaa | 1080 |
| ttttgtattt cccttaaatt ccataatcaa gactattcaa ccaagggttg aaaagaaaaa | 1140 |
| gcttgatggc tttatgggta gaattcgatc tgtctatcca gttgcgtcac caaatgaatg | 1200 |
| caaccaaatg tgccttttcaa ctctcatgaa gtgtgatcat tgtggtgaaa cttcatggca | 1260 |
| gacgggcgat tttgttaaag ccacttgcga attttgtggc actgagaatt tgactaaaga | 1320 |
| aggtgccact acttgtggtt acttaccca aaatgctgtt gttaaaattt attgtccagc | 1380 |

```
atgtcacaat tcagaagtag gacctgagca tagtcttgcc gaataccata atgaatctgg    1440
cttgaaaacc attcttcgta agggtggtcg cactattgcc tttggaggct gtgtgttctc    1500
ttatgttggt tgccataaca agtgtgccta ttgggttcca cgtgctagcg ctaacatagg    1560
ttgtaaccat acaggtgttg ttggagaagg ttccgaaggt cttaatgaca accttcttga    1620
aatactccaa aaagagaaag tcaacatcaa tattgttggt gactttaaac ttaatgaaga    1680
gatcgccatt attttggcat cttttctgc ttccacaagt gcttttgtgg aaactgtgaa     1740
aggtttggat tataaagcat tcaaacaaat tgttgaatcc tgtggtaatt ttaaagttac    1800
aaaaggaaaa gctaaaaaag gtgcctggaa tattggtgaa cagaaatcaa tactgagtcc    1860
tctttatgca tttgcatcag aggctgctcg tgttgtacga tcaatttct cccgcactct     1920
tgaaactgct caaaattctg tgcgtgtttt acagaaggcc gctataacaa tactagatgg    1980
aatttcacag tattcactga gactcattga tgctatgatg ttcacatctg atttggctac    2040
taacaatcta gttgtaatgg cctacattac aggtggtgtt gttcagttga cttcgcagtg    2100
gctaactaac atctttggca ctgtttatga aaaactcaaa cccgtccttg attggcttga    2160
agagaagttt aaggaaggtg tagagtttct tagagacggt tgggaaattg ttaaattat     2220
ctcaacctgt gcttgtgaaa ttgtcggtgg acaaattgtc acctgtgcaa aggaaattaa    2280
ggagagtgtt cagacattct ttaagcttgt aaataaattt ttggctttgt gtgctgactc    2340
tatcattatt ggtggagcta aacttaaagc cttgaattta ggtgaaacat tgtcacgca    2400
ctcaaaggga ttgtacagaa agtgtgttaa atccagagaa gaaactggcc tactcatgcc    2460
tctaaaagcc ccaaaagaaa ttatcttctt agagggagaa acacttccca cagaagtgtt    2520
aacagaggaa gttgtcttga aaactggtga tttacaacca ttagaacaac ctactagtga    2580
agctgttgaa gctccattgg ttggtacacc agtttgtatt aacgggctta tgttgctcga    2640
aatcaaagac acagaaaagt actgtgccct tgcacctaat atgatggtaa caaacaatac    2700
cttcacactc aaaggcggtg caccaacaaa ggttactttt ggtgatgaca ctgtgataga    2760
agtgcaaggt tacaagagtg tgaatatcac ttttgaactt gatgaaagga ttgataaagt    2820
acttaatgag aagtgctctg cctatacagt tgaactcggt acagaagtaa atgagttcgc    2880
ctgtgttgtg gcagatgctg tcataaaaac tttgcaacca gtatctgaat tacttacacc    2940
actgggcatt gatttagatg agtggagtat ggctacatac tacttatttg atgagtctgg    3000
tgagtttaaa ttggcttcac atatgtattg ttctttctac cctccagatg aggatgaaga    3060
agaaggtgat tgtgaagaag aagagtttga gccatcaact caatatgagt atggtactga    3120
agatgattac caaggtaaac ctttggaatt tggtgccact tctgctgctc ttcaacctga    3180
agaagagcaa gaagaagatt ggttagatga tgatagtcaa caaactgttg gtcaacaaga    3240
cggcagtgag gacaatcaga caactactat tcaaacaatt gttgaggttc aacctcaatt    3300
agagatggaa cttacaccag ttgttcagac tattgaagtg aatagtttta gtggttattt    3360
aaaacttact gacaatgtat acattaaaaa tgcagacatt gtggaagaag ctaaaaaggt    3420
aaaaccaaca gtggttgtta atgcagccaa tgtttacctt aaacatggag gaggtgttgc    3480
aggagcctta aataaggcta ctaacaatgc catgcaagtt gaatctgatg attacatagc    3540
tactaatgga ccacttaaag tgggtggtag ttgtgtttta agcggacaca atcttgctaa    3600
acactgtctt catgttgtcg gcccaaatgt aacaaaggt gaagcattc aacttcttaa      3660
gagtgcttat gaaaatttta atcagcacga agttctactt gcaccattat tatcagctgg    3720
```

```
tattttttggt gctgaccccta tacattcttt aagagtttgt gtagatactg ttcgcacaaa    3780
tgtctactta gctgtctttg ataaaaatct ctatgacaaa cttgtttcaa gcttttttgga    3840 aatgaagagt gaaaagcaag ttgaacaaaa gatcgctgag attcctaaag aggaagttaa    3900
gccatttata actgaaagta aaccttcagt tgaacagaaa aaacaagatg ataagaaaat    3960
caaagcttgt gttgaagaag ttacaacaac tctggaagaa actaagttcc tcacagaaaa    4020
cttgttactt tatattgaca ttaatggcaa tcttcatcca gattctgcca ctcttgttag    4080
tgacattgac atcactttct taaagaaaga tgctccatat atagtgggtg atgttgttca    4140
agagggtgtt ttaactgctg tggttatacc tactaaaaag gctggtggca ctactgaaat    4200
gctagcgaaa gctttgagaa aagtgccaac agacaattat ataaccactt acccgggtca    4260
gggtttaaat ggttacactg tagaggaggc aaagacagtg cttaaaaagt gtaaaagtgc    4320
cttttacatt ctaccatcta ttatctctaa tgagaagcaa gaaattcttg gaactgtttc    4380
ttggaatttg cgagaaatgc ttgcacatgc agaagaaaca cgcaaattaa tgcctgtctg    4440
tgtggaaact aaagccatag tttcaactat acagcgtaaa tataagggta ttaaaataca    4500
agagggtgtg gttgattatg gtgctagatt ttacttttac accagtaaaa caactgtagc    4560
gtcacttatc aacacactta acgatctaaa tgaaactctt gttacaatgc cacttggcta    4620
tgtaacacat ggcttaaatt tggaagaagc tgctcggtat atgagatctc tcaaagtgcc    4680
agctacagtt tctgtttctt cacctgatgc tgttacagcg tataatggtt atcttacttc    4740
ttcttctaaa acacctgaag aacattttat tgaaaccatc tcacttgctg gttcctataa    4800
agattggtcc tattctggac aatctacaca actaggtata gaatttctta agagaggtga    4860
taaaagtgta tattcacacta gtaatcctac cacattccac ctagatggtg aagttatcac    4920
ctttgacaat cttaagacac ttctttcttt gagagaagtg aggactatta ggtgtttac    4980 aacagtagac aacattaacc tccacacgca agttgtggac atgtcaatga catatggaca    5040
acagtttggt ccaacttatt tggatggagc tgatgttact aaaataaaac ctcataattc    5100
acatgaaggt aaaacatttt atgttttacc taatgatgac actctacgtg ttgaggcttt    5160
tgagtactac cacacaactg atcctagttt tctgggtagg tacatgtcag cattaaatca    5220
cactaaaaag tggaaatacc cacaagttaa tggtttaact tctattaaat gggcagataa    5280
caactgttat cttgccactg cattgttaac actccaacaa atagagttga agtttaatcc    5340
acctgctcta caagatgctt attacagagc aagggctggt gaagctgcta acttttgtgc    5400
acttatctta gcctactgta ataagacagt aggtgagtta ggtgatgtta gagaaacaat    5460
gagttacttg tttcaacatg ccaatttaga ttcttgcaaa agagtcttga acgtggtgtg    5520 taaaaacttgt ggacaacagc agacaacccct aagggtgta gaagctgtta tgtacatggg    5580
cacactttct tatgaacaat ttaagaaagg tgttcagata ccttgtacgt gtggtaaaca    5640
agctacaaaa tatctagtac aacaggagtc acctttttgt atgatgtcag caccacctgc    5700
tcagtatgaa cttaagcatg gtacatttac ttgtgctagt gagtacactg gtaattacca    5760
gtgtggtcac tataaacata actttctaa agaaactttg tattgcatag acggtgcttt    5820
acttacaaag tcctcagaat acaaaggtcc tattacggat gttttctaca agaaaaacag    5880
ttacacaaca accataaaac cagttactta taaattggat ggtgttgttt gtacagaaat    5940 tgacccctaag ttggacaatt attataagaa agacaattct tatttcacag agcaaccaat    6000
tgatcttgta ccaaaccaac catatccaaa cgcaagcttc gataatttta gtttgtatg    6060 tgataatatc aaatttgctg atgatttaaa ccagttaact ggttataaga aacctgcttc    6120
```

| | | | | | |
|---|---|---|---|---|---|
| aagagagctt | aaagttacat | ttttccctga | cttaaatggt | gatgtggtgg | ctattgatta | 6180 |
| taaacactac | acaccctctt | ttaagaaagg | agctaaattg | ttacataaac | ctattgtttg | 6240 |
| gcatgttaac | aatgcaacta | ataaagccac | gtataaacca | aatacctggt | gtatacgttg | 6300 |
| tctttggagc | acaaaaccag | ttgaaacatc | aaattcgttt | gatgtactga | agtcagagga | 6360 |
| cgcgcaggga | atggataatc | ttgcctgcga | agatctaaaa | ccagtctctg | aagaagtagt | 6420 |
| ggaaaatcct | accatacaga | aagacgttct | tgagtgtaat | gtgaaaacta | ccgaagttgt | 6480 |
| aggagacatt | atacttaaac | cagcaaataa | tagtttaaaa | attacagaag | aggttggcca | 6540 |
| cacagatcta | atggctgctt | atgtagacaa | ttcagtctt | actattaaga | aacctaatga | 6600 |
| attatctaga | gtattaggtt | tgaaaaccct | tgctactcat | ggtttagctg | ctgttaatag | 6660 |
| tgtcccttgg | gatactatag | ctaattatgc | taagcctttt | cttaacaaag | ttgttagtac | 6720 |
| aactactaac | atagttacac | ggtgtttaaa | ccgtgtttgt | actaattata | tgccttattt | 6780 |
| ctttacttta | ttgctacaat | tgtgtacttt | tactagaagt | acaaattcta | gaattaaagc | 6840 |
| atctatgccg | actactatag | caaagaatac | tgttaagagt | gtcggtaaat | tttgtctaga | 6900 |
| ggcttcattt | aattatttga | agtcacctaa | ttttttctaaa | ctgataaata | ttataatttg | 6960 |
| gttttacta | ttaagtgttt | gcctaggttc | tttaatctac | tcaaccgctg | ctttaggtgt | 7020 |
| tttaatgtct | aatttaggca | tgccttctta | ctgtactggt | tacagagaag | ctatttgaa | 7080 |
| ctctactaat | gtcactattg | caacctactg | tactggttct | ataccttgta | gtgtttgtct | 7140 |
| tagtggttta | gattctttag | acaccctatcc | ttctttagaa | actatacaaa | ttaccatttc | 7200 |
| atctttaaa | tgggatttaa | ctgcttttgg | cttagttgca | gagtggtttt | tggcatatat | 7260 |
| tcttttcact | aggttttttct | atgtacttgg | attggctgca | atcatgcaat | tgtttttcag | 7320 |
| ctattttgca | gtacattta | ttagtaattc | ttggcttatg | tggttaataa | ttaatcttgt | 7380 |
| acaaatggcc | ccgatttcag | ctatggttag | aatgtacatc | ttctttgcat | cattttatta | 7440 |
| tgtatggaaa | agttatgtgc | atgttgtaga | cggttgtaat | tcatcaactt | gtatgatgtg | 7500 |
| ttacaaacgt | aatagagcaa | caagagtcga | atgtacaact | attgttaatg | gtgttagaag | 7560 |
| gtcctttat | gtctatgcta | atggaggtaa | aggcttttgc | aaactacaca | attggaattg | 7620 |
| tgttaattgt | gatacattct | gtgctggtag | tacatttatt | agtgatgaag | ttgcgagaga | 7680 |
| cttgtcacta | cagtttaaaa | gaccaataaa | tcctactgac | cagtcttctt | acatcgttga | 7740 |
| tagtgttaca | gtgaagaatg | gttccatcca | tctttacttt | gataaagctg | gtcaaaagac | 7800 |
| ttatgaaaga | cattctctct | ctcatttttgt | taacttagac | aacctgagag | ctaataacac | 7860 |
| taaaggttca | ttgcctatta | atgttatagt | ttttgatggt | aaatcaaaat | gtgaagaatc | 7920 |
| atctgcaaaa | tcagcgtctg | tttactacag | tcagcttatg | tgtcaaccta | tactgttact | 7980 |
| agatcaggca | ttagtgtctg | atgttggtga | tagtgcggaa | gttgcagtta | aatgtttga | 8040 |
| tgcttacgtt | aatacgtttt | catcaacttt | taacgtacca | atggaaaaac | tcaaaacact | 8100 |
| agttgcaact | gcagaagctg | aacttgcaaa | gaatgtgtcc | ttagacaatg | tcttatctac | 8160 |
| ttttatttca | gcagctcggc | aagggtttgt | tgattcagat | gtagaaacta | aagatgttgt | 8220 |
| tgaatgtctt | aaattgtcac | atcaatctga | catagaagtt | actggcgata | gttgtaataa | 8280 |
| ctatatgctc | acctataaca | aagttgaaaa | catgacaccc | cgtgaccttg | gtgcttgtat | 8340 |
| tgactgtagt | gcgcgtcata | ttaatgcgca | ggtagcaaaa | agtcacaaca | ttgctttgat | 8400 |
| atggaacgtt | aaagatttca | tgtcattgtc | tgaacaacta | cgaaaacaaa | tacgtagtgc | 8460 |

```
tgctaaaaag aataacttac cttttaagtt gacatgtgca actactagac aagttgttaa    8520
tgttgtaaca acaaagatag cacttaaggg tggtaaaatt gttaataatt ggttgaagca    8580
gttaattaaa gttacacttg tgttcctttt tgttgctgct attttctatt taataacacc    8640
tgttcatgtc atgtctaaac atactgactt ttcaagtgaa atcataggat acaaggctat    8700
tgatggtggt gtcactcgtg acatagcatc tacagatact tgttttgcta acaaacatgc    8760
tgattttgac acatggttta gccagcgtgg tggtagttat actaatgaca agcttgccc     8820
attgattgct gcagtcataa caagagaagt gggttttgtc gtgcctggtt tgcctggcac    8880
gatattacgc acaactaatg tgacttttt gcatttctta cctagagttt ttagtgcagt     8940
tggtaacatc tgttacacac catcaaaact tatagagtac actgactttg caacatcagc    9000
ttgtgttttg gctgctgaat gtacaatttt taaagatgct tctggtaagc cagtaccata    9060
ttgttatgat accaatgtac tagaaggttc tgttgcttat gaaagtttac gccctgacac    9120
acgttatgtg ctcatggatg gctctattat tcaatttcct aacacctacc ttgaaggttc    9180
tgttagagtg gtaacaactt ttgattctga gtactgtagg cacggcactt gtgaaagatc    9240
agaagctggt gtttgtgtat ctactagtgg tagatgggta cttaacaatg attattacag    9300
atctttacca ggagttttct gtggtgtaga tgctgtaaat ttacttacta atatgttac    9360
accactaatt caacctattg gtgctttgga catatcagca tctatagtag ctggtggtat    9420
tgtagctatc gtagtaacat gccttgccta ctattttatg aggtttagaa gagcttttgg    9480
tgaatacagt catgtagttg cctttaatac tttactattc cttatgtcat tcactgtact    9540
ctgtttaaca ccagtttact cattcttacc tggtgtttat tctgttattt acttgtactt    9600
gacattttat cttactaatg atgtttcttt tttagcacat attcagtgga tggttatgtt    9660
cacacccttta gtaccttct ggataacaat tgcttatatc atttgtattt ccacaaagca    9720
tttctattgg ttctttagta attacctaaa gagacgtgta gtcttaatg gtgtttcctt    9780
tagtactttt gaagaagctg cgctgtgcac ctttttgtta aataaagaaa tgtatctaaa    9840
gttgcgtagt gatgtgctat tacctcttac gcaatataat agatacttag ctctttataa    9900
taagtacaag tattttagtg gagcaatgga tacaactagc tacagagaag ctgcttgttg    9960
tcatctcgca aaggctctca atgacttcag taactcaggt tctgatgttc tttaccaacc   10020
accacaaacc tctatcacct cagctgtttt gcagagtggt tttagaaaaa tggcattccc   10080
atctggtaaa gttgagggtt gtatggtaca agtaacttgt ggtacaacta cacttaacgg   10140
tctttggctt gatgacgtag tttactgtcc aagacatgtg atctgcacct ctgaagacat   10200
gcttaaccct aattatgaag atttactcat tcgtaagtct aatcataatt tcttggtaca   10260
ggctggtaat gttcaactca gggttattgg acattctatg caaaattgtg tacttaagct   10320
taaggttgat acagccaatc ctaagacacc taagtataag tttgttcgca ttcaaccagg   10380
acagactttt tcagtgttag cttgttcaa tggttcacca tctggtgttt accaatgtgc   10440
tatgaggccc aatttcacta ttaagggttc attccttaat ggttcatgtg gtagtgttgg   10500
ttttaacata gattatgact gtgtctcttt tgttacatg caccatatgg aattaccaac   10560
tggagttcat gctggcacag acttagaagg taactttat ggacccttg ttgacaggca    10620
aacagcacaa gcagctggta cggacacaac tattacagtt aatgttttag cttggttgta   10680
cgctgctgtt ataaatggag acaggtggtt tctcaatcga tttaccacaa ctcttaatga   10740
ctttaacctt gtggctatga agtacaatta tgaacctcta acacaagacc atgttgacat   10800
actaggacct ctttctgctc aaactggaat tgccgttta gatatgtgtg cttcattaaa   10860
```

```
agaattactg caaaatggta tgaatggacg taccatattg ggtagtgctt tattagaaga   10920
tgaatttaca cctttttgatg ttgttagaca atgctcaggt gttactttcc aaagtgcagt   10980
gaaaagaaca atcaagggta cacaccactg gttgttactc acaattttga cttcactttt   11040
agttttagtc cagagtactc aatggtcttt gttcttttt ttgtatgaaa atgccttttt    11100
acctttgct  atgggtatta ttgctatgtc tgcttttgca atgatgtttg tcaaacataa   11160
gcatgcattt ctctgtttgt ttttgttacc ttctcttgcc actgtagctt attttaatat   11220
ggtctatatg cctgctagtt gggtgatgcg tattatgaca tggttggata tggttgatac   11280
tagtttgtct ggttttaagc taaaagactg tgttatgtat gcatcagctg tagtgttact   11340
aatccttatg acagcaagaa ctgtgtatga tgatggtgct aggagagtgt ggacacttat   11400
gaatgtcttg acactcgttt ataaagttta ttatggtaat gctttagatc aagccatttc   11460
catgtgggct cttataatct ctgttacttc taactactca ggtgtagtta caactgtcat   11520
gttttttggcc agaggtattg ttttatgtg tgttgagtat tgccctattt tcttcataac    11580
tggtaataca cttcagtgta taatgctagt ttattgtttc ttaggctatt tttgtacttg   11640
ttactttggc ctcttttgtt tactcaaccg ctactttaga ctgactcttg gtgtttatga   11700
ttacttagtt tctacacagg agtttagata tatgaattca cagggactac tcccacccaa   11760
gaatagcata gatgccttca aactcaacat taaattgttg ggtgttggtg caaaccttg    11820
tatcaaagta gccactgtac agtctaaaat gtcagatgta aagtgcacat cagtagtctt   11880
actctcagtt ttgcaacaac tcagagtaga atcatcatct aaattgtggg ctcaatgtgt   11940
ccagttacac aatgacattc tcttagctaa agatactact gaagcctttg aaaaaatggt   12000
ttcactactt tctgttttgc tttccatgca gggtgctgta gacataaaca agctttgtga   12060
agaaatgctg gacaacaggg caaccttaca agctatagcc tcagagttta gttcccttcc   12120
atcatatgca gcttttgcta ctgctcaaga agcttatgag caggctgttg ctaatggtga   12180
ttctgaagtt gttcttaaaa agttgaagaa gtctttgaat gtggctaaat ctgaatttga   12240
ccgtgatgca gccatgcaac gtaagttgga aaagatggct gatcaagcta tgacccaaat   12300
gtataaacag gctagatctg aggacaagag ggcaaaagtt actagtgcta tgcagacaat   12360
gcttttcact atgctagaa  agttggataa tgatgcactc aacaacatta tcaacaatgc   12420
aagagatggt tgtgttccct tgaacataat acctcttaca acagcagcca actaatggt    12480
tgtcatacca gactataaca catataaaaa tacgtgtgat ggtacaacat ttacttatgc   12540
atcagcattg tgggaaatcc aacaggttgt agatgcagat agtaaaattg ttcaacttag   12600
tgaaattagt atggacaatt cacctaattt agcatggcct cttattgtaa cagctttaag   12660
ggccaattct gctgtcaaat tacagaataa tgagcttagt cctgttgcac tacgacagat   12720
gtcttgtgct gccggtacta cacaaactgc ttgcactgat gacaatgcgt tagcttacta   12780
caacacaaca aagggaggta ggtttgtact tgcactgtta tccgatttac aggatttgaa   12840
atgggctaga ttcccctaaga gtgatggaac tggtactatc tatacagaac tggaaccacc   12900
ttgtaggttt gttacagaca cacctaaagg tcctaaagtg aagtatttat acttttattaa   12960
aggattaaac aacctaaata gaggtatggt acttggtagt ttagctgcca cagtacgtct   13020
acaagctggt aatgcaacag aagtgcctgc caattcaact gtattatctt tctgtgctt    13080
tgctgtagat gctgctaaag cttacaaaga ttatctagct agtgggggac aaccaatcac   13140
taattgtgtt aagatgttgt gtacacacac tggtactggt caggcaataa cagttacacc   13200
```

```
ggaagccaat atggatcaag aatcctttgg tggtgcatcg tgttgtctgt actgccgttg    13260
ccacatagat catccaaatc ctaaaggatt ttgtgactta aaaggtaagt atgtacaaat    13320
acctacaact tgtgctaatg accctgtggg ttttacactt aaaaacacag tctgtaccgt    13380
ctgcggtatg tggaaaggtt atggctgtag ttgtgatcaa ctccgcgaac ccatgcttca    13440
gtcagctgat gcacaatcgt ttttaaacgg gtttgcggtg taagtgcagc ccgtcttaca    13500
ccgtgcggca caggcactag tactgatgtc gtatacaggg cttttgacat ctacaatgat    13560
aaagtagctg gttttgctaa attcctaaaa actaattgtt gtcgcttcca agaaaaggac    13620
gaagatgaca atttaattga ttcttacttt gtagttaaga gacacacttt ctctaactac    13680
caacatgaag aaacaattta taatttactt aaggattgtc cagctgttgc taaacatgac    13740
ttctttaagt ttagaataga cggtgacatg gtaccacata tatcacgtca acgtcttact    13800
aaatacacaa tggcagacct cgtctatgct ttaaggcatt ttgatgaagg taattgtgac    13860
acattaaaag aaatacttgt cacatacaat tgttgtgatg atgattattt caataaaaag    13920
gactggtatg attttgtaga aaacccagat atattacgcg tatacgccaa cttaggtgaa    13980
cgtgtacgcc aagctttgtt aaaaacagta caattctgtg atgccatgcg aaatgctggt    14040
attgttggtg tactgacatt agataatcaa gatctcaatg gtaactggta tgatttcggt    14100
gatttcatac aaaccacgcc aggtagtgga gttcctgttg tagattctta ttattcattg    14160
ttaatgccta tattaacctt gaccagggct ttaactgcag agtcacatgt tgacactgac    14220
ttaacaaagc cttacattaa gtgggattg ttaaaatatg acttcacgga agagaggtta    14280
aaactctttg accgttattt taaatattgg gatcagacat accacccaaa ttgtgttaac    14340
tgtttggatg acagatgcat tctgcattgt gcaaacttta atgtttttatt ctctacagtg    14400 ttcccaccta caagttttgg accactagtg agaaaaatat ttgttgatgg tgttccattt    14460
gtagtttcaa ctggatacca cttcagagag ctaggtgttg tacataatca ggatgtaaac    14520
ttacatagct ctagacttag ttttaaggaa ttacttgtgt atgctgctga ccctgctatg    14580
cacgctgctt ctggtaatct attactagat aaacgcacta cgtgcttttc agtagctgca    14640
cttactaaca atgttgcttt tcaaactgtc aaacccggta attttaacaa agacttctat    14700
gactttgctg tgtctaaggg tttctttaag gaaggaagtt ctgttgaatt aaaacacttc    14760
ttctttgctc aggatggtaa tgctgctatc agcgattatg actactatcg ttataatcta    14820
ccaacaatgt gtgatatcag acaactacta tttgtagttg aagttgttga taagtacttt    14880
gattgttacg atggtggctg tattaatgct aaccaagtca tcgtcaacaa cctagacaaa    14940
tcagctggtt ttccatttaa taaatgggt aaggctagac tttattatga ttcaatgagt    15000
tatgaggatc aagatgcact tttcgcatat acaaaacgta atgtcatccc tactataact    15060
caaatgaatc ttaagtatgc cattagtgca aagaatagag ctcgcaccgt agctggtgtc    15120
tctatctgta gtactatgac caatagacag tttcatcaaa aattattgaa atcaatagcc    15180
gccactagag gagctactgt agtaattgga acaagcaaat tctatggtgg ttggcacaac    15240
atgttaaaaa ctgtttatag tgatgtagaa aaccctcacc ttatggggttg ggattatcct    15300 aaatgtgata gagccatgcc taacatgctt agaattatgg cctcacttgt tcttgctcgc    15360
aaacatacaa cgtgttgtag cttgtcacac cgtttctata ttagctaa tgagtgtgct    15420 caagtattga gtgaaatggt catgtgtggc ggttcactat atgttaaacc aggtggaacc    15480
tcatcaggag atgccacaac tgcttatgct aatagtgttt ttaacatttg tcaagctgtc    15540
acggccaatg ttaatgcact tttatctact gatggtaaca aaattgccga taagtatgtc    15600
```

```
cgcaatttac aacacagact ttatgagtgt ctctatagaa atagagatgt tgacacagac   15660
tttgtgaatg agttttacgc atatttgcgt aaacatttct caatgatgat actctctgac   15720
gatgctgttg tgtgtttcaa tagcacttat gcatctcaag gtctagtggc tagcataaag   15780
aactttaagt cagttcttta ttatcaaaac aatgttttta tgtctgaagc aaaatgttgg   15840
actgagactg accttactaa aggacctcat gaattttgct ctcaacatac aatgctagtt   15900
aaacagggtg atgattatgt gtaccttcct tacccagatc catcaagaat cctaggggcc   15960
ggctgttttg tagatgatat cgtaaaaaca gatggtacac ttatgattga acggttcgtg   16020
tctttagcta tagatgctta cccacttact aaacatccta atcaggagta tgctgatgtc   16080
tttcatttgt acttacaata cataagaaag ctacatgatg agttaacagg acacatgtta   16140
gacatgtatt ctgttatgct tactaatgat aacacttcaa ggtattggga acctgagttt   16200
tatgaggcta tgtacacacc gcatacagtc ttacaggctg ttggggcttg tgttctttgc   16260
aattcacaga cttcattaag atgtggtgct tgcatacgta gaccattctt atgttgtaaa   16320
tgctgttacg accatgtcat atcaacatca cataaattag tcttgtctgt taatccgtat   16380
gtttgcaatg ctccaggttg tgatgtcaca gatgtgactc aactttactt aggaggtatg   16440
agctattatt gtaaatcaca taaaccaccc attagttttc cattgtgtgc taatggacaa   16500 gttttttggtt tatataaaaa tacatgtgtt ggtagcgata atgttactga ctttaatgca   16560
attgcaacat gtgactggac aaatgctggt gattacattt tagctaacac ctgtactgaa   16620
agactcaagc tttttgcagc agaaacgctc aaagctactg aggagacatt taaactgtct   16680
tatggtattg ctactgtacg tgaagtgctg tctgacagag aattacatct ttcatgggaa   16740
gttggtaaac ctagaccacc acttaaccga aattatgtct ttactggtta tcgtgtaact   16800
aaaaacagta agtacaaat aggagagtac acctttgaaa aaggtgacta tggtgatgct   16860
gttgtttacc gaggtacaac aacttacaaa ttaaatgttg gtgattattt tgtgctgaca   16920
tcacatacag taatgccatt aagtgcacct acactagtgc cacaagagca ctatgttaga   16980
attactggct tatacccaac actcaatatc tcagatgagt tttctagcaa tgttgcaaat   17040
tatcaaaagg ttggtatgca aaagtattct acactccagg gaccacctgg tactggtaag   17100
agtcattttg ctattggcct agctctctac taccctttctg ctcgcatagt gtatacagct   17160
tgctctcatg ccgctgttga tgcactatgt gagaaggcat taaaatattt gcctatagat   17220
aaatgtagta gaattatacc tgcacgtgct cgtgtagagt gttttgataa attcaaagtg   17280
aattcaacat tagaacagta tgtcttttgt actgtaaatg cattgcctga acgacagca   17340 gatatagttg tctttgatga aatttcaatg gccacaaatt atgatttgag tgttgtcaat   17400
gccagattac gtgctaagca ctatgtgtac attggcgacc ctgctcaatt acctgcacca   17460
cgcacattgc taactaaggg cacactagaa ccagaatatt tcaattcagt gtgtagactt   17520
atgaaaacta taggtccaga catgttcctc ggaacttgtc ggcgttgtcc tgctgaaatt   17580
gttgacactg tgagtgcttt ggtttatgat aataagctta aagcacataa agacaaatca   17640
gctcaatgct ttaaaatgtt ttataagggt gttatcacgc atgatgtttc atctgcaatt   17700
aacaggccac aaataggcgt ggtaagagaa ttccttacac gtaaccctgc ttggagaaaa   17760
gctgtcttta tttcacctta taattcacag aatgctgtag cctcaaagat tttgggacta   17820
ccaactcaaa ctgttgattc atcacagggc tcagaatatg actatgtcat attcactcaa   17880
accactgaaa cagctcactc ttgtaatgta aacagattta atgttgctat taccagagca   17940
```

```
aaagtaggca tactttgcat aatgtctgat agagaccttt atgacaagtt gcaatttaca   18000
agtcttgaaa ttccacgtag gaatgtggca actttacaag ctgaaaatgt aacaggactc   18060
tttaaagatt gtagtaaggt aatcactggg ttacatccta cacaggcacc tacacacctc   18120
agtgttgaca ctaaattcaa aactgaaggt ttatgtgttg acatacctgg catacctaag   18180
gacatgacct atagaagact catctctatg atgggtttta aaatgaatta tcaagttaat   18240
ggttacccta acatgtttat cacccgcgaa gaagctataa gacatgtacg tgcatggatt   18300
ggcttcgatg tcgaggggtg tcatgctact agagaagctg ttggtaccaa tttacccttta  18360
cagctaggtt tttctacagg tgttaaccta gttgctgtac ctacaggtta tgttgataca   18420
cctaataata cagattttc cagagttagt gctaaaccac cgcctggaga tcaatttaaa    18480
cacctcatac cacttatgta caaaggactt ccttggaatg tagtgcgtat aaagattgta   18540
caaatgttaa gtgacacact aaaaatctc tctgacagag tcgtatttgt cttatgggca    18600
catggctttg agttgacatc tatgaagtat tttgtgaaaa taggacctga gcgcacctgt   18660
tgtctatgtg atagacgtgc cacatgcttt tccactgctt cagacactta tgcctgttgg   18720
catcattcta ttggatttga ttacgtctat aatccgttta tgattgatgt tcaacaatgg   18780
ggttttacag gtaacctaca aagcaaccat gatctgtatt gtcaagtcca tggtaatgca   18840
catgtagcta ttgtgatgc aatcatgact aggtgtctag ctgtccacga gtgctttgtt    18900
aagcgtgttg actggactat tgaatatcct ataattggtg atgaactgaa gattaatgcg   18960
gcttgtagaa aggttcaaca catggttgtt aaagctgcat tattagcaga caaattccca   19020
gttcttcacg acattggtaa ccctaaagct attaagtgtg tacctcaagc tgatgtagaa   19080
tggaagttct atgatgcaca gccttgtagt gacaaagctt ataaaataga agaattattc   19140
tattcttatg ccacacattc tgacaaattc acagatggtg tatgcctatt ttggaattgc   19200
aatgtcgata gatatcctgc taattccatt gtttgtagat ttgacactag agtgctatct   19260
aaccttaact tgcctggttg tgatggtggc agtttgtatg taaataaaca tgcattccac   19320
acaccagctt ttgataaaag tgcttttgtt aatttaaaac aattaccatt tttctattac   19380
tctgacagtc catgtgagtc tcatggaaaa caagtagtgt cagatataga ttatgtacca   19440
ctaaagtctg ctacgtgtat aacacgttgc aatttaggtg gtgctgtctg tagacatcat   19500
gctaatgagt acagattgta tctcgatgct tataacatga tgatctcagc tggctttagc   19560
ttgtgggttt acaaacaatt tgatacttat aacctctgga acactttac aagacttcag   19620
agtttagaaa atgtggcttt taatgttgta aataagggac actttgatgg acaacagggt   19680
gaagtaccag tttctatcat taataacact gtttacacaa aagttgatgg tgttgatgta   19740
gaattgtttg aaaataaaac aacattacct gttaatgtag catttgagct ttgggctaag   19800
cgcaacatta accagtacc agaggtgaaa atactcaata atttgggtgt ggacattgct   19860
gctaatactg tgatctggga ctacaaaaga gatgctccag cacatatatc tactattggt   19920
gtttgttcta tgactgacat agccaagaaa ccaactgaaa cgatttgtgc accactcact   19980
gtctttttg atggtagagt tgatggtcaa gtagacttat ttagaaatgc ccgtaatggt   20040
gttcttatta cagaaggtag tgttaaaggt ttacaaccat ctgtaggtcc caaacaagct   20100
agtcttaatg gagtcacatt aattggagaa gccgtaaaaa cacagttcaa ttattataag   20160
aaagttgatg gtgttgtcca acaattaccct gaaacttact ttactcagag tagaaattta  20220
caagaattta aacccaggag tcaaatggaa attgatttct tagaattagc tatggatgaa   20280
ttcattgaac ggtataaatt agaaggctat gccttcgaac atatcgttta tggagatttt   20340
```

```
agtcatagtc agttaggtgg tttacatcta ctgattggac tagctaaacg ttttaaggaa    20400
tcaccttttg aattagaaga ttttattcct atggacagta cagttaaaaa ctatttcata    20460
acagatgcgc aaacaggttc atctaagtgt gtgtgttctg ttattgattt attacttgat    20520
gattttgttg aaataataaa atcccaagat ttatctgtag tttctaaggt tgtcaaagtg    20580
actattgact atacagaaat ttcatttatg ctttggtgta aagatggcca tgtagaaaca    20640
ttttacccaa aattacaatc tagtcaagcg tggcaaccgg gtgttgctat gcctaatctt    20700
tacaaaatgc aaagaatgct attagaaaag tgtgaccttc aaaattatgg tgatagtgca    20760
acattaccta aaggcataat gatgaatgtc gcaaaatata ctcaactgtg tcaatattta    20820
aacacattaa cattagctgt accctataat atgagagtta tacattttgg tgctggttct    20880
gataaaggag ttgcaccagg tacagctgtt ttaagacagt ggttgcctac gggtacgctg    20940
cttgtcgatt cagatcttaa tgactttgtc tctgatgcag attcaacttt gattggtgat    21000
tgtgcaactg tacatacagc taataaatgg gatctcatta ttagtgatat gtacgaccct    21060
aagactaaaa atgttacaaa agaaaatgac tctaagagag gttttttcac ttacatttgt    21120
gggtttatac aacaaaagct agctcttgga ggttccgtgg ctataaagat aacagaacat    21180
tcttggaatg ctgatctttt aagctcatg ggacacttcg catggtggac agcctttgtt    21240
actaatgtga atgcgtcatc atctgaagca ttttttaattg gatgtaatta tcttggcaaa    21300
ccacgcgaac aaatagatgg ttatgtcatg catgcaaatt acatattttg gaggaataca    21360
aatccaattc agttgtcttc ctattcttta tttgacatga gtaaatttcc ccttaaatta    21420
aggggtactg ctgttatgtc tttaaaagaa ggtcaaatca atgatatgat tttatctctt    21480
cttagtaaag gtagacttat aattagaaa acaacagag ttgttatttc tagtgatgtt    21540
cttgttaaca actaaacgaa caatgtttgt ttttcttgtt ttattgccac tagtctctag    21600
tcagtgtgtt aatcttacaa ccagaactca attacccccct gcatacacta attctttcac    21660
acgtggtgtt tattaccctg acaaagtttt cagatcctca gttttacatt caactcagga    21720
cttgttctta cctttctttt ccaatgttac ttggttccat gctatacatg tctctgggac    21780
caatggtact aagaggtttg ataaccctgt cctaccattt aatgatggtg tttatttgc    21840 ttccactgag aagtctaaca taataagagg ctggattttt ggtactactt tagattcgaa    21900
gacccagtcc ctacttattg ttaataacgc tactaatgtt gttattaaag tctgtgaatt    21960
tcaattttgt aatgatccat ttttgggtgt ttattaccac aaaaacaaca aaagttggat    22020
ggaaagtgag ttcagagttt attctagtgc gaataattgc acttttgaat atgtctctca    22080
gccttttctt atggaccttg aaggaaaaca gggtaatttc aaaaatctta gggaatttgt    22140
gtttaagaat attgatggtt attttaaaat atattctaag cacacgccta ttaatttagt    22200
gcgtgatctc cctcagggtt tttcggcttt agaaccattg gtagatttgc caataggtat    22260
taacatcact aggtttcaaa ctttacttgc tttacataga agttatttga ctcctggtga    22320
ttcttcttca ggttggacag ctggtgctgc agcttattat gtgggttatc ttcaacctag    22380
gacttttcta ttaaaatata tgaaaatgg aaccattaca gatgctgtag actgtgcact    22440
tgacccctct tcagaaacaa agtgtacgtt gaaatccttc actgtagaaa aaggaatcta    22500
tcaaacttct aactttagag tccaaccaac agaatctatt gttagatttc ctaatattac    22560
aaacttgtgc ccttttggtg aagtttttaa cgccaccaga tttgcatctg tttatgcttg    22620
gaacaggaag agaatcagca actgtgttgc tgattattct gtcctatata attccgcatc    22680
```

```
attttccact tttaagtgtt atggagtgtc tcctactaaa ttaaatgatc tctgctttac   22740
taatgtctat gcagattcat ttgtaattag aggtgatgaa gtcagacaaa tcgctccagg   22800
gcaaactgga aagattgctg attataatta taaattacca gatgatttta caggctgcgt   22860
tatagcttgg aattctaaca atcttgattc taaggttggt ggtaattata attacctgta   22920
tagattgttt aggaagtcta atctcaaacc ttttgagaga gatatttcaa ctgaaatcta   22980
tcaggccggt agcacacctt gtaatggtgt tgaaggtttt aattgttact ttcctttaca   23040
atcatatggt ttccaaccca ctaatggtgt tggttaccaa ccatacagag tagtagtact   23100
ttcttttgaa cttctacatg caccagcaac tgtttgtgga cctaaaaagt ctactaattt   23160
ggttaaaaac aaatgtgtca atttcaactt caatggttta acaggcacag gtgttcttac   23220
tgagtctaac aaaaagtttc tgcctttcca acaatttggc agagacattg ctgacactac   23280
tgatgctgtc cgtgatccac agacacttga gattcttgac attacaccat gttcttttgg   23340
tggtgtcagt gttataacac caggaacaaa tacttctaac caggttgctg ttctttatca   23400
ggatgttaac tgcacagaag tccctgttgc tattcatgca gatcaactta ctcctacttg   23460
gcgtgtttat tctacaggtt ctaatgtttt tcaaacacgt gcaggctgtt taataggggc   23520
tgaacatgtc aacaactcat atgagtgtga catacccatt ggtgcaggta tatgcgctag   23580
ttatcagact cagactaatt ctcctcggcg ggcacgtagt gtagctagtc aatccatcat   23640
tgcctacact atgtcacttg gtgcagaaaa ttcagttgct tactctaata actctattgc   23700
catacccaca aattttacta ttagtgttac cacagaaatt ctaccagtgt ctatgaccaa   23760
gacatcagta gattgtacaa tgtacatttg tggtgattca actgaatgca gcaatctttt   23820
gttgcaatat ggcagttttt gtacacaatt aaaccgtgct ttaactggaa tagctgttga   23880
acaagacaaa aacacccaag aagtttttgc acaagtcaaa caaatttaca aaacaccacc   23940
aattaaagat tttggtggtt ttaattttc acaaatatta ccagatccat caaaaccaag   24000
caagaggtca tttattgaag atctactttt caacaaagtg acacttgcag atgctggctt   24060
catcaaacaa tatggtgatt gccttggtga tattgctgct agagacctca tttgtgcaca   24120
aaagtttaac ggccttactg ttttgccacc tttgctcaca gatgaaatga ttgctcaata   24180
cacttctgca ctgttagcgg gtacaatcac ttctggttgg acctttggtg caggtgctgc   24240
attacaaata ccatttgcta tgcaaatggc ttataggttt aatggtattg gagttacaca   24300
gaatgttctc tatgagaacc aaaaattgat tgccaaccaa tttaatagtg ctattggcaa   24360
aattcaagac tcacttttct tccacagcaag tgcacttgga aaacttcaag atgtggtcaa   24420
ccaaaatgca caagctttaa acacgcttgt taaacaactt agctccaatt ttggtgcaat   24480
ttcaagtgtt ttaaatgata tcctttcacg tcttgacaaa gttgaggctg aagtgcaaat   24540
tgataggttg atcacaggca gacttcaaag tttgcagaca tatgtgactc aacaattaat   24600
tagagctgca gaaatcagag cttctgctaa tcttgctgct actaaaatgt cagagtgtgt   24660
acttggacaa tcaaaaagag ttgattttg tggaaagggc tatcatctta tgtccttccc   24720
tcagtcagca cctcatggtg tagtcttctt gcatgtgact tatgtccctg cacaagaaaa   24780
gaacttcaca actgctcctg ccatttgtca tgatggaaaa gcacactttc ctcgtgaagg   24840
tgtctttgtt tcaaatggca cacactggtt tgtaacacaa aggaattttt atgaaccaca   24900
aatcattact acagacaaca catttgtgtc tggtaactgt gatgttgtaa taggaattgt   24960
caacaacaca gtttatgatc ctttgcaacc tgaattagac tcattcaagg aggagttaga   25020
taaatatttt aagaatcata catcaccaga tgttgattta ggtgacatct ctggcattaa   25080
```

```
tgcttcagtt gtaaacattc aaaaagaaat tgaccgcctc aatgaggttg ccaagaattt   25140
aaatgaatct ctcatcgatc tccaagaact tggaaagtat gagcagtata taaaatggcc   25200
atggtacatt tggctaggtt ttatagctgg cttgattgcc atagtaatgg tgacaattat   25260
gctttgctgt atgaccagtt gctgtagttg tctcaagggc tgttgttctt gtggatcctg   25320
ctgcaaattt gatgaagacg actctgagcc agtgctcaaa ggagtcaaat tacattacac   25380
ataaacgaac ttatggattt gtttatgaga atcttcacaa ttggaactgt aactttgaag   25440
caaggtgaaa tcaaggatgc tactccttca gattttgttc gcgctactgc aacgataccg   25500
atacaagcct cactcccttt cggatggctt attgttggcg ttgcacttct tgctgttttt   25560
cagagcgctt ccaaaatcat aaccctcaaa agagatggc aactagcact ctccaagggt   25620
gttcactttg tttgcaactt gctgttgttg tttgtaacag tttactcaca cctttttgctc   25680 gttgctgctg gccttgaagc ccctttttctc tatctttatg ctttagtcta cttcttgcag   25740
agtataaact ttgtaagaat aataatgagg ctttggcttt gctggaaatg ccgttccaaa   25800
aacccattac tttatgatgc caactatttt ctttgctggc atactaattg ttacgactat   25860 tgtataccttt acaatagtgt aacttcttca attgtcatta cttcaggtga tggcacaaca   25920
agtcctattt ctgaacatga ctaccagatt ggtggttata ctgaaaaatg ggaatctgga   25980
gtaaaagact gtgttgtatt acacagttac ttcacttcag actattacca gctgtactca   26040
actcaattga gtacagacac tggtgttgaa catgttacct tcttcatcta caataaaatt   26100
gttgatgagc ctgaagaaca tgtccaaatt cacacaatcg acggttcatc cggagttgtt   26160
aatccagtaa tggaaccaat ttatgatgaa ccgacgacga ctactagcgt gcctttgtaa   26220
gcacaagctg atgagtacga acttatgtac tcattcgttt cggaagagac aggtacgtta   26280
atagttaata gcgtacttct ttttcttgct ttcgtggtat tcttgctagt tacactagcc   26340
atccttactg cgcttcgatt gtgtgcgtac tgctgcaata ttgttaacgt gagtcttgta   26400
aaaccttctt tttacgttta ctctcgtgtt aaaaatctga attcttctag agttcctgat   26460
cttctggtct aaacgaacta atatattat tagttttttct gtttggaact ttaatttttag   26520 ccatggcaga ttccaacggt actattaccg ttgaagagct taaaaagctc cttgaacaat   26580
ggaacctagt aataggtttc ctattcctta catggatttg tcttctacaa tttgcctatg   26640
ccaacaggaa taggtttttg tatataatta agttaatttt cctctggctg ttatggccag   26700
taactttagc ttgttttgtg cttgctgctg tttacagaat aaattggatc accggtggaa   26760
ttgctatcgc aatggcttgt cttgtaggct tgatgtggct cagctacttc attgcttct   26820 tcagactgtt tgcgcgtacg cgttccatgt ggtcattcaa tccagaaact aacattcttc   26880
tcaacgtgcc actccatggc actattctga ccagaccgct tctagaaagt gaactcgtaa   26940
tcggagctgt gatccttcgt ggacatcttc gtattgctgg acaccatcta ggacgctgtg   27000
acatcaagga cctgcctaaa gaaatcactg ttgctcatc acgaacgctt tcttattaca   27060
aattgggagc ttcgcagcgt gtagcaggtg actcaggttt tgctgcatac agtcgctaca   27120
ggattggcaa ctataaatta aacacagacc attccagtag cagtgacaat attgctttgc   27180
ttgtacagta agtgacaaca gatgtttcat ctcgttgact ttcaggttac tatagcagag   27240
atattactaa ttattatgag gacttttaaa gtttccattt ggaatcttga ttacatcata   27300
aacctcataa ttaaaaattt atctaagtca ctaactgaga ataaatattc tcaattagat   27360
gaagagcaac caatggagat tgattaaacg aacatgaaaa ttattctttt cttggcactg   27420
```

```
ataacactcg ctacttgtga gctttatcac taccaagagt gtgttagagg tacaacagta   27480
cttttaaaag aaccttgctc ttctggaaca tacgagggca attcaccatt tcatcctcta   27540
gctgataaca aatttgcact gacttgcttt agcactcaat ttgcttttgc ttgtcctgac   27600
ggcgtaaaac acgtctatca gttacgtgcc agatcagttt cacctaaact gttcatcaga   27660
caagaggaag ttcaagaact ttactctcca attttttctta ttgttgcggc aatagtgttt   27720
ataacacttt gcttcacact caaaagaaag acagaatgat tgaactttca ttaattgact   27780
tctatttgtg cttttagcc tttctgctat tccttgtttt aattatgctt attatcttt    27840 ggttctcact tgaactgcaa gatcataatg aaacttgtca cgcctaaacg aacatgaaat   27900
ttcttgtttt cttaggaatc atcacaactg tagctgcatt tcaccaagaa tgtagtttac   27960
agtcatgtac tcaacatcaa ccatatgtag ttgatgaccc tgtcctatt cacttctatt    28020 ctaaatggta tattagagta ggagctagaa aatcagcacc tttaattgaa ttgtgcgtgg   28080
atgaggctgg ttctaaatca cccattcagt acatcgatat cggtaattat acagtttcct   28140
gtttaccttt tacaattaat tgccaggaac ctaaattggg tagtcttgta gtgcgttgtt   28200
cgttctatga agacttttta gagtatcatg acgttcgtgt tgttttagat ttcatctaaa   28260
cgaacaaact aaaatgtctg ataatggacc ccaaaatcag cgaaatgcac cccgcattac   28320
gtttggtgga cccctcagatt caactggcag taaccagaat ggagaacgca gtggggcgcg   28380
atcaaaacaa cgtcggcccc aaggtttacc caataatact gcgtcttggt tcaccgctct   28440
cactcaacat ggcaaggaag accttaaatt ccctcgagga caaggcgttc caattaacac   28500
caatagcagt ccagatgacc aaattggcta ctaccgaaga gctaccagac gaattcgtgg   28560
tggtgacggt aaaatgaaag atctcagtcc aagatggtat ttctactacc taggaactgg   28620
gccagaagct ggacttccct atggtgctaa caaagacggc atcatatggg ttgcaactga   28680
gggagccttg aatacaccaa aagatcacat tggcacccgc aatcctgcta caatgctgc    28740 aatcgtgcta caacttcctc aaggaacaac attgccaaaa ggcttctacg cagaaggag    28800 cagaggcggc agtcaagcct cttctcgttc ctcatcacgt agtcgcaaca gttcaagaaa   28860
ttcaactcca ggcagcagta ggggaacttc tcctgctaga atggctggca atggcggtga   28920
tgctgctctt gctttgctgc tgcttgacag attgaaccag cttgagagca aaatgtctgg   28980
taaaggccaa caacaacaag gccaaactgt cactaagaaa tctgctgctg aggcttctaa   29040
gaagcctcgg caaaaacgta ctgccactaa agcatacaat gtaacacaag ctttcggcag   29100
acgtggtcca aacaaaccc aaggaaattt tggggaccag gaactaatca gacaaggaac   29160
tgattacaaa cattggccgc aaattgcaca atttgcccccc agcgcttcag cgttcttcgg   29220
aatgtcgcgc attggcatgg aagtcacacc ttcgggaacg tggttgacct acacaggtgc   29280
catcaaattg gatgacaaag atccaaattt caaagatcaa gtcattttgc tgaataagca   29340
tattgacgca tacaaaacat tcccaccaac agagcctaaa aaggacaaaa agaagaaggc   29400
tgatgaaact caagccttac cgcagagaca gaagaaacag caaactgtga ctcttcttcc   29460
tgctgcagat ttggatgatt tctccaaaca attgcaacaa tccatgagca gtgctgactc   29520
aactcaggcc taaactcatg cagaccacac aaggcagatg ggctatataa acgttttcgc   29580
ttttccgttt acgatatata gtctactctt gtgcagaatg aattctcgta actacatagc   29640
acaagtagat gtagttaact ttaatctcac atagcaatct ttaatcagtg tgtaacatta   29700
gggaggactt gaaagagcca ccacatttc accgaggcca cgcggagtac gatcgagtgt   29760
acagtgaaca atgctaggga gagctgccta tatggaagag ccctaatgtg taaaattaat   29820
```

```
tttagtagtg ctatccccat gtgatttta a tagcttctta ggagaatgac aaaaaaaaaa    29880
aaaaaaaaaa aaaaaaaaaa aaa                                            29903
```

<210> SEQ ID NO 53
<211> LENGTH: 26
<212> TYPE: DNA
<213> ORGANISM: Artificial Sequence
<220> FEATURE:
<223> OTHER INFORMATION: Oligonucleotide

<400> SEQUENCE: 53

```
acactagcca tccttactgc gcttcg                                         26
```

<210> SEQ ID NO 54
<211> LENGTH: 21
<212> TYPE: PRT
<213> ORGANISM: Artificial Sequence
<220> FEATURE:
<223> OTHER INFORMATION: Oligopeptide

<400> SEQUENCE: 54

```
Met Ala Tyr Ala Ala Gln Pro Phe Leu Leu Arg Asn Gly Ala Asn Glu
1               5                   10                  15

Gly Phe His Glu Ala
            20
```

<210> SEQ ID NO 55
<211> LENGTH: 805
<212> TYPE: PRT
<213> ORGANISM: Homo sapiens

<400> SEQUENCE: 55

```
Met Ser Ser Ser Ser Trp Leu Leu Leu Ser Leu Val Ala Val Thr Ala
1               5                   10                  15

Ala Gln Ser Thr Ile Glu Glu Gln Ala Lys Thr Phe Leu Asp Lys Phe
            20                  25                  30

Asn His Glu Ala Glu Asp Leu Phe Tyr Gln Ser Ser Leu Ala Ser Trp
        35                  40                  45

Asn Tyr Asn Thr Asn Ile Thr Glu Glu Asn Val Gln Asn Met Asn Asn
    50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
    130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205
```

```
Val Asn Gly Val Asp Gly Tyr Asp Tyr Ser Arg Gly Gln Leu Ile Glu
    210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
            260                 265                 270

Arg Phe Trp Thr Asn Leu Tyr Ser Leu Thr Val Pro Phe Gly Gln Lys
        275                 280                 285

Pro Asn Ile Asp Val Thr Asp Ala Met Val Asp Gln Ala Trp Asp Ala
    290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
            340                 345                 350

Lys Gly Asp Phe Arg Ile Leu Met Cys Thr Lys Val Thr Met Asp Asp
        355                 360                 365

Phe Leu Thr Ala His His Glu Met Gly His Ile Gln Tyr Asp Met Ala
    370                 375                 380

Tyr Ala Ala Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
                405                 410                 415

His Leu Lys Ser Ile Gly Leu Leu Ser Pro Asp Phe Gln Glu Asp Asn
            420                 425                 430

Glu Thr Glu Ile Asn Phe Leu Leu Lys Gln Ala Leu Thr Ile Val Gly
        435                 440                 445

Thr Leu Pro Phe Thr Tyr Met Leu Glu Lys Trp Arg Trp Met Val Phe
    450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ser Asn Asp Tyr Ser Phe
            500                 505                 510

Ile Arg Tyr Tyr Thr Arg Thr Leu Tyr Gln Phe Gln Phe Gln Glu Ala
        515                 520                 525

Leu Cys Gln Ala Ala Lys His Glu Gly Pro Leu His Lys Cys Asp Ile
    530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Leu Leu Asn Tyr Phe Glu Pro Leu Phe
            580                 585                 590

Thr Trp Leu Lys Asp Gln Asn Lys Asn Ser Phe Val Gly Trp Ser Thr
        595                 600                 605

Asp Trp Ser Pro Tyr Ala Asp Gln Ser Ile Lys Val Arg Ile Ser Leu
    610                 615                 620
```

```
Lys Ser Ala Leu Gly Asp Arg Ala Tyr Glu Trp Asn Asp Asn Glu Met
625                 630                 635                 640

Tyr Leu Phe Arg Ser Ser Val Ala Tyr Ala Met Arg Gln Tyr Phe Leu
            645                 650                 655

Lys Val Lys Asn Gln Met Ile Leu Phe Gly Glu Glu Asp Val Arg Val
        660                 665                 670

Ala Asn Leu Lys Pro Arg Ile Ser Phe Asn Phe Phe Val Thr Ala Pro
    675                 680                 685

Lys Asn Val Ser Asp Ile Ile Pro Arg Thr Glu Val Glu Lys Ala Ile
690                 695                 700

Arg Met Ser Arg Ser Arg Ile Asn Asp Ala Phe Arg Leu Asn Asp Asn
705                 710                 715                 720

Ser Leu Glu Phe Leu Gly Ile Gln Pro Thr Leu Gly Pro Pro Asn Gln
            725                 730                 735

Pro Pro Val Ser Ile Trp Leu Ile Val Phe Gly Val Val Met Gly Val
            740                 745                 750

Ile Val Val Gly Ile Val Ile Leu Ile Phe Thr Gly Ile Arg Asp Arg
        755                 760                 765

Lys Lys Lys Asn Lys Ala Arg Ser Gly Glu Asn Pro Tyr Ala Ser Ile
770                 775                 780

Asp Ile Ser Lys Gly Glu Asn Asn Pro Gly Phe Gln Asn Thr Asp Asp
785                 790                 795                 800

Val Gln Thr Ser Phe
            805

<210> SEQ ID NO 56
<211> LENGTH: 385
<212> TYPE: PRT
<213> ORGANISM: Homo sapiens

<400> SEQUENCE: 56

Glu Glu Gln Ala Lys Thr Phe Leu Asp Lys Phe Asn His Glu Ala Glu
1               5                   10                  15

Asp Leu Phe Tyr Gln Ser Ser Leu Ala Ser Trp Asn Tyr Asn Thr Asn
            20                  25                  30

Ile Thr Glu Glu Asn Val Gln Asn Met Asn Asn Ala Gly Asp Lys Trp
        35                  40                  45

Ser Ala Phe Leu Lys Glu Gln Ser Thr Leu Ala Gln Met Tyr Pro Leu
    50                  55                  60

Gln Glu Ile Gln Asn Leu Thr Val Lys Leu Gln Leu Gln Ala Leu Gln
65                  70                  75                  80

Gln Asn Gly Ser Ser Val Leu Ser Glu Asp Lys Ser Lys Arg Leu Asn
                85                  90                  95

Thr Ile Leu Asn Thr Met Ser Thr Ile Tyr Ser Thr Gly Lys Val Cys
            100                 105                 110

Asn Pro Asp Asn Pro Gln Glu Cys Leu Leu Leu Glu Pro Gly Leu Asn
        115                 120                 125

Glu Ile Met Ala Asn Ser Leu Asp Tyr Asn Glu Arg Leu Trp Ala Trp
    130                 135                 140

Glu Ser Trp Arg Ser Glu Val Gly Lys Gln Leu Arg Pro Leu Tyr Glu
145                 150                 155                 160

Glu Tyr Val Val Leu Lys Asn Glu Met Ala Arg Ala Asn His Tyr Glu
                165                 170                 175

Asp Tyr Gly Asp Tyr Trp Arg Gly Asp Tyr Glu Val Asn Gly Val Asp
            180                 185                 190
```

```
Gly Tyr Asp Tyr Ser Arg Gly Gln Leu Ile Glu Asp Val Glu His Thr
            195                 200                 205

Phe Glu Glu Ile Lys Pro Leu Tyr Glu His Leu His Ala Tyr Val Arg
    210                 215                 220

Ala Lys Leu Met Asn Ala Tyr Pro Ser Tyr Ile Ser Pro Ile Gly Cys
225                 230                 235                 240

Leu Pro Ala His Leu Leu Gly Asp Met Trp Gly Arg Phe Trp Thr Asn
                245                 250                 255

Leu Tyr Ser Leu Thr Val Pro Phe Gly Gln Lys Pro Asn Ile Asp Val
            260                 265                 270

Thr Asp Ala Met Val Asp Gln Ala Trp Asp Ala Gln Arg Ile Phe Lys
        275                 280                 285

Glu Ala Glu Lys Phe Phe Val Ser Val Gly Leu Pro Asn Met Thr Gln
    290                 295                 300

Gly Phe Trp Glu Asn Ser Met Leu Thr Asp Pro Gly Asn Val Gln Lys
305                 310                 315                 320

Ala Val Cys His Pro Thr Ala Trp Asp Leu Gly Lys Gly Asp Phe Arg
                325                 330                 335

Ile Leu Met Cys Thr Lys Val Thr Met Asp Asp Phe Leu Thr Ala His
            340                 345                 350

His Glu Met Gly His Ile Gln Tyr Asp Met Ala Tyr Ala Ala Gln Pro
        355                 360                 365

Phe Leu Leu Arg Asn Gly Ala Asn Glu Gly Phe His Glu Ala Val Gly
    370                 375                 380

Glu
385

<210> SEQ ID NO 57
<211> LENGTH: 65
<212> TYPE: DNA
<213> ORGANISM: Artificial Sequence
<220> FEATURE:
<223> OTHER INFORMATION: Oligonucleotide

<400> SEQUENCE: 57
gccttgtccc tggtttcaac gagaattcaa gagattctcg ttgaaaccag ggacaaggct    60
ttttt                                                                65

<210> SEQ ID NO 58
<211> LENGTH: 65
<212> TYPE: DNA
<213> ORGANISM: Artificial Sequence
<220> FEATURE:
<223> OTHER INFORMATION: Oligonucleotide

<400> SEQUENCE: 58
aaaaaatatc agaggcacgt caacatctta atctcttgaa ttaagatgtt gacgtgcctc    60
tgata                                                                65

<210> SEQ ID NO 59
<211> LENGTH: 65
<212> TYPE: DNA
<213> ORGANISM: Artificial Sequence
<220> FEATURE:
<223> OTHER INFORMATION: Oligonucleotide

<400> SEQUENCE: 59
caggcactag tactgatgtc gtatattcaa gagatatacg acatcagtac tagtgcctgt    60
```

```
<210> SEQ ID NO 60
<211> LENGTH: 71
<212> TYPE: DNA
<213> ORGANISM: Artificial Sequence
<220> FEATURE:
<223> OTHER INFORMATION: Oligonucleotide

<400> SEQUENCE: 60
aaactaaaat gtctgataat ggaccttcaa gagaggtcca ttatcagaca ttttagtttt    60
tttttggtac c                                                         71

<210> SEQ ID NO 61
<211> LENGTH: 1273
<212> TYPE: PRT
<213> ORGANISM: Artificial Sequence
<220> FEATURE:
<223> OTHER INFORMATION: SARS-COV-2

<400> SEQUENCE: 61
```

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala

```
            275                 280                 285
Val Asp Cys Ala Leu Asp Pro Leu Ser Glu Thr Lys Cys Thr Leu Lys
290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
            325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
            355                 360                 365

Tyr Asn Ser Ala Ser Phe Ser Thr Phe Lys Cys Tyr Gly Val Ser Pro
370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
            405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
            435                 440                 445

Tyr Asn Tyr Leu Tyr Arg Leu Phe Arg Lys Ser Asn Leu Lys Pro Phe
450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
            485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
            515                 520                 525

Lys Ser Thr Asn Leu Val Lys Asn Lys Cys Val Asn Phe Asn Phe Asn
            530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
            565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
            595                 600                 605

Ala Val Leu Tyr Gln Asp Val Asn Cys Thr Glu Val Pro Val Ala Ile
            610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
            645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
            675                 680                 685

Ser Gln Ser Ile Ile Ala Tyr Thr Met Ser Leu Gly Ala Glu Asn Ser
            690                 695                 700
```

```
Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
            725                 730                 735

Asp Cys Thr Met Tyr Ile Cys Gly Asp Ser Thr Glu Cys Ser Asn Leu
        740                 745                 750

Leu Leu Gln Tyr Gly Ser Phe Cys Thr Gln Leu Asn Arg Ala Leu Thr
    755                 760                 765

Gly Ile Ala Val Glu Gln Asp Lys Asn Thr Gln Glu Val Phe Ala Gln
770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
            805                 810                 815

Phe Ile Glu Asp Leu Leu Phe Asn Lys Val Thr Leu Ala Asp Ala Gly
        820                 825                 830

Phe Ile Lys Gln Tyr Gly Asp Cys Leu Gly Asp Ile Ala Ala Arg Asp
    835                 840                 845

Leu Ile Cys Ala Gln Lys Phe Asn Gly Leu Thr Val Leu Pro Pro Leu
850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
            885                 890                 895

Pro Phe Ala Met Gln Met Ala Tyr Arg Phe Asn Gly Ile Gly Val Thr
        900                 905                 910

Gln Asn Val Leu Tyr Glu Asn Gln Lys Leu Ile Ala Asn Gln Phe Asn
    915                 920                 925

Ser Ala Ile Gly Lys Ile Gln Asp Ser Leu Ser Ser Thr Ala Ser Ala
930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
            965                 970                 975

Leu Asn Asp Ile Leu Ser Arg Leu Asp Lys Val Glu Ala Glu Val Gln
        980                 985                 990

Ile Asp Arg Leu Ile Thr Gly Arg Leu Gln Ser Leu Gln Thr Tyr Val
    995                 1000                1005

Thr Gln Gln Leu Ile Arg Ala Ala Glu Ile Arg Ala Ser Ala Asn
    1010                1015                1020

Leu Ala Ala Thr Lys Met Ser Glu Cys Val Leu Gly Gln Ser Lys
    1025                1030                1035

Arg Val Asp Phe Cys Gly Lys Gly Tyr His Leu Met Ser Phe Pro
    1040                1045                1050

Gln Ser Ala Pro His Gly Val Val Phe Leu His Val Thr Tyr Val
    1055                1060                1065

Pro Ala Gln Glu Lys Asn Phe Thr Thr Ala Pro Ala Ile Cys His
    1070                1075                1080

Asp Gly Lys Ala His Phe Pro Arg Glu Gly Val Phe Val Ser Asn
    1085                1090                1095

Gly Thr His Trp Phe Val Thr Gln Arg Asn Phe Tyr Glu Pro Gln
    1100                1105                1110
```

-continued

```
Ile Ile Thr Thr Asp Asn Thr Phe Val Ser Gly Asn Cys Asp Val
    1115                1120                1125

Val Ile Gly Ile Val Asn Asn Thr Val Tyr Asp Pro Leu Gln Pro
    1130                1135                1140

Glu Leu Asp Ser Phe Lys Glu Glu Leu Asp Lys Tyr Phe Lys Asn
    1145                1150                1155

His Thr Ser Pro Asp Val Asp Leu Gly Asp Ile Ser Gly Ile Asn
    1160                1165                1170

Ala Ser Val Val Asn Ile Gln Lys Glu Ile Asp Arg Leu Asn Glu
    1175                1180                1185

Val Ala Lys Asn Leu Asn Glu Ser Leu Ile Asp Leu Gln Glu Leu
    1190                1195                1200

Gly Lys Tyr Glu Gln Tyr Ile Lys Trp Pro Trp Tyr Ile Trp Leu
    1205                1210                1215

Gly Phe Ile Ala Gly Leu Ile Ala Ile Val Met Val Thr Ile Met
    1220                1225                1230

Leu Cys Cys Met Thr Ser Cys Cys Ser Cys Leu Lys Gly Cys Cys
    1235                1240                1245

Ser Cys Gly Ser Cys Cys Lys Phe Asp Glu Asp Ser Glu Pro
    1250                1255                1260

Val Leu Lys Gly Val Lys Leu His Tyr Thr
    1265                1270

<210> SEQ ID NO 62
<211> LENGTH: 15
<212> TYPE: PRT
<213> ORGANISM: Artificial Sequence
<220> FEATURE:
<223> OTHER INFORMATION: SARS-COV-2

<400> SEQUENCE: 62

Thr Phe Leu Asp Lys Phe Asn His Glu Ala Glu Asp Leu Phe Tyr
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Oligopeptide

<400> SEQUENCE: 63

Thr Phe Leu Asp Lys Phe Asn His Glu Ala Glu Asp Leu Phe Tyr
1               5                   10                  15

<210> SEQ ID NO 64
<211> LENGTH: 20
<212> TYPE: PRT
<213> ORGANISM: Artificial Sequence
<220> FEATURE:
<223> OTHER INFORMATION: Oligopeptide

<400> SEQUENCE: 64

Gln Ala Lys Thr Phe Leu Asp Lys Phe Asn His Glu Ala Glu Asp Leu
1               5                   10                  15

Phe Tyr Gln Ser
            20

<210> SEQ ID NO 65
<211> LENGTH: 26
<212> TYPE: PRT
```

```
<213> ORGANISM: Artificial Sequence
<220> FEATURE:
<223> OTHER INFORMATION: Oligopeptide

<400> SEQUENCE: 65

Thr Ile Glu Glu Gln Ala Lys Thr Phe Leu Asp Lys Phe Asn His Glu
1               5                   10                  15

Ala Glu Asp Leu Phe Tyr Gln Ser Ser Leu
                20                  25

<210> SEQ ID NO 66
<211> LENGTH: 30
<212> TYPE: PRT
<213> ORGANISM: Artificial Sequence
<220> FEATURE:
<223> OTHER INFORMATION: Oligopeptide

<400> SEQUENCE: 66

Gln Ser Thr Ile Glu Glu Gln Ala Lys Thr Phe Leu Asp Lys Phe Asn
1               5                   10                  15

His Glu Ala Glu Asp Leu Phe Tyr Gln Ser Ser Leu Ala Ser
                20                  25                  30

<210> SEQ ID NO 67
<211> LENGTH: 15
<212> TYPE: PRT
<213> ORGANISM: Artificial Sequence
<220> FEATURE:
<223> OTHER INFORMATION: Oligopeptide

<400> SEQUENCE: 67

Glu Gln Ser Thr Leu Ala Gln Met Tyr Pro Leu Gln Glu Ile Gln
1               5                   10                  15

<210> SEQ ID NO 68
<211> LENGTH: 20
<212> TYPE: PRT
<213> ORGANISM: Artificial Sequence
<220> FEATURE:
<223> OTHER INFORMATION: Oligopeptide

<400> SEQUENCE: 68

Leu Lys Glu Gln Ser Thr Leu Ala Gln Met Tyr Pro Leu Gln Glu Ile
1               5                   10                  15

Gln Asn Leu Thr
                20

<210> SEQ ID NO 69
<211> LENGTH: 25
<212> TYPE: PRT
<213> ORGANISM: Artificial Sequence
<220> FEATURE:
<223> OTHER INFORMATION: Oligopeptide

<400> SEQUENCE: 69

Trp Ser Ala Phe Leu Lys Glu Gln Ser Thr Leu Ala Gln Met Tyr Pro
1               5                   10                  15

Leu Gln Glu Ile Gln Asn Leu Thr Val
                20                  25

<210> SEQ ID NO 70
<211> LENGTH: 30
<212> TYPE: PRT
<213> ORGANISM: Artificial Sequence
<220> FEATURE:
```

<223> OTHER INFORMATION: Oligopeptide

<400> SEQUENCE: 70

Asp Lys Trp Ser Ala Phe Leu Lys Glu Gln Ser Thr Leu Ala Gln Met
1               5                   10                  15
Tyr Pro Leu Gln Glu Ile Gln Asn Leu Thr Val Lys Leu Gln
            20                  25                  30

<210> SEQ ID NO 71
<211> LENGTH: 15
<212> TYPE: PRT
<213> ORGANISM: Artificial Sequence
<220> FEATURE:
<223> OTHER INFORMATION: Oligopeptide

<400> SEQUENCE: 71

Thr Gln Gly Phe Trp Glu Asn Ser Met Leu Thr Asp Pro Gly Asn
1               5                   10                  15

<210> SEQ ID NO 72
<211> LENGTH: 20
<212> TYPE: PRT
<213> ORGANISM: Artificial Sequence
<220> FEATURE:
<223> OTHER INFORMATION: Oligopeptide

<400> SEQUENCE: 72

Leu Pro Asn Met Thr Gln Gly Phe Trp Glu Asn Ser Met Leu Thr Asp
1               5                   10                  15
Pro Gly Asn Val
            20

<210> SEQ ID NO 73
<211> LENGTH: 25
<212> TYPE: PRT
<213> ORGANISM: Artificial Sequence
<220> FEATURE:
<223> OTHER INFORMATION: Oligopeptide

<400> SEQUENCE: 73

Val Gly Leu Pro Asn Met Thr Gln Gly Phe Trp Glu Asn Ser Met Leu
1               5                   10                  15
Thr Asp Pro Gly Asn Val Gln Lys Ala
            20                  25

<210> SEQ ID NO 74
<211> LENGTH: 30
<212> TYPE: PRT
<213> ORGANISM: Artificial Sequence
<220> FEATURE:
<223> OTHER INFORMATION: Oligopeptide

<400> SEQUENCE: 74

Val Ser Val Gly Leu Pro Asn Met Thr Gln Gly Phe Trp Glu Asn Ser
1               5                   10                  15
Met Leu Thr Asp Pro Gly Asn Val Gln Lys Ala Val Cys His
            20                  25                  30

<210> SEQ ID NO 75
<211> LENGTH: 15
<212> TYPE: PRT
<213> ORGANISM: Artificial Sequence
<220> FEATURE:
<223> OTHER INFORMATION: Oligopeptide

```
<400> SEQUENCE: 75

Trp Asp Leu Gly Lys Gly Asp Phe Arg Ile Leu Met Cys Thr Lys
1               5                   10                  15

<210> SEQ ID NO 76
<211> LENGTH: 20
<212> TYPE: PRT
<213> ORGANISM: Artificial Sequence
<220> FEATURE:
<223> OTHER INFORMATION: Oligopeptide

<400> SEQUENCE: 76

Pro Thr Ala Trp Asp Leu Gly Lys Gly Asp Phe Arg Ile Leu Met Cys
1               5                   10                  15

Thr Lys Val Thr
            20

<210> SEQ ID NO 77
<211> LENGTH: 25
<212> TYPE: PRT
<213> ORGANISM: Artificial Sequence
<220> FEATURE:
<223> OTHER INFORMATION: Oligopeptide

<400> SEQUENCE: 77

Val Cys His Pro Thr Ala Trp Asp Leu Gly Lys Gly Asp Phe Arg Ile
1               5                   10                  15

Leu Met Cys Thr Lys Val Thr Met Asp
            20                  25

<210> SEQ ID NO 78
<211> LENGTH: 30
<212> TYPE: PRT
<213> ORGANISM: Artificial Sequence
<220> FEATURE:
<223> OTHER INFORMATION: Oligopeptide

<400> SEQUENCE: 78

Lys Ala Val Cys His Pro Thr Ala Trp Asp Leu Gly Lys Gly Asp Phe
1               5                   10                  15

Arg Ile Leu Met Cys Thr Lys Val Thr Met Asp Asp Phe Leu
            20                  25                  30

<210> SEQ ID NO 79
<211> LENGTH: 15
<212> TYPE: PRT
<213> ORGANISM: Artificial Sequence
<220> FEATURE:
<223> OTHER INFORMATION: Oligopeptide

<400> SEQUENCE: 79

Ala Gln Pro Phe Leu Leu Arg Asn Gly Ala Asn Glu Gly Phe His
1               5                   10                  15

<210> SEQ ID NO 80
<211> LENGTH: 20
<212> TYPE: PRT
<213> ORGANISM: Artificial Sequence
<220> FEATURE:
<223> OTHER INFORMATION: Oligopeptide

<400> SEQUENCE: 80

Ala Tyr Ala Ala Gln Pro Phe Leu Leu Arg Asn Gly Ala Asn Glu Gly
1               5                   10                  15
```

```
Phe His Glu Ala
        20

<210> SEQ ID NO 81
<211> LENGTH: 25
<212> TYPE: PRT
<213> ORGANISM: Artificial Sequence
<220> FEATURE:
<223> OTHER INFORMATION: Oligopeptide

<400> SEQUENCE: 81

Tyr Asp Met Ala Tyr Ala Ala Gln Pro Phe Leu Leu Arg Asn Gly Ala
1               5                   10                  15

Asn Glu Gly Phe His Glu Ala Val Gly
            20                  25

<210> SEQ ID NO 82
<211> LENGTH: 31
<212> TYPE: PRT
<213> ORGANISM: Artificial Sequence
<220> FEATURE:
<223> OTHER INFORMATION: Oligopeptide

<400> SEQUENCE: 82

Ile Gln Tyr Asp Met Ala Tyr Ala Ala Gln Pro Phe Leu Leu Arg Asn
1               5                   10                  15

Gly Ala Asn Glu Gly Phe His Glu Ala Val Gly Glu Ile Met Ser
            20                  25                  30
```